US009453224B2

(12) United States Patent
Thibonnier

(10) Patent No.: US 9,453,224 B2
(45) Date of Patent: Sep. 27, 2016

(54) MIRNA MODULATORS OF THERMOGENESIS

(71) Applicant: APTAMIR THERAPEUTICS, INC., Austin, TX (US)

(72) Inventor: Marc Thibonnier, Austin, TX (US)

(73) Assignee: AptamiR Therapeutics, Inc., Austin, TX (US)

( * ) Notice: Subject to any disclaimer, the term of this patent is extended or adjusted under 35 U.S.C. 154(b) by 0 days.

(21) Appl. No.: 14/714,470

(22) Filed: May 18, 2015

(65) Prior Publication Data

US 2015/0329861 A1     Nov. 19, 2015

Related U.S. Application Data

(63) Continuation of application No. 13/826,775, filed on Mar. 14, 2013, now Pat. No. 9,034,839.

(60) Provisional application No. 61/636,059, filed on Apr. 20, 2012, provisional application No. 61/681,750, filed on Aug. 10, 2012.

(51) Int. Cl.
    *A61K 48/00*     (2006.01)
    *C12N 15/113*    (2010.01)
    *C12Q 1/68*      (2006.01)

(52) U.S. Cl.
    CPC .............. *C12N 15/113* (2013.01); *C12Q 1/68* (2013.01); *C12N 2310/141* (2013.01); *C12N 2310/16* (2013.01); *C12N 2310/3519* (2013.01); *C12N 2320/11* (2013.01); *C12N 2320/32* (2013.01)

(58) Field of Classification Search
    None
    See application file for complete search history.

(56) References Cited

U.S. PATENT DOCUMENTS

| 6,107,094 A | 8/2000 | Crooke .......................... 435/455 |
| 2008/0311040 A1 | 12/2008 | Berry et al. ................... 514/1.1 |
| 2010/0255545 A1 | 10/2010 | Smolke et al. .............. 435/91.1 |
| 2011/0224286 A1 | 9/2011 | Yu et al. ..................... 514/44 R |
| 2013/0331440 A1 | 12/2013 | Scheideler et al. ............. 514/44 |

FOREIGN PATENT DOCUMENTS

| EP | 1 800 695 A1 | 6/2007 |
| WO | WO/2010/108126 | 9/2010 |
| WO | WO/2010/135714 | 11/2010 |
| WO | WO/2011/079263 | 6/2011 |
| WO | WO/2011/138457 | 11/2011 |
| WO | WO 2011153542 | 12/2011 |
| WO | WO/2012/007725 | 1/2012 |
| WO | WO 2013181613 | 12/2013 |

OTHER PUBLICATIONS

Alexander, et al., Exp Opin Therap Targets. 15(5):623-36, 2011.
Andersen, et al., Int J Obes. 37(2):175-81, 2013.
Bader, et al., Gene Ther. 18(12):1121-26, 2011.
Borgdorff, et al., Oncogene. 29(15):2262-71, 2010.
Broderick, et al., Gene Ther. 18(12):1104-1110, 2011.
Cerchia, et al., Pharmaceut. 4(12):1434-49, 2011.
Chen, et al., J Biol Chem. 284:5362-5369, 2009.
Czech, et al., Nat Rev Endocrinol. 7(8):473-84, 2011.
Davidson, et al., Nat Rev Genet. 12(5):329-40, 2011.
Dehwah, et al., J Genet Genom. 39(1):11-18, 2011.
Ebert, et al., Nature Methods. 4(9):721-26, 2007.
Elmen, et al., Nature. 452:896-99, 2008.
Esau, et al., Cell Metab. 3(2):87-98, 2006.
Esterbauer, et al., Nat Genet. 28(2):178-83, 2001.
Friedman, et al., BMC Bioinformatics. 26(15):1920-1, 2010.
Fujiki, et al., BMC Biol. 7:38, 2009.
Gallagher, et al., Genome Med. 2(2):9, 2010.
Hao, et al., Mol Biosyst. 8(11): 2828-38, 2012.
Hao, et al., Mol Biosyst. 8(2):663-70, 2012.
Hsu, et al., Nucleic Acids Res. 39(Database Issue):D163-9, 2011.
Kanasaki, et al., J Biomed Biotechnol. 2011:197636, 2011.
Kanwar, et al., Crit Rec Biochem Mol Biol. 46(6):459-77, 2011.
Kim, et al., Biomat. 33(1):20-17, 2011.
Krutzfeldt, et al., Nature. 438:685-9, 2005.
Lennox, et al., Gene Ther. 18(12):1111-1120, 2011.
Liu, et al., Cancer Invest. 30(8):577-82, 2012.
Liu, et al., Gene. 514(1):41-7, 2013.
Liu, et al., PLoS One. 7(5):e37789, 2012.
Lowell, et al., Nature. 404(6778):652-60, 2000.
McGregor, et al., Curr Mol Med. 11(4):304-16, 2011.
Okada, et al., J Androl. 31(1):75-8, 2010.
Petrovic, et al., J Biol Chem. 285(10):7153-64, 2010.
Rantalainen, et al., PLoS One. 6(11):1-12, 2011.
Rieger, et al., Frontiers in Genetics. 2:39, 2011.
Rosen & Spiegelman, Cell. 156:20-45, 2014.
Search Report and Written Opinion in International Application No. PCT/US2013/037579 mailed Oct. 25, 2013.
Search Report and Written Opinion in International Application No. PCT/US2013/053613 mailed Jan. 2, 2014.
Snead, et al., Nucleic Acid Ther. 22(3):139-46, 2012.
Speakman, et al., Obes Rev. 8(Suppl 1): 55-61, 2007.
Sun, et al., Mol Endocrinol. 23:925-31, 2009.
Sun, et al., Nature Cell Biol. 13(8):958-65, 2011.
Thorsen, et al., Cancer J. 18(3):275-84, 2012.
Tivnan, et al., PLoS One. 7(5):e38129, 2012.
Van Rooij, et al., Circ Res. 110(3):496-507, 2012.
Wang, et al., Am J Physiol. 286(1):E1-7, 2004.
Wang, et al., Meth Mol Biol. 821:421-433, 2012.
Wu, et al., Int J Nanomed. 6:1747-56, 2011.
Xiao, et al., J Cell Physiol. 212:285-92, 2007.
Yin, et al., Cell Metabl. 17(2):210-224, 2013.

(Continued)

*Primary Examiner* — Kimberly Chong
(74) *Attorney, Agent, or Firm* — Norton Rose Fulbright US LLP

(57) ABSTRACT

Provided are novel methods and compositions for the modulation of thermogenesis. Such methods are particularly advantageous in that they allow for the reduction of body fat in a subject without the subject having to adjust their caloric intake through dieting, modify their physical activity or undergo bariatric surgery. Accordingly, the methods of the invention are particularly useful for treating or preventing obesity. Also provided are methods of screening for novel agents that modulate the activity of thermogenic regulators.

14 Claims, 26 Drawing Sheets

(56) References Cited

OTHER PUBLICATIONS

Zaragosi, et al., Genoma Biol. 12:1-13, 2011.
Chen et al., *PLoS One* 7(4):e34116, 2012.
Hajer et al., *European Heart Journal* 29:2959-2971, 2008.
He et al., *Experimental Biology and Medicine* 236:1116-1121, 2011.
Kaur et al., *Mol. BioSyst.* 7:3234-3244, 2011.
TargetScan 5.2, "Predicted MiRNA Targets of miR-22", Jun. 2011. Retrieved on Mar. 23, 2016.
Cao et al., "White to Brown Fat Phenotypic Switch Induced by Genetic and Environmental Activation of a Hypothalamic-Adipocyte Axis", *Cell Metabolism* 14:324-338, 2011.
Ho et al., "Mitochondrial Uncoupling Protein-2 (UCP2) Mediates Leptin Protection Against MPP+ Toxicity in Neuronal Cells", *Neurotox Res.* 17:332-343, 2010.
Partial Supplementary European Search Report for EP13777669.6, mailed May 10, 2016.
Sun et al., "MicroRNA-15a Positively Regulates Insulin Synthesis by Inhibiting Uncoupling Protein-2 Expression", *Diabetes Research and Clinical Practice* 91:94-100, 2011.

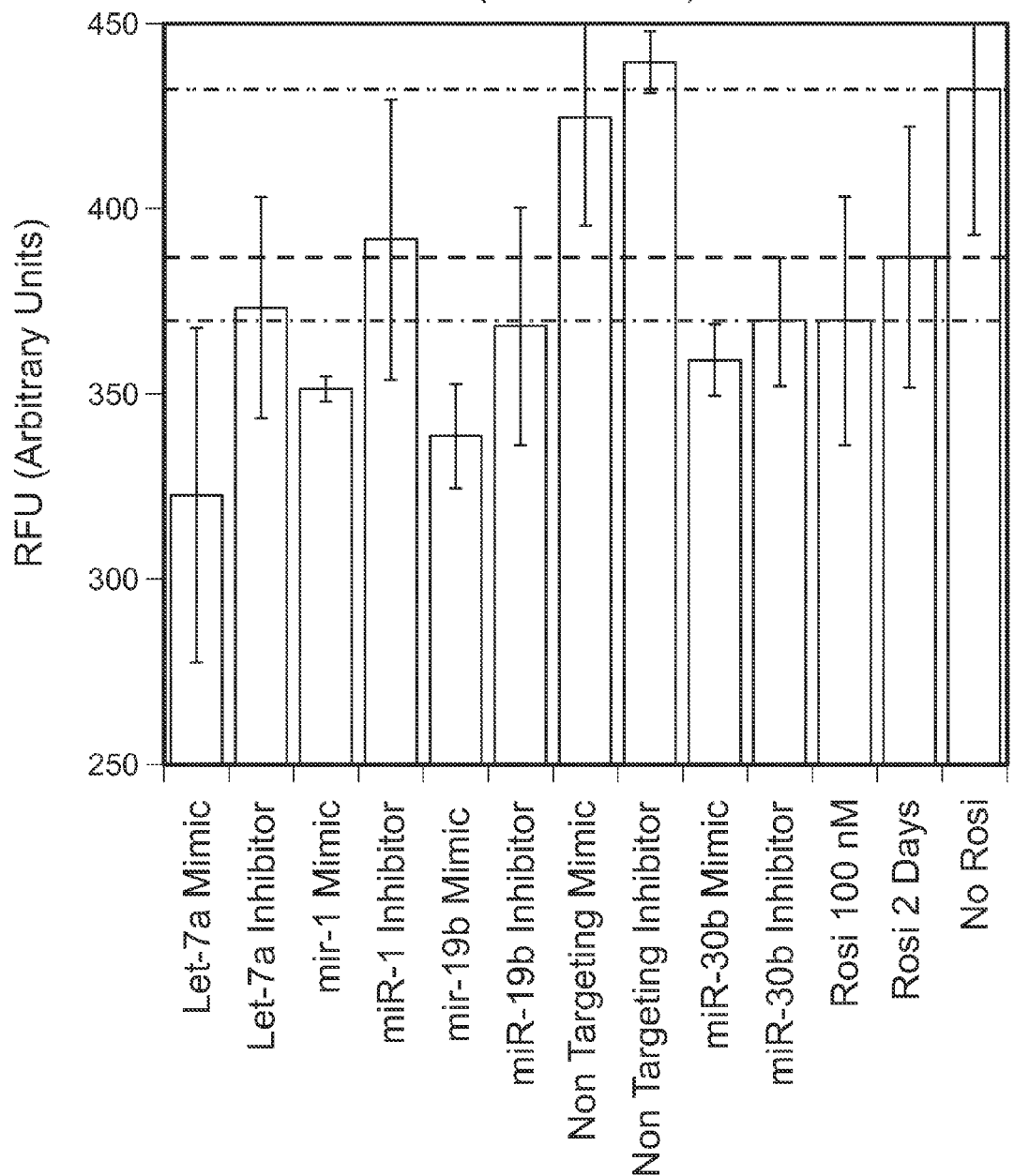

SEQUENCE LISTING

<160> NUMBER OF SEQ ID NOS: 383

<210> SEQ ID NO 1
<211> LENGTH: 16
<212> TYPE: DNA
<213> ORGANISM: Homo sapiens

<400> SEQUENCE: 1
cctctctgct tcttct                                                      16

<210> SEQ ID NO 2
<211> LENGTH: 10
<212> TYPE: DNA
<213> ORGANISM: Homo sapiens

<400> SEQUENCE: 2
ctccttggaa                                                             10

<210> SEQ ID NO 3
<211> LENGTH: 13
<212> TYPE: DNA
<213> ORGANISM: Homo sapiens

<400> SEQUENCE: 3
ttgcccttgc tca                                                         13

<210> SEQ ID NO 4
<211> LENGTH: 16
<212> TYPE: DNA
<213> ORGANISM: Homo sapiens

<400> SEQUENCE: 4

```
acgtcataaa gggtca                                                   16
```

```
<210> SEQ ID NO 5
<211> LENGTH: 16
<212> TYPE: DNA
<213> ORGANISM: Homo sapiens
<220> FEATURE:
<221> NAME/KEY: misc_feature
<222> LOCATION: (7)..(10)
<223> OTHER INFORMATION: n is an a, t, g, c, other or unknown

<400> SEQUENCE: 5
rgktcannnn rgktca                                                   16

<210> SEQ ID NO 6
<211> LENGTH: 14
<212> TYPE: DNA
<213> ORGANISM: Homo sapiens

<400> SEQUENCE: 6
gctcatactg acct                                                     14

<210> SEQ ID NO 7
<211> LENGTH: 13
<212> TYPE: DNA
<213> ORGANISM: Homo sapiens

<400> SEQUENCE: 7
gttaatgtgt tct                                                      13

<210> SEQ ID NO 8
<211> LENGTH: 17
<212> TYPE: DNA
<213> ORGANISM: Homo sapiens

<400> SEQUENCE: 8
tgaccacagt ttgatca                                                  17

<210> SEQ ID NO 9
<211> LENGTH: 20
<212> TYPE: DNA
<213> ORGANISM: Homo sapiens

<400> SEQUENCE: 9
aatgtaatgc agataagcta                                               20

<210> SEQ ID NO 10
<211> LENGTH: 20
<212> TYPE: DNA
<213> ORGANISM: Homo sapiens

<400> SEQUENCE: 10
acatgtttta attacaattc                                               20

<210> SEQ ID NO 11
<211> LENGTH: 12
<212> TYPE: DNA
<213> ORGANISM: Homo sapiens

<400> SEQUENCE: 11
gattggcagc tt                                                       12

<210> SEQ ID NO 12
<211> LENGTH: 23
```

```
<212> TYPE: DNA
<213> ORGANISM: Homo sapiens

<400> SEQUENCE: 12
gatttttaat gtttagagtc cag                                            23

<210> SEQ ID NO 13
<211> LENGTH: 20
<212> TYPE: DNA
<213> ORGANISM: Homo sapiens

<400> SEQUENCE: 13
tttagagctg gagggtactt                                                20

<210> SEQ ID NO 14
<211> LENGTH: 20
<212> TYPE: DNA
<213> ORGANISM: Homo sapiens

<400> SEQUENCE: 14
tttagagctg gagggtactt                                                20

<210> SEQ ID NO 15
<211> LENGTH: 19
<212> TYPE: DNA
<213> ORGANISM: Homo sapiens

<400> SEQUENCE: 15
gacagaggaa cagtttgag                                                 19

<210> SEQ ID NO 16
<211> LENGTH: 22
<212> TYPE: DNA
<213> ORGANISM: Homo sapiens

<400> SEQUENCE: 16
attttggcag gattgctact ag                                             22

<210> SEQ ID NO 17
<211> LENGTH: 19
<212> TYPE: DNA
<213> ORGANISM: Homo sapiens

<400> SEQUENCE: 17
ttttgagatc tatacctgg                                                 19

<210> SEQ ID NO 18
<211> LENGTH: 23
<212> TYPE: DNA
<213> ORGANISM: Homo sapiens

<400> SEQUENCE: 18
attttaagct aaatccaagg att                                            23

<210> SEQ ID NO 19
<211> LENGTH: 22
<212> TYPE: DNA
<213> ORGANISM: Homo sapiens

<400> SEQUENCE: 19
tgaccatttc tggagtgcaa tt                                             22

<210> SEQ ID NO 20
```

```
<211> LENGTH: 10
<212> TYPE: DNA
<213> ORGANISM: Homo sapiens

<400> SEQUENCE: 20
acagtttgat                                                              10

<210> SEQ ID NO 21
<211> LENGTH: 10
<212> TYPE: DNA
<213> ORGANISM: Homo sapiens

<400> SEQUENCE: 21
acagtttgag                                                              10

<210> SEQ ID NO 22
<211> LENGTH: 19
<212> TYPE: DNA
<213> ORGANISM: Homo sapiens

<400> SEQUENCE: 22
ctggagtgca attgtgtga                                                    19

<210> SEQ ID NO 23
<211> LENGTH: 20
<212> TYPE: DNA
<213> ORGANISM: Homo sapiens

<400> SEQUENCE: 23
ttttaatgtt tagagtccag                                                   20

<210> SEQ ID NO 24
<211> LENGTH: 22
<212> TYPE: DNA
<213> ORGANISM: Homo sapiens

<400> SEQUENCE: 24
tgatgacatc tctaacaact tc                                                22

<210> SEQ ID NO 25
<211> LENGTH: 20
<212> TYPE: DNA
<213> ORGANISM: Homo sapiens

<400> SEQUENCE: 25
agaaactgag tgaaatgcag                                                   20

<210> SEQ ID NO 26
<211> LENGTH: 17
<212> TYPE: DNA
<213> ORGANISM: Homo sapiens

<400> SEQUENCE: 26
tgaccatttc tggagtg                                                      17

<210> SEQ ID NO 27
<211> LENGTH: 13
<212> TYPE: DNA
<213> ORGANISM: Homo sapiens

<400> SEQUENCE: 27
tactctgaat gtt                                                          13
```

```
<210> SEQ ID NO 28
<211> LENGTH: 16
<212> TYPE: DNA
<213> ORGANISM: Homo sapiens

<400> SEQUENCE: 28
ttaaccacag ttgtca                                                     16

<210> SEQ ID NO 29
<211> LENGTH: 20
<212> TYPE: DNA
<213> ORGANISM: Homo sapiens

<400> SEQUENCE: 29
caagttcact agaatacaag                                                 20

<210> SEQ ID NO 30
<211> LENGTH: 22
<212> TYPE: DNA
<213> ORGANISM: Homo sapiens

<400> SEQUENCE: 30
aaggttacag gctgccagac at                                              22

<210> SEQ ID NO 31
<211> LENGTH: 13
<212> TYPE: DNA
<213> ORGANISM: Homo sapiens

<400> SEQUENCE: 31
gtgtgaatga atg                                                        13

<210> SEQ ID NO 32
<211> LENGTH: 23
<212> TYPE: DNA
<213> ORGANISM: Homo sapiens

<400> SEQUENCE: 32
taggcatgaa cctactctga atg                                             23

<210> SEQ ID NO 33
<211> LENGTH: 20
<212> TYPE: DNA
<213> ORGANISM: Homo sapiens

<400> SEQUENCE: 33
aaactgagtg aaatgcagtt                                                 20

<210> SEQ ID NO 34
<211> LENGTH: 20
<212> TYPE: DNA
<213> ORGANISM: Homo sapiens

<400> SEQUENCE: 34
aaactgagtg aaatgcagtt                                                 20

<210> SEQ ID NO 35
<211> LENGTH: 23
<212> TYPE: DNA
<213> ORGANISM: Homo sapiens

<400> SEQUENCE: 35
tttattaacc acagttgtca gtt                                             23
```

<210> SEQ ID NO 36
<211> LENGTH: 11
<212> TYPE: DNA
<213> ORGANISM: Homo sapiens

<400> SEQUENCE: 36
aagtatcctt t                                                            11

<210> SEQ ID NO 37
<211> LENGTH: 10
<212> TYPE: DNA
<213> ORGANISM: Homo sapiens

<400> SEQUENCE: 37
atgggacaca                                                              10

<210> SEQ ID NO 38
<211> LENGTH: 11
<212> TYPE: DNA
<213> ORGANISM: Homo sapiens

<400> SEQUENCE: 38
ttattttccc t                                                            11

<210> SEQ ID NO 39
<211> LENGTH: 10
<212> TYPE: DNA
<213> ORGANISM: Homo sapiens

<400> SEQUENCE: 39
tgacaactgt                                                              10

<210> SEQ ID NO 40
<211> LENGTH: 10
<212> TYPE: DNA
<213> ORGANISM: Homo sapiens

<400> SEQUENCE: 40
agggaactga                                                              10

<210> SEQ ID NO 41
<211> LENGTH: 10
<212> TYPE: DNA
<213> ORGANISM: Homo sapiens

<400> SEQUENCE: 41
tgtgaactgg                                                              10

<210> SEQ ID NO 42
<211> LENGTH: 10
<212> TYPE: DNA
<213> ORGANISM: Homo sapiens

<400> SEQUENCE: 42
acttttgcgg                                                              10

<210> SEQ ID NO 43
<211> LENGTH: 10
<212> TYPE: DNA
<213> ORGANISM: Homo sapiens

<400> SEQUENCE: 43
ttcctttatc                                                              10

<210> SEQ ID NO 44
<211> LENGTH: 10
<212> TYPE: DNA
<213> ORGANISM: Homo sapiens

<400> SEQUENCE: 44
ttcctctgtc                                                                   10

<210> SEQ ID NO 45
<211> LENGTH: 10
<212> TYPE: DNA
<213> ORGANISM: Homo sapiens

<400> SEQUENCE: 45
tagcttatct                                                                   10

<210> SEQ ID NO 46
<211> LENGTH: 11
<212> TYPE: DNA
<213> ORGANISM: Homo sapiens

<400> SEQUENCE: 46
ttccctatct c                                                                 11

<210> SEQ ID NO 47
<211> LENGTH: 9
<212> TYPE: DNA
<213> ORGANISM: Homo sapiens

<400> SEQUENCE: 47 cagcaagca                                                                     9

<210> SEQ ID NO 48
<211> LENGTH: 10
<212> TYPE: DNA
<213> ORGANISM: Homo sapiens

<400> SEQUENCE: 48
aagctgccaa                                                                   10

<210> SEQ ID NO 49
<211> LENGTH: 11
<212> TYPE: DNA
<213> ORGANISM: Homo sapiens

<400> SEQUENCE: 49
agttcttcac a                                                                 11

<210> SEQ ID NO 50
<211> LENGTH: 10
<212> TYPE: DNA
<213> ORGANISM: Homo sapiens

<400> SEQUENCE: 50
cattttcttg                                                                   10

<210> SEQ ID NO 51
<211> LENGTH: 10
<212> TYPE: DNA
<213> ORGANISM: Homo sapiens

<400> SEQUENCE: 51
ccaatccttg                                                                      10

<210> SEQ ID NO 52
<211> LENGTH: 10
<212> TYPE: DNA
<213> ORGANISM: Homo sapiens

<400> SEQUENCE: 52
cctttcatg                                                                       10

<210> SEQ ID NO 53
<211> LENGTH: 10
<212> TYPE: DNA
<213> ORGANISM: Homo sapiens

<400> SEQUENCE: 53
gtaaccttcc                                                                      10

<210> SEQ ID NO 54
<211> LENGTH: 10
<212> TYPE: DNA
<213> ORGANISM: Homo sapiens

<400> SEQUENCE: 54
cagagtaggt                                                                      10

<210> SEQ ID NO 55
<211> LENGTH: 10
<212> TYPE: DNA
<213> ORGANISM: Homo sapiens

<400> SEQUENCE: 55
ccttgtaggc                                                                      10

<210> SEQ ID NO 56
<211> LENGTH: 10
<212> TYPE: DNA
<213> ORGANISM: Homo sapiens

<400> SEQUENCE: 56
ctgttcctct                                                                      10

<210> SEQ ID NO 57
<211> LENGTH: 10
<212> TYPE: DNA
<213> ORGANISM: Homo sapiens

<400> SEQUENCE: 57
atccttggat                                                                      10

<210> SEQ ID NO 58
<211> LENGTH: 10
<212> TYPE: DNA
<213> ORGANISM: Homo sapiens

<400> SEQUENCE: 58
aattgcactc                                                                      10

<210> SEQ ID NO 59
<211> LENGTH: 10
<212> TYPE: DNA
<213> ORGANISM: Homo sapiens

<400> SEQUENCE: 59

```
aagtgcctgc                                                         10

<210> SEQ ID NO 60
<211> LENGTH: 10
<212> TYPE: DNA
<213> ORGANISM: Homo sapiens

<400> SEQUENCE: 60
tctcaaactg                                                         10

<210> SEQ ID NO 61
<211> LENGTH: 10
<212> TYPE: DNA
<213> ORGANISM: Homo sapiens

<400> SEQUENCE: 61
actggccttg                                                         10

<210> SEQ ID NO 62
<211> LENGTH: 10
<212> TYPE: DNA
<213> ORGANISM: Homo sapiens

<400> SEQUENCE: 62
attcattcac                                                         10

<210> SEQ ID NO 63
<211> LENGTH: 15
<212> TYPE: DNA
<213> ORGANISM: Homo sapiens

<400> SEQUENCE: 63
gaagttgtta gagat                                                   15

<210> SEQ ID NO 64
<211> LENGTH: 9
<212> TYPE: DNA
<213> ORGANISM: Homo sapiens

<400> SEQUENCE: 64 agattagaa                                                           9

<210> SEQ ID NO 65
<211> LENGTH: 10
<212> TYPE: DNA
<213> ORGANISM: Homo sapiens

<400> SEQUENCE: 65
attaactgac                                                         10

<210> SEQ ID NO 66
<211> LENGTH: 10
<212> TYPE: DNA
<213> ORGANISM: Homo sapiens

<400> SEQUENCE: 66
ctcaaaagac                                                         10

<210> SEQ ID NO 67
<211> LENGTH: 10
<212> TYPE: DNA
<213> ORGANISM: Homo sapiens
```

```
<400> SEQUENCE: 67
tgtgtgcctt                                                          10

<210> SEQ ID NO 68
<211> LENGTH: 10
<212> TYPE: DNA
<213> ORGANISM: Homo sapiens

<400> SEQUENCE: 68
aatggggaag                                                          10

<210> SEQ ID NO 69
<211> LENGTH: 10
<212> TYPE: DNA
<213> ORGANISM: Homo sapiens

<400> SEQUENCE: 69
atgcatcagg                                                          10

<210> SEQ ID NO 70
<211> LENGTH: 23
<212> TYPE: DNA
<213> ORGANISM: Homo sapiens

<400> SEQUENCE: 70
tattctagtg aacttgactc tta                                           23

<210> SEQ ID NO 71
<211> LENGTH: 10
<212> TYPE: DNA
<213> ORGANISM: Homo sapiens

<400> SEQUENCE: 71
atggtgcatt                                                          10

<210> SEQ ID NO 72
<211> LENGTH: 11
<212> TYPE: DNA
<213> ORGANISM: Homo sapiens

<400> SEQUENCE: 72
cagcaagcac t                                                        11

<210> SEQ ID NO 73
<211> LENGTH: 10
<212> TYPE: DNA
<213> ORGANISM: Homo sapiens

<400> SEQUENCE: 73
tgacaactgt                                                          10

<210> SEQ ID NO 74
<211> LENGTH: 10
<212> TYPE: DNA
<213> ORGANISM: Homo sapiens

<400> SEQUENCE: 74
atgaatatag                                                          10

<210> SEQ ID NO 75
<211> LENGTH: 10
<212> TYPE: DNA
<213> ORGANISM: Homo sapiens
```

<400> SEQUENCE: 75
actggtatgt                                                              10

<210> SEQ ID NO 76
<211> LENGTH: 10
<212> TYPE: DNA
<213> ORGANISM: Homo sapiens

<400> SEQUENCE: 76
tcttgtattc                                                              10

<210> SEQ ID NO 77
<211> LENGTH: 10
<212> TYPE: DNA
<213> ORGANISM: Homo sapiens

<400> SEQUENCE: 77
ccttgtaggc                                                              10

<210> SEQ ID NO 78
<211> LENGTH: 10
<212> TYPE: DNA
<213> ORGANISM: Homo sapiens

<400> SEQUENCE: 78
acatgcatgc                                                              10

<210> SEQ ID NO 79
<211> LENGTH: 10
<212> TYPE: DNA
<213> ORGANISM: Homo sapiens

<400> SEQUENCE: 79
ttaaaataag                                                              10

<210> SEQ ID NO 80
<211> LENGTH: 10
<212> TYPE: DNA
<213> ORGANISM: Homo sapiens

<400> SEQUENCE: 80
ttaggttaaa                                                              10

<210> SEQ ID NO 81
<211> LENGTH: 10
<212> TYPE: DNA
<213> ORGANISM: Homo sapiens

<400> SEQUENCE: 81
tcatgataag                                                              10

<210> SEQ ID NO 82
<211> LENGTH: 10
<212> TYPE: DNA
<213> ORGANISM: Homo sapiens

<400> SEQUENCE: 82
tatctcttct                                                              10

<210> SEQ ID NO 83
<211> LENGTH: 10
<212> TYPE: DNA

```
<213> ORGANISM: Homo sapiens

<400> SEQUENCE: 83
tatgtatact                                                            10

<210> SEQ ID NO 84
<211> LENGTH: 10
<212> TYPE: DNA
<213> ORGANISM: Homo sapiens

<400> SEQUENCE: 84
gactgactcc                                                            10

<210> SEQ ID NO 85
<211> LENGTH: 10
<212> TYPE: DNA
<213> ORGANISM: Homo sapiens

<400> SEQUENCE: 85
attgcactcc                                                            10

<210> SEQ ID NO 86
<211> LENGTH: 10
<212> TYPE: DNA
<213> ORGANISM: Homo sapiens

<400> SEQUENCE: 86
aagctggctc                                                            10

<210> SEQ ID NO 87
<211> LENGTH: 10
<212> TYPE: DNA
<213> ORGANISM: Homo sapiens

<400> SEQUENCE: 87
acttttgcgg                                                            10

<210> SEQ ID NO 88
<211> LENGTH: 10
<212> TYPE: DNA
<213> ORGANISM: Homo sapiens

<400> SEQUENCE: 88
agttttacaa                                                            10

<210> SEQ ID NO 89
<211> LENGTH: 10
<212> TYPE: DNA
<213> ORGANISM: Homo sapiens

<400> SEQUENCE: 89
agttttgtat                                                            10

<210> SEQ ID NO 90
<211> LENGTH: 10
<212> TYPE: DNA
<213> ORGANISM: Homo sapiens

<400> SEQUENCE: 90
agtcttgaag                                                            10

<210> SEQ ID NO 91
<211> LENGTH: 10
```

```
<212> TYPE: DNA
<213> ORGANISM: Homo sapiens

<400> SEQUENCE: 91
aggtttgtag                                                            10

<210> SEQ ID NO 92
<211> LENGTH: 10
<212> TYPE: DNA
<213> ORGANISM: Homo sapiens

<400> SEQUENCE: 92
agtattgaag                                                            10

<210> SEQ ID NO 93
<211> LENGTH: 10
<212> TYPE: DNA
<213> ORGANISM: Homo sapiens

<400> SEQUENCE: 93
aggcttgcag                                                            10

<210> SEQ ID NO 94
<211> LENGTH: 10
<212> TYPE: DNA
<213> ORGANISM: Homo sapiens

<400> SEQUENCE: 94
aatttggcag                                                            10

<210> SEQ ID NO 95
<211> LENGTH: 10
<212> TYPE: DNA
<213> ORGANISM: Homo sapiens

<400> SEQUENCE: 95
agttttggaa                                                            10

<210> SEQ ID NO 96
<211> LENGTH: 10
<212> TYPE: DNA
<213> ORGANISM: Homo sapiens

<400> SEQUENCE: 96
tagcttatct                                                            10

<210> SEQ ID NO 97
<211> LENGTH: 10
<212> TYPE: DNA
<213> ORGANISM: Homo sapiens

<400> SEQUENCE: 97
aagctgccaa                                                            10

<210> SEQ ID NO 98
<211> LENGTH: 10
<212> TYPE: DNA
<213> ORGANISM: Homo sapiens

<400> SEQUENCE: 98
aagcttccag                                                            10

<210> SEQ ID NO 99
```

```
<211> LENGTH: 11
<212> TYPE: DNA
<213> ORGANISM: Homo sapiens

<400> SEQUENCE: 99
agttcttcac a                                                          11

<210> SEQ ID NO 100
<211> LENGTH: 11
<212> TYPE: DNA
<213> ORGANISM: Homo sapiens

<400> SEQUENCE: 100
aattcttcag g                                                          11

<210> SEQ ID NO 101
<211> LENGTH: 11
<212> TYPE: DNA
<213> ORGANISM: Homo sapiens

<400> SEQUENCE: 101
ggttcttcag c                                                          11

<210> SEQ ID NO 102
<211> LENGTH: 12
<212> TYPE: DNA
<213> ORGANISM: Homo sapiens

<400> SEQUENCE: 102
tgcctactgg cc                                                         12

<210> SEQ ID NO 103
<211> LENGTH: 10
<212> TYPE: DNA
<213> ORGANISM: Homo sapiens

<400> SEQUENCE: 103
cctttcatg                                                             10

<210> SEQ ID NO 104
<211> LENGTH: 10
<212> TYPE: DNA
<213> ORGANISM: Homo sapiens

<400> SEQUENCE: 104
ccaatccttg                                                            10

<210> SEQ ID NO 105
<211> LENGTH: 10
<212> TYPE: DNA
<213> ORGANISM: Homo sapiens

<400> SEQUENCE: 105
cattttcttg                                                            10

<210> SEQ ID NO 106
<211> LENGTH: 10
<212> TYPE: DNA
<213> ORGANISM: Homo sapiens

<400> SEQUENCE: 106
cctactcttc                                                            10
```

```
<210> SEQ ID NO 107
<211> LENGTH: 10
<212> TYPE: DNA
<213> ORGANISM: Homo sapiens

<400> SEQUENCE: 107
acgattcttg                                                          10

<210> SEQ ID NO 108
<211> LENGTH: 10
<212> TYPE: DNA
<213> ORGANISM: Homo sapiens

<400> SEQUENCE: 108
tctattcttt                                                          10

<210> SEQ ID NO 109
<211> LENGTH: 10
<212> TYPE: DNA
<213> ORGANISM: Homo sapiens

<400> SEQUENCE: 109 catattttttg                                                         10

<210> SEQ ID NO 110
<211> LENGTH: 10
<212> TYPE: DNA
<213> ORGANISM: Homo sapiens

<400> SEQUENCE: 110
gctagtcttg                                                          10

<210> SEQ ID NO 111
<211> LENGTH: 10
<212> TYPE: DNA
<213> ORGANISM: Homo sapiens

<400> SEQUENCE: 111
catatttttg                                                          10

<210> SEQ ID NO 112
<211> LENGTH: 10
<212> TYPE: DNA
<213> ORGANISM: Homo sapiens

<400> SEQUENCE: 112
ccttttcttt                                                          10

<210> SEQ ID NO 113
<211> LENGTH: 10
<212> TYPE: DNA
<213> ORGANISM: Homo sapiens

<400> SEQUENCE: 113
cccattctcg                                                          10

<210> SEQ ID NO 114
<211> LENGTH: 10
<212> TYPE: DNA
<213> ORGANISM: Homo sapiens

<400> SEQUENCE: 114
tttattcttg                                                          10
```

```
<210> SEQ ID NO 115
<211> LENGTH: 10
<212> TYPE: DNA
<213> ORGANISM: Homo sapiens

<400> SEQUENCE: 115
cctttacttg                                                          10

<210> SEQ ID NO 116
<211> LENGTH: 10
<212> TYPE: DNA
<213> ORGANISM: Homo sapiens

<400> SEQUENCE: 116
gcgattcttg                                                          10

<210> SEQ ID NO 117
<211> LENGTH: 10
<212> TYPE: DNA
<213> ORGANISM: Homo sapiens

<400> SEQUENCE: 117
agagcttagg                                                          10

<210> SEQ ID NO 118
<211> LENGTH: 10
<212> TYPE: DNA
<213> ORGANISM: Homo sapiens

<400> SEQUENCE: 118
gtaaccttcc                                                          10

<210> SEQ ID NO 119
<211> LENGTH: 10
<212> TYPE: DNA
<213> ORGANISM: Homo sapiens

<400> SEQUENCE: 119
gtaaccatca                                                          10

<210> SEQ ID NO 120
<211> LENGTH: 10
<212> TYPE: DNA
<213> ORGANISM: Homo sapiens

<400> SEQUENCE: 120
gtaatcatac                                                          10

<210> SEQ ID NO 121
<211> LENGTH: 10
<212> TYPE: DNA
<213> ORGANISM: Homo sapiens

<400> SEQUENCE: 121
gtcaacatca                                                          10

<210> SEQ ID NO 122
<211> LENGTH: 10
<212> TYPE: DNA
<213> ORGANISM: Homo sapiens

<400> SEQUENCE: 122
gtaaacataa                                                          10
```

```
<210> SEQ ID NO 123
<211> LENGTH: 10
<212> TYPE: DNA
<213> ORGANISM: Homo sapiens

<400> SEQUENCE: 123
gtactcatcc                                                              10

<210> SEQ ID NO 124
<211> LENGTH: 10
<212> TYPE: DNA
<213> ORGANISM: Homo sapiens

<400> SEQUENCE: 124
ctatacatcc                                                              10

<210> SEQ ID NO 125
<211> LENGTH: 10
<212> TYPE: DNA
<213> ORGANISM: Homo sapiens

<400> SEQUENCE: 125
ctaaacatct                                                              10

<210> SEQ ID NO 126
<211> LENGTH: 10
<212> TYPE: DNA
<213> ORGANISM: Homo sapiens

<400> SEQUENCE: 126
attgcactcc                                                              10

<210> SEQ ID NO 127
<211> LENGTH: 10
<212> TYPE: DNA
<213> ORGANISM: Homo sapiens

<400> SEQUENCE: 127
attgcactag                                                              10

<210> SEQ ID NO 128
<211> LENGTH: 10
<212> TYPE: DNA
<213> ORGANISM: Homo sapiens

<400> SEQUENCE: 128
caaagtgctg                                                              10

<210> SEQ ID NO 129
<211> LENGTH: 10
<212> TYPE: DNA
<213> ORGANISM: Homo sapiens

<400> SEQUENCE: 129
caaagtgctg                                                              10

<210> SEQ ID NO 130
<211> LENGTH: 11
<212> TYPE: DNA
<213> ORGANISM: Homo sapiens

<400> SEQUENCE: 130
```
actcctgggc t	11

<210> SEQ ID NO 131
<211> LENGTH: 11
<212> TYPE: DNA
<213> ORGANISM: Homo sapiens

<400> SEQUENCE: 131
actgataagc t	11

<210> SEQ ID NO 132
<211> LENGTH: 11
<212> TYPE: DNA
<213> ORGANISM: Homo sapiens

<400> SEQUENCE: 132
actcctgacc t	11

<210> SEQ ID NO 133
<211> LENGTH: 11
<212> TYPE: DNA
<213> ORGANISM: Homo sapiens

<400> SEQUENCE: 133
aatcatgtgc c	11

<210> SEQ ID NO 134
<211> LENGTH: 10
<212> TYPE: DNA
<213> ORGANISM: Homo sapiens

<400> SEQUENCE: 134 aagctggctc	10

<210> SEQ ID NO 135
<211> LENGTH: 10
<212> TYPE: DNA
<213> ORGANISM: Homo sapiens

<400> SEQUENCE: 135 aaactctttc	10

<210> SEQ ID NO 136
<211> LENGTH: 10
<212> TYPE: DNA
<213> ORGANISM: Homo sapiens

<400> SEQUENCE: 136 aatcttgttc	10

<210> SEQ ID NO 137
<211> LENGTH: 10
<212> TYPE: DNA
<213> ORGANISM: Homo sapiens

<400> SEQUENCE: 137 aagctccttt	10

<210> SEQ ID NO 138
<211> LENGTH: 10
<212> TYPE: DNA
<213> ORGANISM: Homo sapiens

<400> SEQUENCE: 138
aagctccttt                                                                      10

<210> SEQ ID NO 139
<211> LENGTH: 10
<212> TYPE: DNA
<213> ORGANISM: Homo sapiens

<400> SEQUENCE: 139
aagctctgtc                                                                      10

<210> SEQ ID NO 140
<211> LENGTH: 10
<212> TYPE: DNA
<213> ORGANISM: Homo sapiens

<400> SEQUENCE: 140
caacctcgag                                                                      10

<210> SEQ ID NO 141
<211> LENGTH: 10
<212> TYPE: DNA
<213> ORGANISM: Homo sapiens

<400> SEQUENCE: 141
cgagctcctg                                                                      10

<210> SEQ ID NO 142
<211> LENGTH: 10
<212> TYPE: DNA
<213> ORGANISM: Homo sapiens

<400> SEQUENCE: 142
gaagcttgtg                                                                      10

<210> SEQ ID NO 143
<211> LENGTH: 10
<212> TYPE: DNA
<213> ORGANISM: Homo sapiens

<400> SEQUENCE: 143
caaactcctg                                                                      10

<210> SEQ ID NO 144
<211> LENGTH: 10
<212> TYPE: DNA
<213> ORGANISM: Homo sapiens

<400> SEQUENCE: 144
tccagtagat                                                                      10

<210> SEQ ID NO 145
<211> LENGTH: 10
<212> TYPE: DNA
<213> ORGANISM: Homo sapiens

<400> SEQUENCE: 145
acgcgcagat                                                                      10

<210> SEQ ID NO 146
<211> LENGTH: 10
<212> TYPE: DNA
<213> ORGANISM: Homo sapiens

```
<400> SEQUENCE: 146
caaagtgctg                                                              10

<210> SEQ ID NO 147
<211> LENGTH: 10
<212> TYPE: DNA
<213> ORGANISM: Homo sapiens

<400> SEQUENCE: 147
caaagtgctg                                                              10

<210> SEQ ID NO 148
<211> LENGTH: 11
<212> TYPE: DNA
<213> ORGANISM: Homo sapiens

<400> SEQUENCE: 148
ttattttccc t                                                            11

<210> SEQ ID NO 149
<211> LENGTH: 11
<212> TYPE: DNA
<213> ORGANISM: Homo sapiens

<400> SEQUENCE: 149
ctcttttcag t                                                            11

<210> SEQ ID NO 150
<211> LENGTH: 11
<212> TYPE: DNA
<213> ORGANISM: Homo sapiens

<400> SEQUENCE: 150
ctctcttcac t                                                            11

<210> SEQ ID NO 151
<211> LENGTH: 11
<212> TYPE: DNA
<213> ORGANISM: Homo sapiens

<400> SEQUENCE: 151
ctcttttccc c                                                            11

<210> SEQ ID NO 152
<211> LENGTH: 11
<212> TYPE: DNA
<213> ORGANISM: Homo sapiens

<400> SEQUENCE: 152
ctttttcccc t                                                            11

<210> SEQ ID NO 153
<211> LENGTH: 11
<212> TYPE: DNA
<213> ORGANISM: Homo sapiens

<400> SEQUENCE: 153
ctattttccg t                                                            11

<210> SEQ ID NO 154
<211> LENGTH: 11
<212> TYPE: DNA
<213> ORGANISM: Homo sapiens
```

```
<400> SEQUENCE: 154
ttcctttccc t                                                              11

<210> SEQ ID NO 155
<211> LENGTH: 11
<212> TYPE: DNA
<213> ORGANISM: Homo sapiens

<400> SEQUENCE: 155
ctctttgccc c                                                              11

<210> SEQ ID NO 156
<211> LENGTH: 11
<212> TYPE: DNA
<213> ORGANISM: Homo sapiens

<400> SEQUENCE: 156
ctcctttcct t                                                              11

<210> SEQ ID NO 157
<211> LENGTH: 10
<212> TYPE: DNA
<213> ORGANISM: Homo sapiens

<400> SEQUENCE: 157
tttggtgccc                                                                10

<210> SEQ ID NO 158
<211> LENGTH: 9
<212> TYPE: DNA
<213> ORGANISM: Homo sapiens

<400> SEQUENCE: 158 ggtgcagtg                                                                  9

<210> SEQ ID NO 159
<211> LENGTH: 10
<212> TYPE: DNA
<213> ORGANISM: Homo sapiens

<400> SEQUENCE: 159
tgagatgagg                                                                10

<210> SEQ ID NO 160
<211> LENGTH: 10
<212> TYPE: DNA
<213> ORGANISM: Homo sapiens

<400> SEQUENCE: 160
tgagatggag                                                                10

<210> SEQ ID NO 161
<211> LENGTH: 10
<212> TYPE: DNA
<213> ORGANISM: Homo sapiens

<400> SEQUENCE: 161
ttagatgaag                                                                10

<210> SEQ ID NO 162
<211> LENGTH: 10
<212> TYPE: DNA
```

```
<213> ORGANISM: Homo sapiens

<400> SEQUENCE: 162
tgtgaactgg                                                            10

<210> SEQ ID NO 163
<211> LENGTH: 10
<212> TYPE: DNA
<213> ORGANISM: Homo sapiens

<400> SEQUENCE: 163
agggaactga                                                            10

<210> SEQ ID NO 164
<211> LENGTH: 10
<212> TYPE: DNA
<213> ORGANISM: Homo sapiens

<400> SEQUENCE: 164
tgacaactgt                                                            10

<210> SEQ ID NO 165
<211> LENGTH: 10
<212> TYPE: DNA
<213> ORGANISM: Homo sapiens

<400> SEQUENCE: 165
taagaactaa                                                            10

<210> SEQ ID NO 166
<211> LENGTH: 10
<212> TYPE: DNA
<213> ORGANISM: Homo sapiens

<400> SEQUENCE: 166
ttagaacaga                                                            10

<210> SEQ ID NO 167
<211> LENGTH: 10
<212> TYPE: DNA
<213> ORGANISM: Homo sapiens

<400> SEQUENCE: 167
tgagaagtgc                                                            10

<210> SEQ ID NO 168
<211> LENGTH: 10
<212> TYPE: DNA
<213> ORGANISM: Homo sapiens

<400> SEQUENCE: 168
tgaaaactta                                                            10

<210> SEQ ID NO 169
<211> LENGTH: 10
<212> TYPE: DNA
<213> ORGANISM: Homo sapiens

<400> SEQUENCE: 169
acagaactga                                                            10

<210> SEQ ID NO 170
<211> LENGTH: 10
```

```
<212> TYPE: DNA
<213> ORGANISM: Homo sapiens

<400> SEQUENCE: 170
tgagaccaga                                                          10

<210> SEQ ID NO 171
<211> LENGTH: 10
<212> TYPE: DNA
<213> ORGANISM: Homo sapiens

<400> SEQUENCE: 171
tgagaaataa                                                          10

<210> SEQ ID NO 172
<211> LENGTH: 11
<212> TYPE: DNA
<213> ORGANISM: Homo sapiens

<400> SEQUENCE: 172
tgtgtggata a                                                        11

<210> SEQ ID NO 173
<211> LENGTH: 11
<212> TYPE: DNA
<213> ORGANISM: Homo sapiens

<400> SEQUENCE: 173
tttgtgcaaa t                                                        11

<210> SEQ ID NO 174
<211> LENGTH: 12
<212> TYPE: DNA
<213> ORGANISM: Homo sapiens

<400> SEQUENCE: 174
ctaacatatg aa                                                       12

<210> SEQ ID NO 175
<211> LENGTH: 10
<212> TYPE: DNA
<213> ORGANISM: Homo sapiens

<400> SEQUENCE: 175
tgtaacagca                                                          10

<210> SEQ ID NO 176
<211> LENGTH: 10
<212> TYPE: DNA
<213> ORGANISM: Homo sapiens

<400> SEQUENCE: 176
ccctgtgttc                                                          10

<210> SEQ ID NO 177
<211> LENGTH: 10
<212> TYPE: DNA
<213> ORGANISM: Homo sapiens

<400> SEQUENCE: 177
taataatgcc                                                          10

<210> SEQ ID NO 178
```

```
<210> SEQ ID NO 178
<211> LENGTH: 10
<212> TYPE: DNA
<213> ORGANISM: Homo sapiens

<400> SEQUENCE: 178
gaatactgcc                                                          10

<210> SEQ ID NO 179
<211> LENGTH: 10
<212> TYPE: DNA
<213> ORGANISM: Homo sapiens

<400> SEQUENCE: 179
ttcctctgtc                                                          10

<210> SEQ ID NO 180
<211> LENGTH: 10
<212> TYPE: DNA
<213> ORGANISM: Homo sapiens

<400> SEQUENCE: 180
ttcctttatc                                                          10

<210> SEQ ID NO 181
<211> LENGTH: 11
<212> TYPE: DNA
<213> ORGANISM: Homo sapiens

<400> SEQUENCE: 181
ttccctatct c                                                        11

<210> SEQ ID NO 182
<211> LENGTH: 11
<212> TYPE: DNA
<213> ORGANISM: Homo sapiens

<400> SEQUENCE: 182
tcccctctgt c                                                        11

<210> SEQ ID NO 183
<211> LENGTH: 11
<212> TYPE: DNA
<213> ORGANISM: Homo sapiens

<400> SEQUENCE: 183
ttcccttgct c                                                        11

<210> SEQ ID NO 184
<211> LENGTH: 11
<212> TYPE: DNA
<213> ORGANISM: Homo sapiens

<400> SEQUENCE: 184
ttcccattct c                                                        11

<210> SEQ ID NO 185
<211> LENGTH: 10
<212> TYPE: DNA
<213> ORGANISM: Homo sapiens

<400> SEQUENCE: 185
cgcgtcccct                                                          10
```

```
<210> SEQ ID NO 186
<211> LENGTH: 10
<212> TYPE: DNA
<213> ORGANISM: Homo sapiens

<400> SEQUENCE: 186
ccttgtaggc                                                              10

<210> SEQ ID NO 187
<211> LENGTH: 10
<212> TYPE: DNA
<213> ORGANISM: Homo sapiens

<400> SEQUENCE: 187
cagagtaggt                                                              10

<210> SEQ ID NO 188
<211> LENGTH: 10
<212> TYPE: DNA
<213> ORGANISM: Homo sapiens

<400> SEQUENCE: 188
ccaagtagct                                                              10

<210> SEQ ID NO 189
<211> LENGTH: 10
<212> TYPE: DNA
<213> ORGANISM: Homo sapiens

<400> SEQUENCE: 189
ccaagtagct                                                              10

<210> SEQ ID NO 190
<211> LENGTH: 10
<212> TYPE: DNA
<213> ORGANISM: Homo sapiens

<400> SEQUENCE: 190
ctgttcctct                                                              10

<210> SEQ ID NO 191
<211> LENGTH: 10
<212> TYPE: DNA
<213> ORGANISM: Homo sapiens

<400> SEQUENCE: 191
ctggctccct                                                              10

<210> SEQ ID NO 192
<211> LENGTH: 10
<212> TYPE: DNA
<213> ORGANISM: Homo sapiens

<400> SEQUENCE: 192
ctggcccttc                                                              10

<210> SEQ ID NO 193
<211> LENGTH: 10
<212> TYPE: DNA
<213> ORGANISM: Homo sapiens

<400> SEQUENCE: 193
ctggcactca                                                              10
```

```
<210> SEQ ID NO 194
<211> LENGTH: 10
<212> TYPE: DNA
<213> ORGANISM: Homo sapiens

<400> SEQUENCE: 194
ctggctttct                                                              10

<210> SEQ ID NO 195
<211> LENGTH: 10
<212> TYPE: DNA
<213> ORGANISM: Homo sapiens

<400> SEQUENCE: 195
ctgcccctcc                                                              10

<210> SEQ ID NO 196
<211> LENGTH: 10
<212> TYPE: DNA
<213> ORGANISM: Homo sapiens

<400> SEQUENCE: 196
ctgggccgct                                                              10

<210> SEQ ID NO 197
<211> LENGTH: 10
<212> TYPE: DNA
<213> ORGANISM: Homo sapiens

<400> SEQUENCE: 197
ctggagctct                                                              10

<210> SEQ ID NO 198
<211> LENGTH: 10
<212> TYPE: DNA
<213> ORGANISM: Homo sapiens

<400> SEQUENCE: 198
ctgacccttt                                                              10

<210> SEQ ID NO 199
<211> LENGTH: 10
<212> TYPE: DNA
<213> ORGANISM: Homo sapiens

<400> SEQUENCE: 199
caaagcacac                                                              10

<210> SEQ ID NO 200
<211> LENGTH: 10
<212> TYPE: DNA
<213> ORGANISM: Homo sapiens

<400> SEQUENCE: 200
ctaggtgtgg                                                              10

<210> SEQ ID NO 201
<211> LENGTH: 10
<212> TYPE: DNA
<213> ORGANISM: Homo sapiens

<400> SEQUENCE: 201
atccttggat                                                              10
```

```
<210> SEQ ID NO 202
<211> LENGTH: 10
<212> TYPE: DNA
<213> ORGANISM: Homo sapiens

<400> SEQUENCE: 202
aattgcactc                                                          10

<210> SEQ ID NO 203
<211> LENGTH: 10
<212> TYPE: DNA
<213> ORGANISM: Homo sapiens

<400> SEQUENCE: 203
aaatgcactt                                                          10

<210> SEQ ID NO 204
<211> LENGTH: 10
<212> TYPE: DNA
<213> ORGANISM: Homo sapiens

<400> SEQUENCE: 204
aagtgcctgc                                                          10

<210> SEQ ID NO 205
<211> LENGTH: 10
<212> TYPE: DNA
<213> ORGANISM: Homo sapiens

<400> SEQUENCE: 205
aagagccgac                                                          10

<210> SEQ ID NO 206
<211> LENGTH: 10
<212> TYPE: DNA
<213> ORGANISM: Homo sapiens

<400> SEQUENCE: 206
acgtgccacc                                                          10

<210> SEQ ID NO 207
<211> LENGTH: 10
<212> TYPE: DNA
<213> ORGANISM: Homo sapiens

<400> SEQUENCE: 207
aagtgcctct                                                          10

<210> SEQ ID NO 208
<211> LENGTH: 10
<212> TYPE: DNA
<213> ORGANISM: Homo sapiens

<400> SEQUENCE: 208
aagtgcaccc                                                          10

<210> SEQ ID NO 209
<211> LENGTH: 10
<212> TYPE: DNA
<213> ORGANISM: Homo sapiens

<400> SEQUENCE: 209
```

-continued tctcaaactg 10

<210> SEQ ID NO 210
<211> LENGTH: 10
<212> TYPE: DNA
<213> ORGANISM: Homo sapiens

<400> SEQUENCE: 210
tcatcagatt 10

<210> SEQ ID NO 211
<211> LENGTH: 10
<212> TYPE: DNA
<213> ORGANISM: Homo sapiens

<400> SEQUENCE: 211
agcacacaaa 10

<210> SEQ ID NO 212
<211> LENGTH: 10
<212> TYPE: DNA
<213> ORGANISM: Homo sapiens

<400> SEQUENCE: 212
actggccttg 10

<210> SEQ ID NO 213
<211> LENGTH: 10
<212> TYPE: DNA
<213> ORGANISM: Homo sapiens

<400> SEQUENCE: 213
actggtcttg 10

<210> SEQ ID NO 214
<211> LENGTH: 10
<212> TYPE: DNA
<213> ORGANISM: Homo sapiens

<400> SEQUENCE: 214
ctcctgcctc 10

<210> SEQ ID NO 215
<211> LENGTH: 10
<212> TYPE: DNA
<213> ORGANISM: Homo sapiens

<400> SEQUENCE: 215
ctcctgcctc 10

<210> SEQ ID NO 216
<211> LENGTH: 10
<212> TYPE: DNA
<213> ORGANISM: Homo sapiens

<400> SEQUENCE: 216
ctcctgtctc 10

<210> SEQ ID NO 217
<211> LENGTH: 10
<212> TYPE: DNA
<213> ORGANISM: Homo sapiens

<400> SEQUENCE: 217

```
ctcctaactc                                                              10

<210> SEQ ID NO 218
<211> LENGTH: 10
<212> TYPE: DNA
<213> ORGANISM: Homo sapiens

<400> SEQUENCE: 218
attcattcac                                                              10

<210> SEQ ID NO 219
<211> LENGTH: 10
<212> TYPE: DNA
<213> ORGANISM: Homo sapiens

<400> SEQUENCE: 219
ctcaaaagac                                                              10

<210> SEQ ID NO 220
<211> LENGTH: 10
<212> TYPE: DNA
<213> ORGANISM: Homo sapiens

<400> SEQUENCE: 220
attaactgac                                                              10

<210> SEQ ID NO 221
<211> LENGTH: 10
<212> TYPE: DNA
<213> ORGANISM: Homo sapiens

<400> SEQUENCE: 221
aacatcagac                                                              10

<210> SEQ ID NO 222
<211> LENGTH: 10
<212> TYPE: DNA
<213> ORGANISM: Homo sapiens

<400> SEQUENCE: 222
atcaactgag                                                              10

<210> SEQ ID NO 223
<211> LENGTH: 10
<212> TYPE: DNA
<213> ORGANISM: Homo sapiens

<400> SEQUENCE: 223
atcaacaggt                                                              10

<210> SEQ ID NO 224
<211> LENGTH: 10
<212> TYPE: DNA
<213> ORGANISM: Homo sapiens

<400> SEQUENCE: 224
atcaaaagat                                                              10

<210> SEQ ID NO 225
<211> LENGTH: 11
<212> TYPE: DNA
<213> ORGANISM: Homo sapiens
```

```
<400> SEQUENCE: 225
agcgggaagg t                                                          11

<210> SEQ ID NO 226
<211> LENGTH: 10
<212> TYPE: DNA
<213> ORGANISM: Homo sapiens

<400> SEQUENCE: 226
tgtgtgcctt                                                            10

<210> SEQ ID NO 227
<211> LENGTH: 10
<212> TYPE: DNA
<213> ORGANISM: Homo sapiens

<400> SEQUENCE: 227
tctgtgcctt                                                            10

<210> SEQ ID NO 228
<211> LENGTH: 10
<212> TYPE: DNA
<213> ORGANISM: Homo sapiens

<400> SEQUENCE: 228
tatgtgcttt                                                            10

<210> SEQ ID NO 229
<211> LENGTH: 10
<212> TYPE: DNA
<213> ORGANISM: Homo sapiens

<400> SEQUENCE: 229
aatcatacag                                                            10

<210> SEQ ID NO 230
<211> LENGTH: 10
<212> TYPE: DNA
<213> ORGANISM: Homo sapiens

<400> SEQUENCE: 230
aatggggaag                                                            10

<210> SEQ ID NO 231
<211> LENGTH: 10
<212> TYPE: DNA
<213> ORGANISM: Homo sapiens

<400> SEQUENCE: 231
agagggacc                                                             10

<210> SEQ ID NO 232
<211> LENGTH: 10
<212> TYPE: DNA
<213> ORGANISM: Homo sapiens

<400> SEQUENCE: 232
agttgggcac                                                            10

<210> SEQ ID NO 233
<211> LENGTH: 10
<212> TYPE: DNA
<213> ORGANISM: Homo sapiens
```

```
<400> SEQUENCE: 233
agtagagaac                                                          10

<210> SEQ ID NO 234
<211> LENGTH: 10
<212> TYPE: DNA
<213> ORGANISM: Homo sapiens

<400> SEQUENCE: 234
ggtgaggaac                                                          10

<210> SEQ ID NO 235
<211> LENGTH: 10
<212> TYPE: DNA
<213> ORGANISM: Homo sapiens

<400> SEQUENCE: 235
agcggggcac                                                          10

<210> SEQ ID NO 236
<211> LENGTH: 10
<212> TYPE: DNA
<213> ORGANISM: Homo sapiens

<400> SEQUENCE: 236
agtgggaaat                                                          10

<210> SEQ ID NO 237
<211> LENGTH: 10
<212> TYPE: DNA
<213> ORGANISM: Homo sapiens

<400> SEQUENCE: 237
atgcatcagg                                                          10

<210> SEQ ID NO 238
<211> LENGTH: 10
<212> TYPE: DNA
<213> ORGANISM: Homo sapiens

<400> SEQUENCE: 238
atccaccggg                                                          10

<210> SEQ ID NO 239
<211> LENGTH: 10
<212> TYPE: DNA
<213> ORGANISM: Homo sapiens

<400> SEQUENCE: 239
aggcaccagg                                                          10

<210> SEQ ID NO 240
<211> LENGTH: 10
<212> TYPE: DNA
<213> ORGANISM: Homo sapiens

<400> SEQUENCE: 240
tgattatagc                                                          10

<210> SEQ ID NO 241
<211> LENGTH: 10
<212> TYPE: DNA
```

```
<213> ORGANISM: Homo sapiens

<400> SEQUENCE: 241
tgagtgtagc                                                            10

<210> SEQ ID NO 242
<211> LENGTH: 10
<212> TYPE: DNA
<213> ORGANISM: Homo sapiens

<400> SEQUENCE: 242
cagtgctgtc                                                            10

<210> SEQ ID NO 243
<211> LENGTH: 10
<212> TYPE: DNA
<213> ORGANISM: Homo sapiens

<400> SEQUENCE: 243
aagtgctctc                                                            10

<210> SEQ ID NO 244
<211> LENGTH: 10
<212> TYPE: DNA
<213> ORGANISM: Homo sapiens

<400> SEQUENCE: 244
atggtgcatt                                                            10

<210> SEQ ID NO 245
<211> LENGTH: 10
<212> TYPE: DNA
<213> ORGANISM: Homo sapiens

<400> SEQUENCE: 245
atcttgcttc                                                            10

<210> SEQ ID NO 246
<211> LENGTH: 11
<212> TYPE: DNA
<213> ORGANISM: Homo sapiens

<400> SEQUENCE: 246
cagcaagcac t                                                          11

<210> SEQ ID NO 247
<211> LENGTH: 11
<212> TYPE: DNA
<213> ORGANISM: Homo sapiens

<400> SEQUENCE: 247
cagaacacat t                                                          11

<210> SEQ ID NO 248
<211> LENGTH: 11
<212> TYPE: DNA
<213> ORGANISM: Homo sapiens

<400> SEQUENCE: 248
ctgcaaacac t                                                          11

<210> SEQ ID NO 249
<211> LENGTH: 10
```

<212> TYPE: DNA
<213> ORGANISM: Homo sapiens

<400> SEQUENCE: 249
tgacaactgt                                                          10

<210> SEQ ID NO 250
<211> LENGTH: 10
<212> TYPE: DNA
<213> ORGANISM: Homo sapiens

<400> SEQUENCE: 250
gcgaggtctc                                                          10

<210> SEQ ID NO 251
<211> LENGTH: 10
<212> TYPE: DNA
<213> ORGANISM: Homo sapiens

<400> SEQUENCE: 251
gagaggcccc                                                          10

<210> SEQ ID NO 252
<211> LENGTH: 10
<212> TYPE: DNA
<213> ORGANISM: Homo sapiens

<400> SEQUENCE: 252
gagaggacct                                                          10

<210> SEQ ID NO 253
<211> LENGTH: 10
<212> TYPE: DNA
<213> ORGANISM: Homo sapiens

<400> SEQUENCE: 253
atgaatatag                                                          10

<210> SEQ ID NO 254
<211> LENGTH: 10
<212> TYPE: DNA
<213> ORGANISM: Homo sapiens

<400> SEQUENCE: 254
atggaaatat                                                          10

<210> SEQ ID NO 255
<211> LENGTH: 10
<212> TYPE: DNA
<213> ORGANISM: Homo sapiens

<400> SEQUENCE: 255
ttggatatag                                                          10

<210> SEQ ID NO 256
<211> LENGTH: 10
<212> TYPE: DNA
<213> ORGANISM: Homo sapiens

<400> SEQUENCE: 256
gtggagatgg                                                          10

<210> SEQ ID NO 257

```
<211> LENGTH: 10
<212> TYPE: DNA
<213> ORGANISM: Homo sapiens

<400> SEQUENCE: 257
atggagatcc                                                            10

<210> SEQ ID NO 258
<211> LENGTH: 10
<212> TYPE: DNA
<213> ORGANISM: Homo sapiens

<400> SEQUENCE: 258
atggagggag                                                            10

<210> SEQ ID NO 259
<211> LENGTH: 10
<212> TYPE: DNA
<213> ORGANISM: Homo sapiens

<400> SEQUENCE: 259
ctggagaaag                                                            10

<210> SEQ ID NO 260
<211> LENGTH: 10
<212> TYPE: DNA
<213> ORGANISM: Homo sapiens

<400> SEQUENCE: 260
atccagatag                                                            10

<210> SEQ ID NO 261
<211> LENGTH: 10
<212> TYPE: DNA
<213> ORGANISM: Homo sapiens

<400> SEQUENCE: 261
atggggctag                                                            10

<210> SEQ ID NO 262
<211> LENGTH: 10
<212> TYPE: DNA
<213> ORGANISM: Homo sapiens

<400> SEQUENCE: 262
agggagagag                                                            10

<210> SEQ ID NO 263
<211> LENGTH: 10
<212> TYPE: DNA
<213> ORGANISM: Homo sapiens

<400> SEQUENCE: 263
caggagatag                                                            10

<210> SEQ ID NO 264
<211> LENGTH: 10
<212> TYPE: DNA
<213> ORGANISM: Homo sapiens

<400> SEQUENCE: 264
ttggagagag                                                            10
```

```
<210> SEQ ID NO 265
<211> LENGTH: 10
<212> TYPE: DNA
<213> ORGANISM: Homo sapiens

<400> SEQUENCE: 265
acggagcgcg                                                        10

<210> SEQ ID NO 266
<211> LENGTH: 10
<212> TYPE: DNA
<213> ORGANISM: Homo sapiens

<400> SEQUENCE: 266
agggagggcg                                                        10

<210> SEQ ID NO 267
<211> LENGTH: 10
<212> TYPE: DNA
<213> ORGANISM: Homo sapiens

<400> SEQUENCE: 267
acatgcatgc                                                        10

<210> SEQ ID NO 268
<211> LENGTH: 10
<212> TYPE: DNA
<213> ORGANISM: Homo sapiens

<400> SEQUENCE: 268
ccttgtaggc                                                        10

<210> SEQ ID NO 269
<211> LENGTH: 10
<212> TYPE: DNA
<213> ORGANISM: Homo sapiens

<400> SEQUENCE: 269
tcttgtattc                                                        10

<210> SEQ ID NO 270
<211> LENGTH: 10
<212> TYPE: DNA
<213> ORGANISM: Homo sapiens

<400> SEQUENCE: 270
actggtatgt                                                        10

<210> SEQ ID NO 271
<211> LENGTH: 10
<212> TYPE: DNA
<213> ORGANISM: Homo sapiens

<400> SEQUENCE: 271
acttctattc                                                        10

<210> SEQ ID NO 272
<211> LENGTH: 10
<212> TYPE: DNA
<213> ORGANISM: Homo sapiens

<400> SEQUENCE: 272
acttttctgc                                                        10
```

```
<210> SEQ ID NO 273
<211> LENGTH: 10
<212> TYPE: DNA
<213> ORGANISM: Homo sapiens

<400> SEQUENCE: 273
gcttgtaagc                                                          10

<210> SEQ ID NO 274
<211> LENGTH: 10
<212> TYPE: DNA
<213> ORGANISM: Homo sapiens

<400> SEQUENCE: 274
agttgtatgt                                                          10

<210> SEQ ID NO 275
<211> LENGTH: 10
<212> TYPE: DNA
<213> ORGANISM: Homo sapiens

<400> SEQUENCE: 275
acttggaagc                                                          10

<210> SEQ ID NO 276
<211> LENGTH: 10
<212> TYPE: DNA
<213> ORGANISM: Homo sapiens

<400> SEQUENCE: 276
acttgtgtgg                                                          10

<210> SEQ ID NO 277
<211> LENGTH: 10
<212> TYPE: DNA
<213> ORGANISM: Homo sapiens

<400> SEQUENCE: 277
acttgtttga                                                          10

<210> SEQ ID NO 278
<211> LENGTH: 10
<212> TYPE: DNA
<213> ORGANISM: Homo sapiens

<400> SEQUENCE: 278
acatgtttgc                                                          10

<210> SEQ ID NO 279
<211> LENGTH: 9
<212> TYPE: DNA
<213> ORGANISM: Homo sapiens

<400> SEQUENCE: 279 aggaggcac                                                            9

<210> SEQ ID NO 280
<211> LENGTH: 9
<212> TYPE: DNA
<213> ORGANISM: Homo sapiens

<400> SEQUENCE: 280 agaaggcag                                                            9
```

```
<210> SEQ ID NO 281
<211> LENGTH: 9
<212> TYPE: DNA
<213> ORGANISM: Homo sapiens

<400> SEQUENCE: 281 aggagccag                                                                  9

<210> SEQ ID NO 282
<211> LENGTH: 9
<212> TYPE: DNA
<213> ORGANISM: Homo sapiens

<400> SEQUENCE: 282 atgaggcag                                                                  9

<210> SEQ ID NO 283
<211> LENGTH: 10
<212> TYPE: DNA
<213> ORGANISM: Homo sapiens

<400> SEQUENCE: 283
tcatgataag                                                                10

<210> SEQ ID NO 284
<211> LENGTH: 10
<212> TYPE: DNA
<213> ORGANISM: Homo sapiens

<400> SEQUENCE: 284
ttaggttaaa                                                                10

<210> SEQ ID NO 285
<211> LENGTH: 10
<212> TYPE: DNA
<213> ORGANISM: Homo sapiens

<400> SEQUENCE: 285
ttaaaataag                                                                10

<210> SEQ ID NO 286
<211> LENGTH: 10
<212> TYPE: DNA
<213> ORGANISM: Homo sapiens

<400> SEQUENCE: 286
ttagcataac                                                                10

<210> SEQ ID NO 287
<211> LENGTH: 10
<212> TYPE: DNA
<213> ORGANISM: Homo sapiens

<400> SEQUENCE: 287
ttatgatgag                                                                10

<210> SEQ ID NO 288
<211> LENGTH: 10
<212> TYPE: DNA
<213> ORGANISM: Homo sapiens

<400> SEQUENCE: 288
```

-continued tttggatgag    10

<210> SEQ ID NO 289
<211> LENGTH: 10
<212> TYPE: DNA
<213> ORGANISM: Homo sapiens

<400> SEQUENCE: 289
tgagtataag    10

<210> SEQ ID NO 290
<211> LENGTH: 10
<212> TYPE: DNA
<213> ORGANISM: Homo sapiens

<400> SEQUENCE: 290
ttacaataag    10

<210> SEQ ID NO 291
<211> LENGTH: 10
<212> TYPE: DNA
<213> ORGANISM: Homo sapiens

<400> SEQUENCE: 291
taaggataaa    10

<210> SEQ ID NO 292
<211> LENGTH: 10
<212> TYPE: DNA
<213> ORGANISM: Homo sapiens

<400> SEQUENCE: 292
tgtggataag    10

<210> SEQ ID NO 293
<211> LENGTH: 10
<212> TYPE: DNA
<213> ORGANISM: Homo sapiens

<400> SEQUENCE: 293
gtaggatagg    10

<210> SEQ ID NO 294
<211> LENGTH: 10
<212> TYPE: DNA
<213> ORGANISM: Homo sapiens

<400> SEQUENCE: 294
ctaggaaaag    10

<210> SEQ ID NO 295
<211> LENGTH: 10
<212> TYPE: DNA
<213> ORGANISM: Homo sapiens

<400> SEQUENCE: 295
ctatgataag    10

<210> SEQ ID NO 296
<211> LENGTH: 10
<212> TYPE: DNA
<213> ORGANISM: Homo sapiens

<400> SEQUENCE: 296

```
taaggatagg                                                                    10

<210> SEQ ID NO 297
<211> LENGTH: 10
<212> TYPE: DNA
<213> ORGANISM: Homo sapiens

<400> SEQUENCE: 297
tatgtatact                                                                    10

<210> SEQ ID NO 298
<211> LENGTH: 10
<212> TYPE: DNA
<213> ORGANISM: Homo sapiens

<400> SEQUENCE: 298
tatctcttct                                                                    10

<210> SEQ ID NO 299
<211> LENGTH: 10
<212> TYPE: DNA
<213> ORGANISM: Homo sapiens

<400> SEQUENCE: 299
tctatctgct                                                                    10

<210> SEQ ID NO 300
<211> LENGTH: 10
<212> TYPE: DNA
<213> ORGANISM: Homo sapiens

<400> SEQUENCE: 300
aatgtctggt                                                                    10

<210> SEQ ID NO 301
<211> LENGTH: 10
<212> TYPE: DNA
<213> ORGANISM: Homo sapiens

<400> SEQUENCE: 301
tatgtttcct                                                                    10

<210> SEQ ID NO 302
<211> LENGTH: 10
<212> TYPE: DNA
<213> ORGANISM: Homo sapiens

<400> SEQUENCE: 302
tttttctgct                                                                    10

<210> SEQ ID NO 303
<211> LENGTH: 10
<212> TYPE: DNA
<213> ORGANISM: Homo sapiens

<400> SEQUENCE: 303
tatgtctttt                                                                    10

<210> SEQ ID NO 304
<211> LENGTH: 10
<212> TYPE: DNA
<213> ORGANISM: Homo sapiens
```

```
<400> SEQUENCE: 304
tatatctgca                                                          10

<210> SEQ ID NO 305
<211> LENGTH: 10
<212> TYPE: DNA
<213> ORGANISM: Homo sapiens

<400> SEQUENCE: 305
tatgtaggct                                                          10

<210> SEQ ID NO 306
<211> LENGTH: 10
<212> TYPE: DNA
<213> ORGANISM: Homo sapiens

<400> SEQUENCE: 306
ctccagcccc                                                          10

<210> SEQ ID NO 307
<211> LENGTH: 10
<212> TYPE: DNA
<213> ORGANISM: Homo sapiens

<400> SEQUENCE: 307
ctccagcccc                                                          10

<210> SEQ ID NO 308
<211> LENGTH: 10
<212> TYPE: DNA
<213> ORGANISM: Homo sapiens

<400> SEQUENCE: 308
cctggaaata                                                          10

<210> SEQ ID NO 309
<211> LENGTH: 10
<212> TYPE: DNA
<213> ORGANISM: Homo sapiens

<400> SEQUENCE: 309
cctagaaaca                                                          10

<210> SEQ ID NO 310
<211> LENGTH: 10
<212> TYPE: DNA
<213> ORGANISM: Homo sapiens

<400> SEQUENCE: 310
gactgactcc                                                          10

<210> SEQ ID NO 311
<211> LENGTH: 10
<212> TYPE: DNA
<213> ORGANISM: Homo sapiens

<400> SEQUENCE: 311
gactgacagc                                                          10

<210> SEQ ID NO 312
<211> LENGTH: 10
<212> TYPE: DNA
<213> ORGANISM: Homo sapiens
```

```
<400> SEQUENCE: 312
tacttggaag                                                          10

<210> SEQ ID NO 313
<211> LENGTH: 10
<212> TYPE: DNA
<213> ORGANISM: Homo sapiens

<400> SEQUENCE: 313
atccgactgt                                                          10

<210> SEQ ID NO 314
<211> LENGTH: 10
<212> TYPE: DNA
<213> ORGANISM: Homo sapiens

<400> SEQUENCE: 314
tccctgctgt                                                          10

<210> SEQ ID NO 315
<211> LENGTH: 10
<212> TYPE: DNA
<213> ORGANISM: Homo sapiens

<400> SEQUENCE: 315
tcccagctgt                                                          10

<210> SEQ ID NO 316
<211> LENGTH: 10
<212> TYPE: DNA
<213> ORGANISM: Homo sapiens

<400> SEQUENCE: 316
agcccgctgt                                                          10

<210> SEQ ID NO 317
<211> LENGTH: 10
<212> TYPE: DNA
<213> ORGANISM: Homo sapiens

<400> SEQUENCE: 317
acccgggcgt                                                          10

<210> SEQ ID NO 318
<211> LENGTH: 11
<212> TYPE: DNA
<213> ORGANISM: Homo sapiens

<400> SEQUENCE: 318
aagtatcctt t                                                        11

<210> SEQ ID NO 319
<211> LENGTH: 11
<212> TYPE: DNA
<213> ORGANISM: Homo sapiens

<400> SEQUENCE: 319
atgcattctg t                                                        11

<210> SEQ ID NO 320
<211> LENGTH: 11
<212> TYPE: DNA
```

```
<213> ORGANISM: Homo sapiens

<400> SEQUENCE: 320
atgcattctc t                                                          11

<210> SEQ ID NO 321
<211> LENGTH: 10
<212> TYPE: DNA
<213> ORGANISM: Homo sapiens

<400> SEQUENCE: 321
ctccacctcc                                                            10

<210> SEQ ID NO 322
<211> LENGTH: 10
<212> TYPE: DNA
<213> ORGANISM: Homo sapiens

<400> SEQUENCE: 322
agagggaaat                                                            10

<210> SEQ ID NO 323
<211> LENGTH: 10
<212> TYPE: DNA
<213> ORGANISM: Homo sapiens

<400> SEQUENCE: 323
ggaaggaaat                                                            10

<210> SEQ ID NO 324
<211> LENGTH: 10
<212> TYPE: DNA
<213> ORGANISM: Homo sapiens

<400> SEQUENCE: 324
gtagggaga                                                             10

<210> SEQ ID NO 325
<211> LENGTH: 10
<212> TYPE: DNA
<213> ORGANISM: Homo sapiens

<400> SEQUENCE: 325
atgggacaca                                                            10

<210> SEQ ID NO 326
<211> LENGTH: 10
<212> TYPE: DNA
<213> ORGANISM: Homo sapiens

<400> SEQUENCE: 326
tttggatata                                                            10

<210> SEQ ID NO 327
<211> LENGTH: 10
<212> TYPE: DNA
<213> ORGANISM: Homo sapiens

<400> SEQUENCE: 327
ttagggcata                                                            10

<210> SEQ ID NO 328
<211> LENGTH: 10
```

```
<212> TYPE: DNA
<213> ORGANISM: Homo sapiens

<400> SEQUENCE: 328
ttggaacaga                                                              10

<210> SEQ ID NO 329
<211> LENGTH: 10
<212> TYPE: DNA
<213> ORGANISM: Homo sapiens

<400> SEQUENCE: 329
ctgggactta                                                              10

<210> SEQ ID NO 330
<211> LENGTH: 10
<212> TYPE: DNA
<213> ORGANISM: Homo sapiens

<400> SEQUENCE: 330
gtgggaaata                                                              10

<210> SEQ ID NO 331
<211> LENGTH: 10
<212> TYPE: DNA
<213> ORGANISM: Homo sapiens

<400> SEQUENCE: 331
ttgtgagata                                                              10

<210> SEQ ID NO 332
<211> LENGTH: 10
<212> TYPE: DNA
<213> ORGANISM: Homo sapiens

<400> SEQUENCE: 332
ctgggaaata                                                              10

<210> SEQ ID NO 333
<211> LENGTH: 10
<212> TYPE: DNA
<213> ORGANISM: Homo sapiens

<400> SEQUENCE: 333
tcaagacaga                                                              10

<210> SEQ ID NO 334
<211> LENGTH: 10
<212> TYPE: RNA
<213> ORGANISM: Homo sapiens

<400> SEQUENCE: 334
agcccuuacc                                                              10

<210> SEQ ID NO 335
<211> LENGTH: 10
<212> TYPE: RNA
<213> ORGANISM: Homo sapiens

<400> SEQUENCE: 335
uagcagcacg                                                              10

<210> SEQ ID NO 336
```

```
<211> LENGTH: 10
<212> TYPE: RNA
<213> ORGANISM: Homo sapiens

<400> SEQUENCE: 336
acugcccuaa                                                          10

<210> SEQ ID NO 337
<211> LENGTH: 10
<212> TYPE: RNA
<213> ORGANISM: Homo sapiens

<400> SEQUENCE: 337
aguuuugcag                                                          10

<210> SEQ ID NO 338
<211> LENGTH: 10
<212> TYPE: RNA
<213> ORGANISM: Homo sapiens

<400> SEQUENCE: 338
uugugcuuga                                                          10

<210> SEQ ID NO 339
<211> LENGTH: 10
<212> TYPE: RNA
<213> ORGANISM: Homo sapiens

<400> SEQUENCE: 339
uucacagugg                                                          10

<210> SEQ ID NO 340
<211> LENGTH: 11
<212> TYPE: RNA
<213> ORGANISM: Homo sapiens

<400> SEQUENCE: 340
agggcuuagc u                                                        11

<210> SEQ ID NO 341
<211> LENGTH: 10
<212> TYPE: RNA
<213> ORGANISM: Homo sapiens

<400> SEQUENCE: 341
aaggagcuca                                                          10

<210> SEQ ID NO 342
<211> LENGTH: 10
<212> TYPE: RNA
<213> ORGANISM: Homo sapiens

<400> SEQUENCE: 342
gaacggcuuc                                                          10

<210> SEQ ID NO 343
<211> LENGTH: 11
<212> TYPE: RNA
<213> ORGANISM: Homo sapiens

<400> SEQUENCE: 343
aaucacuaac c                                                        11
```

```
<210> SEQ ID NO 344
<211> LENGTH: 11
<212> TYPE: RNA
<213> ORGANISM: Homo sapiens

<400> SEQUENCE: 344
acucaaaaug g                                                              11

<210> SEQ ID NO 345
<211> LENGTH: 12
<212> TYPE: RNA
<213> ORGANISM: Homo sapiens

<400> SEQUENCE: 345 ugauuggguac gu                                                            12

<210> SEQ ID NO 346
<211> LENGTH: 10
<212> TYPE: RNA
<213> ORGANISM: Homo sapiens

<400> SEQUENCE: 346
acucagccuu                                                                10

<210> SEQ ID NO 347
<211> LENGTH: 11
<212> TYPE: RNA
<213> ORGANISM: Homo sapiens

<400> SEQUENCE: 347
ucuccaaaag g                                                              11

<210> SEQ ID NO 348
<211> LENGTH: 10
<212> TYPE: RNA
<213> ORGANISM: Homo sapiens

<400> SEQUENCE: 348
caaaacuggc                                                                10

<210> SEQ ID NO 349
<211> LENGTH: 10
<212> TYPE: RNA
<213> ORGANISM: Homo sapiens

<400> SEQUENCE: 349 ggggguccccc                                                               10

<210> SEQ ID NO 350
<211> LENGTH: 12
<212> TYPE: RNA
<213> ORGANISM: Homo sapiens

<400> SEQUENCE: 350
gcagguucuc ac                                                             12

<210> SEQ ID NO 351
<211> LENGTH: 50
<212> TYPE: DNA
<213> ORGANISM: Homo sapiens

<400> SEQUENCE: 351
gtcggttcaa aaaacagaaa tcgggtttgc tgcccggcgg acaggcgtga                    50
```

<210> SEQ ID NO 352
<211> LENGTH: 202
<212> TYPE: DNA
<213> ORGANISM: Homo sapiens

<400> SEQUENCE: 352
agagcaaggg aaaggaactt cctccacctt cggggctgga gcccttttcc tctgcatctc    60
cagtctctga gtgaagatgg ggggcctgac agcctcggac gtacacccga ccctgggggt   120
ccagctcttc tcagctggaa tagcggcgtg cttggcggac gtgatcacct tcccgctgga   180
cacggccaaa gtccggctcc ag                                             202

<210> SEQ ID NO 353
<211> LENGTH: 50
<212> TYPE: DNA
<213> ORGANISM: Homo sapiens

<400> SEQUENCE: 353
gtagctaggc agagggtaa gacaatgttc tgcacctttc ttatttccag                50

<210> SEQ ID NO 354
<211> LENGTH: 199
<212> TYPE: DNA
<213> ORGANISM: Homo sapiens

<400> SEQUENCE: 354
gtccaaggtg aatgcccgac gtccagtgtt attaggtata aagtgtcct gggaacaatc     60 accgctgtgg taaaaacaga agggcggatg aaactctaca gcgggctgcc tgcggggctt   120
cagcggcaaa tcagctccgc ctctctcagg atcggcctct acgacacggt ccaggagttc   180
ctcaccgcag ggaaagaaa                                                 199

<210> SEQ ID NO 355
<211> LENGTH: 50
<212> TYPE: DNA
<213> ORGANISM: Homo sapiens

<400> SEQUENCE: 355
gtaagccgtg agcgttcctg ggaggaataa ttttttttct ctctggatag                50

<210> SEQ ID NO 356
<211> LENGTH: 199
<212> TYPE: DNA
<213> ORGANISM: Homo sapiens

<400> SEQUENCE: 356
cagcacctag tttaggaagc aagattttag ctggtctaac gactggagga gtggcagtat    60
tcattgggca acccacagag gtcgtgaaag tcagacttca agcacagcca tctccacgga   120
atcaaacctc gctacacggg gacttataat gcgtacagaa taatagcaac aaccgaaggc   180
ttgacgggtc tttggaaag                                                 199

<210> SEQ ID NO 357
<211> LENGTH: 50
<212> TYPE: DNA
<213> ORGANISM: Homo sapiens

<400> SEQUENCE: 357
gtaactaact tcaaaatggg ttttaacatt ttcttttttt ttttcccag                50

```
<210> SEQ ID NO 358
<211> LENGTH: 102
<212> TYPE: DNA
<213> ORGANISM: Homo sapiens

<400> SEQUENCE: 358
ggactactcc caatctgatg agaagtgtca tcatcaattg tacagagcta gtaacatatg     60
atctaatgaa ggaggccttt gtgaaaaaca acatattagc ag                      102

<210> SEQ ID NO 359
<211> LENGTH: 50
<212> TYPE: DNA
<213> ORGANISM: Homo sapiens

<400> SEQUENCE: 359
gtaacttccc atttcatata acaaagacct gtttcatcga tccattttag                50

<210> SEQ ID NO 360
<211> LENGTH: 181
<212> TYPE: DNA
<213> ORGANISM: Homo sapiens

<400> SEQUENCE: 360
atgacgtccc ctgccacttg gtgtcggctc ttatcgctgg attttgcgca acagctatgt     60
cctccccggt ggatgtagta aaaaccagat ttattaattc tccaccagga cagtacaaaa    120
gtgtgcccaa ctgtgcaatg aaagtgttca ctaacgaagg accaacggct ttcttcaagg    180
g                                                                   181

<210> SEQ ID NO 361
<211> LENGTH: 50
<212> TYPE: DNA
<213> ORGANISM: Homo sapiens

<400> SEQUENCE: 361
gtaagatatg atcttgtgta tctgtcgaac gatgacatgc acttttctag                50

<210> SEQ ID NO 362
<211> LENGTH: 578
<212> TYPE: DNA
<213> ORGANISM: Homo sapiens

<400> SEQUENCE: 362
gttggtacct tccttcttgc gacttggatc ctggaacgtc attatgtttg tgtgctttga     60
acaactgaaa cgagaactgt caaagtcaag gcagactatg gactgtgcca cataatcagc    120
ttcaagaaaa tgatgtaaca taccagtggg aatcttgctg actggatcat aaaaacaaac    180
aaaacttatt cacttatttt aacctaaaaa gataaaggaa ttttggcaga gaattttgga    240
cttttttata taaaaagag gaaaattaat gcctatttca tataactttt ttttttctc    300 agtgtcttaa gaaggggaaa gcaaaacatt cagcatatac cctggcaaat gtaatgcaga    360
taagctactg catttgacca tttctggagt gcaattgtgt gaatgaatgt gaagaacttt    420
aacatgtttt aattacaatt ccaactggtg gaaaagaaac tgagtgaaat gcagtttata    480
tttataaata cttaaaaatg aagttattaa aaatattagt ttttattaac cacagttgtc    540
agttaatata ttcaataaaa gtattgctaa tacctttt                            578

<210> SEQ ID NO 363
<211> LENGTH: 50
<212> TYPE: DNA
```

<213> ORGANISM: Homo sapiens

<400> SEQUENCE: 363

| aaagtttgtc ttttgagatc tatacctggg tgtaagagtc aagttcacta | 50 |

<210> SEQ ID NO 364
<211> LENGTH: 10572
<212> TYPE: DNA
<213> ORGANISM: Homo sapiens

<400> SEQUENCE: 364

| agagaaggcc gcaaggtgcc tgcaagatgt ctggggagtt ggaggaatgg aagagtgccc | 60 |
| cgctcttcct tctgggagag ctccagctag gcagaacctt tcaccaaggc tctgatatcg | 120 |
| tgctggtttc cgaaagcccc agccgaaggt gtgcagccaa aggtgacag aaggtgaggc | 180 |
| acgtgcgggg gcgcgggtgc tgaccgccgc ggtgcgccct ccctccgacg tgcggtgtgc | 240 |
| ggggcgcaga caaccagcgg ccggcccagg gctttcgggg agcgaagcag ggctcccgag | 300 |
| gcaccgagcg agaatgggaa tgggaggga ccggtgctcc cggacacgcc cccggcaggt | 360 |
| cccacgcccg ggtcttctga gacctcgcgc ggcccagccc gggagcggcc cagctatata | 420 |
| agtcccagcg gaagaccgga acgcagaggg tcctgctggc gcgaggtgg gtaggagggg | 480 |
| acgcggggac tcggccccca acaccgcgct ccgtctgcag ccgccgcctc tgcaccgccg | 540 |
| ctgcccggcg gtcggttcaa aaacagaaa tcgggtttgc tgcccggcgg acaggcgtga | 600 |
| agagcaaggg aaaggaactt cctccaccctt cggggctgga gccctttttcc tctgcatctc | 660 |
| cagtctctga gtgaagatgg ggggcctgac agcctcggac gtacacccga ccctgggggt | 720 |
| ccagctcttc tcagctggaa tagcggcgtg cttggcggac gtgatcacct tcccgctgga | 780 |
| cacggccaaa gtccggctcc agtagctag gcagagggga aagacaaggg gtctcaggac | 840 |
| agaggggacg ctgttgcgtg cattccattt attctctgct ttggtgtaac cactgtttct | 900 |
| aggtagggta ggtgaccttc caaagcagtc tggccttgtc ccagggctgg tgctttagga | 960 |
| tgggaaactg gaacttttttc tgggattagc tgaagaacca ccagggccac agagaatggg | 1020 |
| ttgaccatga ctactaccaa attctcccaa aatttagggt gcacttagta tttttaagagc | 1080 |
| tgagaatatt ggcctctcct gagtttacta gtcaggtgct ttttcctttc tttgattctt | 1140 |
| cgggggttct gtcctatcct actgccctag gggttctgga gagttcctgg ggaggggat | 1200 |
| attcaaaatg tgcattgtag ccagcctccc tccatctgcg cgtgagcgaa cacacacaca | 1260 |
| cacacacaca cacacacaca cacacacaca cacacacggt agagggaggt ggatggaaga | 1320 |
| ggaatgttgc tgagaaaaga aacggaaaat aggaacacag ggggaaatct tggcttaaga | 1380 |
| gtgaactcaa tttcgctccc ttctgttctg cacctttctt atttccaggt ccaaggtgaa | 1440 |
| tgcccgacgt ccagtgttat taggtataaa ggtgtcctgg gaacaatcac cgctgtggta | 1500 |
| aaaacagaag ggcggatgaa actctacagc gggctgcctg cggggcttca gcggcaaatc | 1560 |
| agctccgcct ctctcaggat cggcctctac gacacggtcc aggagttcct caccgcaggg | 1620 |
| aaagaaagta agccgtgagc gttcctggga ggggcagaaa agccttgggc tccgctctgt | 1680 |
| tccaaaaagt gtaacacaca gaggagtggt tttcataaca aattggcgag aaaacattca | 1740 |
| tatttgaact ctcccttccc caaacattag ctcattgttc atagaaaaaa gtatgcaaaa | 1800 |
| tcgattttt agatgcagat atatacttgt aaaggtcacc cagtcatgga agttttgtgc | 1860 |
| ccagtttgga tctccatctg gagaatatgg gtgggctaca gaaaaatgtt taacttaaag | 1920 |
| ttctccaaag agggaagtat atcagaaaca tctatggagc ttgtcagaaa tccaaacgag | 1980 |

```
gactaccatg gtcctctgag tctgaatcct caggctagag accagagtgt ctttccacaa    2040
gcttccctca tcatttgtgt atgcaacaaa gttcaaagcc ttctgtttga agcaaagaaa    2100
gccagacttt gtgaagagag ttgaaaggac aggaaaagac atatttcctc ttaagaggtt    2160
cctcatcagg tccaggaaag accagagcag aaaaagtgga cgaatgctgc agggagtttg    2220
tttaggggaa aaagaaaagg aaacatattt cctgagtgcc agtgcactct aagaattcct    2280
gtcactttag gtagcattta tttgagggct taactatgaa ccagacattg ttctaagtgc    2340
ttcagataca ttataactgg aagggtatta gtaccattat cccttggcag atgggaaaac    2400
tgaacacaga gcagattcat cacttgccca aggtcacaca gctgggaggg ggcagagcca    2460
gggttcaaac ccaggcagtc tggcctcgga ctccaggctc ctaaccctgt tctctactgc    2520
cttctgcact tctcatatga ttctgcccat cattcaaacc gcacaacact gctgtgagta    2580
aaaagtgtta gccgaatatc agggtagtta agtaacatgc acaaaatcac acagctaatc    2640
aacatcagag gcactttcat gtggagtaga caagccagag agaagatgtg ctgatggcac    2700
aatgaataca ttaagtgaaa tccaccttgt agatttcatc atttctgctg tgagtaacct    2760
tcaatactat aattttatgg gataaattat aaatgttgtc tatacaaata tataagttat    2820
acttatccac acaagtactt tcaaagtgaa gataaagtct ggatgttact agatcaaaac    2880 tgcattttt tatttataga gtagcaaga gaggaaacac aaaggaggta aagctgcccg     2940
```

```
ttcaggtggt tttcttcaca gattgactgt tctaccaatt gttgtggact tgggcacca     3000 aattaatagg atatatgttg gcagtgttct atgttatata gattcagttt atttagtagg    3060
ctttattgaa ctgccatgtg ccagtaacta tgttagatgt ttagatggca gatgtgtctc    3120
tagacagagc ttacagttga gagtatgggt tgtgtgggga gaagtgaata gatgactata    3180
ttccatgata catgctgtat tacaatacag tcctacttca cttaacgatg gggatacatt    3240
ctcagaaatg agttaggagg caaattggtt gttgaatgaa catcacagag agcacttaca    3300
caaacctaga tggcatagcc acacctaggc tatatggtat aatctattgc tcctaggcta    3360
caaacctgtg cagcatgttg gtattgaata ctacaggcaa ttgttacata agttaagtg     3420 tttgtgtacc taaaaataga aaaggtaatg cattacacta cagtcttatg gggctgggat    3480
gtcactaggt gataggaatt tttcagctct gttctaatct tacgggacca ccatcatgta    3540
tgcagcacat gactaactgt aattacaaga tggtggctat attaaacaga actacttaag    3600
ctagccatgg aggtatggtc cgtgagattt tcctgaagaa ttaacgtctg gatcaattct    3660
ggaagggcca gcaggagtac tccagcaaa ggggtgagaa aggagcttcc aagtagagtg     3720
aaggtcatgt gcaaagactc agtgaggagt cgagtgaaca tagcacaggg aggacatgtt    3780
ggtgaggaag gaggggtgaa gccacagaga caggagggga ccagatgaca gaaggccttg    3840
caggcggtgc taaggagttt ggattttatc cttacagtgg tgggaagtca ttgtaaaaat    3900
attaagcaag ggagtggcat aaacaattta cattttcaaa agatcacttt ggcagcagat    3960
agagtatata tgtaaaagga gtaagaaaga ggtaagttag aaagcaagaa atgatcaggg    4020
tatgccctaa aacactggca atagggaaaa agagatgtca atcagaaaga ttgagaaagt    4080
ataattgaat tgacttggtg aacaaataga agtaaggcat aagggacagg tagaaatatg    4140
agatgacttc caagtttctg tttaaagata ccctttattg agagaggatg tatagaagct    4200
gtcttagggg gaagacaaga aatttggttt aggccatgtc aacaggtaat ggccagtagg    4260
cacatgattc agtttattta gtgggctcct tttaggagaa aatctgagcc agattccagg    4320
```

```
aagtcacagc agggactacc aatagggtca aacagcagag agtgtggaaa ggactgaaaa    4380
gtgatcattg tacataacaa atagaagctc actgattttc tagcaaaaac atcttcagca    4440
gagtagcgtg gtataagcta tattgtaggg gactgaggaa gaaatgggct ctgagaagta    4500
aagacaaaca atatgttttg taaataaatt tcttttagtt cttaaaaaaa aagcctcttt    4560
tccagcttga ttgggaagtg aagagaggga tttgaaagtt ggagattgga ggataggatg    4620
agtacatcaa gatacactac gttgtagtgc agtgcattac aaatgtgagc taaaagtgaa    4680
ggcatttgta atcatatgat attgctaatt aaaagacagc tgtcagtcat atgcccagct    4740
cctggtaaag catgatgaga agagtacaat catggtagtg attttaaaaat tgctgccagt    4800 tttgtggatt ttcttttatgc tagacagtgt aagctcttta tcaatattat ttaactcaca    4860
caactctaag aggtagatat tattatccct ttttgacaaa ttaggaaaca gaattataat    4920
gactgagaaa gtctctgctg agtaaatgtt actgaacctt aattttatgt ttacttaatg    4980
atagaaatga atattgggct tcaagactat ttgtacttaa tgaaatctgt cttgagcaac    5040
ataagctatt tttttcaaaa ttttaagaca aaaatcactt tcttctctcc tgtcttctta    5100
tttttgttcc cttacatgt tgtagcctaa cactacttga tggcccatttt tggtgcagtt     5160 tgtccactgg gcttcatcta aggccaccaa gtcccataat taacatgatc attcgtggga    5220
gaaagatcaa gcctcattgg tgatgggtgc ctcctcacag tcggataata ctgaaaagag    5280
agctaaatgt gggaaagaac caagttgaac acaggaaaga atcaggccac tgtgaaaata    5340
agcattgtgt tttcttgttc cttgaaagtc ttcattttta aaaaatttca gacacctgaa    5400
gttttctagc cttactctga gttgacgcac atttagtaca tgatcaacac ataaacaagc    5460
attagagaaa tagaaaagct gtaagaatac aaaaatatgg gccaggtggg tggctcatac    5520
ctgtaatcct agcactttgg gaggccgagg cagacggatc acctgaggtc aggagttcaa    5580
gactagcctg gccaatatag tgaaaccctg tctctactaa aaatacaaaa cttagcaggc    5640
tgtggtggca cgtgcctata atcccagcta cttgggaggc tgaggcagga gaatctcttg    5700
aacccgggag gcggagattg cagtgagcca agatcacacc actgcactct agcctagata    5760
acagagcaag actccatctc aaaaaaaaaa aaaatacaaa aatatgaacc actgaaaatt    5820
aaaaagacat gcatgcattc taggtctttta attttttttc ttaataattt ttttctctc    5880 tggatagcag cacctagttt aggaagcaag attttagctg gtctaacgac tggaggagtg    5940
gcagtattca ttgggcaacc cacagaggtc gtgaaagtca gacttcaagc acagagccat    6000
ctccacggaa tcaaacctcg ctacacgggg acttataatg cgtacagaat aatagcaaca    6060
accgaaggct tgacgggtct ttggaaaggt aactaacttc aaaatggggtt ttataaccac    6120 caaagcacat acatacaact agcaacttat tgtaaagtag agttaataaa cattttcttt    6180
ttttttttcc ccagggacta ctcccaatct gatgagaagt gtcatcatca attgtacaga    6240
gctagtaaca tatgatctaa tgaaggaggc ctttgtgaaa aacaacatat tagcaggtaa    6300
cttcccattt catataacaa acaggtctgc acctttagaa gttcatcttg gagcttctgc    6360
agccacctta tactcaatct cttaactcca atagttttct ctttttaaaa attaagtaat    6420
tttgaaccat atataacttt gtgagaagca ggaaaagacc aaaatattaa gtttaagaag    6480
ttttgccaca acaaaaatat tttgcaacaa aaataacagg caatttcatg tcagcattat    6540
tctcatttaa tactaatata tgggactttt gttagaatct tattctttat acagcagaat    6600
tcaggaggta agtccatcct gcatactata tccaaaagat ctagttataa aaggagctta    6660
tcagtggtct catccaaaaa gtaataccat aagataggtt cttaaaaata atattctaac    6720
```

-continued

| | |
|---|---|
| aacttctaga gacattgaaa tttcccttat ttcaataaaa aagtattaga tgctcatata | 6780 |
| ttaggcatta ttacaggcct taaaggcaca gaggaaacta acagtttact ttcctaaagt | 6840 |
| gttaacaatc tattaagcca tttactcttt accttctttt tctagtgcaa tacctttctt | 6900 |
| attttatttt atttatttat aagacatctt cattgaccta ctgttatcaa taggtttata | 6960 |
| aagatatgac agataactaa attgcaagcc cccaaaagtc tgatgttgac ctgtttcatc | 7020 |
| gatccatttt agatgacgtc ccctgccact tggtgtcggc tcttatcgct ggattttgcg | 7080 |
| caacagctat gtcctccccg gtggatgtag taaaaaccag atttattaat tctccaccag | 7140 |
| gacagtacaa aagtgtgccc aactgtgcaa tgaaagtgtt cactaacgaa ggaccaacgg | 7200 |
| ctttcttcaa ggggtaagat atgatcttgt gtatctgtaa tgtgttctgg ctgtctgtgt | 7260 |
| gctttgggac actctcatgt caagcaaccg acatttagct tacaagcctt agtatattca | 7320 |
| tatacttagt attgactttt ccttgccaca gatttctcca atccaccaat tccactgtgc | 7380 |
| cagaaagtaa aaagccatga tattcaaatt ttctcaactt tgatcaaagg ctcattcaag | 7440 |
| accagtgcct tttccactgg tcccaatcta ctggaaatgc agacagtatt ttgccttctc | 7500 |
| tgggcaagaa agttataaag tagagggaaa tcataataga gagctatgag agaacaagat | 7560 |
| ttgatttgat ttaatttgat ggactcaagt tttaacattg taaaactaga gataagacat | 7620 |
| caccaccaat ctagaaaagt gatgcagaaa agtatttgat ttgggtaatt attcactca | 7680 |
| cctagaaaca agtgttgtgt aatagattac atatttccat aatgcaatgt tgtatcagaa | 7740 |
| actaccttcc taagaaaata tagtatgggc tcggcgtggt ggctcgcacc tgtaatccca | 7800 |
| gcactttggg agatggaggc aggaggatca cttgagccca gactgggcaa caaagcgaga | 7860 |
| ccctgtctca acaaaaaatt taaaaattag ctgagtgtgg tggcacgcac tgatggtccc | 7920 |
| ctctacttgg gaagctgagg caagaggatc tcctgagccc aggagttcaa ggtttcagcg | 7980 |
| agctatgatt gtgccactgc actccagcct gggagacaga gcaagtccct gtctcaaaaa | 8040 |
| agaagaagga gaaggaggag aaaatacagt attaagtaat ctgtcaatat attccacaag | 8100 |
| gattacacta gtggtttaat aataaaatta tattaccttt ttaaattgta aggccattcc | 8160 |
| tcaagcttta taaattaagc atgaatgcat catacacatt ttataaaaag ttccaactca | 8220 |
| tcataatctg tacttatgat acattaatac aaatgaagtt cattataaaa ttaacttaaa | 8280 |
| atggatatac cagttattaa accattaacc atttaataat tttattttttt tcaaatttaa | 8340 |
| aaaccttttg gggaagaaat actacaacat ggatgaacct tgaaaacgtt atgctaagtg | 8400 |
| aaataagcca gacacaaaag gacaaatact gtatgattac acttaaatga ggtacctaga | 8460 |
| gtagtcaaat tcatagagac agaaagaata gaagttacca ggggctggag gtaggaaaaa | 8520 |
| atggagagct gtttaatggg tagagagttt cttttggggg tgacaaaaag gttctagaga | 8580 |
| tggatagtgg tgatggttac acacaatgtg tgtgtactta atgctactga aatgtaattt | 8640 |
| tatgattttt ttttttttgca gcaaaatacc ccacattggg aagtgaagag aaacatgtta | 8700 |
| agagacttga aggaaaaaaa ttggggcaga ggggtgtttt ttataggtta aacaataaaa | 8760 |
| gccatttaaa cagtaacaat ttctctaagg acaagaatcg tcaagattga cagcactg | 8820 |
| atttcttgac tctactcaat acttctttgg tttctcttct tccttccccc ttctaatagt | 8880 |
| ttcctacctc ccattcagaa agcaaagcaa aacaagcaaa aattcccccct tccctcaaaa | 8940 |
| aaggaaagag ttttttgaaaa agttcatgtc agtgaagaaa agacatgttt tgggagtgaa | 9000 |
| ggatatttgt ggatttgtat agatgtgatc atcagggctg tgttgttttg aagtaatata | 9060 |

| | |
|---|---|
| ggacatctag aggaaaattt attttcagca gaggagggaa agatgaagag taggtacttt | 9120 |
| taagcatctt cacttgagga gtggcaaaat gagaagcata acctgctata atcactttaa | 9180 |
| gaatttcagg ctgagtgtgg tggtgcagtc tctagtccca gttactccag gaggctcagg | 9240 |
| tgggaggatc acttaagccc aggagctcga ggttgcagtg agctatgatt acactactgc | 9300 |
| attccagcct gggcggcagg gtgaagcctc atctcaaaaa ttaaaaaaaa aaaaaatcaa | 9360 |
| acaaattaat cgaacgatga catgcacttt tctaggttgg taccttcctt cttgcgactt | 9420 |
| ggatcctgga acgtcattat gtttgtgtgc tttgaacaac tgaaacgaga actgtcaaag | 9480 |
| tcaaggcaga ctatggactg tgccacataa tcagcttcaa gaaatgatg taacatacca | 9540 |
| gtgggaatct tgctgactgg atcataaaaa caaacaaaac ttattcactt atttttaacct | 9600 |
| aaaaagataa aggaattttg gcagagaatt ttggactttt ttatataaaa agaggaaaa | 9660 |
| ttaatgccta tttcatataa cttttttttt ttctcagtgt cttaagaagg ggaaagcaaa | 9720 |
| acattcagca tataccctgg caaatgtaat gcagataagc tactgcattt gaccatttct | 9780 |
| ggagtgcaat tgtgtgaatg aatgtgaaga actttaacat gttttaatta caattccaac | 9840 |
| tggtggaaaa gaaactgagt gaaatgcagt ttatatttat aaatacttaa aaatgaagtt | 9900 |
| attaaaaata ttagttttta ttaaccacag ttgtcagtta atatattcaa taagtattg | 9960 |
| ctaataccctt ttaaagtttg tcttttgaga tctatacctg ggtgtaagag tcaagttcac | 10020 |
| tagaatacaa gactgcccaa tagcaaatgc aggtctttag aatcataggc atgaacctac | 10080 |
| tctgaatgtt attagtatag attttaatg tttagagtcc agatttgatg acatctctaa | 10140 |
| caacttctaa tctaagacac tatattcatt ttggcaggat tgctactaga gtcttggtat | 10200 |
| ctgtgctagc atcacataat tttagagctg gagggtactt ctgggaagac agaggaacag | 10260 |
| tttgagattc ctactgagat gaaaacgaat cttcatggaa tctttcagca aagccaaatt | 10320 |
| caaattcatc attagcacct gtagtaacct tttcaatgcc tacaaactgc atgcagaaga | 10380 |
| gatagggaaa cagtaaaaca gatattaaaa gaagttttta agacaaagcc cagcctgatt | 10440 |
| ttaagctaaa tccaaggatt ggcagcttgg atgagcagga aggttacagg ctgccagaca | 10500 |
| tcattctagt tctgttttaa tcaactccat gttacattta ctatcaggga ttctcacctc | 10560 |
| accctcatgc at | 10572 |

<210> SEQ ID NO 365
<211> LENGTH: 15910
<212> TYPE: DNA
<213> ORGANISM: Homo sapiens

<400> SEQUENCE: 365

| | |
|---|---|
| ctgtacagct ctccgacaat cccacatcta gatgccaagc tgaggttggc attctcacta | 60 |
| atttgctgtt ataatatta agctatcata agcgttagcc tacatatgac tctttcatat | 120 |
| gttagttaat tattttaggg tagaaatcca aaagtggagt taccagaagt ggatatagac | 180 |
| attctggctg ggtgtgatgg ttcatgcctg taatcccagc actttgggag gcagaggcag | 240 |
| gcggatcact tgaggccagg agtttgagat cagcctgggc aacacagcg aaaccccatc | 300 |
| tctactaaaa attccaaaac tagccaggca tagtggcaca tgcctgtact cccagctact | 360 |
| tgggaggcta agacacaaga atcgcttgaa cccgggaggg aggtggaggt tgcggtgagc | 420 |
| tgagattgtg ccaccgtact ccagcctggg tgacacagct agactctgtt tcaaaaaaaa | 480 |
| aaagaaaaag aaaagaaaaa aatagacttt ctccttggctc agtgtatact gccaaattgt | 540 |
| tttccaaaaa aattgtgtca atgtataaca ccatcactaa tatagtattg atattatggt | 600 |

```
tattacattt taaaattcat aatttgtaat tataacattc ataatttatt actatttata    660
atattaatgt aaatgtatat tatatataaa tgttatagta attataactt tggtagtgac    720
aaagtattaa tttattaggt gaagtatatg cttttttatt agtgataata aatatatcct    780
ctctcccatt ataaaagttt gtatttcttc ttttagaaat tgattcttct gtcatttgca    840
catttatctg tataattata acagggtatt tcccagtggt ggctaatgag agaattatgg    900
gaaagtatag aacactattc aaatgcaaag cactgtatga tttttattta ataggaagac    960
attttgtgca gcgatttctg attgaccaca gtttgatcaa gtgcatttgt taatgtgttc   1020
tacattttca aaaggaaag gagaatttgt tacattcaga acttgctgcc actcctttgc    1080
tacgtcataa agggtcagtt gcccttgctc atactgacct attctttacc tctctgcttc   1140
ttctttgtgc cagaagagta gaaatctgac cctttgggga taccaccctc tccctactg    1200 ctctctccaa cctgaggcaa actttctcct acttcccaga gcctgtcaga agtggtgaag   1260
ccagcctgct ccttggaatc cagaactact ttcagaatct tgaacttctg tgacctctca   1320 gggtccctt gtgtgaagtt tttgacgtca gcttctcctg tgacccttag aagtcactct    1380
tgtgtctagc acatcccagg tgctcagtca ccattgaact acagtcatac tatctcctgg   1440
caaaggctct taactgtcca tgttagcctg atattaatat cctggaagct tatactgtcg   1500
ttcttccttc caggtttaaa taaggcagcc cctttatcct gtcacaggtc ctctctccct   1560
acctatcctt acctgttttg gataacaacc tttcttattt ctaatagatt tatttatttc   1620
tcacatttcc ttcccttatc atagttttcc tctcactttc tcctctagtt tgtcatactc   1680
tggctttaaa acatgcaaac atgtgcctta tggggaaaaa aagacaattt taatttacct   1740
tgcttcttct ttacaaatgt attgtggctt cttcttatag tccaaatcta aaactcttta   1800
cccacccact gccttgaact ccttcctcgt tgtgaaagta ggatggggca aagagagaat   1860
gcatgcccct cccaactgct caaacaagta aaggtgctgt tacagttatc ttttgctacc   1920
ttaatacaat aattatttta ttatatctca caattttatg gatcaggaat ttagactggg   1980
ctcagctagg cgattcttct gctttactga catcatagga gatcacttgg tggtattcaa   2040
ctgtcaggta ggcttatctg gagggtccaa gatagctgta ctctggtgcc tggtgccttg   2100
gtaaagaggg atgatgatgt ggggcctctc cagcatgaac agcctcagag aagtttgctt   2160
tcttacatgc tggcccaggg ctccaagagc aaatgttgca gtgagtaaag cagaagatac   2220
aaggactttt ataatctggt ctcagaagcc acatggcatc agttctgtat tattctattg   2280
gtcaaaacat tcataagcct gccagatgca aggggaaggc atatgtaccc tcatcttttg   2340
atgggaggaa tgtgatggat ttgcaattat gttttaaaac tactacagac agaaccactg   2400
agaaagattc atgggtagct ttggggtgag gactgggaat taacctgttg atagcagagg   2460
ttcactagag tcaacaagga ataaggtctc ctcttgtaca ctttagtcat actataccaa   2520
cattcttaac cactgcttag ccatcagcct cacaacataa caactccatc atagttgtac   2580
tccctaagat caccaacaat gttagagtca atccggtag gttttctttt gttttgtcc    2640 tcctgacatt ttttctaaac ttgacactgg tcagacccaa tctttcttta atcatattct   2700
taaataccag ttctatcact ggatatgtta ctgtttcttg ttctcactct accttttgaca  2760 aagccattct ttccagacta taactctggg tctgggtccc cctatggttt ggcccttgaa   2820
ttcttttcct agtcctattt gactagcccc attttcccgt gaaaagcatg ccccttttcat  2880 tgcatccata tcatgactac caaatacctc ctctatttct tcctcttttta gcatgttaaa  2940
```

```
tgcagcttcc taagctctct atctggatat caacagtatt ctctccaaat aattctaaga   3000
ctttaaaaat tggtttaatc ttcttacccc taaaatcacc cccttacca actgcctcat    3060
gacaatcatt ggtactgtca ctgagcttgc aacccatgtt cttaaacata gagtaatctt   3120
tgactccaca tctaatcatt cataaagctg tattgtctat caattaaat ctgacattta    3180
tgtgagagca cttcatagtc tgtaaagcac tacacaggtg ataacatgaa gctacactca   3240
taatggattt gcaggctctg cttctcattt ggcttctaca gcctcatccc tcaccaactt   3300
cttgccctac ctctctcttt cttccccatc acccaatttc ccagtcagtc aggccaacag   3360
aatgcattct atatacgcga cttgctttcc ccaacatctt tgcctgtatg catgccactt   3420
atttgcctca gttgatcttt atttcaacaa gtgtttgcag aggagaaacc tcgctggctc   3480
cttctccttt ctatttttt tcagaggcta cccgtcaggt caacattgcc ttttcaggg    3540
aagctctgca agcctgacct cccttggaag tgccttagga ctggcttctt gcacagtaca   3600
caacctttac ttatagaggg tttggagatt attctttatt catgtcttat ttctcctgct   3660
cctggaggag atgactctga cttccactga ctcttttggg gggcttaagt cagggttgag   3720
taccagaggc cctaaatagc tggacgtgga ttctggtaat atcaaatcca tctttggctt   3780
aactgagagg ttctgaaagc tgggacctga ccttgtccat ttccctcttt ctccagtttc   3840
ctattatttc ccactgtttt ttttaaaagt ttttgtttt cttaagtttt cacaagaata    3900
aacattgaaa ataaaatttg cacaaagatc gaactaggaa aggccacaca accaacacat   3960
attacatcat tataggtaag ttagcaggga gatttcagac ctgggctagc tctggaacca   4020
cattttacac tgttgaaaat aaaagctgga gtacagatga cttccccagg ttcacagagt   4080
tggtaagctg gagagctgca cctggagcca agcaacctgc cctgtccttt ccactgcacc   4140
ctctaagaaa tctaattaga aggaacaggt ggtatctcat tttgtacggt gctttagcaa   4200
tgtactattt gctttctagt gtgtctattg tctcgtttga catcttctct caaaaagtga   4260
tgaaacgaaa cgctctttt gacaagttca gagtgctctt ggttcctgtg tgggattctt    4320
ccaagtctga atttggtagt gggaagagaa ggaatccgga ggaaggagga tgagaagttt   4380
aaaggagagg aaagggaagc agagaaggcc gcaaggtgcc tgcaagatgt ctggggagtt   4440
ggaggaatgg aagagtgccc cgctcttcct tctgggagag ctccagctag cagaaccttt   4500
tcaccaaggc tctgatatcg tgctggtttc cgaaagcccc agccgaaggt gtgcagccaa   4560
agggtgacag aaggtgaggc acgtgcgggg gcgcgggtgc tgaccgccgc ggtgcgccct   4620
ccctccgacg tgcggtgtgc ggggcgcaga caaccagcgg ccggcccagg gctttcgggg   4680
agcgaagcag ggctcccgag gcaccgagcg agaatgggaa tgggagggac ccggtgctcc   4740
cggacacgcc cccggcaggt cccacgcccg ggtcttctga gacctcgcgc ggcccagccc   4800
gggagcggcc cagctatata agtcccagcg gaagaccgga acgcagaggg tcctgctggc   4860
gcgagggtgg gtaggagggg acgcggggac tcggccccca acaccgcgct ccgtctgcag   4920
ccgccgcctc tgcaccgccg ctgccgcg gtcggttcaa aaaacagaaa tcgggtttgc     4980
tgcccggcgg acaggcgtga agagcaaggg aaaggaactt cctccacctt cggggctgga   5040
gcccttttcc tctgcatctc cagtctctga gtgaagatgg ggggcctgac agcctcggac   5100
gtacacccga ccctgggggt ccagctcttc tcagctggaa tagcggcgtg cttggcggac   5160
gtgatcacct tcccgctgga cacggccaaa gtccggctcc aggtagctag gcagagggt    5220
aagacaaggg gtctcaggac agaggggacg ctgttgcgtg cattccattt attctctgct   5280
ttggtgtaac cactgtttct aggtagggta ggtgaccttc caaagcagtc tggccttgtc   5340
```

```
ccagggctgg tgctttagga tgggaaactg gaacttttc tgggattagc tgaagaacca    5400
ccagggccac agagaatggg ttgaccatga ctactaccaa attctcccaa aatttagggt    5460
gcacttagta ttttaagagc tgagaatatt ggcctctcct gagtttacta gtcaggtgct    5520
ttttcctttc tttgattctt cggggtct gtcctatcct actgcccag ggttctgga     5580
gagttcctgg ggaggggat attcaaaatg tgcattgtag ccagcctccc tccatctgcg    5640
cgtgagcgaa cacacacaca cacacacaca cacacacaca cacacacaca cacacacggt    5700
agagggaggt ggatggaaga ggaatgttgc tgagaaaaga aacggaaaat aggaacacag    5760
ggggaaatct tggcttaaga gtgaactcaa tttcgctccc ttctgttctg cacctttctt    5820
atttccaggt ccaaggtgaa tgcccgacgt ccagtgttat taggtataaa ggtgtcctgg    5880
gaacaatcac cgctgtggta aaaacagaag ggcggatgaa actctacagc gggctgcctg    5940
cggggcttca gcggcaaatc agctccgcct ctctcaggat cggcctctac gacacggtcc    6000
aggagttcct caccgcaggg aaagaaagta agccgtgagc gttcctggga ggggcagaaa    6060
agccttgggc tccgctctgt tccaaaaagt gtaacacaca gaggagtggt tttcataaca    6120
aattggcgag aaacattca tatttgaact ctcccttccc caaacattag ctcattgttc    6180
atagaaaaaa gtatgcaaaa tcgatttttt agatgcagat atatacttgt aaaggtcacc    6240
cagtcatgga agttttgtgc ccagtttgga tctccatctg gagaatatgg gtgggctaca    6300
gaaaaatgtt taacttaaag ttctccaaag agggaagtat atcagaaaca tctatggagc    6360
ttgtcagaaa tccaaacgag gactaccatg gtcctctgag tctgaatcct caggctagag    6420
accagagtgt ctttccacaa gcttccctca tcatttgtgt atgcaacaaa gttcaaagcc    6480
ttctgtttga agcaaagaaa gccagacttt gtgaagagag ttgaaaggac aggaaaagac    6540
atatttcctc ttaagaggtt cctcatcagg tccaggaaag accagagcag aaaaagtgga    6600
cgaatgctgc agggagttg tttaggggaa aagaaaagg aaacatattt cctgagtgcc    6660
agtgcactct aagaattcct gtcactttag gtagcattta tttgagggct taactatgaa    6720
ccagacattg ttctaagtgc ttcagataca ttataactgg aagggtatta gtaccattat    6780
cccttggcag atgggaaaac tgaacacaga gcagattcat cacttgccca aggtcacaca    6840
gctgggaggg ggcagagcca gggttcaaac ccaggcagtc tggcctcgga ctccaggctc    6900
ctaaccctgt tctctactgc cttctgcact tctcatatga ttctgcccat cattcaaacc    6960
gcacaacact gctgtgagta aaaagtgtta gccgaatatc agggtagtta agtaacatgc    7020
acaaaatcac acagctaatc aacatcagag gcactttcat gtggagtaga caagccagag    7080
agaagatgtg ctgatggcac aatgaataca ttaagtgaaa tccaccttgt agatttcatc    7140
atttctgctg tgagtaacct tcaatactat aattttatgg gataatttat aaatgttgtc    7200
tatacaaata tataagttat acttatccac acaagtactt tcaaagtgaa gataaagtct    7260
ggatgttact agatcaaaac tgcatttttt tattatatga tgtagcaaga gaggaaacac    7320
aaaggaggta aagctgcccg ttcaggtggt tttcttcaca gattgactgt tctaccaatt    7380
gttgtggact ttgggcacca aattaatagg atatatgttg gcagtgttct atgttatata    7440
gattcagttt atttagtagg ctttattgaa ctgccatgtg ccagtaacta tgttagatgt    7500
ttagatggca gatgtgtctc tagacagagc ttacagttga gagtatgggt tgtgtgggga    7560
gaagtgaata gatgactata ttccatgata catgctgtat tacaatacag tcctacttca    7620
cttaacgatg gggatacatt ctcagaaatg agttaggagg caaattggtt gttgaatgaa    7680
```

```
catcacagag agcacttaca caaacctaga tggcatagcc acacctaggc tatatggtat    7740
aatctattgc tcctaggcta caaacctgtg cagcatgttg gtattgaata ctacaggcaa    7800
ttgttacata aagttaagtg tttgtgtacc taaaaataga aaaggtaatg cattacacta    7860
cagtcttatg gggctgggat gtcactaggt gataggaatt tttcagctct gttctaatct    7920
tacgggacca ccatcatgta tgcagcacat gactaactgt aattacaaga tggtggctat    7980
attaaacaga actacttaag ctagccatgg aggtatggtc cgtgagattt tcctgaagaa    8040
ttaacgtctg gatcaattct ggaagggcca gcaggagtac tccaggcaaa ggggtgagaa    8100
aggagcttcc aagtagagtg aaggtcatgt gcaaagactc agtgaggagt cgagtgaaca    8160
tagcacaggg aggacatgtt ggtgaggaag gaggggtgaa gccacagaga caggagggag    8220
ccagatgaca gaaggccttg caggcggtgc taaggagttt ggattttatc cttacagtgg    8280
tgggaagtca ttgtaaaaat attaagcaag ggagtggcat aaacaattta cattttcaaa    8340
agatcacttt ggcagcagat agagtatata tgtaaaagga gtaagaaaga ggtaagttag    8400
aaagcaagaa atgatcaggg tatgccctaa aacactggca atagggaaaa agagatgtca    8460
atcagaaaga ttgagaaagt ataattgaat tgacttggtg aacaaataga agtaaggcat    8520
aagggacagg tagaaatatg agatgacttc caagtttctg tttaaagata ccctttattg    8580
agagaggatg tatagaagct gtcttagggg gaagacaaga aatttggttt aggccatgtc    8640
aacaggtaat ggccagtagg cacatgattc agtttattta gtgggctcct tttaggagaa    8700
aatctgagcc agattccagg aagtcacagc agggactacc aatagggtca acagcagag    8760 agtgtggaaa ggactgaaaa gtgatcattg tacataacaa atagaagctc actgattttc    8820
tagcaaaaac atcttcagca gagtagcgtg gtataagcta tattgtaggg gactgaggaa    8880
gaaatgggct ctgagaagta aagacaaaca atatgttttg taaataaatt tcttttagtt    8940
cttaaaaaaa aagcctcttt tccagcttga ttgggaagtg aagagaggga tttgaaagtt    9000
ggagattgga ggataggatg agtacatcaa gatacactac gttgtagtgc agtgcattac    9060
aaatgtgagc taaaagtgaa ggcatttgta atcatatgat attgctaatt aaaagacagc    9120
tgtcagtcat atgcccagct cctggtaaag catgatgaga agagtacaat catggtagtg    9180
atttaaaaat tgctgccagt tttgtggatt ttcttatgc tagacagtgt aagctcttta    9240
tcaatattat ttaactcaca caactctaag aggtagatat tattatccct ttttgacaaa    9300
ttaggaaaca gaattataat gactgagaaa gtctctgctg agtaaatgtt actgaacctt    9360
aattttatgt ttacttaatg atagaaatga atattgggct tcaagactat ttgtacttaa    9420
tgaaatctgt cttgagcaac ataagctatt tttttcaaaa ttttaagaca aaaatcactt    9480
tcttctctcc tgtcttctta tttttgttcc cttcacatgt tgtagcctaa cactacttga    9540
tggcccattt tggtgcagtt tgtccactgg gcttcatcta aggccaccaa gtcccataat    9600
taacatgatc attcgtggga gaaagatcaa gcctcattgg tgatgggtgc ctcctcacag    9660
tcggataata ctgaaaagag agctaaatgt gggaaagaac caagttgaac acaggaaaga    9720
atcaggccac tgtgaaaata agcattgtgt tttcttgttc cttgaaagtc ttcattttta    9780
aaaaatttca gacacctgaa gttttctagc cttactctga gttgacgcac atttagtaca    9840
tgatcaacac ataaacaagc attagagaaa tagaaaagct gtaagaatac aaaaatatgg    9900
gccaggtggg tggctcatac ctgtaatcct agcactttgg gaggccgagg cagacggatc    9960
acctgaggtc aggagttcaa gactagcctg gccaatatag tgaaaccctg tctctactaa   10020
aaatacaaaa cttagcaggc tgtggtggca cgtgcctata atcccagcta cttgggaggc   10080
```

```
tgaggcagga gaatctcttg aacccgggag gcggagattg cagtgagcca agatcacacc   10140
actgcactct agcctagata acagagcaag actccatctc aaaaaaaaaa aaaatacaaa   10200
aatatgaacc actgaaaatt aaaaagacat gcatgcattc taggtcttta attttttttc   10260
ttaataattt tttttctctc tggatagcag cacctagttt aggaagcaag attttagctg   10320
gtctaacgac tggaggagtg gcagtattca ttgggcaacc cacagaggtc gtgaaagtca   10380
gacttcaagc acagagccat ctccacggaa tcaaacctcg ctacacgggg acttataatg   10440
cgtacagaat aatagcaaca accgaaggct tgacgggtct ttggaaaggt aactaacttc   10500
aaaatgggtt ttataaccac caaagcacat acatacaact agcaacttat tgtaaagtag   10560
agttaataaa cattttcttt ttttttttcc ccagggacta ctcccaatct gatgagaagt   10620
gtcatcatca attgtacaga gctagtaaca tatgatctaa tgaaggaggc ctttgtgaaa   10680
aacaacatat tagcaggtaa cttcccattt catataacaa acaggtctgc acctttagaa   10740
gttcatcttg gagcttctgc agccacctta tactcaatct cttaactcca atagttttct   10800
ctttttaaaa attaagtaat tttgaaccat atataacttt gtgagaagca ggaaaagacc   10860
aaaatattaa gtttaagaag ttttgccaca acaaaaaatat tttgcaacaa aaataacagg   10920
caatttcatg tcagcattat tctcatttaa tactaatata tgggactttt gttagaatct   10980
tattctttat acagcagaat tcaggaggta agtccatcct gcatactata tccaaaagat   11040
ctagttataa aaggagctta tcagtggtct catccaaaaa gtaataccat aagataggtt   11100
cttaaaaata atattctaac aacttctaga gacattgaaa tttcccttat ttcaataaaa   11160
aagtattaga tgctcatata ttaggcatta ttacaggcct taaaggcaca gaggaaacta   11220
acagtttact ttcctaaagt gttaacaatc tattaagcca tttactcttt accttctttt   11280
tctagtgcaa tacctttctt attttatttt atttatttat aagacatctt cattgaccta   11340
ctgttatcaa taggtttata aagatatgac agataactaa attgcaagcc cccaaaagtc   11400
tgatgttgac ctgtttcatc gatccatttt agatgacgtc ccctgccact tggtgtcggc   11460
tcttatcgct ggattttgcg caacagctat gtcctccccg gtggatgtag taaaaaccag   11520
atttattaat tctccaccag gacagtacaa aagtgtgccc aactgtgcaa tgaaagtgtt   11580
cactaacgaa ggaccaacgg cttcttcaa ggggtaagat atgatcttgt gtatctgtaa   11640
tgtgttctgg ctgtctgtgt gctttgggac actctcatgt caagcaaccg acatttagct   11700
tacaagcctt agtatattca tatacttagt attgactttt ccttgccaca gatttctcca   11760
atccaccaat tccactgtgc cagaaagtaa aaagccatga attcaaatt ttctcaactt   11820
tgatcaaagg ctcattcaag accagtgcct tttccactgg tcccaatcta ctggaaatgc   11880
agacagtatt ttgccttctc tgggcaagaa agttataaag tagagggaaa tcataataga   11940
gagctatgag agaacaagat ttgatttgat ttaatttgat ggactcaagt tttaacattg   12000
taaaactaga gataagacat caccaccaat ctagaaaagt gatgcagaaa agtatttgat   12060
ttgggtaatt атtcacactca cctagaaaca agtgttgtgt aatagattac atattccat   12120
aatgcaatgt tgtatcagaa actaccttcc taagaaaata tagtatgggc tcggcgtggt   12180
ggctcgcacc tgtaatccca gcactttggg agatggaggc aggaggatca cttgagccca   12240
gactgggcaa caaagcgaga ccctgtctca acaaaaaatt taaaaattag ctgagtgtgg   12300
tggcacgcac tgatggtccc ctctacttgg gaagctgagg caagaggatc tcctgagccc   12360
aggagttcaa ggtttcagcg agctatgatt gtgccactgc actccagcct gggagacaga   12420
```

```
gcaagtccct gtctcaaaaa agaagaagga gaaggaggag aaaatacagt attaagtaat    12480
ctgtcaatat attccacaag gattacacta gtggtttaat aataaaatta tattaccttt    12540
ttaaattgta aggccattcc tcaagcttta taaattaagc atgaatgcat catacacatt    12600
ttataaaaag ttccaactca tcataatctg tacttatgat acattaatac aaatgaagtt    12660
cattataaaa ttaacttaaa atggatatac cagttattaa accattaacc atttaataat    12720 tttattttt tcaaatttaa aaaccttttg gggaagaaat actacaacat ggatgaacct    12780
tgaaaacgtt atgctaagtg aaataagcca gacacaaaag gacaaatact gtatgattac    12840
acttaaatga ggtacctaga gtagtcaaat tcatagagac agaagaata gaagttacca    12900 ggggctggag gtaggaaaaa atggagagct gtttaatggg tagagagttt cttttttggg    12960
tgacaaaaag gttctagaga tggatagtgg tgatggttac acacaatgtg tgtgtactta    13020
atgctactga aatgtaattt tatgattttt ttttttgca gcaaaatacc ccacattggg    13080
aagtgaagag aaacatgtta agagacttga aggaaaaaaa ttggggcaga ggggtgtttt    13140
ttataggtta aacaataaaa gccatttaaa cagtaacaat ttctctaagg acaagaatcg    13200
tcaagattga gacagcactg atttcttgac tctactcaat acttctttgg tttctcttct    13260
tccttccccc ttctaatagt ttcctacctc ccattcagaa agcaaagcaa aacaagcaaa    13320 aattcccct tccctcaaaa aaggaaagag ttttttgaaaa agttcatgtc agtgaagaaa    13380
agacatgttt tgggagtgaa ggatatttgt ggatttgtat agatgtgatc atcagggctg    13440
tgttgttttg aagtaatata ggacatctag aggaaaattt attttcagca gaggagggaa    13500
agatgaagag taggtacttt taagcatctt cacttgagga gtggcaaaat gagaagcata    13560
acctgctata atcactttaa gaatttcagg ctgagtgtgg tggtgcagtc tctagtccca    13620
gttactccag gaggctcagg tgggaggatc acttaagccc aggagctcga ggttgcagtg    13680
agctatgatt acactactgc attccagcct gggcggcagg gtgaagcctc atctcaaaaa    13740
ttaaaaaaaa aaaaatcaa acaaattaat cgaacgatga catgcacttt tctaggttgg    13800
taccttcctt cttgcgactt ggatcctgga acgtcattat gtttgtgtgc tttgaacaac    13860
tgaaacgaga actgtcaaag tcaaggcaga ctatggactg tgccacataa tcagcttcaa    13920
gaaaatgatg taacatacca gtgggaatct tgctgactgg atcataaaaa caaacaaaac    13980
ttattcactt attttaacct aaaaagataa aggaattttg gcagagaatt ttggactttt    14040
ttatataaaa aagaggaaaa ttaatgccta tttcatataa cttttttttt ttctcagtgt    14100
cttaagaagg ggaaagcaaa acattcagca tatacccctgg caaatgtaat gcagataagc    14160
tactgcattt gaccatttct ggagtgcaat tgtgtgaatg aatgtgaaga actttaacat    14220
gttttaatta caattccaac tggtggaaaa gaaactgagt gaaatgcagt ttatatttat    14280
aaatacttaa aaatgaagtt attaaaaata ttagttttta ttaaccacag ttgtcagtta    14340
atatattcaa taagtattg ctaataccttt ttaaagtttg tcttttgaga tctataccctg    14400 ggtgtaagag tcaagttcac tagaatacaa gactgcccaa tagcaaatgc aggtctttag    14460
aatcataggc atgaacctac tctgaatgtt attagtatag attttttaatg tttagagtcc    14520 agatttgatg acatctctaa caacttctaa tctaagacac tatattcatt ttggcaggat    14580
tgctactaga gtcttggtat ctgtgctagc atcacataat tttagagctg gagggtactt    14640
ctgggaagac agaggaacag tttgagattc ctactgagat gaaaacgaat cttcatggaa    14700
tctttcagca aagccaaatt caaattcatc attagcacct gtagtaacct tttcaatgcc    14760
tacaaactgc atgcagaaga gatagggaaa cagtaaaaca gatattaaaa gaagttttta    14820
```

```
agacaaagcc cagcctgatt ttaagctaaa tccaaggatt ggcagcttgg atgagcagga    14880
aggttacagg ctgccagaca tcattctagt tctgttttaa tcaactccat gttacattta    14940
ctatcaggga ttctcacctc accctcatgc atgtcttccc cattcattac ccgcaaaagt    15000
gtcttgtagc agatgtcttc tgtgtcccat acataccatt ttgctctttta gtgcttgctg    15060 gcctgacttc ctattgtcat gtcagcatct gccctttta gggtctctgg ccaccagagc      15120
cagctttact cacctgtgca tggcattcta gaagagcagc agggaaaata acacagcccc    15180
agtgcagccc ttaaccacca ataactggta gtagttggtg tacaaatatc tcagttccct    15240
caactgtcag gtggaatacc gctgagggat caaactctag taacacacag tagtgttttg    15300
cttactatgg ttaactaaaa aatcacaggg tcttcatgca tttggaaagg atactttatt    15360
tcttacaaag ggttacagcc tacaaggtgg tcattctgca ggctagaaag cgtaacctcc    15420
agcaaagacc ggaggcaggc acttctaggg aaggaagagt aagacagaaa tttaaattga    15480
atgggttggc caagtataca tattcaacag gctacaggtg gattcatgaa tattcatgaa    15540
ggcagtcctg atgcatgcat gttacacctt ggggtggagg cttaacattt aaatgtatta    15600
cagttaggcc ctatacatga aaaggtgaag cagtaacacg aaggcacaca atgcaccatt    15660
tctgtaaaca ggccagagcc agttcacagt ggttggtctc ttatcatgag aaagctacta    15720
aaatcctctt gtccagttaa aactgtagtt atggctggtg gaaaatgggc tggagtcagt    15780
caacacttgg tgaagctgca gttgcttcag acactcaagg ccagtgtttg tttagctgct    15840
cgagaaaaag aaaaatcttg tggcagttag aacatagttt attctttaag tgtaggagtg    15900
tgtgacttaa                                                          15910

<210> SEQ ID NO 366
<211> LENGTH: 50
<212> TYPE: DNA
<213> ORGANISM: Homo sapiens

<400> SEQUENCE: 366
aatcgacagc gaggccggtc gcgaggcccc agtcccgccc tgcaggagcc                50

<210> SEQ ID NO 367
<211> LENGTH: 587
<212> TYPE: DNA
<213> ORGANISM: Homo sapiens

<400> SEQUENCE: 367
agccgcgcgc tcgctcgcag gagggtgggt agtttgccca gcgtaggggg gctgggccca     60
taaaagagga agtgcactta agacacggcc ccgctggacg ctgttagaaa ccgtcctggc    120
tgggaaggca agaggtgtgt gactggacaa gacttgtttc tggcggtcag tcttgccatc    180
ctcacagagg ttggcggccc gagagagtgt gaggcagagg cggggagtgg caagggagtg    240
accatctcgg ggaacgaagg agtaaacgcg gtgatgggac gcacggaaac gggagtggag    300
aaagtcatgg agagaaccct aggcggggcg gtccccgcgg aaaggcggct gctccagggt    360
ctccgcaccc aagtaggagc tggcaggccc ggccccgccc cgcaggcccc acccgggcc     420 ccgcccccga ggcttaagcc gcgccgccgc ctgcgcggag ccccactgcg aagcccagct    480
gcgcgcgcct tgggattgac tgtccacgct cgcccggctc gtccgacgcg ccctccgcca    540
gccgacagac acagccgcac gcactgccgt gttctccctg cggctcg                  587

<210> SEQ ID NO 368
```

```
<211> LENGTH: 50
<212> TYPE: DNA
<213> ORGANISM: Homo sapiens

<400> SEQUENCE: 368
gtgagcctgg ccccagccct gcgccactct ctgcctttgc tcacccacag           50

<210> SEQ ID NO 369
<211> LENGTH: 157
<212> TYPE: DNA
<213> ORGANISM: Homo sapiens

<400> SEQUENCE: 369
gacacatagt atgaccatta ggtgtttcgt ctcccaccca ttttctatgg aaaaccaagg   60
ggatcgggcc atgatagcca ctggcagctt tgaagaacgg dacaccttta gagaagcttg  120
atcttggagg cctcaccgtg agaccttaca aagccgg                           157

<210> SEQ ID NO 370
<211> LENGTH: 50
<212> TYPE: DNA
<213> ORGANISM: Homo sapiens

<400> SEQUENCE: 370
gtaagagtcc agtccaagga agaggtgggg cttttctcct cttggcttag            50

<210> SEQ ID NO 371
<211> LENGTH: 225
<212> TYPE: DNA
<213> ORGANISM: Homo sapiens

<400> SEQUENCE: 371
attccggcag agttcctcta tctcgtcttg ttgctgatta aggtgcccc tgtctccagt    60 ttttctccat ctcctgggac gtagcaggaa atcagcatca tggttgggtt caaggccaca  120
gatgtgcccc ctactgccac tgtgaagttt cttggggctg gcacagctgc ctgcatcgca  180
gatctcatca cctttcctct ggatactgct aaagtccggt tacag                  225

<210> SEQ ID NO 372
<211> LENGTH: 50
<212> TYPE: DNA
<213> ORGANISM: Homo sapiens

<400> SEQUENCE: 372 gtgagggat gaagcctggg agtcttagct accctgtctt ggccttgcag              50

<210> SEQ ID NO 373
<211> LENGTH: 211
<212> TYPE: DNA
<213> ORGANISM: Homo sapiens

<400> SEQUENCE: 373
atccaaggag aaagtcaggg gccagtgcgc gctacagcca gcgcccagta ccgcggtgtg   60
atgggcacca ttctgaccat ggtgcgtact gagggccccc gaagcctcta caatgggctg  120
gttgccggcc tgcagcgcca aatgagcttt gcctctgtcc gcatcggcct gtatgattct  180
gtcaaacagt tctacaccaa gggctctgag c                                 211

<210> SEQ ID NO 374
<211> LENGTH: 50
<212> TYPE: DNA
<213> ORGANISM: Homo sapiens
```

<400> SEQUENCE: 374
gtgagtatgg agcaagggtg taggccactg accccatggc tcgcccacag        50

<210> SEQ ID NO 375
<211> LENGTH: 195
<212> TYPE: DNA
<213> ORGANISM: Homo sapiens

<400> SEQUENCE: 375
atgccagcat tgggagccgc ctcctagcag gcagcaccac aggtgccctg gctgtggctg        60
tggcccagcc cacggatgtg gtaaaggtcc gattccaagc tcaggcccgg gctggaggtg       120
gtcggagata ccaaagcacc gtcaatgcct acaagaccat gcccgagag gaagggttcc        180 ggggcctctg gaaag                                                        195

<210> SEQ ID NO 376
<211> LENGTH: 50
<212> TYPE: DNA
<213> ORGANISM: Homo sapiens

<400> SEQUENCE: 376
gtgtgtacca gttgttttcc cttccaccca ggatcttcct cctcctacag        50

<210> SEQ ID NO 377
<211> LENGTH: 102
<212> TYPE: DNA
<213> ORGANISM: Homo sapiens

<400> SEQUENCE: 377
ggacctctcc caatgttgct cgtaatgcca ttgtcaactg tgctgagctg gtgacctatg        60
acctcatcaa ggatgccctc ctgaaagcca acctcatgac ag                          102

<210> SEQ ID NO 378
<211> LENGTH: 50
<212> TYPE: DNA
<213> ORGANISM: Homo sapiens

<400> SEQUENCE: 378
gtgagtcatg aggtagacgg tgctgtgcct tgcctgctcc tccttggcag        50

<210> SEQ ID NO 379
<211> LENGTH: 181
<212> TYPE: DNA
<213> ORGANISM: Homo sapiens

<400> SEQUENCE: 379
atgacctccc ttgccacttc acttctgcct ttggggcagg cttctgcacc actgtcatcg        60
cctcccctgt agacgtggtc aagacgagat acatgaactc tgccctgggc cagtacagta       120
gcgctggcca ctgtgccctt accatgctcc agaaggaggg gccccgagcc ttctacaaag       180
g                                                                       181

<210> SEQ ID NO 380
<211> LENGTH: 50
<212> TYPE: DNA
<213> ORGANISM: Homo sapiens

<400> SEQUENCE: 380
gtgagcctct ggtcctcccc acccaatgac ctgtgatttt tctcctctag        50

<210> SEQ ID NO 381
<211> LENGTH: 455
<212> TYPE: DNA
<213> ORGANISM: Homo sapiens

<400> SEQUENCE: 381

```
gttcatgccc tcctttctcc gcttgggttc ctggaacgtg gtgatgttcg tcacctatga      60
gcagctgaaa cgagccctca tggctgcctg cacttcccga gaggctccct tctgagcctc     120
tcctgctgct gacctgatca cctctggctt tgtctctagc cgggccatgc tttccttttc     180
ttccttcttt ctcttccctc cttcccttct ctccttccct cttccccac ctcttccttc      240
cgctccttta cctaccacct tccctctttc tacattctca tctactcatt gtctcagtgc     300
tggtggagtt gacatttgac agtgtgggag gcctcgtacc agccaggatc ccaagcgtcc     360
cgtcccttgg aaagttcagc cagaatcttc gtcctgcccc cgacagccca gcctagccca     420
cttgtcatcc ataaagcaag ctcaaccttg gcgtc                                455
```

<210> SEQ ID NO 382
<211> LENGTH: 50
<212> TYPE: DNA
<213> ORGANISM: Homo sapiens

<400> SEQUENCE: 382

```
tcctccctct cttgtagctc ttaccagagg tcttggtcca atggcctttt                 50
```

<210> SEQ ID NO 383
<211> LENGTH: 15174
<212> TYPE: DNA
<213> ORGANISM: Homo sapiens

<400> SEQUENCE: 383

```
tccagcctgg gcaacaagag tgaaactcgg tctcaaaaaa aaaaaaaga gaagaagaag       60
aaagaaaact aggtggagtg tggtggcttg cacctataat cccagcactt tgggaggccg     120
aggtgggtgg atctattgag gctaggagtt caagatcaac ctgccaacat gacgaaaccc     180
cacctctact aaaaatacaa aaaattagca cggcgtggtg tgtgtgcctg taatcctagc     240
tacttggaag gctgaggcag gaatcgcttg aacctggggg gcagaggttg cagtgagcca     300
agatcttgcc actgcactcc aggctgggcg acacagcaca actctatctc aaaaaaaaaa     360
agaaaaaaca aaagaaaact aatatatcaa ataaatttct agttagttgg attcactcac     420
ttattcattc aatgacttat tgaattatca tatattacta gtgctttttta atacatacct    480
tctacaattt ttcaactgaa aattacttca ttgatcaggg ctctttaaac tgatctccat     540
ttgcattgtt ttactaacta tagttattat tcatgtatta gcactctgag cctactgtaa     600
tgatgtgtac cttaataaag aactgaatat ttgtaatggc tggcagtgaa tttagtagtt     660
cttgaattta gagctcaaaa tatgggagta atttgctgct ttatttcctt tgagaggtaa     720
tagaggaaaa acagaatcta ataacaatca cagattttcg ggaaagcact gtaaaaccat     780
atgatcaatt ctagcttctt atgtaaacat ggaaagattg ccagctgaac acctgtcatg     840
ctctaagaag ttggggagaa tttgcatttt tagaactgtg agcaaaatga gaacgactgc     900
tatgttcatg ctttgtgaat ttagctttat ttcattcaca caattcatgg gaaaaaatgc     960
atcttttaac tcggtgtttt tcaattcaac ttttaaaata caggagtggg ccagacccgg    1020
tggctcacac ctgtaatctc atcacttggg gaggccgagg caggtggacc acaaggtcaa    1080
gagatagaca ccatcctggc caacatggtg aaaccccatc tccactaaaa atacaaaaat    1140
```

```
tagctgggca tgttggcacg tacctgtaat cccagctact cgggagactg aggcaggaga    1200
atcgcttgaa cctgggagat ggaggttaca gtaagccgag atcgcgccac tgcactccag    1260
cctggcgaca gagcaagact ccatctcaaa aaaaaaaaaa aaaaaaaaaa aaaaaaaaaa    1320
aaaaaaccag gatgtgttac caaggaaaat tcatttacaa tggttaatta tgtgacaaac    1380
atgtcaagta attccatctg gctttgtgtc accatttccc cacccttttt tcagaaacca    1440
aaaccaagaa gaagaacaaa catcaaaatg gacatggaaa ttaacaaata tatgattcaa    1500
tttaatctcc taagaggttt tttaaaatta ttttattttg agacggagtc ttgctctgtc    1560
gccaggctgg agtgcagtgg caggatctca gctcactgca acctccatct cccaggttca    1620
agcgattctc ctgcttcagc ctcccaagta gctggaacta caggcaagca ccaccacacc    1680
cagctaatgt ttgtattttt ggtagagatg gggtttcacc atgttggcca ggatggtctc    1740
gatctcttga cctcatgatc cacccgcctt ggcctcccaa agtgctggga ttacaggtat    1800
tttttatttt ttttgagaca gggtcaccct gtcacccagg ctggagtgta gtggcacaat    1860
catggctcac tgcagcctca acctcccagg ctcaggtgat cctccatgtc agcctcccaa    1920
gtagctggaa ctataggcgt gcaacaccat gcccagctaa ttttttgtatt ttttgtagag    1980
acagggattt gccatgttgg ccaggctggt cttcaactcc tggcctcaag tgatccaccc    2040
gtctcaacct cccaaactgc taggattaca ggtgtgagcc accgtgcccc atctcatctg    2100
ctaagtgggt ttaaagaaat tcagtttcat gtcaattttt aaaatgtatg gttatcaaat    2160
tcgacttctt tttaaaaatg caatcagata actgtatgct tgtttgatga ggggaggaaa    2220
gttaatatag ccaatctact caatattttt agcagaaatt atcagagact aaggaaatgt    2280
ttaagttttt ctcatgttgg ttttaattac ctaatgtttt cagttttctc tttcattctt    2340
gtgtcttttt ttcatttttca gtgtttcaaa tacagtttgt atttaaagat ttagaagttc    2400
caaaactgta agcacagtgg attgtttcct gggatgatgt taaaattata caacaaaata    2460
tatgaaactt tgtcaatttg gttattggca catacaaaat atttacaaat aaacgtgtgt    2520
gtgtgtgcgt gtacacacaa ttcaatgaaa tagatgtgaa acaagttttc tttttttttt    2580
ttttgagaca gagtcttgct ctgtcgccca ggctggagtg caatgtcgca gtctcagctc    2640
actgcaacct ctgcctcccg ggttcaagcg attctcctgc ctcagcctcc cgagtagctg    2700
ggactacagg cacctaccac cactcccagc taattttttgt gttttttagta gagacagggt    2760
ttcaccatgt tagccaggct agtctccaac tcctgacctc aggtgatctg cccgcctcag    2820
cctcccaaag tgctgggatt gcaggcgtga gccacctcac ctggctacaa gttttcaaaa    2880
tacatttatc tgtacccata cattctccag tttgtccaca ggacatctta tgacttgagc    2940
aagctgctaa aaatccaagg gtgcagcgtt tgtatgtcta taggattgct cagatctgcc    3000
cccacccctga aagaatttaa gagaatttct tgaggccagg cacagtggct cacacctgta    3060
attccagtac tgtgagagtc cgaggtcaga ggactgcttg aggccaggag ttcaagagca    3120
gcctggacaa catagggaga cctgtcacta caaagaataa ataaattagc caggcttagt    3180
ggctcatccc tgtggtccca gctactaggg aggcagaagt aggactgctt gtcccaggag    3240
gtcaagactc cagtgagctg agacccagcc acctgcattc cagcctgggc aacaaaaga    3300
gaccctgtct caaaaaataa gttaaataaa taaataataa aaatagttta aaccctaaac    3360
acatcttctt tttcaaagag gacttcttaa ggacttcatg ctgcgtcctg ttgatctcca    3420
cttcccttttt tcagcgtcca cacttttaac agtctctttt gccaaggata ataagtatat    3480
```

```
agtttctgga atccagattc ttccctgttt ggacagccag ggggacaatt tttggtctgc    3540
aggcctttgc atctgttctg ctgttgctca gcaatctcac agcaaatttg ccgagcctct    3600
ccggaatgca cagccagaca gagctcagcg caaaagctag agaacctggc ggagggagac    3660
tcacagtgcc acaaaaaaac tttatctttt cttttttttt ttcttttctt tctttctctt    3720
tctttcttgt ctttctgtct ttcctctctc tctctctgtc tttctttcct ctctttcttt    3780
ctttttttcct acatggcaag atctcctcat ggcagaaata atctgccttg acttctgttt    3840
ccacgctgct tctgccagga ccatgcgctc ggcgtgtttt tctttccgct ataattatcc    3900
aggcccatcc cagctctggt cccctcagct gttccctggc agtcccttct gctggtgaaa    3960
acacatatgg cgccggcctg accagggtgt aagtgtgtga atatcaggaa gatgactgaa    4020
cgtctttggg actccgtttc ctcattgtaa aatggaggtt aataccagcc ttcttctact    4080
ccccaaacgc acgtgtttgt cccggccaga gggcccaatt gttggctgtt cacgcgtcag    4140
ttaccccac aggacgggtc agccaattaa aggcgaacca ggcccggtcc atctcctgac    4200
gccttttctc atcccagggc tggacaggca gctggcctgg gcccggctct gccttgtcac    4260
gtgcggggc cggccgtttt gcttgtctgt gtgtaggagc gtgaggtcac gctgggtgct    4320
cccgccccgc cggggccttt agtgtcctgg tccctaaacg ccaggccgct ccaccggggg    4380
agaaggcgcg aaccccagcc gagcccaacg gctgttgtcg gttgccgggc cacctgttgc    4440
tgcagttctg attggttcct tcccccgaca acgcggcggc tgtaaccaat cgacagcgag    4500
gccggtcgcg aggccccagt cccgccctgc aggagccagc cgcgcgctcg ctcgcaggag    4560
ggtgggtagt ttgcccagcg tagggggggct gggcccataa aagaggaagt gcacttaaga    4620
cacggccccg ctggacgctg ttagaaaccg tcctggctgg gaaggcaaga ggtgtgtgac    4680
tggacaagac ttgtttctgg cggtcagtct tgccatcctc acagaggttg gcggcccgag    4740
agagtgtgag gcagaggcgg ggagtggcaa gggagtgacc atctcgggga acgaaggagt    4800
aaacgcggtg atgggacgca cggaaacggg agtggagaaa gtcatggaga gaaccctagg    4860
cggggcggtc cccgcggaaa ggcggctgct ccagggtctc cgcacccaag taggagctgg    4920
caggcccggc cccgccccgc aggccccacc ccgggccccg ccccgaggc ttaagccgcg    4980
ccgccgcctg cgcggagccc cactgcgaag cccagctgcg cgcgccttgg gattgactgt    5040
ccacgctcgc ccggctcgtc cgacgcgccc tccgccagcc gacagacaca gccgcacgca    5100
ctgccgtgtt ctccctgcgg ctcggtgagc ctggcccag ccctgcgccc tttgcgcccc    5160
ccacgcttgt tctgcgtgcg ctgcccgctc ttccatttac cttctctccc acccaagttt    5220
gtactctttt ctttctctcg gttttatttt ttgttttgt ttgttgttt gagacaggct    5280
ttcgctctgt ctcccaggct ggagtgcagt ggcgcgatct cggctcactg cagcctccac    5340
ctcccaggtt caagcgatcc gcctgccgag tagctgggat tacaggcgcc cgccaccacg    5400
cctggctaat ttttgtgttt tgtagagatg gggtttcgcc atgttggcca ggctggcctc    5460
gaactgctga gctcaagcaa tccgcccgcc tcggcctcac aaagtcctag aattttaggc    5520
atgagcctcc gggtccggcc tgtgctaatc cttctctgtcc ttggttctttt atttctcttc    5580
tctcttttc ttagtcccctt tgttctttc cctctcccgt tcagttggct gtcgtttgag    5640
cctccacctt ttcactccct cctttccacc acgatgccga gccctgcctt ggatggggac    5700
catcagcgat gaccacaatg acctctccct taccaggcag ctccaggcag tgttcctgca    5760
ccgccttttcc cagggcttgg gggctttttc tagtgggctt tgagctgctc aatctggcct    5820
ctgcagggcc ggctcccagc ccttccaacc tcctcacagc ccgacctggg acctagccaa    5880
```

```
ttcccggaga gtctctgtcc catcgtgacc ccctcacaac tctcccactc accaaagtct   5940
gatgactgtg ctaggggtg cttatataga gtactgagtg ttacaaaagc agaagtctgg    6000
atgagaacca atttgtgata ttaagcaggt ggggtggggg tggggagtgt acctaggttc   6060
attttccgcc ctgcttttcc cctttccagt gtgtgcactt aaccagtccc tgggccctgt   6120
tccccatccc cctccaaggc atggattggg tgggcttgtg tgtcttgggg caggtggccc   6180
tttctaaact ctctgccttt gctcacccac aggacacata gtatgaccat taggtgtttc   6240
gtctcccacc cattttctat ggaaaaccaa gggatcggg ccatgatagc cactggcagc    6300
tttgaagaac gggacacctt tagagaagct tgatcttgga ggcctcaccg tgagacctta   6360
caaagccggg taagagtcca gtccaaggaa gaggtctctt gctgcctcct aaccctgtgg   6420
tctaggggca ggagtcagca gggcattaac aaaaataatt accatcccca ccccgacag    6480
tgaagtggct ctttccagtt cacagagcac tctcacacct ccccgctctc attctggccc   6540
ttcagctgac tcggacaagc caaggatctt ggtccccatt ttataaagga gaaaactgag   6600
gcccacgtgt aacagtgatt ggccccaagt catcccggga gccagcagaa gagctaggac   6660
aggaacctat tgttctaact tcatattgat gctagctttt gactatccct gaaaccgaga   6720
ttggtaatca gcccggctct gaaactggtt atttgctggg gactgtaaaa taggattaac   6780
tatttctagt cctgcatttt aattgctgtt agtagggcca tcttacccac cctctgaagg   6840
acctgacttg gcaagcccaa ggcaacattc agaatatggc agctgaacct ctgtgcactt   6900
gtctttgggc agcagctggg tcttattctt ctctggcctt cacaacatcc tgcaacccag   6960
ctcaaggtca ggaatgtgac agactcatgt catcatatct ctgatgccca gagaagggat   7020
accatttgcc tgagccttct cagtactgtt taatcagcct gtgagaactt tccttgtgaa   7080
aggccctgtc tgtgcctggg gctgataaaa cagcaagaac gaactgagga gctgggcagc   7140
agtgcaaagc aaatactacc agctttggtg cctgtaagtg tggctcttac tcatctcaca   7200
tggaaataag ggcagccacc ttgcagggct gctctgagga ttgagctaat acagtgccct   7260
gggcgttggg gtggggaaag ttgtggagca cctcctgggg gaaggggtg tcagagcagg    7320
gaatctgggg agtccgaggg caccttcatc aacccaatct gtcatttgag caccagtctt   7380
cactgagcct cgtgggcaag ctggaggaa acaggaataa ggtcaggccc tgttctatag    7440
gtcccagtgt agttgctatg gtgagtatct tcatttccct gcttgcccca gccacctgga   7500
gtgagaagcc caagaggaag ctgggtgagc tgtttgtttc catgggtctc tgtgttcaca   7560
gctgactccc ttcaccagcc agccctttca cctgagcccc agcaacaaag gcagtcaggc   7620
ggggctcaaa gcagctgctc caatgaagtc aaagaaataa gctcagggga agaagcaggt   7680
caccctcccc cactagggtg ctgggctcac ttcctcctgg ggcagtggag gagggtgtgg   7740
ttccaactca gaacaaaatg gggcttttgg tttactttat cactcttcac agctctgacc   7800
tggacccctc atccctgcct gtcttgtggt gtaagtgcgg atccccctaa gttggaggaa   7860
aggaaactgg cccaaacaaa aaggagagca gttttctctg catcacatgg taggccagga   7920
ggagtctaat gccccagagt ttactctcag cccccaaaat cacctagcta aatgttacct   7980
tatctaagaa gtccttaggt ttttggggt ttgtttttttt tttttttgag acaaggtctc    8040
actctctcac ccagactgga gcacagtggc acaatcacag ctcactgcag cctcaacctc   8100
ctgggctcaa gcaatcgtcc caagtagctg ggactatagg cctgcaccac catgtccagc   8160
taatttattt ttatttatat tttttagaca gggtctcatt atgttgccct ggctggtctt   8220
```

```
gaactcctgg gttcaagcag tcctcccacc tctgcctccc aaagtgctag gttttttttt    8280
gtttgtttgt ctgttttttg aaacagagtc ttgctctgtc gcctaggctg gagtgcagtg    8340
gcacgatctc agctactgca acctccacct cctgggttca agtgattctc ctgcctcagc    8400
ctcctaagta gttgggaata caggcgtgtg ccaacacacc cagctcattt ttgtattttt    8460
agcggagatg gggttttgcc atgttggcca agctggtctc aaactcctga cctcaggtga    8520
ttcgcccgcc tcagcctccc aaagtgctgg gtttacaggc gtgagccacc acacccagcc    8580
caagaagtct tttctgatca cccactcttc cttctctccc aatggcatta gttgttccct    8640
cctttgcatt ttgagagtat gtcctgtaag ccccaaatgc agcttgaatc atctgcccat    8700
ccaccccctg tgcccaacag taagcctcct ctagagtaga tactatctcc tgcatctcag    8760
tgaaccactg cccagcaaag cagtcttgct aaaacaatga ctctagagat cctaagctgt    8820
gtgagagctg gaggagagaa ttagactgat ggtctgggaa gggattgaat tagtcatctt    8880
gtacctttc ttcttgactt aagttccaga cctgtagcaa ccattcctgc ttagacatcc    8940
agaacataag cctatgggtc tgtgcctgtt gggtcttagt ctgggtgaaa cttttctcta    9000
cttctgtcag ctctccagat gaaccacaga agcaggaatg tgggcatcat cagtgaaatc    9060
tctgcataca gcagacaaag ggctggtcca gtggctgttt atgaggcagc gctaggagag    9120
ctctgatcca gactctccct gcagtgaaag ggagggagcc cttcatgaag tattgactgc    9180
ttgagcagga attgcttcac cagcacctaa ctgagtgcct ctcgagctca catcggtttt    9240
ccctcatgag gccacttgga gtcttgctga gggacttggt tctattaggg aaggtgagtt    9300
tggggatggt gagcagggag ggcctgggga cattgtggct aatggggctt ttctcctctt    9360
ggcttagatt ccggcagagt tcctctatct cgtcttgttg ctgattaaag gtgcccctgt    9420
ctccagttttt tctccatctc ctgggacgta gcaggaaatc agcatcatgg ttgggttcaa    9480
ggccacagat gtgcccccta ctgccactgt gaagtttctt ggggctggca cagctgcctg    9540
catcgcagat ctcatcacct ttcctctgga tactgctaaa gtccggttac aggtgagggg    9600
atgaagcctg ggagtcttga tggtgtctac tctgttccct ccccaaagac acagacccct    9660
caagggccag tgtttggagc atcgagatga ctggaggtgg gaagggcaac atgcttatcc    9720
ctgtagctac cctgtcttgg ccttgcagat ccaaggagaa agtcaggggc cagtgcgcgc    9780
tacagccagc gcccagtacc gcggtgtgat gggcaccatt ctgaccatgg tgcgtactga    9840
gggcccccga agcctctaca atgggctggt tgccggcctg cagcgccaaa tgagctttgc    9900
ctctgtccgc atcggcctgt atgattctgt caaacagttc tacaccaagg gctctgagcg    9960
tgagtatgga gcaagggtgt aggccccttg gccctttttt ctcagtgatg attgatctta   10020
gttcattcag ccatatagtt ttttaggccc cacgatccct aggaagatca ggggaacaga   10080
gaactggaag gggccctggt cctccacata gttcctaagc acctgggcta taccaggctc   10140
tgagcagggc gtcatcccat cacagtcttc aacaccacct tgggagtagg tagtatcatc   10200
ccagtgttat agaagaagag actgaggtgg gaaggcagtg ggtagagtgg ggacttggcc   10260
aggggcacac agtagagagc cagaaaacac acagtagaga gccaggacac tcgtctctaa   10320
ggccagcgtt cttcccttc acctccttag tatgccatgc caaccctcca ttttacacat   10380
gacgaaacag agccccagac aaaaggttgt ctttcccaga tcacatggca ggaagaagta   10440
aagctgacct gagatcccaa gtcttaggaa tcccagtcct cagaaagcca cttctctctg   10500
agccttggtt ttcacatttg tcagatggaa atgattgtga tttctcaggg ctgttgagca   10560
ggtaaatgaa aatgttttat gaaagaaagc accaagtttc attttggtct tagcccttgc   10620
```

```
tatgtcccta gcaagaagta gatattcata gggatatttt gtttgatgtg aggagttctt    10680
acagcaagag cttgtagaag gccaaaagct tctggattct attcccaaaa gcaggagatg    10740
acagtgacag ggtggttttg gtgaggagag atgaggtaga aaatgagtgc aagcccgctg    10800
gccactgacc ccatggctcg cccacagatg ccagcattgg gagccgcctc ctagcaggca    10860
gcaccacagg tgccctggct gtggctgtgg cccagcccac ggatgtggta aaggtccgat    10920
tccaagctca ggcccgggct ggaggtggtc ggagatacca aagcaccgtc aatgcctaca    10980
agaccattgc ccgagaggaa gggttccggg gcctctggaa aggtgtgtac cagttgtttt    11040
cccttcccct tttcctcctc cccgatactc tggtctcacc caggatcttc ctcctcctac    11100
agggacctct cccaatgttg ctcgtaatgc cattgtcaac tgtgctgagc tggtgaccta    11160
tgacctcatc aaggatgccc tcctgaaagc aacctcatg acaggtgagt catgaggtag    11220
acggtgctgg gtctcaccct tcccccatgc caggagcagg tgcggggggtc tagctgacac    11280
cagaagacca catcttttca tcctatttgc cctttgcagg gagagtaaga tatctcttac    11340
ttgccatatt gaagccaatt gggatgaagc tcccactttg cacattgagg aactgaggct    11400
agattggcaa aatgactctt tcaggtcctc agaagatgtc tcagctggag tccctgtctg    11460
ttttttgtttt tttgtttgtt tgtttttttgt tttttttgag atagagtctc actctgttac    11520
ccgtgtaatc tcagctcact gcaaccttct cctcctgggt tcaagcgatt cttgtgcctc    11580
agcctcccga gtagctggga tgacaggtgt gcaccagcac actggctaat ttttgtattt    11640
ttagtagaga tggagtttca ccatgttagc caggctggtc tcgaactcct ggcctcaagt    11700
gatctgccca ccttggcctc ccaatgtgct gggattacag gtgtgagcct ctgcgcccca    11760
tcctcttgtt tgttttttga dacagggtct tgctcggttg cccaggctgg agtgcagtgg    11820
ggtgattaat ggctcattgc agcctcgacc tccctgactc aagcaatcct cccacctcag    11880
cctcctgagt agctggggct gactacaggc atgcacactg tgcctggcta atttttgtat    11940
tttgtagaga cagggttttt gccatgttac ccagtctggt cttgaactcc tgggctcaag    12000
tgatccaccc acctcggcct ccaaaagaag tcctggatta caggcatgag acattgtgcc    12060
cagcctctct gtctctttaa aatcatgaaa actcgtagct acttaagtaa ttctcctgcc    12120
ttctggaatg atgggtgaag atcttgactg ccttgcctgc tcctccttgg cagatgacct    12180
cccttgccac ttcacttctg cctttgggc aggcttctgc accactgtca tcgcctcccc    12240
tgtagacgtg gtcaagacga gatacatgaa ctctgccctg ggccagtaca gtagcgctgg    12300
ccactgtgcc cttaccatgc tccagaagga ggggccccga gccttctaca aagggtgagc    12360
ctctggtcct ccccacccag ttcaggcctc ttggctatgc atgtctattg tgggtgggag    12420
agaaccacct ggaagtgagt agcagccaag tgtgactatt tctgatcctg gtcctggcat    12480
ttcaccagca ttcacctatc cccttaattc cttcctccca gaattgctac catcactgtt    12540
tattaggtgt aaatggaga ctcaaaggga attcatgctt atagccaagc agctgtgagc    12600
tcagttcatt gagtcctccc agcctccttt gggacagagc aactggggttg gattgaatac    12660
caggcccagt gagggaagtg ggaggtggag gtgccccccat gacctgtgat ttttctcctc    12720
taggttcatg ccctccttc tccgcttggg ttcctggaac gtggtgatgt tcgtcaccta    12780
tgagcagctg aaacgagccc tcatggctgc ctgcacttcc cgagaggctc ccttctgagc    12840
ctctcctgct gctgacctga tcacctctgg ctttgtctct agccgggcca tgctttcctt    12900
ttcttccttc tttctcttcc ctccttccct tctctccttc cctctttccc cacctcttcc    12960
```

```
ttccgctcct ttacctacca ccttccctct ttctacattc tcatctactc attgtctcag    13020
tgctggtgga gttgacattt gacagtgtgg gaggcctcgt accagccagg atcccaagcg    13080
tcccgtccct tggaaagttc agccagaatc ttcgtcctgc ccccgacagc ccagcctagc    13140
ccacttgtca tccataaagc aagctcaacc ttggcgtctc ctccctctct tgtagctctt    13200
accagaggtc ttggtccaat ggccttttg  gtacctggtg ggcagggag gaaccacctg     13260 actttgaaaa tgggtgtgat ccaccttcca cctccagcat ccaatctgaa gcccgtgtag    13320
gtcatctggt ccatttctct ctagacccag gccctgtact aacatgggga gtgcaggagc    13380
cacctgagag acagcagtgc ctcccttcc  tttgccgggc cacttgagct cttactcaga    13440
atctggtact ctagtgcctg ccatcccaac cccccacccc agccgcaggc ctgtttatct    13500
gcacaacaag agtgctcctg tgtgccctgc atctcctgca gttccagagg aacatgagac    13560
tcttagatgc tgttgacttt attttattcc attttacaaa tggaaggaag acccacctcc    13620
cccaaagtcc cagaccttgt gagaacaagt cagtcagcct ccttccaccc tccacagcca    13680
cagccacacc cacagaggaa atgttactga actgggtgga gcaggccctg actccacaga    13740
gggtgggtgg aggctgcagg gcaaacatct ggtctctgcc tgaggatact ttccatttgt    13800
gttttttgtt gttttgagac agagtctcac ttgctgtcac ccaggctgga gtgcagtggt    13860
gcaatcttgg ctcactgcaa cctctcccag gttcaggcga ttctcctgcc tcagcctccc    13920
aagtagctgg gattacaggc atacaccatc atacctggct aattttgtg ttttggtag     13980 aaacggggtt ttgccatgtt ggccaggctg gtctcaaact cctgacctca agtgatccac    14040
ctacctcagc ctcccaaagt gctgggatta caggcatgag ccactgtgcc tggccaggat    14100
attttccatt tggagtctca ccaccacaac ccccctccac ctgcccctgc cccagctagg    14160
catccaagga ggccgcaaga agccagggcc ttggctgcac aggggtctcc gcttctctgt    14220
ccctgttctt atcacctgca ctcagaggca ggtgggcagg ggtactacaa tttcaaggag    14280
tggagactgt gaggtcctgg aatcccaagg catctcctgt agggctgggc cttagaatt    14340 atgtcactca gacccagttt gtaggtgtct gaagaaactg aggcctgaca caggtgatgc    14400
aggcaagaac acccagaaag tccactactg aactgggacc gggacccagt cctccttccc    14460
cttgtggact cccccagaga ccagtgctgg ggtccttggg gaagcctgtt tggcagctgt    14520
ggagctaggc cctgagaaca cgaccaccct ccctcttccc tcagcctcaa gccgctgaag    14580
ccactgctgc ttcgccgcct cgtaagccca atggtcagag ctggaggcta gacccttcag    14640
tgcttgggtt gagggccagg gtgttagatt ggttttgga  gaaggaacga gggcccagga    14700
ttcttcagct tcttagtttt tgacaaattg agctgaggcc ccatagtcct cgggagggac    14760
agggttgagt gccataagtc ggcaaaccag ggtaaaggtg acaggcagct cagccaggct    14820
gcagggggtg gcatatacag aggacctggc cactacttta tgtaccttct tacactaatt    14880
ctgtgaggca ggctgtttgt tagctctgct ctggacggga agaagtaggg gcagtttggt    14940
aggtgtgtgt caaagctaaa caggctgggt gggcatgagc aagtcagctg gttcattcag    15000
cagccttaat agacacgagg ctacccaact tcactgtggt tctgggtgtg gccttaggac    15060
aatgagctgg gaacagtggt aggaaccact ggaaaacata ccagtgggtc tcattcattc    15120
tgatcacagg tagatcactt ctctttggtt cccaacccct taatgcctat taag          15174
```

MIRNA MODULATORS OF THERMOGENESIS

CROSS-REFERENCE TO RELATED APPLICATIONS

This application is a continuation of U.S. patent application Ser. No. 13/826,775, filed Mar. 14, 2013, which claims priority to U.S. Provisional Patent Application No. 61/636,059, filed Apr. 20, 2012, and U.S. Provisional Patent Application No. 61/681,750, filed Aug. 10, 2012. The entire contents of each of the above-referenced disclosures are specifically incorporated herein by reference without disclaimer.

BACKGROUND OF THE INVENTION

Obesity has reached pandemic proportions, affecting all ages and socioeconomic groups. The World Health Organization estimated that in 2008, 1.5 billion adults aged 20 years and older were overweight and over 200 million men and 300 million women were obese. These figures are estimated to increase to 2.16 billion overweight and 1.12 billion obese individuals by 2030. Obesity is the source of lost earnings, restricted activity days, absenteeism, lower productivity at work (presenteeism), reduced quality of life, permanent disability, significant morbidity and mortality, and shortened lifespan. Indeed, the total annual economic cost of overweight and obesity in the United States and Canada caused by medical costs, excess mortality and disability was estimated to be about $300 billion in 2009. International studies on the economic costs of obesity have shown that they account for between 2% and 10% of total health care costs.

Obesity is the result of a chronic imbalance between energy intake and expenditure. This leads to storage of excess energy into adipocytes, which typically exhibit both hypertrophy (increase in cell size) and hyperplasia (increase in cell number or adipogenesis). The recent worsening of obesity is due to the combination of excessive consumption of energy-dense foods high in saturated fats and sugars, and reduced physical activity.

The current symptomatic medical treatments of obesity fail to achieve their long-term therapeutic goals, largely due to limited drug efficacy and patients' poor adherence with lifestyle changes and therapies. Several obesity drugs have been removed from the market for safety reasons and small molecules currently in development are struggling to gain regulatory approval because of their modest short-term efficacy and unknown safety profile. Presently, only restrictive and malabsorptive bariatric surgery can achieve significant long-term reduction of weight excess with some favorable cardiovascular benefits.

Accordingly, there is a need in the art for novel treatments for obesity.

SUMMARY OF THE INVENTION

Obesity is the consequence of a chronic imbalance of energy intake over expenditure, leading to the storage of excess energy inside white adipocytes. This disclosure features a novel treatment for obesity targeting peripheral adipocytes, including energy-storing lipid-filled white adipocytes (WAT), and energy-expending mitochondria-rich brown adipocytes (BAT). In addition, the disclosure provides methods for the modulation of thermogenesis (the process of heat production in organisms) using microRNA (miRNAs) agents. The methods described herein generally involve the direct and/or indirect modulation of at least one thermogenic regulator (e.g., a mitochondrial uncoupler, such as Uncoupling Protein 1 (UCP1 also known as Thermogenin) or Uncoupling Protein 2 (UCP2)) in a cell, tissue and/or subject using an isolated miRNA agent. UCPs uncouple oxidative phosphorylation from ATP synthesis. In certain instances, this uncoupling results in energy dissipated as heat. Such methods are particularly advantageous in that they allow for the reduction of body fat in a subject without the subject having to adjust their caloric intake through dieting, modify their physical activity or undergo bariatric surgery. Accordingly, the methods of the invention are particularly useful for treating or preventing obesity.

The invention also provides novel miRNA agent compositions (e.g., miRNA, agomirs, and antagomirs) that can modulate the activity of thermogenic regulators. Yet further, the invention provides methods of screening for novel miRNA agents that modulate the activity of thermogenic regulators. Further still, the invention provides novel agent compositions (e.g. aptamer-miRNA complexes or "aptamirs") that provide cell/tissue-specific delivery of the miRNA agents.

Accordingly, in one aspect, the invention provides a method of modulating respiratory chain uncoupling in a cell, the method comprising contacting the cell with an isolated miRNA agent that modulates the expression level and/or activity of at least one mitochondrial uncoupler. In some embodiments, the method further comprises the step of selecting a subject in need of modulating respiratory chain uncoupling (e.g., an obese patient). In one embodiment, the miRNA agent increases the expression level and/or activity of the at least one mitochondrial uncoupler. In certain embodiments, the mitochondrial uncoupler is UCP1 or UCP2. In some embodiments, the method increases respiratory chain uncoupling in a cell in vivo. In other embodiments, the method increases respiratory chain uncoupling in a cell ex vivo. In certain embodiments, the method further comprises determining the level of expression (mRNA or protein) or activity of the mitochondrial uncoupler. In certain embodiments, the cell is a pre-adipocyte, adipocyte, adipose tissue derived mesenchymal stem cell, hepatocyte, myocyte, or a precursor thereof. Optionally, adipocytes can be white fat or brown fat adipocytes.

In another aspect, the invention provides a method of modulating thermogenesis in a tissue, the method comprising contacting the tissue with an isolated miRNA agent that modulates the expression level and/or activity of at least one mitochondrial uncoupler. In some embodiments, the method further comprises the step of selecting a subject in need of modulating thermogenesis (e.g., an obese patient). In one embodiment, the miRNA agent increases the expression level and/or activity of the at least one mitochondrial uncoupler. In certain embodiments, the mitochondrial uncoupler is UCP1 or UCP2. In certain embodiments, the method involves increasing thermogenesis. In certain embodiments, the method further comprises determining the level of expression (mRNA or protein) or activity of the mitochondrial uncoupler. In certain embodiments, the tissue is brown fat, white fat, subcutaneous adipose tissue, liver or muscle. In certain embodiments, the tissue is contacted with the miRNA agent ex vivo.

In another aspect, the invention provides a method of treating obesity in human subject in need of treatment thereof, the method generally comprising administering to the human subject an effective amount of a miRNA agent that modulates activity of at least one mitochondrial uncoupler. In certain embodiments, the human subject selected for treatment has a genetic or epigenetic predisposition to obesity. In certain embodiments, the mitochondrial uncoupler is UCP1 or UCP2.

In certain embodiments of all of the above aspects, the miRNA agent is an isolated miRNA selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-mir-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a. In certain embodiments of all of the above aspects, the miRNA agent is an isolated miRNA that is 80%, 85%, 90%, 91%, 92%, 93%, 94%, 95%, 96%, 97%, 98%, or 99% identical to the sequence of a miRNA listed above. In certain embodiments of all of the above aspects, the miRNA agent is a seed sequence of a miRNA listed above.

In certain embodiments of all of the above aspects, the miRNA agent is an isolated miRNA selected from the group consisting of the 536 miRNAs set forth in Table A. In certain embodiments of all of the above aspects, the miRNA agent is an isolated miRNA that is 80%, 85%, 90%, 91%, 92%, 93%, 94%, 95%, 96%, 97%, 98%, or 99% identical to the sequence of a miRNA listed in Table A. In certain embodiments of all of the above aspects, the miRNA agent is a seed sequence of a miRNA listed in Table A.

TABLE A

Adipocyte miRNAs listed in ascending order
(miRBase 19 nomenclature)

hsa-let-7a-3p
hsa-let-7a-5p
hsa-let-7b-3p
hsa-let-7b-5p
hsa-let-7c
hsa-let-7d-3p
hsa-let-7d-5p
hsa-let-7e-5p
hsa-let-7f-1-3p
hsa-let-7f-5p
hsa-let-7g-3p
hsa-let-7g-5p
hsa-let-7i-3p
hsa-let-7i-5p
hsa-miR-1
hsa-miR-100-5p
hsa-miR-101-3p
hsa-miR-101-5p
hsa-miR-103a-2-5p
hsa-miR-103a-3p
hsa-miR-103b
hsa-miR-105-5p
hsa-miR-106a-5p
hsa-miR-106b-3p
hsa-miR-106b-5p
hsa-miR-107

TABLE A-continued

Adipocyte miRNAs listed in ascending order
(miRBase 19 nomenclature)

hsa-miR-10a-3p
hsa-miR-10a-5p
hsa-miR-10b-3p
hsa-miR-10b-5p
hsa-miR-1179
hsa-miR-1185-5p
hsa-miR-1208
hsa-miR-122-5p
hsa-miR-1227-3p
hsa-miR-1228-5p
hsa-miR-1229-3p
hsa-miR-124-3p
hsa-miR-125a-3p
hsa-miR-125a-5p
hsa-miR-125b-1-3p
hsa-miR-125b-2-3p
hsa-miR-125b-5p
hsa-miR-126-3p
hsa-miR-126-5p
hsa-miR-1260a
hsa-miR-1260b
hsa-miR-1268a
hsa-miR-127-3p
hsa-miR-127-5p
hsa-miR-1271-5p
hsa-miR-1273a
hsa-miR-1277-3p
hsa-miR-128
hsa-miR-128-2
hsa-miR-1285-3p
hsa-miR-1287
hsa-miR-1288
hsa-miR-129-5p
hsa-miR-1290
hsa-miR-1292-5p
hsa-miR-1301
hsa-miR-1305
hsa-mir-1307-3p
hsa-miR-130a-3p
hsa-miR-130b-3p
hsa-miR-130b-5p
hsa-miR-132-3p
hsa-miR-132-5p
hsa-miR-1323
hsa-miR-133a
hsa-miR-133b
hsa-miR-134
hsa-miR-135a-5p
hsa-miR-135b-5p
hsa-miR-136-3p
hsa-miR-136-5p
hsa-miR-137
hsa-miR-138-1-3p
hsa-miR-138-5p
hsa-miR-139-3p
hsa-miR-139-5p
hsa-miR-140-3p
hsa-miR-140-5p
hsa-miR-141-3p
hsa-miR-142-3p
hsa-miR-142-5p
hsa-miR-143-3p
hsa-miR-143-5p
hsa-miR-144-3p
hsa-miR-144-5p
hsa-miR-145-3p
hsa-miR-145-5p
hsa-miR-1468
hsa-miR-146a-5p
hsa-miR-146b-3p
hsa-miR-146b-5p
hsa-miR-147a
hsa-miR-148a-3p
hsa-miR-148a-5p
hsa-miR-148b-3p
hsa-miR-148b-5p
hsa-miR-149-5p

TABLE A-continued

Adipocyte miRNAs listed in ascending order
(miRBase 19 nomenclature)

hsa-miR-150-3p
hsa-miR-150-5p
hsa-miR-151a-3p
hsa-miR-151a-5p
hsa-miR-151b
hsa-miR-152
hsa-miR-153
hsa-miR-1539
hsa-miR-154-3p
hsa-miR-154-5p
hsa-miR-155-5p
hsa-miR-15a-3p
hsa-miR-15a-5p
hsa-miR-15b-3p
hsa-miR-15b-5p
hsa-miR-16-1-3p
hsa-miR-16-2-3p
hsa-miR-16-5p
hsa-miR-17-3p
hsa-miR-17-5p
hsa-miR-181a-2-3p
hsa-miR-181a-3p
hsa-miR-181a-5p
hsa-miR-181b-5p
hsa-miR-181c-3p
hsa-miR-181c-5p
hsa-miR-181d
hsa-miR-182-5p
hsa-miR-183-5p
hsa-miR-184
hsa-miR-185-3p
hsa-miR-185-5p
hsa-miR-186-3p
hsa-miR-186-5p
hsa-miR-187-3p
hsa-miR-188-5p
hsa-miR-18a-3p
hsa-miR-18a-5p
hsa-miR-18b-5p
hsa-miR-1909-3p
hsa-miR-190a
hsa-miR-190b
hsa-miR-191-3p
hsa-miR-191-5p
hsa-miR-192-5p
hsa-miR-193a-3p
hsa-miR-193a-5p
hsa-miR-193b-3p
hsa-miR-193b-5p
hsa-miR-194-5p
hsa-miR-195-3p
hsa-miR-195-5p
hsa-miR-196a-5p
hsa-miR-196b-5p
hsa-miR-197-3p
hsa-miR-198
hsa-miR-199a-3p
hsa-miR-199a-5p
hsa-miR-199b-3p
hsa-miR-199b-5p
hsa-miR-19a-3p
hsa-miR-19b-3p
hsa-miR-200a-3p
hsa-miR-200a-5p
hsa-miR-200b-3p
hsa-miR-200c-3p
hsa-miR-202-3p
hsa-miR-203a
hsa-miR-204-5p
hsa-miR-205-5p
hsa-miR-206
hsa-miR-20a-3p
hsa-miR-20a-5p
hsa-miR-20b-5p
hsa-miR-21-3p
hsa-miR-21-5p
hsa-miR-210

TABLE A-continued

Adipocyte miRNAs listed in ascending order
(miRBase 19 nomenclature)

hsa-miR-211-5p
hsa-miR-2110
hsa-miR-212-3p
hsa-miR-214-3p
hsa-miR-214-5p
hsa-miR-215
hsa-miR-216a-5p
hsa-miR-217
hsa-miR-218-5p
hsa-miR-219-1-3p
hsa-miR-219-5p
hsa-miR-22-3p
hsa-miR-22-5p
hsa-miR-221-3p
hsa-miR-221-5p
hsa-miR-222-3p
hsa-miR-222-5p
hsa-miR-223-3p
hsa-miR-223-5p
hsa-miR-224-3p
hsa-miR-224-5p
hsa-miR-2355-3p
hsa-miR-23a-3p
hsa-miR-23b-3p
hsa-miR-23b-5p
hsa-miR-24-1-5p
hsa-miR-24-2-5p
hsa-miR-24-3p
hsa-miR-25-3p
hsa-miR-26a-2-3p
hsa-miR-26a-5p
hsa-miR-26b-3p
hsa-miR-26b-5p
hsa-miR-27a-3p
hsa-miR-27a-5p
hsa-miR-27b-3p
hsa-miR-27b-5p
hsa-miR-28-3p
hsa-miR-28-5p
hsa-miR-296-5p
hsa-miR-297
hsa-miR-298
hsa-miR-299-3p
hsa-miR-299-5p
hsa-miR-29a-3p
hsa-miR-29a-5p
hsa-miR-29b-1-5
hsa-miR-29b-2-5p
hsa-miR-29b-3p
hsa-miR-29c-3p
hsa-miR-29c-5p
hsa-miR-301a-3p
hsa-miR-301b
hsa-miR-302a-5p
hsa-miR-302b-5p
hsa-miR-302c-5p
hsa-miR-302d-3p
hsa-miR-3065-3p
hsa-miR-3065-5p
hsa-miR-3074-3p
hsa-miR-3074-5p
hsa-miR-30a-3p
hsa-miR-30a-5p
hsa-miR-30b-3p
hsa-miR-30b-5p
hsa-miR-30c-1-3p
hsa-miR-30c-2-3p
hsa-miR-30c-5p
hsa-miR-30d-3p
hsa-miR-30d-5p
hsa-miR-30e-3p
hsa-miR-30e-5p
hsa-miR-31-3p
hsa-miR-31-5p
hsa-miR-3120-3p
hsa-miR-3120-5p
hsa-miR-3184-5p TABLE A-continued Adipocyte miRNAs listed in ascending order
(miRBase 19 nomenclature)

hsa-miR-32-3p
hsa-miR-32-5p
hsa-miR-320a
hsa-miR-320b
hsa-miR-320c
hsa-miR-323a-3p
hsa-miR-324-3p
hsa-miR-324-5p
hsa-miR-325
hsa-miR-326
hsa-miR-328
hsa-miR-329
hsa-miR-330-3p
hsa-miR-330-5p
hsa-miR-331-3p
hsa-miR-331-5p
hsa-miR-335-3p
hsa-miR-335-5p
hsa-miR-337-3p
hsa-miR-337-5p
hsa-miR-338-3p
hsa-miR-338-5p
hsa-miR-339-3p
hsa-miR-339-5p
hsa-miR-33a-5p
hsa-miR-33b-5p
hsa-miR-340-3p
hsa-miR-340-5p
hsa-miR-342-3p
hsa-miR-342-5p
hsa-miR-345-5p
hsa-miR-346
hsa-miR-34a-5p
hsa-miR-34b-3p
hsa-miR-34b-5p
hsa-miR-34c-5p
hsa-miR-3545-5p
hsa-miR-3591-3p
hsa-miR-361-3p
hsa-miR-361-5p
hsa-miR-3613-5p
hsa-miR-3615
hsa-miR-362-3p
hsa-miR-362-5p
hsa-miR-363-3p
hsa-miR-363-5p
hsa-mir-365a-3p
hsa-mir-3653
hsa-miR-3656
hsa-miR-365a-3p
hsa-miR-365a-5p
hsa-miR-367-3p
hsa-mir-3676-3p
hsa-miR-369-3p
hsa-miR-369-5p
hsa-miR-370
hsa-miR-371a-3p
hsa-miR-373-3p
hsa-miR-373-5p
hsa-miR-374a-3p
hsa-miR-374a-5p
hsa-miR-374b-3p
hsa-miR-374b-5p
hsa-miR-375
hsa-mir-376a-2-5p
hsa-miR-376a-3p
hsa-miR-376a-5p
hsa-miR-376b-3p
hsa-miR-376c-3p
hsa-miR-377-3p
hsa-miR-378a-3p
hsa-miR-378a-5p
hsa-miR-378c
hsa-miR-378d
hsa-miR-379-5p
hsa-miR-380-3p
hsa-miR-381-3p
hsa-miR-382-5p
hsa-miR-383
hsa-miR-384
hsa-miR-3912
hsa-miR-3928
hsa-miR-409-3p
hsa-miR-409-5p
hsa-miR-410
hsa-miR-411-5p
hsa-miR-421
hsa-miR-422a
hsa-miR-422b
hsa-miR-423-3p
hsa-miR-423-5p
hsa-miR-424-3p
hsa-miR-424-5p
hsa-miR-425-3p
hsa-miR-425-5p
hsa-miR-429
hsa-miR-431-5p
hsa-miR-432-5p
hsa-miR-433
hsa-miR-4421
hsa-miR-449a
hsa-miR-450a-5p
hsa-miR-450b-3p
phsa-miR-450b-5p
hsa-miR-4510
hsa-miR-4516
hsa-miR-451a
hsa-miR-452-3p
hsa-miR-452-5p
hsa-miR-454-3p
hsa-miR-454-5p
hsa-miR-455-3p
hsa-miR-455-5p
hsa-miR-4634
hsa-miR-4732-5p
hsa-miR-4792
hsa-miR-483-3p
hsa-miR-483-5p
hsa-miR-484
hsa-miR-485-5p
hsa-miR-486-3p
hsa-miR-486-5p
hsa-miR-487b
hsa-miR-488-3p
hsa-miR-489
hsa-miR-491-3p
hsa-miR-491-5p
hsa-miR-492
hsa-miR-493-3p
hsa-miR-493-5p
hsa-miR-494
hsa-miR-495-3p
hsa-miR-497-5p
hsa-miR-498
hsa-miR-499a-5p
hsa-miR-500a-3p
hsa-miR-501-3p
hsa-miR-501-5p
hsa-miR-502-3p
hsa-miR-502-5p
hsa-miR-503-5p
hsa-miR-504
hsa-miR-505-3p
hsa-miR-505-5p
hsa-miR-506-3p
hsa-miR-509-3p
hsa-miR-511
hsa-miR-513a-3p
hsa-miR-513a-5p
hsa-miR-513b
hsa-miR-514a-3p
hsa-miR-515-3p
hsa-miR-516b-3p
hsa-miR-516b-5p

TABLE A-continued

Adipocyte miRNAs listed in ascending order
(miRBase 19 nomenclature)

hsa-miR-518b
hsa-miR-518e-3p
hsa-miR-518e-5p
hsa-miR-518f-3p
hsa-miR-519a-5p
hsa-miR-519b-5p
hsa-miR-519c-3p
hsa-miR-519c-5p
hsa-miR-519d
hsa-miR-520c-3p
hsa-miR-520e
hsa-miR-520f
hsa-miR-520g
hsa-miR-520h
hsa-miR-521
hsa-miR-522-5p
hsa-miR-523-5p
hsa-miR-525-3p
hsa-miR-532-3p
hsa-miR-532-5p
hsa-miR-539-5p
hsa-miR-542-3p
hsa-miR-542-5p
hsa-miR-545-3p
hsa-miR-545-5p
hsa-miR-548d-3p
hsa-miR-548e
hsa-miR-548i
hsa-miR-548m
hsa-miR-550a-5p
hsa-miR-551b-3p
hsa-miR-552
hsa-miR-553
hsa-miR-554
hsa-miR-557
hsa-miR-563
hsa-miR-564
hsa-miR-567
hsa-miR-569
hsa-miR-570-3p
hsa-miR-572
hsa-miR-574-3p
hsa-miR-574-5p
hsa-miR-575
hsa-miR-576-3p
hsa-miR-576-5p
hsa-miR-582-3p
hsa-miR-582-5p
hsa-miR-583
hsa-miR-584-5p
hsa-miR-585
hsa-miR-586
hsa-miR-589-5p
hsa-miR-590-3p
hsa-miR-590-5p
hsa-miR-595
hsa-miR-598
hsa-miR-601
hsa-miR-602
hsa-miR-603
hsa-miR-605
hsa-miR-606
hsa-miR-609
hsa-miR-611
hsa-miR-615-3p
hsa-miR-619
hsa-miR-625-5p
hsa-miR-627
hsa-miR-628-3p
hsa-miR-628-5p
hsa-miR-629-3p
hsa-miR-629-5p
hsa-miR-630
hsa-miR-636
hsa-miR-638
hsa-miR-639
hsa-miR-641
hsa-miR-642a-3p
hsa-miR-642a-5p
hsa-miR-646
hsa-miR-649
hsa-miR-651
hsa-miR-652-3p
hsa-miR-653
hsa-miR-654-3p
hsa-miR-659-3p
hsa-miR-660-5p
hsa-miR-663a
hsa-miR-664a-3p
hsa-miR-664a-5p
hsa-miR-668
hsa-miR-671-5p
hsa-miR-675-3p
hsa-miR-675-5p
hsa-miR-7-2-3p
hsa-miR-7-5p
hsa-miR-708-3p
hsa-miR-708-5p
hsa-miR-718
hsa-miR-744-5p
hsa-miR-765
hsa-miR-769-5p
hsa-miR-770-5p
hsa-miR-874
hsa-miR-885-3p
hsa-miR-887
hsa-miR-889
hsa-miR-890
hsa-miR-891a
hsa-miR-891b
hsa-miR-9-5p
hsa-miR-92a-3p
hsa-miR-92b-3p
hsa-miR-93-3p
hsa-miR-93-5p
hsa-miR-935
hsa-miR-942
hsa-miR-95
hsa-miR-96-3p
hsa-miR-96-5p
hsa-miR-98-5p
hsa-miR-99a-3p
hsa-miR-99a-5p
hsa-miR-99b-3p
hsa-miR-99b-5p In certain embodiments of all of the above aspects, the miRNA agent is a miRNA selected from the group consisting of the isolated miRNAs set forth in Table 7. In certain embodiments of all of the above aspects, the miRNA agent is an isolated miRNA that is 80%, 85%, 90%, 91%, 92%, 93%, 94%, 95%, 96%, 97%, 98%, or 99% identical to the sequence of a miRNA listed in Table 8. In certain embodiments of all of the above aspects, the miRNA agent is a seed sequence of a miRNA listed in Table 8.

In certain embodiments of all of the above aspects, the miRNA agent is an agomir or antagomir of a miRNA selected from the group consisting of the miRNAs set forth in Table A.

In certain embodiments of all of the above aspects, the miRNA agent is an agomir or antagomir of a miRNA selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-miR-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a.

In certain embodiments of all of the above aspects, the miRNA agent is an agomir or antagomir of a miRNA selected from the group consisting of the miRNAs set forth in Table 7.

In certain embodiments of all of the above aspects, the miRNA agent is an antagomir of a miRNA selected from the group consisting of hsa-miR-19b-2-5p, hsa-miR-21-5p, hsa-miR-130b-5p, hsa-miR-211, hsa-miR-325, hsa-miR-382-3p/5p, hsa-miR-543, hsa-miR-515-3p, and hsa-miR-545.

In certain embodiments of all of the above aspects, the miRNA agent is an antagomir of a miRNA selected from the group consisting of hsa-miR-331-5p, hsa-miR-552, hsa-miR-620, and hsa-miR-1179.

In certain embodiments of all of the above aspects, the miRNA agent is linked to a targeting moiety (e.g., an aptamer). In one embodiment, the targeting moiety delivers the miRNA agent to a specific cell type or tissue.

In certain embodiments of all of the above aspects, the miRNA agent directly binds to the mRNA or promoter region of at least one mitochondrial uncoupler.

In certain embodiments of all of the above aspects, the miRNA agent directly binds to the 5'UTR or coding sequence of the mRNA of at least one mitochondrial uncoupler.

In certain embodiments of all of the above aspects, the miRNA agent directly binds to the 3'UTR of the mRNA of at least one mitochondrial uncoupler.

In certain embodiments of all of the above aspects, the miRNA agent modulates the activity of an activator or repressor of a mitochondrial uncoupling protein. In one embodiment, the miRNA agent directly binds to the mRNA or promoter region of the activator or repressor. In one embodiment, the miRNA agent directly binds to the 5'UTR or coding sequence of the mRNA of the activator or repressor. In one embodiment, the miRNA agent directly binds to the 3'UTR of the mRNA of the activator or repressor. In one embodiment, the activator or repressor is selected from the group listed in Table 1.

In certain embodiments of all of the above aspects, the mRNA or protein expression of the mitochondrial uncoupling protein is upregulated.

In certain embodiments of all of the above aspects, the mitochondrial uncoupling activity of the mitochondrial uncoupling protein is upregulated.

In another aspect, the invention provides a method of screening for a miRNA agent that modulates thermogenesis, the method generally comprising: providing an indicator cell; contacting the indicator cell with a test miRNA agent; and determining the cellular activity of at least one thermogenic regulator in the indicator cell in the presence and absence of the miRNA agent, wherein a change in the activity of the thermogenic regulator in the presence of the test miRNA agent identifies the test miRNA agent as a miRNA agent that modulates thermogenesis. The indicator cell can be a mammalian cell. In certain embodiments, the indicator cell is a human cell comprising at least a portion of a human genome.

In certain embodiments, the cell is a pre-adipocyte, adipocyte, adipose tissue derived mesenchymal stem cell, hepatocyte, myocyte, or a precursor thereof.

In certain embodiments, the cellular activity of the thermogenic regulator determined in the method is the mRNA expression level, protein expression level or mitochondrial uncoupling activity of the thermogenic regulator.

In certain embodiments, the test miRNA agent increases the activity of the thermogenic regulator compared to the level of activity of the thermogenic regulator in the absence of the test miRNA agent.

In certain embodiments, the thermogenic regulator is UCP1 or UCP2.

In another aspect, the invention provides an agomir or antagomir that modulates the activity of at least one thermogenic regulator in a cell.

In certain embodiments, the agomir or antagomir is an agomir or antagomir of a miRNA selected from the group consisting of the miRNAs set forth in Table 8.

In certain embodiments, the agomir or antagomir is an agomir or antagomir of a miRNA selected from the group consisting of the miRNAs set forth in Table A.

In certain embodiments, the agomir or antagomir is an agomir or antagomir of a miRNA selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-miR-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a.

In certain embodiments, the agomir or antagomir is an antagomir of a miRNA selected from the group consisting of hsa-miR-19b-2-5p, ha-miR-21-5p, hsa-miR-130b-5p, hsa-miR-211, hsa-miR-325, hsa-miR-382-3p/5p, hsa-miR-543, hsa-miR-515-3p, and hsa-miR-545.

In certain embodiments, the agomir or antagomir is an antagomir of a miRNA selected from the group consisting of hsa-miR-331-5p, hsa-miR-552, hsa-miR-620, and hsa-miR-1179.

In certain embodiments, the agomir or antagomir is linked to a targeting moiety. In certain embodiments, the targeting moiety is an aptamer.

In certain embodiments, the targeting moiety delivers the agomir or antagomir to a specific cell type or tissue.

In certain embodiments, the agomir or antagomir directly binds to the mRNA or promoter region of at least one mitochondrial uncoupler.

In certain embodiments, the agomir or antagomir directly binds to the 5'UTR or coding sequence of the mRNA of at least one mitochondrial uncoupler.

In certain embodiments, the agomir or antagomir directly binds to the 3'UTR of the mRNA of at least one mitochondrial uncoupler.

In certain embodiments, the agomir or antagomir modulates the activity of an activator or repressor of a mitochondrial uncoupling protein.

In certain embodiments, the activator or repressor is selected from the group listed in Table 1.

In certain embodiments, the agomir or antagomir directly binds to the mRNA or promoter region of the activator or repressor.

In certain embodiments, the agomir or antagomir directly binds to the 5'UTR or coding sequence of the mRNA of the activator or repressor. In other embodiments, the agomir or antagomir directly binds to the 3'UTR of the mRNA of the activator or repressor.

The disclosure also provides a pharmaceutical composition comprising two or more miRNAs selected from hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. In certain embodiments the pharmaceutical composition also includes a pharmaceutically acceptable excipient. In certain embodiments, the two or more miRNAs are expressed from a recombinant vector. The recombinant vector can be selected from DNA plasmids, viral vectors and DNA minicircles.

The disclosure also provides a method of inducing pre-adipocytes to differentiate initially into white adipocytes and subsequently into brown adipocytes comprising administering to a population of pre-adipocytes one or more miRNAs selected from hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. The one or more miRNAs can also be selected from hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. In certain embodiments, the induction of pre-adipocytes to differentiate into adipocytes is greater than the differentiation of pre-adipocytes to adipocytes when pre-adipocytes are exposed to 100 mM rosiglitazone for two days followed by maintenance medium. In certain embodiments, the adipocytes are brown adipocytes. In other embodiments, the adipocytes are white adipocytes. Additional criteria for differentiation can be found in the Examples, below.

The disclosure also provides a method for decreasing the lipid content of adipocytes comprising administering to a population of adipocytes one or more miRNAs selected from the group consisting of hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir. In certain embodiments, the lipid content of the adipocytes is less than the lipid content of adipocytes exposed to 100 nM rosiglitazone for two days followed by maintenance medium or less than the fat content of adipocytes exposed to 100 nM rosiglitazone for the duration of culture. The duration of culture can be 8-16, 10-14 or 14 days. The duration of culture can also be 8, 9, 10, 11, 12, 13, 14, 15, 16, 17, 18, 19 or 20 days. Additional criteria for lipid content of adipocytes can be found in the Examples, below.

The disclosure also provides a method for increasing insulin sensitivity in a subject in need thereof comprising administering the subject one or more miRNAs selected from the group consisting of hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir and hsa-miR-30b antagomir.

In certain embodiments, the subject is a mammal.

The disclosure also provides a method of increasing expression or activity of one or more uncoupling proteins in a cell comprising administering to the cell one or more, two or more, or three or more miRNAs selected from the group consisting of hsa-let-7a antagomir, hsa-miR-1 agomir, hsa-miR-19b agomir and hsa-miR-30b agomir. In certain embodiments, the cell is selected from the group consisting of a brown adipocyte, a white adipocyte, a subcutaneous adipocyte, a liver cell or a muscle cell. In other embodiments, the one or more uncoupling proteins include UCP1 or UCP2. In certain embodiments, the method is an ex vivo method. In other embodiments, the method is an in vivo method. In certain embodiments, the method involves selecting a subject (e.g., a human) in need of increasing the level of expression or activity of one or more uncoupling proteins (e.g., UCP1, UCP2). In some embodiments, the subject has, or is at risk of developing, obesity. In certain embodiments, the subject has, or is at risk of developing, diabetes. In certain embodiments, the method further comprises determining the expression level (mRNA or protein) or activity of the one or more uncoupling proteins.

The disclosure also provides a method of causing fat loss in a subject in need thereof comprising administering the subject one or more miRNAs selected from the group consisting of hsa-let-7a antagomir, hsa-miR-1 agomir, hsa-miR-19b agomir and hsa-miR-30b agomir. In certain embodiments, the subject is a mammal. In other embodiments, the mammal is a human.

BRIEF DESCRIPTION OF THE DRAWINGS

FIG. 15 is a bar graph showing the amount of lipids in mature adipocytes using Nile Red Dye exposed to various miRNAs.

DETAILED DESCRIPTION OF THE INVENTION

I. Definitions

Figure 1A:
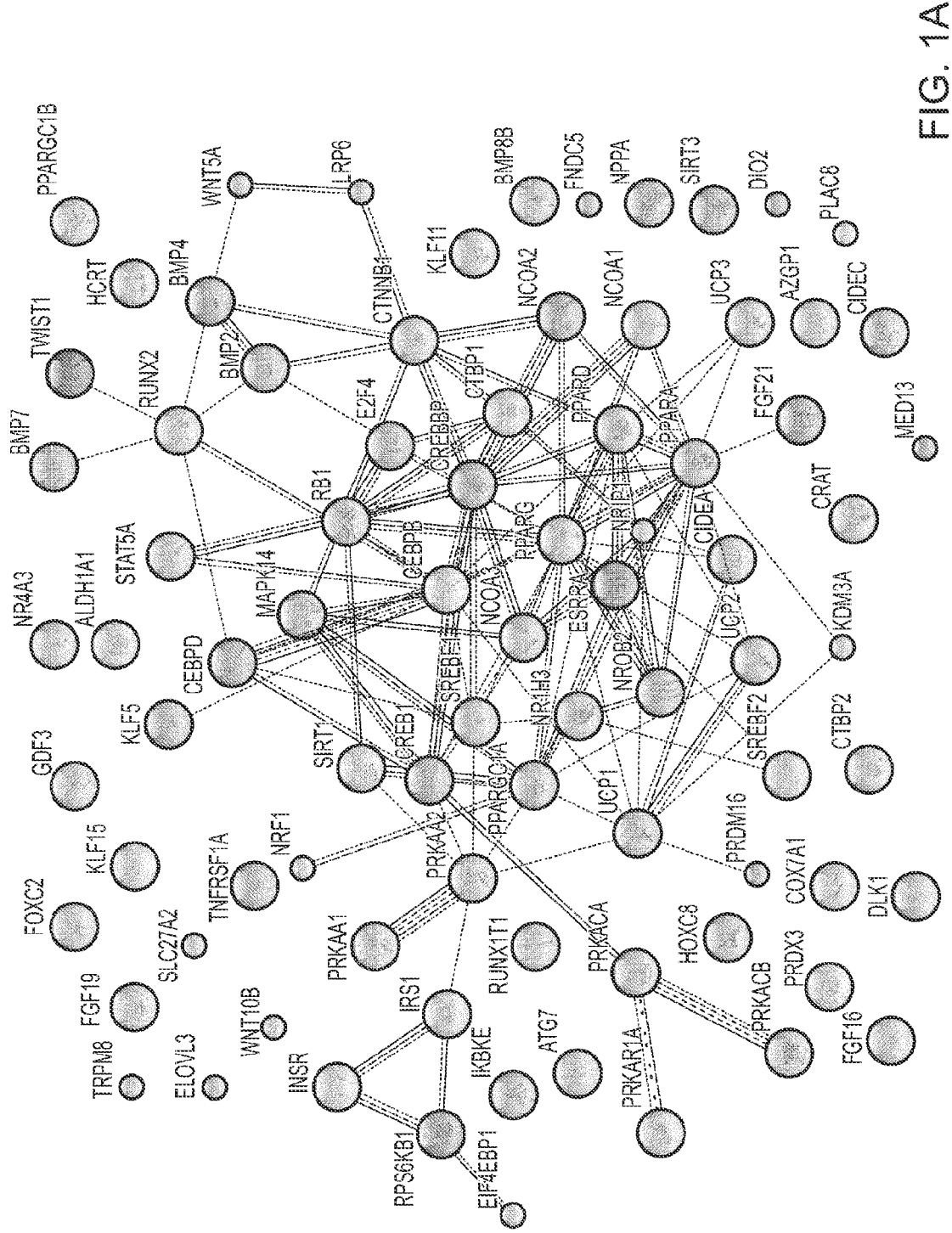
FIGS. 1A and 1B are schematic representations of the interactions of 83 thermogenic regulators determined using the STRING 9.0 database.

Unless otherwise defined, all technical and scientific terms used herein have the same meaning as commonly understood by one of ordinary skill in the art to which this invention belongs. In case of conflict, the present application, including definitions, will control.

As used herein, the term "miRNA agent" refers to an oligonucleotide or oligonucleotide mimetic that directly or indirectly modulates the activity of a thermogenic regulator (e.g., a mitochondrial uncoupler or an activator or repressor thereof). miRNA agents can act on a target gene or on a target miRNA.

As used herein, the term "miRNA" refers to a single-stranded RNA molecule (or a synthetic derivative thereof), which is capable of binding to a target gene (either the mRNA or the DNA) and regulating expression of that gene. In certain embodiments, the miRNA is naturally expressed in an organism.

As used herein, the term "seed sequence" refers to a 6-8 nucleotide (nt) long substring within the first 8 nt at the 5'-end of the miRNA (i.e., seed sequence) that is an important determinant of target specificity.

As used herein, the term "agomir" refers to a synthetic oligonucleotide or oligonucleotide mimetic that functionally mimics a miRNA. An agomir can be an oligonucleotide with the same or similar nucleic acid sequence to a miRNA or a portion of a miRNA. In certain embodiments, the agomir has 1, 2, 3, 4, 5, 6, 7, 8, 9 or 10 nucleotide differences from the miRNA that it mimics. Further, agomirs can have the same length, a longer length or a shorter length than the miRNA that it mimics. In certain embodiments, the agomir has the same sequence as 6-8 nucleotides at the 5' end of the miRNA it mimics. In other embodiments, an agomir can be 5, 6, 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 or 50 nucleotides in length. In other embodiments, an agomir can be 5-10, 6-8, 10-20, 10-15 or 5-500 nucleotides in length. In certain embodiments, agomirs include any of the sequences shown in Table A. These chemically modified synthetic RNA duplexes include a guide strand that is identical or substantially identical to the miRNA of interest to allow efficient loading into the miRISC complex, whereas the passenger strand is chemically modified to prevent its loading to the Argonaute protein in the miRISC complex (Thorsen S B et al., Cancer J., 18(3):275-284 (2012); Broderick J A et al., Gene Ther., 18(12):1104-1110 (2011)).

As used herein, the term "antagomir" refers to a synthetic oligonucleotide or oligonucleotide mimetic having complementarity to a specific microRNA, and which inhibits the activity of that miRNA. In certain embodiments, the antagomir has 1, 2, 3, 4, 5, 6, 7, 8, 9 or 10 nucleotide differences from the miRNA that it inhibits. Further, antagomirs can have the same length, a longer length or a shorter length than the miRNA that it inhibits. In certain embodiments, the antagomir hybridizes to 6-8 nucleotides at the 5' end of the miRNA it inhibits. In other embodiments, an antagomir can be 5, 6, 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 or 50 nucleotides in length. In other embodiments, an antagomir can be 5-10, 6-8, 10-20, 10-15 or 5-500 nucleotides in length. In certain embodiments, antagomirs include nucleotides that are complementary to any of the sequences shown in Table A. The antagomirs are synthetic reverse complements that tightly bind to and inactivate a specific miRNA. Various chemical modifications are used to improve nuclease resistance and binding affinity. The most commonly used modifications to increase potency include various 2'sugar modifications, such as 2'-O-Me, 2'-O-methoxyethyl (2'-MOE), or 2'-fluoro(2'-F). The nucleic acid structure of the miRNA can also be modified into a locked nucleic acid (LNA) with a methylene bridge between the 2'oxygen and the 4' carbon to lock the ribose in the 3'-endo (North) conformation in the A-type conformation of nucleic acids (Lennox K A et al. Gene Ther. December 2011; 18(12):1111-1120; Bader A G et al. Gene Ther. December 2011; 18(12):1121-1126). This modification significantly increases both target specificity and hybridization properties of the molecules.

As used herein, the term "aptamir" refers to the combination of an aptamer (oligonucleic acid or peptide molecule that bind to a specific target molecule) and an agomir or antagomir as defined above, which allows cell or tissue-specific delivery of the miRNA agents.

As used herein, the term "interfering RNA" refers to any double stranded or single stranded RNA sequence capable of inhibiting or down-regulating gene expression by mediating RNA interference. Interfering RNAs include, but are not limited to, small interfering RNA ("siRNA") and small hairpin RNA ("shRNA"). "RNA interference" refers to the selective degradation of a sequence-compatible messenger RNA transcript.

As used herein, the term "small interfering RNA" or "siRNA" refers to any small RNA molecule capable of inhibiting or down regulating gene expression by mediating RNA interference in a sequence specific manner. The small RNA can be, for example, about 16 to 21 nucleotides long.

As used herein, the term "shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA (siRNA) by a cleavage event mediated by the enzyme Dicer, which is a member of the RNase III family.

As used herein, the term "antisense oligonucleotide" refers to a synthetic oligonucleotide or oligonucleotide mimetic that is complementary to a DNA or mRNA sequence (e.g., a miRNA).

As used herein, the term "miR-mask" refers to a single stranded antisense oligonucleotide that is complementary to a miRNA binding site in a target mRNA, and that serves to inhibit the binding of miRNA to the mRNA binding site. See, e.g., Xiao, et al. "Novel approaches for gene-specific interference via manipulating actions of microRNAs: examination on the pacemaker channel genes HCN2 and HCN4," Journal of Cellular Physiology, vol. 212, no. 2, pp. 285-292, 2007, which is incorporated herein in its entirety.

As used herein, the term "miRNA sponge" refers to a synthetic nucleic acid (e.g. a mRNA transcript) that contains multiple tandem-binding sites for a miRNA of interest, and that serves to titrate out the endogenous miRNA of interest, thus inhibiting the binding of the miRNA of interest to its endogenous targets. See, e.g., Ebert et al., "MicroRNA sponges: competitive inhibitors of small RNAs in mammalian cells," Nature Methods, vol. 4, no. 9, pp. 721-726, 2007, which is incorporated herein in its entirety.

As used herein, the term "respiratory chain uncoupling" refers to the dissipation of the mitochondrial inner membrane proton gradient, thereby preventing the synthesis of ATP in the mitochondrion by oxidative phosphorylation.

As used herein, the term "mitochondrial uncoupler" refers to a protein (or the encoding nucleic acid) that can dissipate of the mitochondrial inner membrane proton gradient, thereby preventing the synthesis of ATP in the mitochondrion by oxidative phosphorylation. Exemplary mitochondrial uncouplers include UCP1 and UCP2.

As used herein, the terms "activator" or "repressor" of a mitochondrial uncoupler refers to a protein that serves to upregulate or downregulate, respectively, an activity of a mitochondrial uncoupler.

As used herein, the term "thermogenic regulator" refers to a protein (or the encoding nucleic acid) that regulates thermogenesis either directly or indirectly. The term encompasses mitochondrial uncouplers, and also activators and repressors of mitochondrial uncouplers. Exemplary thermogenic regulators are set forth in Table 1 herein.

As used herein, the term "modulate" refers to increasing or decreasing a parameter. For example, to modulate the activity of a protein that protein's activity could be increased or decreased.

As used herein, the term "activity" of mitochondrial uncoupler or thermogenic regulator refers to any measurable biological activity including, without limitation, mRNA expression, protein expression, or respiratory chain uncoupling.

The "effective amount" of the miRNA agent composition is an amount sufficient to be effective in treating or preventing a disorder or to regulate a physiological condition in humans. In certain embodiments, this physiological condition is obesity.

A "subject" is a vertebrate, including any member of the class Mammalia, including humans, domestic and farm animals, zoo, sports or pet animals, such as mouse, rabbit, pig, sheep, goat, cattle and higher primates.

The term "mammal" refers to any species that is a member of the class mammalia, including rodents, primates, dogs, cats, camelids and ungulates. The term "rodent" refers to any species that is a member of the order rodentia including mice, rats, hamsters, gerbils and rabbits. The term "primate" refers to any species that is a member of the order primates, including monkeys, apes and humans. The term "camelids" refers to any species that is a member of the family camelidae including camels and llamas. The term "ungulates" refers to any species that is a member of the superorder ungulata including cattle, horses and camelids. According to some embodiments, the mammal is a human.

"Treatment", or "treating" as used herein, is defined as the application or administration of a therapeutic agent (e.g., a miRNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

"Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

The "effective amount" of the miRNA agent composition is an amount sufficient to be effective in treating or preventing a disorder or to regulate a physiological condition in humans.

II. Thermogenesis and Obesity

In certain embodiments, the invention provides methods for modulating thermogenesis. These methods generally involve contacting cells or tissue with a miRNA agent that modulates activity of at least one mitochondrial uncoupler (e.g., UCP1 and/or UCP2). Such methods and compositions are particularly useful for treating obesity.

Mammalian adipocytes can be categorized into two major categories based on their functional profiles: 1) energy-storing and releasing, lipid-filled white adipocytes (WAT) and; 2) energy-expending and heat producing, mitochondria-rich brown adipocytes (BAT). Until recently, it was believed that BAT underwent rapid involution in early childhood, leaving only vestigial amounts in adults. However, positron-emission tomography (PET) studies performed in humans with the tracer 18F-fluorodeoxyglucose (18F-FDG) demonstrated that: 1) multiple depots of BAT are still present in the cervical, supraclavicular, axillary and paravertebral regions in adult subjects; 2) BAT in adult humans can be rapidly activated by exposure to cold temperatures; 3) there is an inverse correlation between the activity of BAT and age, body-mass index (BMI), the percentage of body fat, fasting plasma glucose level, beta-blocker use and outdoor temperature; and 4) BAT expansion may drive the weight loss associated with catecholamine-producing phaeochromocytomas, whereas beta3-adrenoreceptor polymorphisms leading to a reduction in receptor function have been linked to weight gain and early onset type 2 diabetes mellitus.

Although WAT and BAT are derived from mesenchymal stem cells, they have distinct lineages, with Myf5 (Myogenic Regulatory Factor 5) (shared with skeletal myocyte progenitors), PGC-lalpha and PRDM16 (PR-domain-containing 16) expression distinguishing the brown from white adipocyte precursors. In addition to the classic brown adipocytes, a different type of brown fat cells can be induced in tissues where WAT predominates. The termed "brite" (brown-in-white) adipocyte has been coined and the appearance of brown-like adipocytes within WAT depots is associated with improved metabolic phenotypes. Increasing BAT mass and/or activity offers a degree of protection from obesity. Heat production by BAT is 300 W/g compared to 1 W/g in all other tissues. Relatively limited amounts of BAT would be required to make significant impact on energy balance, since as little as 50 g of BAT would account for 20% of daily energy expenditure. It has been speculated that the estimated 63 g of BAT found in the supraclavicular/paracervical depot of one subject could combust the energy equivalent of 4.1 kg of WAT over 1 year.

Mitochondrial uncoupling proteins (UCP) are members of the family of mitochondrial anion carrier proteins (MACP). UCPs separate oxidative phosphorylation from ATP synthesis with energy dissipated as heat (also referred to as the "mitochondrial proton leak"). UCPs facilitate the transfer of anions from the inner to the outer mitochondrial membrane and the return transfer of protons from the outer to the inner mitochondrial membrane generating heat in the process. UCPs are the primary proteins responsible for thermogenesis and heat dissipation. Uncoupling Protein 1 (UCP1), also named thermogenin, is a BAT specific protein responsible for thermogenesis and heat dissipation. UCP2 is another Uncoupling Protein also expressed in adipocytes. UCPs are part of network of thermogenic regulator proteins (see FIG. 1). Exemplary thermogenic regulators are set forth in Table 1.

Modulation of thermogenic regulators to induce BAT differentiation and/or mitochondrial uncoupling proteins provides a method to induce thermogenesis in a subject and, hence, to treat obesity. However, chemical pharmacologic approaches cannot target these molecules, as they do not belong to the classic 'target classes' (kinases, ion channels, G-protein coupled receptors, etc.) that dominate the 'druggable space' of traditional drug discovery. Accordingly, the invention provides novel methods and compositions for modulating these thermogenic regulators using miRNA agents.

In certain embodiments, miRNA agents are employed to upregulate the activity of a mitochondrial uncoupler (e.g., the mRNA expression level, protein expression level, or mitochondrial uncoupling activity). Upregulation of a mitochondrial uncoupler can be achieved in several ways. In one embodiment, the miRNA agent directly inhibits the activity of a naturally occurring miRNA that is responsible for downregulation of the activity (e.g., the mRNA expression level, protein expression level) of the mitochondrial uncoupler. In another embodiment, the miRNA agent upregulates the activity (e.g., the mRNA expression level or the protein expression level) of an activator of the mitochondrial uncoupler. This upregulation can be achieved, for example, by directly inhibiting the activity of a naturally occurring miRNA that is responsible for downregulation of the expression of the activator. In yet another embodiment, the miRNA agent downregulates the activity (e.g., the mRNA expression level or the protein expression level) of a repressor of the mitochondrial uncoupler. This downregulation can be achieved, for example, by directly inhibiting the expression of a repressor of a mitochondrial uncoupler using a miRNA agent.

In certain embodiments, miRNA agents are employed that are capable of modulating the activity of multiple thermogenic regulators simultaneously (Pathway-specific miRNA agents as opposed to universal miRNA agents). For example, a single miRNA, agomir or antagomir that binds to multiple thermogenic regulators can be used. This approach is particularly advantageous in that it allows for the modulation of multiple members of an entire signaling pathway using a single miRNA agent.

In certain embodiments, multiple inhibitory miRNA agents (e.g., antagomirs or miR-masks) are employed. These inhibitory miRNA agents can have the same or different miRNA targets.

III. miRNA Agents

In certain embodiments, the invention employs miRNA agents for the modulation of thermogenic regulators (e.g., mitochondrial uncouplers, such as UCP1 and/or UCP2). miRNA agents, suitable for use in the methods disclosed herein, included, without limitation, miRNA, agomirs, antagomirs, miR-masks, miRNA-sponges, siRNA (single- or double-stranded), shRNA, antisense oligonucleotides, ribozymes, or other oligonucleotide mimetics which hybridize to at least a portion of a target nucleic acid and modulate its function.

In certain embodiments, the miRNA agents are miRNA molecules or synthetic derivatives thereof (e.g., agomirs). In one particular embodiment, the miRNA agent is a miRNA. miRNAs are a class of small (e.g., 18-24 nucleotides) non-coding RNAs that exist in a variety of organisms, including mammals, and are conserved in evolution. miR-NAs are processed from hairpin precursors of about 70 nucleotides which are derived from primary transcripts through sequential cleavage by the RNAse III enzymes drosha and dicer. Many miRNAs can be encoded in intergenic regions, hosted within introns of pre-mRNAs or within ncRNA genes. Many miRNAs also tend to be clustered and transcribed as polycistrons and often have similar spatial temporal expression patterns. In general, miRNAs are post-transcriptional regulators that bind to complementary sequences on a target gene (mRNA or DNA), resulting in gene silencing by, e.g., translational repression or target degradation. One miRNA can target many different genes simultaneously. Exemplary miRNA molecules for use in the disclosed methods include without limitation: hsa-miR-1-1, hsa-miR-1-2, hsa-miR-7a-g, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-miR-19a-b, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-mir-367, hsa-mir-371, hsa-mir-371-5p, hsa-mir-377, hsa-mir-378, hsa-mir-378a-5p, hsa-mir-382, hsa-mir-383, hsa-miR-3658, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, hsa-miR-568, hsa-mir-620, hsa-mir-643, hsa-mir-654-3p, hsa-mir-765, hsa-mir-871, hsa-mir-888, hsa-mir-888-3p, hsa-mir-92b, hsa-mir-93, hsa-mir-96, hsa-mir-99a. In other embodiments, exemplary miRNA molecules for use in the disclosed methods miRNA disclosed in Table A and/or Table 8, herein. In one particular embodiment, the miRNA agent is human miR-22, or a functional derivative thereof.

In another particular embodiment, the miRNA agent is an agomir. Agomirs of a particular miRNA can be identified using the screening methods disclosed herein. In one particular embodiment, the agomir is a functional mimetic of human miR-22 (Davidson B L et al., Nat Rev Genet., 12(5):329-340 (2011).

In certain embodiments, the miRNA agents are oligonucleotide or oligonucleotide mimetics that inhibit the activity of one or more miRNA. Examples of such molecules include, without limitation, antagomirs, interfering RNA, antisense oligonucleotides, ribozymes, miRNA sponges and miR-masks. In one particular embodiment, the miRNA agent is an antagomir. In general, antagomirs are chemically modified antisense oligonucleotides that bind to a target miRNA and inhibit miRNA function by preventing binding of the miRNA to its cognate gene target. Antagomirs can include any base modification known in the art. In one particular embodiment, the antagomir inhibits the activity of human miR-22 (van Rooij E et al., Circ Res., 110(3):496-507 (2012); Snead N M et al., Nucleic Acid Ther., 22(3): 139-146 (2012); Czech M P et al., Nat Rev Endocrinol., 7(8):473-484 (2011).

In certain embodiments, the miRNA agents are 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin.

In certain embodiments, the miRNA agents are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In certain embodiments, the miRNA agents comprise at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, a basic residue or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make an oligonucleotide more resistant to nuclease digestion, thereby prolonging in vivo half-life. Specific examples of modified oligonucleotides include those comprising backbones comprising, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N (CH$_3$)—CH$_2$—CH$_2$ backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497), each of which is herein incorporated by reference in its entirety. Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321, 131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol, 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991, each of which is herein incorporated by reference in its entirety. Cyclohexenyl nucleic acid oligonucleotide mimetics are described in Wang et al., J. Am. Chem. Soc., 2000, 122, 8595-8602, the contents of which is incorporated herein in its entirety.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts; see U.S. Pat. Nos. 5,034,506; 5,166,315; 5,185,444; 5,214,134; 5,216, 141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In certain embodiments, miRNA agents comprise one or more substituted sugar moieties, e.g., one of the following at the 2' position: OH, SH, SCH$_3$, F, OCN, OCH$_3$OCH$_3$, OCH$_3$O(CH$_2$)nCH$_3$, O(CH$_2$)nNH$_2$ or O(CH$_2$)nCH$_3$ where n is from 1 to about 10; Ci to CIO lower alkyl, alkoxyalkoxy, substituted lower alkyl, alkaryl or aralkyl; CI; Br; CN; CF3; OCF3; O-, S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacokinetic/pharmacodynamic properties of an oligonucleotide and other substituents having similar properties. A preferred modification includes 2'-methoxyethoxy[2'-O—CH$_2$CH$_2$OCH$_3$, also known as 2'-O-(2-methoxyethyl)] (Martin et al., Helv. Chim. Acta, 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

In certain embodiments, miRNA agents comprise one or more base modifications and/or substitutions. As used herein, "unmodified" or "natural" bases include adenine (A), guanine (G), thymine (T), cytosine (C) and uracil (U). Modified bases include, without limitation, bases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic bases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions can also be included. These have been shown to increase nucleic acid duplex stability by 0.6-1.20C. (Sanghvi, Y. S., in Crooke, S. T. and Lebleu, B., eds., Antisense Research and Applications, CRC Press, Boca Raton, 1993, pp. 276-278). Further suitable modified bases are described in U.S. Pat. No. 3,687,808, as well as U.S. Pat. Nos. 4,845,205; 5,130,302; 5,134,066; 5,175, 273; 5, 367, 066; 5,432,272; 5,457,187; 5,459,255; 5,484,908; 5,502, 177; 5,525,711; 5,552,540; 5,587,469; 5,596,091; 5,614, 617; 5,750,692, and 5,681,941, each of which is herein incorporated by reference.

It is not necessary for all positions in a given oligonucleotide to be uniformly modified, and in fact more than one of the aforementioned modifications may be incorporated in a single oligonucleotide or even at a single nucleoside within an oligonucleotide.

In certain embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone.

Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In certain embodiments, the miRNA agent is linked (covalently or non-covalently) to one or more moieties or conjugates that enhance the activity, cellular distribution, or cellular uptake of the oligonucleotide. Such moieties include, without limitation, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937), each of which is herein incorporated by reference in its entirety. See also U.S. Pat. Nos. 4,828, 979; 4,948,882; 5,218,105; 5,525,465; 5,541,313; 5,545, 730; 5,552, 538; 5,578,717; 5,580,731; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762, 779; 4,789,737; 4,824,941; 4,835, 263; 4,876,335; 4,904,582; 4,958,013; 5,082, 830; 5,112, 963; 5,214,136; 5,082,830; 5,112,963; 5,214,136; 5, 245, 022; 5,254,469; 5,258,506; 5,262,536; 5,272,250; 5,292, 873; 5,317,098; 5,371,241; 5,391,723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928 and 5,688,941, each of which is herein incorporated by reference in its entirety.

In one particular embodiment, the miRNA agent is linked to (covalently or non-covalently) to a nucleic acid aptamer. Aptamers are synthetic oligonucleotides or peptide molecules that bind to a specific target molecule. Aptamers appropriate for use with the miRNA agents provided herein are described in U.S. Provisional Patent Application No. 61/695,477 filed Aug. 31, 2012 and incorporated by reference herein in its entirety.

Accordingly, in a first aspect, the invention provides an adipocyte-specific miRNA modulator composition comprising i) a targeting moiety that selectively binds to a cellular surface marker on an adipose target cell in a human and ii) a thermogenic miRNA modulator moiety, wherein the targeting moiety facilitates uptake of the miRNA modulatory moiety by the target cell such that the miRNA is capable of targeting a thermogenic pathway and upregulating thermogenesis in the target cell.

In one embodiment, the composition comprises an aptamir comprising an aptamer as the targeting moiety.

In certain embodiments, the aptamers used with the miRNAs disclosed herein specifically bind to cell surface marker proteins on an adipose tissue mesenchymal stem cell (ATMSC), white adipose tissue (WAT) adipocytes and brown adipose tissue (BAT) adipocytes. Cell surface markers for ATMSCs include CD9, CD10, CD13, CD29, CD36, CD44, CD49d, CD54, CD55, CD59, CD73, CD90, CD91, CD105, CD137, CD146, CD166, and HLA-ABC. Cell surface markers for WAT adipocytes include Adiponectin, Caveolin-1, Caveolin-2, CD36 (FAT), CLH-22 (Clathrin Heavy Chain Chr 22), FABP4 (Adipocyte protein 2, aP2), SLC27A1 (FATP1), SLC27A2 (FATP2), GLUT4 (Glucose Transporter 4), Perilipin 2 or Resistin. Cell surface markers for all adipocytes include Neprilysin (CD10), FAT (CD36), Thy-1 (CD90), Low density lipoprotein receptor-related protein 1 (LRP1 or CD91), Caveolin-1, Caveolin-2, Fatty acid binding protein 4 (FABP4), Cell surface glycoprotein MUC18 (CD146), Activated leukocyte cell adhesion molecule (CD166) and Natriuretic peptide receptor A (NPR1). According to other embodiments, the aptamers for use with the miRNAs disclosed herein can also specifically bind to markers of adipose tissue including adiponectin, leptin, resistin, FGF 17, FGF 19, BMP7, PYY, MetAP2, RBP4, endostatin, and angiostatin.

In certain embodiments, the aptamers are selected by the Cell-SELEX technology, which uses whole living cells as the target, whereby aptamers that recognize specific molecules in their native conformation in their natural environment on the surface of intact cells are selected by repeated amplification and binding to living cells. In this cell-based selection, specific cell surface molecules or even unknown membrane receptors can be directly targeted within their native environment, allowing a straightforward enrichment of cell-specific aptamers.

In certain exemplary embodiments, the miRNA modulator is combined with an aptamer to create an "AptamiR" composition. There are many different ways to combine an aptamer and miRNA analog(s) to create an aptamir. They include, for example, aptamer-miRNA analog chimeras, aptamer-splice-switching oligonucleotide chimeras, and aptamer conjugated to nanoparticles or liposomes containing the miRNA analog(s). "Escort Aptamers" may be inserted at the surface of functional polymers, liposomes, and nanoparticles, each of which can carry many miRNA analogs. For instance, the size of thioaptamer-conjugated liposomes is about 120 nm. Nanoparticle approaches have several functional advantages, including, for example, cellular uptake, the ability to cross membranes, and triggered nanoparticle disassembly.

In one embodiment, an aptamiR compostion comprises an aptamer that is directly linked or fused to a miRNA modulator. Such aptamiRs are entirely chemically synthesized, which provides more control over the composition of the conjugate. For instance, the stoichiometry (ratio of miRNA analog per aptamer) and site of attachment can be precisely defined. The linkage portion of the conjugate presents a plurality (2 or more) of nucleophilic and/or electrophilic moieties that serve as the reactive attachment point for the aptamers and miRNA analogs. In addition, the aptamir may further comprise a linker between the aptamer and the miRNA analog. In some embodiments, the linker is a polyalkylene glycol, particularly a polyethylene glycol. In other embodiments, the linker is a liposome, exosome, dendrimer, or comb polymer. Other linkers can mediate the conjugation between the aptamer and the miRNA analog, including a biotinstreptavidin bridge, or a ribonucleic acid. Exemplary non-covalent linkers include linkers formed by base pairing a single stranded portion or overhang of the miRNA moiety and a complementary single-stranded portion or overhang of the aptamer moiety.

In another particular embodiment, an aptamer is combined with a miRNA analog in the form of a liposome-based aptamiR. Liposomes are spherical nanostructures made of a lipid bilayer that can be loaded with pharmaceuticals, such as miRNAs. Furthermore, the liposome surface can be loaded with different substances, such as polyethylene glycol (extending their systemic half life) or molecular recognition moieties like aptamers for specific binding to targeted cells. For example, aptamer-modified liposomes have been developed, with each liposome displaying approximately 250 aptamers tethered to its surface to facilitate target binding. In a preferred embodiment, liposomes are created to encapsulate miRNA analog(s) and display at their surface aptamers that specifically bind with high affinity and specificity to molecules (e.g. lipid transporters) highly expressed at the surface of adipocytes and ATMSCs. The fusion of the liposomes with the targeted cells causes the release of the miRNA analog(s) into the cell cytoplasm, which then alter a specific intra-cellular pathway. Alternatively, stable thio-aptamers may be inserted at the surface of liposomes to guide delivery of the liposome miRNA analog(s) load to targeted ATMSCs and adipocytes.

In a further particular embodiment, an aptamer is combined with a miRNA analog in the form of a carrier-based aptamiR. Exemplary carriers include nanoparticles, liposomes or exosomes. Such carrier-based aptamiR compositions have the capability of delivering a cargo of multiple miRNA modulators to the target cell in a single carrier. To accomplish targeting and accumulation, the carriers are formulated to present the targeting moiety on their external surface so they can react/bind with selected cell surface antigens or receptors on the adipose target cell. As an example, carriers may be created to encapsulate miRNA modulators while displaying at their surface aptamers that specifically bind with high affinity and specificity to molecules (e.g. lipid transporters) highly expressed at the surface of adipocytes and ATMSCs. The internalized exosomes release inside the cell cytoplasm their miRNA analog(s) load, which alters a specific intra-cellular pathway.

In one embodiment, the carrier is an exosome. Exosomes, which originate from late endosomes, are naturally occurring nanoparticles that are specifically loaded with proteins, mRNAs, or miRNAs, and are secreted endogenously by cells. Exosomes are released from host cells, are not cytotoxic, and can transfer information to specific cells based on their composition and the substance in/on the exosome. Because exosomes are particles of approximately 20-100 nm in diameter, the exosomes evade clearance by the mononuclear phagocyte system (which clears circulating particles >100 nm in size), and are very efficiently delivered to target tissues.

Moreover, synthetic exosomes may offer several advantages over other carriers. For example, they may deliver their cargo directly into the cytosol, while their inertness avoids attack and clearance in the extracellular environment. The structural constituents of exosomes may include small molecules responsible for processes like signal transduction, membrane transport, antigen presentation, targeting/adhesion, among many others.

The miRNA agents must be sufficiently complementary to the target mRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of a miRNA agent is capable of hydrogen bonding with a base at the corresponding position of a target nucleic acid sequence, then the bases are considered to be complementary to each other at that position. In certain embodiments, 100% complementarity is not required. In other embodiments, 100% complementarity is required.

miRNA agents for use in the methods disclosed herein can be designed using routine methods. While the specific sequences of certain exemplary target nucleic acid sequences and miRNA agents are set forth herein, one of skill in the art will recognize that these serve to illustrate and describe particular embodiments within the scope of the present invention. Additional target segments are readily identifiable by one having ordinary skill in the art in view of this disclosure. Target segments of 5, 6, 7, 8, 9, 10 or more nucleotides in length comprising a stretch of at least five (5) consecutive nucleotides within the seed sequence, or immediately adjacent thereto, are considered to be suitable for targeting a gene. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the miRNA agent contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the miRNA agent contains about 5 to about 30 nucleotides). One having skill in the art armed with the sequences provided herein will be able, without undue experimentation, to identify further preferred regions to target using miRNA agents. Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target nucleic acid sequences), to give the desired effect.

In certain embodiments, miRNA agents used to practice this invention are expressed from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989), Coffin et al. (Retroviruses. (1997) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors can be delivered as described herein, and persist in target cells (e.g., stable transformants).

In certain embodiments, miRNA agents used to practice this invention are synthesized in vitro using chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68: 109; Beaucage (1981) Tetra. Lett. 22: 1859; U.S. Pat. No. 4,458,066, each of which is herein incorporated by reference in its entirety.

IV. Methods of Treatment

In one aspect, the invention provides a method of treating obesity in human subject. The method generally comprises administering to the human subject an effective amount of a miRNA agent that modulates activity of at least one thermogenic regulator, (e.g., a mitochondrial uncoupler, such as UCP1 and/or UCP2).

Such methods of treatment may be specifically tailored or modified, based on knowledge obtained from the field of pharmacogenomics. Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects. miRNA agents can be tested in an appropriate animal model e.g., an obesity model including ob/ob mice (Lindstrom P., ScientificWorld Journal, 7:666-685 (2007) and db/db mice (Sharma K et al., Am J Physiol Renal Physiol., 284(6): F1138-1144 (2003)). For example, a miRNA agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, a miRNA agent can be used in an animal model to determine the efficacy, toxicity, or side effects of treatment with such an agent. Alternatively, an agent can be used in an animal model to determine the mechanism of action of such an agent.

The disclosure also provides a method of inducing pre-adipocytes to differentiate into white adipocytes and white adipocytes into brown adipocytes, comprising administering to a population of pre-adipocytes one or more miRNAs selected from hsa-let-7a agomir, hsa-let-7a antagomir, hsa-miR-1 agomir, hsa-miR-1 antagomir, hsa-miR-19 agomir, hsa-miR-19b agomir, hsa-miR-19b antagomir, hsa-miR-30b agomir and hsa-miR-30b antagomir. In certain embodiments, the induction of pre-adipocytes to differentiate into adipocytes is greater than the differentiation of pre-adipocytes to adipocytes than when pre-adipocytes are exposed to 100 mM rosiglitazone for two days followed by maintenance medium. In certain embodiments, the adipocytes are brown adipocytes. In other embodiments, the adipocytes are white adipocytes.

The disclosure also provides a method for increasing insulin sensitivity in a subject in need thereof comprising administering the subject one or more miRNAs selected from the group consisting of hsa-let-7a agomir, hsa-let-7a antagomir, hsa-miR-1 agomir, hsa-miR-1 antagomir, hsa-miR-19 agomir, hsa-miR-19b agomir, hsa-miR-19b antagomir, hsa-miR-30b agomir and hsa-miR-30b antagomir. In certain embodiments, the subject is a mammal.

The disclosure also provides a method of causing fat loss in a subject in need thereof comprising administering the subject one or more miRNAs selected from the group consisting of hsa-let-7a antagomir, hsa-miR-1 agomir, hsa-miR-19b agomir and hsa-miR-30b agomir. In certain embodiments, the subject is a mammal. In other embodiments, the mammal is a human.

A miRNA agent modified for enhancing uptake into cells (e.g., adipose cells) can be administered at a unit dose less than about 15 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of miRNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular), an inhaled dose, or a topical application. Particularly preferred dosages are less than 2, 1, or 0.1 mg/kg of body weight.

Delivery of a miRNA agent directly to an organ or tissue (e.g., directly to adipose tissue) can be at a dosage on the order of about 0.00001 mg to about 3 mg per organ/tissue, or preferably about 0.0001-0.001 mg per organ/tissue, about 0.03-3.0 mg per organ/tissue, about 0.1-3.0 mg per organ/tissue or about 0.3-3.0 mg per organ/tissue. The dosage can be an amount effective to treat or prevent obesity or to increase insulin sensitivity. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In certain embodiment, a subject is administered an initial dose, and one or more maintenance doses of a miRNA agent. The maintenance dose or doses are generally lower than the initial dose, e.g., one-half less of the initial dose. A maintenance regimen can include treating the subject with a dose or doses ranging from 0.01 mg/kg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in condition, e.g., changes in percentage body fat. The dosage of the compound may either be increased in the event the patient does not respond significantly to current dosage levels, or the dose may be decreased if a decrease in body fat is observed, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., sub-cutaneous, intravenous, intraperitoneal, intracisternal or intracapsular), or reservoir may be advisable. In one embodiment, a pharmaceutical composition includes a plurality of miRNA agent species. In another embodiment, the miRNA agent species has sequences that are non-overlapping and non-adjacent to another species with respect to a naturally occurring target sequence. In another embodiment, the plurality of miRNA agent species is specific for different naturally occurring target genes. In another embodiment, the miRNA agent is allele specific. In another embodiment, the plurality of miRNA agent species target two or more SNP alleles (e.g., two, three, four, five, six, or more SNP alleles).

Following successful treatment, it may be desirable to have the patient undergo maintenance therapy to prevent the recurrence of the disease state, wherein the compound of the invention is administered in maintenance doses, ranging from 0.01 mg per kg to 100 mg per kg of body weight (see U.S. Pat. No. 6,107,094).

The concentration or amount of miRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a miRNA agent can include a single treatment or, preferably, can include a series of treatments. It will also be appreciated that the effective dosage of a miRNA agent for treatment may increase or decrease over the course of a particular treatment. Changes in dosage may result and become apparent from the results of diagnostic assays as described herein. For example, the subject can be monitored after administering a miRNA agent composition. Based on information from the monitoring, an additional amount of the miRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target mRNA (e.g., a thermogenic regulator). The transgenic animal can be deficient for the corresponding endogenous mRNA. In another embodiment, the composition for testing includes a miRNA agent that is complementary, at least in an internal region, to a sequence that is conserved between a nucleic acid sequence in the animal model and the target nucleic acid sequence in a human.

Several studies have reported successful mammalian dosing using miRNA agents. For example, Esau C, et al., Cell Metabolism, 3(2): 87-98 (2006) reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, nontoxic dose. Another study by Krutzfeldt J., et al., Nature, 438, 685-689 (2005), injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg per kg LNA-antimiR, leading to a long-lasting and reversible decrease in total plasma cholesterol without any evidence for LNA-associated toxicities or histopathological changes in the study animals.

In certain embodiments, miRNA agents used to practice this invention are administered through expression from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors can be delivered as described herein, and persist in target cells (e.g., stable transformants).

miRNA agents may be directly introduced into a cell (e.g., an adipocyte); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The miRNA agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The miRNA agents may be introduced along with other components e.g., compounds that enhance miRNA agent uptake by a cell.

In certain embodiments, the methods described herein include co-administration of miRNA agents with other drugs or pharmaceuticals, e.g., compositions for modulating thermogenesis, compositions for treating diabetes, compositions for treating obesity.

Compositions for modulating thermogenesis include beta-3 adrenergic agonists, thyroid hormones, PPARG agonists, leptin, adiponectin, and orexin.

V. Screening Methods

In another aspect, the invention provides a method of screening for a miRNA agent that modulates thermogenesis, decreases obesity, or improves insulin sensitivity. The method generally comprises the steps of: providing an indicator cell; contacting the indicator cell with a test miRNA agent; and determining the expression level and/or cellular activity of at least one thermogenic regulator in the indicator cell in the presence and absence of the miRNA agent, wherein a change in the activity of the thermogenic regulator in the presence of the test miRNA agent identifies the test miRNA agent as a miRNA agent that modulates thermogenesis, decreases obesity, or improves insulin sensitivity. In certain embodiments, the method involves determining an increase the expression level and/or activity of the thermogenic regulator (e.g., UCP1, UCP2). The indicator cell can be a mammalian cell. In certain embodiments, the mammalian cell is a human cell, which comprises at least a portion of a human genome.

Any thermogenic regulator can be assayed in the methods disclosed herein. Exemplary thermogenic regulators are set forth in Table 1. In a preferred embodiment, the thermogenic regulator is a mitochondrial uncoupling protein e.g., UCP1 and/or UCP2.

Any cell in which the activity of a thermogenic regulator can be measured is suitable for use in the methods disclosed herein. Exemplary cells include pre-adipocytes, adipocytes, adipose tissue derived mesenchymal stem cells, hepatocytes, myocytes, or precursors thereof.

Any activity of a thermogenic regulator can be assayed, including, without limitation, mRNA expression level, protein expression level or mitochondrial uncoupling activity of the thermogenic regulator. Methods for determining such activities are well known in the art.

Any miRNA agent can be screened, including, without limitation, miRNA, agomirs, antagomirs, aptamirs, miR-masks, miRNA sponges, siRNA (single- or double-stranded), shRNA, antisense oligonucleotides, ribozymes, or other oligonucleotide mimetics which hybridize to at least a portion of a target nucleic acid and modulate its function.

VI. Pharmaceutical Compositions

In one aspect, the methods disclosed herein can include the administration of pharmaceutical compositions and formulations comprising miRNA agents capable of modulating the activity of at least one thermogenic modulator.

In certain embodiments, the compositions are formulated with a pharmaceutically acceptable carrier. The pharmaceutical compositions and formulations can be administered parenterally, topically, by direct administration into the gastrointestinal tract (e.g., orally or rectally), or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The miRNA agents can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of the invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragées, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragée cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxy-propylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In certain embodiments, oil-based pharmaceuticals are used for administration of the miRNA agents. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

In certain embodiments, the pharmaceutical compositions and formulations are in the form of oil-in-water emulsions. The oily phase can be a vegetable oil or a mineral oil, described above, or a mixture of these. Suitable emulsifying agents include naturally-occurring gums, such as gum *acacia* and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In certain embodiments, the pharmaceutical compositions and formulations are administered by in intranasal, intraocular and intravaginal routes including suppositories, insufflation, powders and aerosol formulations (for examples of steroid inhalants, see e.g., Rohatagi (1995) J. Clin. Pharmacol. 35: 1 187-1193; Tjwa (1995) Ann. Allergy Asthma Immunol. 75: 107-1 11). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In certain embodiments, the pharmaceutical compositions and formulations are delivered transdermally, by a topical route, formulated as applicator sticks, solutions, suspensions, emulsions, gels, creams, ointments, pastes, jellies, paints, powders, and aerosols.

In certain embodiments, the pharmaceutical compositions and formulations are delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In certain embodiments, the pharmaceutical compositions and formulations are parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In certain embodiments, the pharmaceutical compounds and formulations are lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL nucleic acid, about 15 mg/mL sucrose, about 19 mg/mL NaCl, and a sodium citrate buffer having a pH greater than 5.5 but less than 6.5. See, e.g., U.S. 20040028670.

In certain embodiments, the pharmaceutical compositions and formulations are delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46: 1576-1587.

The formulations of the invention can be administered for prophylactic and/or therapeutic treatments. In certain embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in certain embodiments, pharmaceutical compositions of the invention are administered in an amount sufficient to treat obesity in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84: 1 144-1 146; Rohatagi (1995) Pharmazie 50:610-613; Brophy (1983) Eur. J. Clin. Pharmacol. 24: 103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate. Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., treat obesity.

In certain embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

VII. Exemplification

The present invention is further illustrated by the following examples which should not be construed as further limiting. The contents of Sequence Listing, figures and all references, patents and published patent applications cited throughout this application are expressly incorporated herein by reference.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Example 1

In-Silico Analysis of Thermogenic Regulators

Eighty three proteins that are involved in regulation of thermogenesis were selected based upon a critical assessment and review of the available scientific information and our own experimental data. These proteins were categorized as activators or repressors of thermogenesis based upon their functions. These thermogenic regulator proteins are set forth in Table 1.

TABLE 1

Thermogenicregulator proteins.

| | Name | Entrez Gene ID | Ensembl Gene ID |
|---|---|---|---|
| | Activators | | |
| 1 | ALDH1A1 | 216 | ENSG00000165092 |
| 2 | ANP (NPPA) | 4878 | ENSG00000175206 |
| 3 | AZGP1 | 563 | ENSG00000160862 |
| 4 | BMP7 | 655 | ENSG00000101144 |
| 5 | BMP8b | 656 | ENSG00000116985 |
| 6 | CEBPA | 1050 | ENSG00000245848 |
| 7 | CEBPB | 1051 | ENSG00000172216 |
| 8 | CEBPD | 1052 | ENSG00000221869 |
| 9 | CIDEA | 1149 | ENSG00000176194 |
| 10 | COX7A1 | 1346 | ENSG00000161281 |
| 11 | CRAT | 1384 | ENSG00000095321 |
| 12 | CREB1 | 1385 | ENSG00000118260 |
| 13 | CREBBP | 1387 | ENSG00000005339 |
| 14 | CTBP1 | 1487 | ENSG00000159692 |
| 15 | CTBP2 | 1488 | ENSG00000175029 |
| 16 | DIO2 | 1734 | ENSG00000211448 |
| 17 | ELOVL3 | 83401 | ENSG00000119915 |
| 18 | FGF16 | 8823 | ENSG00000196468 |
| 19 | FGF19 | 9965 | ENSG00000162344 |
| 20 | FGF21 | 26291 | ENSG00000105550 |
| 21 | FNDC5 | 252995 | ENSG00000160097 |
| 22 | FOXC2 | 2303 | ENSG00000176692 |
| 23 | GDF3 | 9573 | ENSG00000184344 |

TABLE 1-continued

Thermogenicregulator proteins.

| | Name | Entrez Gene ID | Ensembl Gene ID |
|---|---|---|---|
| 24 | HCRT (OREXIN) | 3060 | ENSG00000161610 |
| 25 | HOXC8 | 3224 | ENSG00000037965 |
| 26 | INSR | 3643 | ENSG00000171105 |
| 27 | IRS1 | 3667 | ENSG00000169783 |
| 28 | KDM3A (JMJD1A) | 55818 | ENSG00000115548 |
| 29 | KLF5 | 688 | ENSG00000102554 |
| 30 | KLF11 | 8462 | ENSG00000172059 |
| 31 | KLF15 | 28999 | ENSG00000163884 |
| 32 | LRP6 | 4040 | ENSG00000070018 |
| 33 | MAPK14 | 1432 | ENSG00000112062 |
| 34 | MED13 | 9969 | ENSG00000108510 |
| 35 | NCOA1 | 8648 | ENSG00000084676 |
| 36 | NCOA2 | 10499 | ENSG00000140396 |
| 37 | NCOA3 | 8202 | ENSG00000124151 |
| 38 | NR4A3 | 8013 | ENSG00000119508 |
| 39 | NRF1 | 4899 | ENSG00000106459 |
| 40 | PLAC8 | 51316 | ENSG00000145287 |
| 41 | PPARA | 5465 | ENSG00000186951 |
| 42 | PPARD | 5467 | ENSG00000112033 |
| 43 | PPARG | 5468 | ENSG00000132170 |
| 44 | PPARGC1A | 10891 | ENSG00000109819 |
| 45 | PPARGC1B | 133522 | ENSG00000155846 |
| 46 | PRDM16 | 63976 | ENSG00000142611 |
| 47 | PRDX3 | 10935 | ENSG00000165672 |
| 48 | PRKAA1 (AMPKA1) | 5562 | ENSG00000132356 |
| 49 | PRKAA2 (AMPKA2) | 5563 | ENSG00000162409 |
| 50 | PRKACA | 5566 | ENSG00000072062 |
| 51 | PRKACB | 5567 | ENSG00000142875 |
| 52 | PRKAR1A | 5573 | ENSG00000108946 |
| 53 | SIRT1 | 23411 | ENSG00000096717 |
| 54 | SIRT3 | 23410 | ENSG00000142082 |
| 55 | SLC27A2 (FATP2) | 11001 | ENSG00000140284 |
| 56 | SREBF1 | 6720 | ENSG00000072310 |
| 58 | SREBF2 | 6721 | ENSG00000198911 |
| 58 | STAT5A | 6776 | ENSG00000126561 |
| 59 | TRPM8 | 79054 | ENSG00000144481 |
| 60 | UCP1 (SLC25A7) | 7350 | ENSG00000109424 |
| 61 | UCP2 (SLC25A8) | 7351 | ENSG00000175567 |
| 62 | UCP3 (SLC25A9) | 7352 | ENSG00000175564 |

Repressors

| | | | |
|---|---|---|---|
| 1 | ATG7 | 10533 | ENSG00000197548 |
| 2 | BMP2 | 650 | ENSG00000125845 |
| 3 | BMP4 | 652 | ENSG00000125378 |
| 4 | CIDEC | 63924 | ENSG00000187288 |
| 5 | CTNNB1 | 1499 | ENSG00000168036 |
| 6 | DLK1 (Pref-1) | 8788 | ENSG00000185559 |
| 7 | E2F4 (p107) | 1874 | ENSG00000205250 |
| 8 | EIF4EBP1 | 1978 | ENSG00000187840 |
| 9 | ESRRA (NR3B1) | 2101 | ENSG00000173153 |
| 10 | IKBKE | 9641 | ENSG00000143466 |
| 11 | NR1H3 (LXRA) | 10062 | ENSG00000025434 |
| 12 | NRIP1 (RIP140) | 8204 | ENSG00000180530 |
| 13 | RB1 (pRb) | 5925 | ENSG00000139687 |
| 14 | NR0B2 (SHP) | 8431 | ENSG00000131910 |
| 15 | RPS6KB1 | 6198 | ENSG00000108443 |
| 16 | RUNX1T1 | 862 | ENSG00000079102 |
| 17 | RUNX2 | 860 | ENSG00000124813 |
| 18 | TNFRSF1A | 7132 | ENSG00000067182 |
| 19 | TWIST1 | 7291 | ENSG00000122691 |

TABLE 1-continued

Thermogenicregulator proteins.

| | Name | Entrez Gene ID | Ensembl Gene ID |
|---|---|---|---|
| 20 | WNT5A | 7474 | ENSG00000114251 |
| 21 | WNT10B | 7480 | ENSG00000169884 |

The STRING 9.0 database of known and predicted protein interactions (string-db.org/) was used to test these 83 candidate molecules. The interactions include direct (physical) and indirect (functional) associations; they are derived from four sources: genomic context; high-throughput experiments; co-expression; and previous knowledge. STRING quantitatively integrates interaction data from these sources for a large number of organisms, and transfers information between these organisms where applicable. The database currently covers 5,214,234 proteins from 1,133 organisms. As an example, the relationships between the 83 thermogenic regulator molecules were centered around UCP1, and molecules having direct and indirect connections with UCP1 could be distinguished using the highest confidence score of 0.90. This relationship is set forth in schematic form in FIG. 1A. From this analysis, it was discovered that nine molecules (CEBPB, CIDEA, KDM3A, NRIP1, PRDM16, PPARG, PPARGC1A, PPKAA2, and UCP2) are directly linked to UCP1, whereas many more molecules are connected to UCP1 on a second or higher degree order.

Figure 1B:
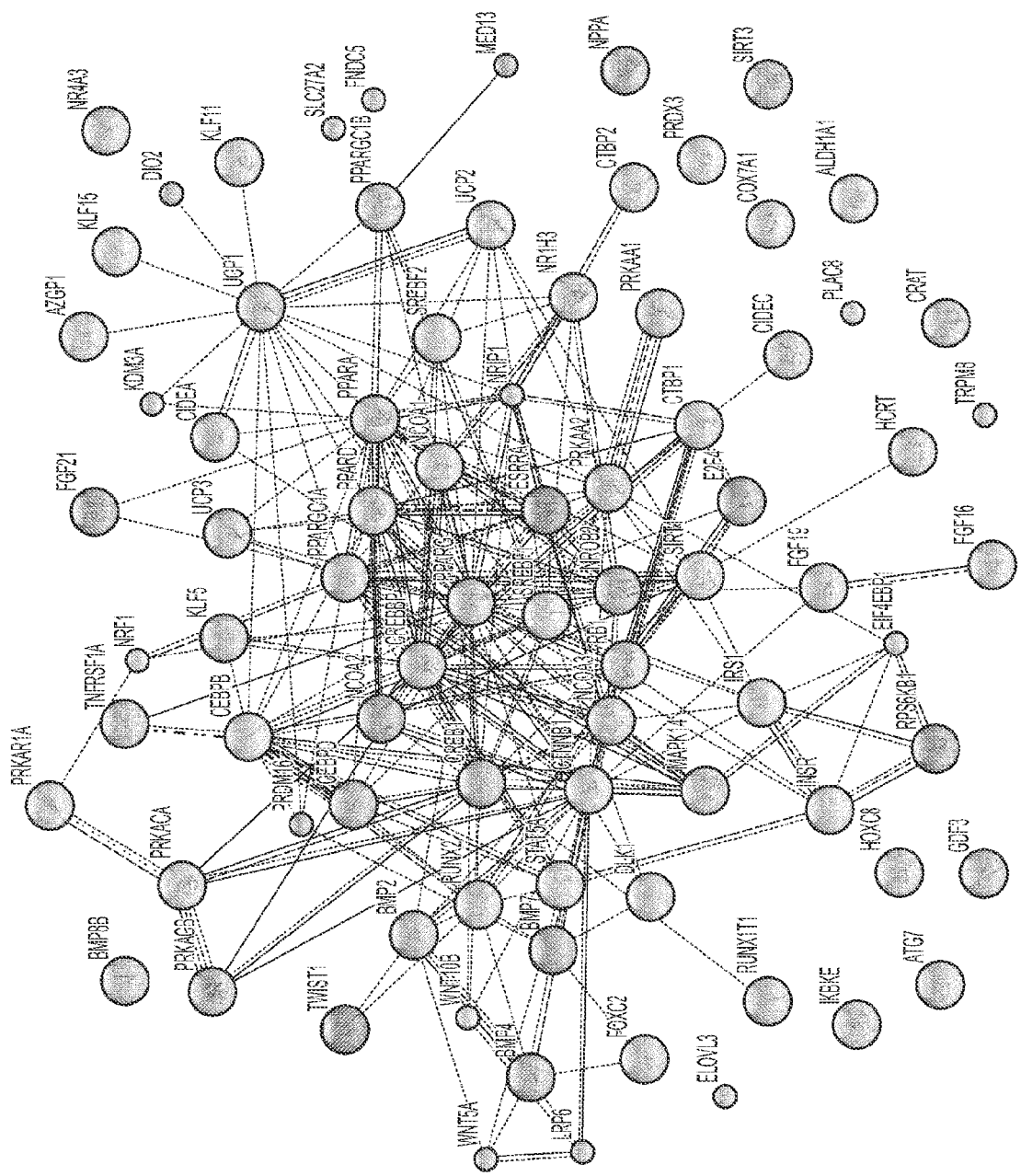

When the degree of confidence was set to high with a score of 0.70, eight additional proteins were found to be directly linked to UCP1 (AZGP1, DIO2, KLF11, KLF15, NR1H3, PPARA, PPARD, and PPARGC1B), FIG. 1B.

Figure 2A:
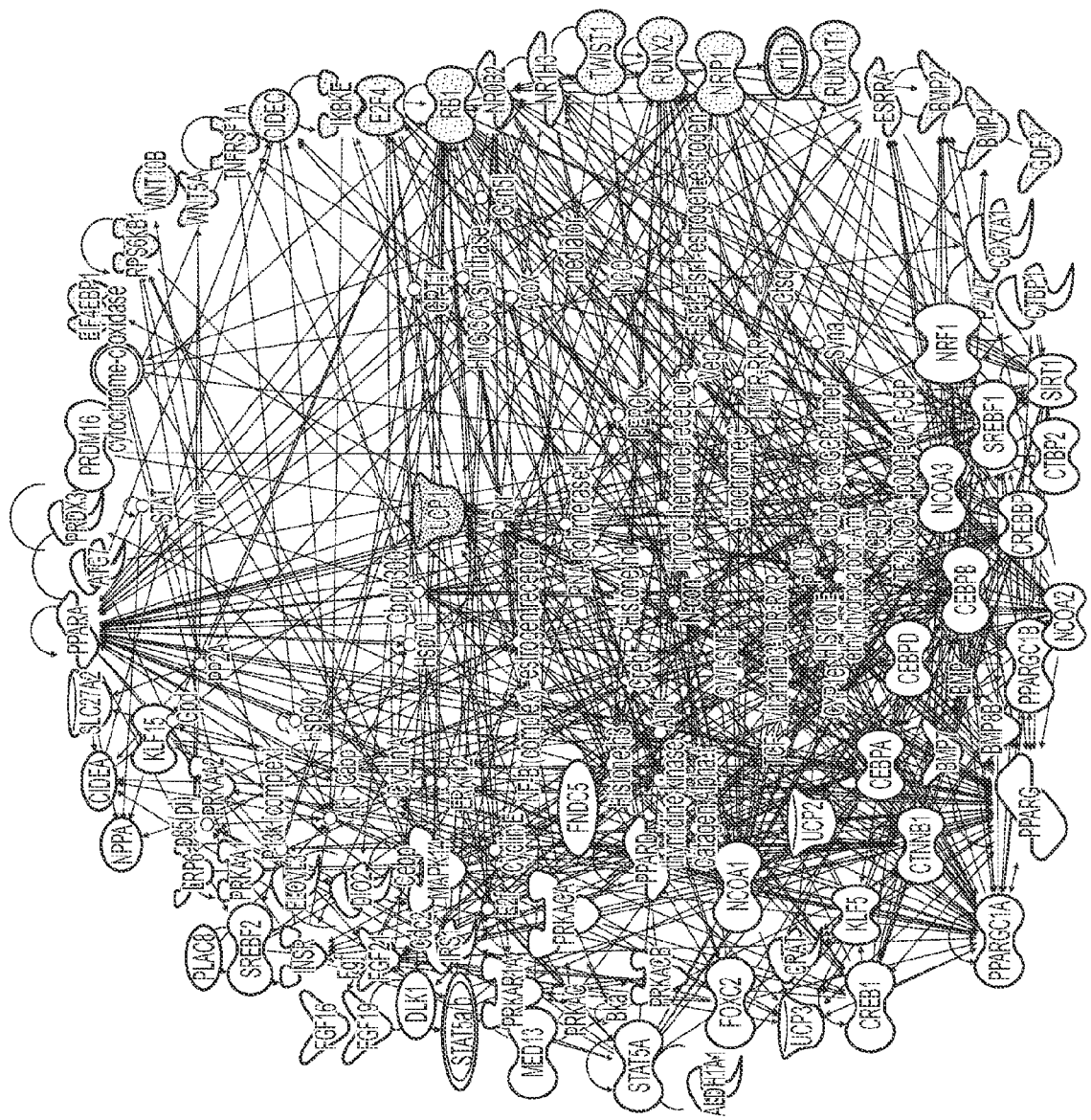
FIG. 2A is a schematic representation of the interaction of 83 thermogenic regulators determined using the Ingenuity Pathway Analysis Software program.
Figure 2B:
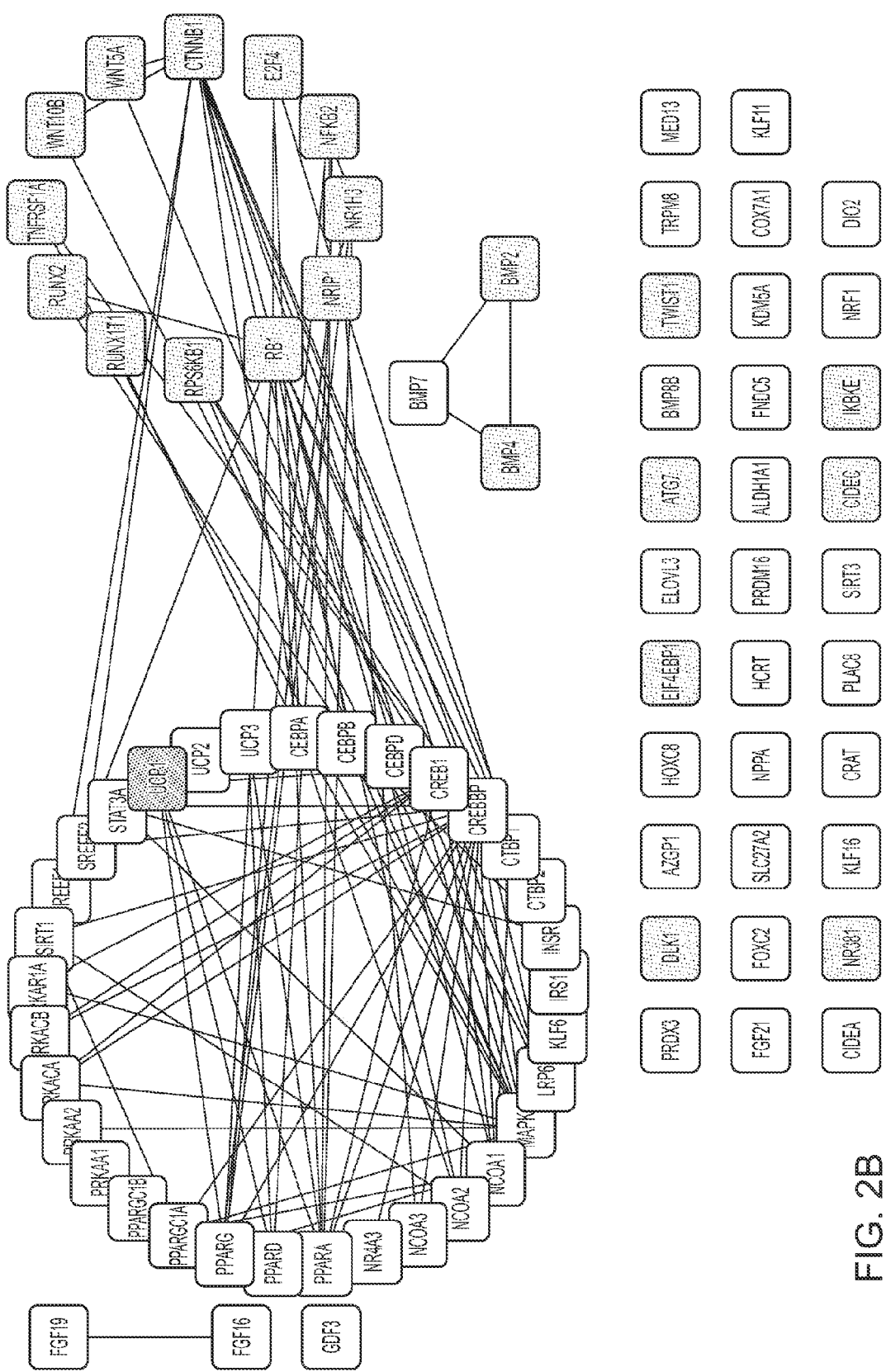
FIG. 2B is a schematic representation of the interaction of 83 thermogenic regulators determined using the Reactome Functional Interaction Network program.

Similarly, the interactions among these 83 thermogenic regulator molecules were independently assessed using other software programs. The interactions predicted by the Ingenuity Pathway Analysis (IPA) Software program (www.ingenuity.com) are shown in FIG. 2A (UCP1 in yellow, activators in green and repressors in purple). The interactions predicted by the Reactome Functional Interaction (Reactome IF) Software program (http://wiki.reactome.org) are shown in FIG. 2B (UCP1 in yellow, activators in green and repressors in purple). The IPA and Reactome IF networks differ from the one set forth in FIG. 1, obtained with the STRING program. It is not surprising that the results of these algorithms are different because they rely on different predefined parameters, sources of information and selection criteria.

Example 2

In-Silico Selection of Relevant miRNA Targets

To select thermogenic regulators suitable as targets for miRNA agents, several internet-based resources were employed to match miRNAs and their targets (the "micronome"). Exemplary tools are set forth in Table 2A.

TABLE 2A

Exemplary bioinformatics tools used to select miRNAs and their targets.

| Field & Name | Function | Web Address |
|---|---|---|
| Integrated Data Mining (8) | | |
| BioCarta | Catalogs and summarizes important resources providing information for over 120,000 genes from multiple species. Find both classical | biocarta.com |

TABLE 2A-continued

Exemplary bioinformatics tools used to select miRNAs and their targets.

| Field & Name | Function | Web Address |
| --- | --- | --- |
| | pathways as well as current suggestions for new pathways | |
| Database for Annotation, Visualization and Integrated Discovery (DAVID) | Integrated biological knowledgebase and analytic tools aimed at systematically extracting biological meaning from large gene/protein lists | david.abcc.ncifcrf.gov/homejsp |
| GeneOntology | Standardizing the representation of gene and gene product attributes across species and databases | geneontology.org/ |
| Gene Set Enrichment Analysis (GSEA) | Computational method that determines whether an a priori defined set of genes shows statistically significant, concordant differences between two biological states (e.g. phenotypes). | broadinstitute.org/gsea/index.jsp |
| KEGG | Kyoto Encyclopedia of Genes and Genomes | genome.jp/kegg/ |
| PubGene | Connecting up-to-date information on genes and related terms | pubgene.org/ |
| Reactome | An open-source, open access, manually curated and peer-reviewed pathway database. | reactome.org/ReactomeGWT/entry point.html |
| STRING | Database of known and predicted protein interactions; direct (physical) and indirect (functional) associations | string-db.org/ |
| miRNA Mining & Mapping (8) | | |
| deepBase | Platform for annotating and discovering small and long ncRNAs (microRNAs, siRNAs, piRNAs . . . ) | deepbase.sysu.edu.cn/ |
| Human microRNA disease database (HMDD) | Contains miRNA names, disease names, dysfunction evidences, and the literature PubMed ID | 202.38.126.151/hmdd/mirna/md/ |
| miRBase V19 | Searchable database of published miRNA sequences and annotation | mirbase.org/ |
| miRGen 2.0 | Database of microRNA genomic information and regulation | diana.cslab.ece.ntua.gr/mirgen/ |
| miRNAMap | Experimentally verified microRNAs Shows tissue expression profile | mirnamap.mbc.nctu.edu.tw/ |
| miRSel | Automated extraction of associations between microRNAs and genes from the biomedical literature | services.bio.ifi.lmu.de/mirsel/ |
| miRStart | Database of human microRNA TSSs (transcription start sites) | mirstart.mbc.nctu.edu.tw/home.php |
| miR2Disease | A manually curated database providing a comprehensive resource of miRNA deregulation in various human diseases | mir2disease.org |
| miRNA Targets & Expression (21) | | |
| DIANA-microT 3.0 | Algorithm based on several parameters calculated individually for each microRNA and it combines conserved and non-conserved microRNA recognition elements into a final prediction score. | diana.cslab.ece.ntua.gr/microT/ |
| DIANA-mirExTra | Algorithm that can identify microRNA effects to the Expression levels of protein-coding transcripts, based on the frequency of six nucleotide long motifs in the 3'UTR sequences of genes. | diana.cslab.ece.ntua.gr/hexamers/ |

TABLE 2A-continued

Exemplary bioinformatics tools used to select miRNAs and their targets.

| Field & Name | Function | Web Address |
|---|---|---|
| GSEA Molecular Signatures Database v3.0 | Gene sets that contain genes sharing a 3'-UTR microRNA binding motif (n = 221) | broadinstitute.org/gsea/index.jsp |
| MicroCosm Targets | Computationally predicted targets for microRNAs across many species. The miRNA sequences are obtained from the miRBase Sequence database and most genomic sequence from EnsEMBL | ebi.ac.uk/enright-srv/microcosm/cgi-bin/targets/v5/download.pl |
| MicroInspector | A scanning software for detection of miRNA binding sites using hybridization temperature and free energy cut-off value | bioinfo.uni-plovdiv.bg/microinspector/ |
| microRNA.org (ex. miRanda) | Predicted microRNA targets & target downregulation scores. Experimentally observed expression patterns. | microrna.org/microrna/home.do |
| miRDB | Online database for miRNA target prediction and functional annotations in animals by a new bioinformatics tool analyzing thousands of genes impacted by miRNAs with an SVM learning machine. | mirdb.org/miRDB/ |
| miRTarBase | Has accumulated more than three thousand miRNA-target interactions (MTIs), which are collected by manually surveying pertinent literature | mirtarbase.mbc.nctu.edu.tw/index.html |
| miRTar.Human | An integrated web server for identifying miRNA-target interactions. Identifies the biological functions and regulatory relationships between a group of known/putative miRNAs and protein coding genes. It also provides perspective of information on the miRNA targets on alternatively spliced transcripts in human | mirtar.mbc.nctu.edu.tw/human/download.php |
| miRvestigator | Takes as input a list of co-expressed genes and will return the most likely miRNA regulating these genes. It does this by searching for an over-represented sequence motif in the 3'UTRs of the genes using Weeder and then comparing this to the miRNA seed sequences in miRBase using our custom built miRvestigator hidden Markov model (HMM) | mirvestigator.systemsbiology.net/ |
| mirZ | A server that provides statistical analysis and data mining tools operating on up-to-date databases of sequencing-based miRNA expression profiles and of predicted miRNA target sites | mirz.unibas.ch/ElMMo2/ |
| MultiMiTar | A Support Vector Machine (SVM) based classifier integrated with a multiobjective metaheuristic based feature selection technique. | isical.ac.in/~bioinfo_miu/multimitar.htm |
| PhenomiR | Provides information about differentially regulated miRNA expression in diseases and other biological processes. The content of PhenomiR is completely generated by manual curation of experienced annotators. Data was extracted from more than 365 scientific articles and resulted in more than 632 database entries as of February 2011 | mips.helmholtz-muenchen.de/phenomir/index.gsp |
| PicTar | Algorithm for the identification of microRNA targets. This searchable website provides details (3'UTR alignments with predicted sites, | pictar.mdc-berlin.de/ |

TABLE 2A-continued

Exemplary bioinformatics tools used to select miRNAs and their targets.

| Field & Name | Function | Web Address |
|---|---|---|
| | links to various public databases, etc.) | |
| PITA | Incorporates the role of target-site accessibility, as determined by base-pairing interactions within the mRNA, in microRNA target recognition. | genie.weizmann.ac.il/pubs/mir07/mir07_data.html |
| RepTar | Database of miRNA target predictions, based on an algorithm that is independent of evolutionary conservation considerations and is not limited to seed pairing sites. | bioinformatics.ekmd.huji.ac.il/reptar/ |
| RNAhybrid | A tool for finding the minimum free energy hybridisation of a long and a short RNA. The hybridisation is performed in a kind of domain mode, ie. the short sequence is hybridised to the best fitting part of the long one. | bibiserv.techfak.uni-bielefeld.de/rnahybrid/ |
| RNA22 | First finds putative microRNA binding sites in the sequence of interest, then identifies the targeted microRNA (IBM). | cbcsrv.watson.ibm.com/rna22.html |
| Sylamer | A system for finding significantly over or under-represented words in sequences according to a sorted gene list. It is used to find significant enrichment or depletion of microRNA or siRNA seed sequences from microarray expression data. | ebi.ac.uk/enright/sylamer/ |
| TarBase 6.0 | Database of experimentally supported microRNA targets. | diana.cslab.ece.ntua.gr/DianaToolsNew/index.php?r=tarbase/index |
| TargetScanHuman 6.2 | Predicts biological targets of miRNAs by searching for the presence of conserved 8mer and 7mer sites that match the seed region of each miRNA, using 6 features: site-type contribution, 3' pairing contribution, local AU contribution, position contribution, TA (target site abundance) contribution, SPS (seed-pairing stability) contribution. | targetscan.org/ |
| Integrated miRNA Targets & Expression Tools (13) | | |
| GOmir | Integrates the predicted target genes from TargetScan, miRanda, RNAhybrid and PicTar computational tools and also providing a full gene description and functional analysis for each target gene. | bioacademy.gr/bioinformatics/projects/GOmir/ |
| MAMI (MetaMiR:Target Inference) | Compiles predictions from five different miRNA target prediction algorithms (TargetScanS, miRanda, microT, miRtarget, and pieTar). | mami.med.harvard.edu/ |
| mimiRNA | Allows the visualization of miRNA expression levels in 188 different tissue or cell types, provides a robust statistical method for discovering functional interactions between miRNAs and mRNA genes. Uses a novel sample classification algorithm, ExParser, that allows mimiRNA to automatically classify imported experiments with minimal curation | mimirna.centenary.org.au/mep/formulaire.html |

TABLE 2A-continued

Exemplary bioinformatics tools used to select miRNAs and their targets.

| Field & Name | Function | Web Address |
| --- | --- | --- |
| MMIA (microRNA and mRNA Integrated Analysis) | Integrates the predicted target genes from TargetScan, PicTar, PITA | 147.46.15.115/MMIA/index.html |
| mirDIP | Integrates twelve microRNA prediction datasets from six microRNA prediction databases, allowing users to customize their microRNA target searches. Combining microRNA predictions allows users to obtain more robust target predictions, giving you more confidence in your microRNA targets. | ophid.utoronto.ca/mirDIP/ |
| miRGator V3.0 | Integrated database of miRNA-associated gene expression, target prediction, disease association and genomic annotation, using mirBridge, miRanda, PITA and TargetScan. Now includes 73 deep sequencing datasets on human samples from GEO, SRA, and TCGA archives | mirgator.kobic.re.kr |
| miRecords | Integrates the predictions form DIANA-microT, MicroInspector, miRanda, mirTarget2, miTarget, NBmiRTar, PicTar, PITA, rna22, RNAhybrid, TargetScan/TargetScanS | mirecords.biolead.org/ |
| MIRNA-DISTILLER | Automatically extracts miRNAs predicted to interact with a given set of target genes from several selectable public databases. | ikp-stuttgart.de/content/languagel/html/10415.asp |
| MiRonTop | Online java web tool that integrates DNA microarrays or high-throughput sequencing data to identify the potential implication of miRNAs on a specific biological system. It allows a rapid characterization of the most pertinent mRNA targets according to several existing miRNA target prediction approaches (Mirbase, miRanda, exact seed, TargetScan or PicTar) | microarray.fr:8080/miRonTop/index |
| miRror | Integrates predictions from a dozen of miRNA resources that are based on complementary algorithms into a unified statistical framework. | proto.cs.huji.ac.il/mirror |
| miRSystem | Database which integrates 7 miRNA target gene prediction programs: DIANA, miRanda, miRBridge, PicTar, PITA, rna22, and TargetScan. | mirsystem.cgm.ntu.edu.tw/ |
| miRWalk | Comprehensive database that provides information on miRNA on their predicted as well as validated binding sites on their target genes. | ma.uni-heidelberg.de/apps/zmf/mirwalk/index.html |
| StarBase | Public platform for decoding microRNA-target and protein-RNA interaction maps from CLIP-Seq (HITS-CLIP, PAR-CLIP) and degradome sequencing (Degradome-Seq, PARE) data. | starbase.sysu.edu.cn/index.php |
| miRNA Secondary Structure (5) | | |
| OligoWalk | An online server calculating thermodynamic features of sense-antisense hybridization. It predicts the free energy changes of oligonucleotides binding to a target RNA. It can be used to design efficient siRNA targeting a given mRNA sequence. | rna.urmc.rochester.edu/cgi-bin/server_exe/oligowalk/oligowalk_form.cgi |

TABLE 2A-continued

Exemplary bioinformatics tools used to select miRNAs and their targets.

| Field & Name | Function | Web Address |
|---|---|---|
| PicTar RNA Studio | The BiBiSery Tool section offers bioinformatics tools for a large variety of tasks, including RNA studio | www.pictar.org/ |
| RNA2D | Suite of programs for discovering structural features in RNAs. | protein3d.ncifcrf.gov/shuyun/rna2d.html |
| Vienna RNA Package | RNA Secondary Structure Prediction and Comparison. | tbi.univie.ac.at/ivo/RNA/ |
| Whitehead siRNA algorithm | Helps select siRNAs to knock down your gene of interest | jura.wi.mit.edu/bioc/siRNAext/ |
| Network Searches & Analyses (8) | | |
| ARIADNE Pathway Studio | Pathway analysis software helping to: Interpret gene expression and other high throughput data Build, expand and analyze pathways Find relationships among genes, proteins, cell processes and diseases Draw publication-quality diagrams | ariadnegenomics.com/products/pathway-studio/ |
| Cytoscape | Open source bioinformatics software platform for visualizing molecular interaction networks and biological pathways and integrating these networks with annotations, gene expression profiles and other state data. | cytoscape.org/ |
| Database for Annotation, Visualization and Integrated Discovery (DAVID) | Integrated biological knowledgebase and analytic tools aimed at systematically extracting biological meaning from large gene/protein lists | david.abcc.ncifcrf.gov/home.jsp |
| Genego MetaCore | An integrated knowledge database and software suite for pathway analysis of experimental data and gene lists based on a proprietary manually curated database of human protein-protein, protein-DNA and protein compound interactions, metabolic and signaling pathways. | genego.com/metacore.php |
| Ingenuity Systems IPA (Ingenuity Pathway Analysis) | To understand biology at multiple levels by integrating data from a variety of experimental platforms and providing insight into the molecular and chemical interactions, cellular phenotypes, and disease processes. | ingenuity.com/products/IPA/microRNA.html |
| MATISSE (Module Analysis via Topology of Interactions and Similarity SEts) | A program for detection of functional modules using interaction networks and expression data | acgt.cs.tau.ac.il/matisse/ |
| MIR@NT@N | a framework integrating transcription factors, microRNAs and their targets to identify sub-network motifs in a meta-regulation network model | mironton.uni.lu |
| NAViGaTOR | Network Analysis, Visualization, & Graphing TORonto is a software package for visualizing and analyzing protein-protein interaction networks. | ophid.utoronto.ca/navigator/index.html |
| Molecular Visualization (4) | | |
| Foldit | Multiplayer online game that enlists players worldwide to solve difficult protein-structure prediction problems. | fold.it/portal/info/science |

TABLE 2A-continued

Exemplary bioinformatics tools used to select miRNAs and their targets.

| Field & Name | Function | Web Address |
|---|---|---|
| PyMOL | A user-sponsored molecular visualization system on an open-source foundation. | .pymol.org/ |
| Qlucore Omics Explorer | To examine and analyze data from miRNA experiments. | qlucore.com/ProdOverviewmiRNA.aspx |
| WebMol | Displays and analyzes structural information contained in the Brookhaven Protein Data Bank (PDB). It can be run as an applet or as a stand-alone application. | cmpharm.ucsf.edu/cgi-bin/webmol.pl |
| Information Integration (1) | | |
| TIBCO Spotfire | Comprehensive software platform that allows customers to analyze data, using predictive and complex statistics in the analysis | |

Specifically, these tools were used to perform: 1) Integrated Data Mining (8 tools); 2) miRNA Mining and Mapping (6 tools); 3) miRNA Target Targets and Expression (21 tools); 4) Integrated miRNA Targets and Expression (13 tools); 5) miRNA Secondary Structure Prediction and Comparison (5 tools); 6) Network Searches and Analyses (8 tools); 7) Molecular Visualization (4 tools); and 8) Information Integration and Exploitation (1 tool).

A single gene target can be controlled by several miRNAs whereas a single miRNA can control several gene targets. Sophisticated bioinformatics resources have been developed to select the most relevant miRNAs to target diseases (Gallagher I J, et al. *Genome medicine.* 2010; Fujiki K, et al. *BMC Biol.* 2009; Okada Y, et al., *J Androl.* 2010; Hao T, et al., *Mol Biosyst.* 2012; Hao T, et al., *Mol Biosyst.* 2012). However, the results of these algorithms are acutely dependent on predefined parameters and the degree of convergence between these algorithms is rather limited. Therefore, there is a need to develop better performing bioinformatics tools with improved sensitivity, specificity and selectivity for the identification of miRNA/target relationships.

The interactions between miRNAs and their targets go beyond the original description of miRNAs as post-transcriptional regulators whose seed region of the driver strand (5' bases 2-7) bind to complementary sequences in the 3' UTR region of target mRNAs, usually resulting in translational repression or target degradation and gene silencing. The interactions can also involve various regions of the driver or passenger strands of the miRNAs as well as the 5'UTR, promoter, and coding regions of the mRNAs.

Upon analysis of the available data, it was decided to favor pathway-specific miRNAs which target multiple genes within one discrete signaling pathway, rather than universal miRNAs which are involved in many signaling pathways, functions or processes. Using 34 publicly available Internet tools predicting miRNA targets, specific huma miRNAs were searched for that could potentially modulate several targets among the 83 thermogenic regulator molecules (which include 36 Transcription Factors) selected in Example 1.

Several paradigms were considered:

a) A One microRNA-Multiple mRNAs Pathway-Specific Paradigm.

A. The methylation state of histones can be dynamically regulated by histone methyltransferases and demethylases. The human lysine (K)-specific demethylase 3A (KDM3A) is critically important in regulating the expression of metabolic genes. Its loss of function results in obesity and hyperlipidemia in mice. Beta-adrenergic stimulation of KDM3A binding to the PPAR responsive element (PPRE) of the UCP1 gene not only decreases levels of H3K9me2 (dimethylation of lysine 9 of histone H3) at the PPRE, but also facilitates the recruitment of PPARG and RXRA and their co-activators PPARGC1A, CREBBP and NCOA1 to the PPRE. The interrogation of the TargetScan Human database (release 6.0) revealed that the human KDM3A 3' UTR 29-35 region is a conserved target for hsa-miR-22. Several other miRNA Targets Databases also confirmed this match between hsa-miR-22 and KDM3A. Therefore, increased production of the demethylase KDM3A by an hsa-miR-22 antagomir should lead to demethylation of the UCP1 gene promoter region, thus facilitating binding of several regulatory elements and increased UCP1 production.

In addition, we used the 34 miRNA Targets and Expression tools (Table 2B) to identify the mRNA targets of a given miRNA.

TABLE 2B

Bioinformatics tools used to select miRNAs and their targets.

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|---|
| *DIANA-microT 3.0* | 1 | x | | | | | | | | | | | | | | | | | | | | | | | | | | | | | | | | | |
| DIANA-mirExTra | 2 | | x | | | | | | | | | | | | | | | | | | | | | | | | | | | | | | | | |
| GOmir | 3 | | | x | | | | | | | | | | | | | | | | | | | | | | | | | | | | | | | |
| GSEA MSD v3.0 | 4 | | | | x | | | | | | | | | | | | | | | | | | | | | | | | | | | | | | |
| MAMI | 5 | ✓ | | | | x | | | ✓ | | | | | | | | | | | | | | | | | | ✓ | | | | ✓ | | | | 4 |
| *MicroCosm Targets* | 6 | | | | | | x | x | ✓ | | | | | | | | | | | | | | | | | | | | | | | | | | 5 |
| *MicroInspector* | 7 | | | | | | | x | | | | | | | | | | | | | | | | | | | | | | | | | | | |
| *microRNA.org* | 8 | | | | | | | | ✓ | x | | | | | | | | | | | | | | | | | | | | | | | | | 4 |
| mimiRNA | 9 | | | | | | | | | x | x | | | | | | | | | | | | | | | | ✓ | | | ✓ | | | | | 3 |
| MMIA | 10 | | | | | | | | | | x | ✓ | | | | | | | | | | | | | | | ✓ | ✓ | | ✓ | | | | | | 7 |
| *miRDB* | 11 | | | | | | | | | | | x | | | | | | | | | | | | | | | ✓ | ✓ | | ✓ | | | | | ✓ | 9 |
| miRDIP | 12 | ✓ | | | | | ✓ | ✓ | ✓ | | ✓ | ✓ | x | | | | | | | | | | | | | | | ✓ | | | | | | | ✓ | 8 |
| miRGator v3.0 | 13 | | | | | | ✓ | ✓ | ✓ | | ✓ | ✓ | | x | | | | | | | | | | | | | | ✓ | | | | | | | ✓ | 3 |
| miRecords | 14 | ✓ | | | | | ✓ | ✓ | ✓ | | ✓ | ✓ | | | x | ✓ | | | | | | | | | | | ✓ | ✓ | | ✓ | ✓ | | | | ✓ | 4 |
| MiRNA Distiller | 15 | ✓ | | | | | ✓ | ✓ | ✓ | | ✓ | ✓ | | | | x | x | | | | | | | | | | | ✓ | | | | | | | ✓ | 9 |
| MiRonTop | 16 | | | | | | | | | | | | | | | | x | | | | | | | | | | ✓ | ✓ | | ✓ | | | | | ✓ | 7 |
| miRror | 17 | | | | | | | | | | | | | | | | | x | | | | | | | | | | | | | | | | | |
| miRSystem | 18 | ✓ | | | | | | | ✓ | | | ✓ | | | | | | | x | | | | | ✓ | | | | | | | | | | | 8 |
| miRTarBase | 19 | | | | | | | | | | | | | | | | | | | x | | | | | | | | | | | | | | | |
| miRTar.Human | 20 | | | | | | | | | | | | | | | | | | | | x | | | | | | | | | | | | | | |
| miRvestigator | 21 | | | | | | | | | | | | | | | | | | | | | x | | | | | | | | | | | | | |
| miRWalk | 22 | ✓ | | | | | | | | | | | | | | | | | | | | | x | | | | | | | | | | | | |
| *mirZ* | 23 | | | | | | | | | | | | | | | | | | | | | | | x | | | | | | | | | | | |
| MultiMiTar | 24 | | | | | | | | | | | | | | | | | | | | | | | | x | | | | | | | | | | |
| PhenomiR | 25 | | | | | | | | | | | | | | | | | | | | | | | | | x | | | | | | | | | |
| *PicTar* | 26 | | | | | | | | | | | | | | | | | | | | | | | | | | x | | | | | | | | |
| *PITA* | 27 | | | | | | | | | | | | | | | | | | | | | | | | | | | x | | | | | | | |
| RepTar | 28 | | | | | | | | | | | | | | | | | | | | | | | | | | | | x | | | | | | |
| *RNA22* | 29 | | | | | | | | | | | | | | | | | | | | | | | | | | | | | x | | | | | |
| *RNAhybrid* | 30 | | | | | | | | | | | | | | | | | | | | | | | | | | | | | | x | | | | |
| StarBase | 31 | | | | | | | | | | | | | | | | | | | | | | | | | | | | | | | x | | | |
| Sylamer | 32 | | | | | | | | | | | | | | | | | | | | | | | | | | | | | | | | x | | |
| TarBase 6.0 | 33 | | | | | | | | | | | | | | | | | | | | | | | | | | | | | | | | | x | ✓ |
| *TargetScanHuman* | 34 | | | | | | | | | | | | | | | | | | | | | | | | | | | | | | | | | | x |
| | | 5 | | | | | 4 | 1 | 10 | | 3 | | | | | | | | | | | | | 1 | | | 10 | 8 | | 7 | 3 | | | | 12 |

Meta Tools in bold (13)
Engines called by Meta Tools in italics (11)

Applying the above in silico strategy, it was discovered that hsa-miR-22-3p and hsa-miR-22-5p interact respectively with a total of 42 and 8 of the chosen 83 thermogenic targets. This data is set forth in Table 3.

TABLE 3

Thermogenic regulators identified as predicted and/or validated targets for hsa-miR-22-3p.

| | | | | |
|---|---|---|---|---|
| ALDH1A1 | DIO2 | NCOA1 | PRKAA1 | STAT5A |
| BMP4 | FGF19 | NPPA | PRKACA | TNFRSF1A |
| BMP7 | FGF21 | NRF1 | PRKACB | TRPM8 |
| CEBPA | FOXC2 | NRIP1 | PRKAR1A | UCP2 |
| CEBPD | INSR | PPARA | RUNX1T1 | WNT10B |
| CIDEC | KDM3A | PPARGC1A | RUNX2 | WNT5A |
| CREB1 | KLF11 | PPARGC1B | SIRT1 | |
| CREBBP | LRP6 | PRDM16 | SREBF1 | |
| CTNNB1 | MAPK14 | PRDX3 | SREBF2 | |

Thermogenic regulators identified as predicted and/or validated targets for hsa-miR-22-5p

| | | | | | | | |
|---|---|---|---|---|---|---|---|
| BMP7 | DIO2 | FNDC5 | IKBKE | INSR | MAPK14 | NR1H3 | PPARA |

B. We also utilized the 34 miRNA Targets and Expression tools (Table 2B) to look for potential relations between any of the adipocyte 536 miRNAs (Table A) and the 83 thermogenic targets (Table 1).

It appears that many adipocyte miRNAs interact (prediction and/or validation) with at least one of the 83 thermogenic targets. For example, miR-17-3p and hsa-miR-17-5p interact respectively with a total of 23 and 65 of the chosen thermogenic 83 targets. This data is set forth in Table 4.

TABLE 4

Thermogenic regulators identified as predicted and/or validated targets for hsa-miR-17-3p.

| | | | | |
|---|---|---|---|---|
| ATG7 | CTBP2 | KLF11 | PPARD | TNFRSF1A |
| BMP2 | E2F4 | MAPK14 | PRDM16 | TWIST1 |
| BMP4 | FGF19 | NCOA3 | RB1 | WNT10B |
| CEBPB | IKBKE | PLAC8 | RUNX1T1 | |
| CREB1 | IRS1 | PPARA | STAT5A | |

Thermogenic regulators identified as predicted and/or validated targets for hsa-miR-17-5p

| | | | | |
|---|---|---|---|---|
| ALDH1A1 | CREB2 | IKBKE | NRIP1 | RB1 |
| ATG7 | CTNNB1 | INSR | PLAC8 | RPS6KB1 |
| BMP2 | CTBP1 | IRS1 | PPARA | RUNX1T1 |
| BMP4 | CTBP2 | KLF11 | PPARD | RUNX2 |
| BMP7 | DIO2 | MAPK14 | PPARG | SIRT1 |
| BMP8b | ELOVL3 | MED13 | PPARGC1A | SIRT3 |
| CEBPA | FGF19 | NCOA1 | PPARGC1B | SREBF1 |
| CEBPB | FGF21 | NCOA2 | PRDX3 | STAT5A |
| CEBPD | FNDC5 | NCOA3 | PRKAA1 | TNFRSF1A |
| CIDEC | FOXC2 | NPPA | PRKAA2 | TWIST1 |
| COX7A1 | GDF3 | NR1H3 | PRKACA | UCP1 |
| CRAT | HCRT | NR4A3 | PRKACB | UCP3 |
| CREB1 | HOXC8 | NRF1 | PRKAR1A | WNT5A |

Once the lists of miRNAs of interest and their mRNA targets were produced, the following filters were applied to refine the results:

Parameters

1 Expression of miRNAs in tissue/cell of interest
2 Number of algorithms predicting one miRNA for a given gene or set of genes
3 Score/percent from algorithms
4 Number of preferred genes targeted by one miRNA
5 Number of binding sites in a target gene for one miRNA
6 Number of binding sites in a target gene for several miRNAs
7 Over-representation of one miRNA seed complementary sequence among target genes (miRvestigator)
8 Validated miRNA-mRNA target couples
9 Genomic location of miRNA binding site (5'UTR-Promoter-CDS-3'UTR)
10 Intronic location of miRNA
11 Clustering of miRNAs
12 Abundance of miRNA in specific tissue/cell of interest Applying the above parameters, it was discovered that 229 miRNAs met at least two of these criteria. This data is set forth in Table 5.

TABLE 5

Ranking of miRNAs according to selection critria.

| | | |
|---|---|---|
| hsa-miR-20b-5p | hsa-let-7c | hsa-miR-30d-5p |
| hsa-miR-27b-3p | hsa-let-7d-5p | hsa-miR-424-5p |
| hsa-miR-103a-3p | hsa-miR-141-3p | hsa-miR-454-3p |
| hsa-miR-22-3p | hsa-miR-183-5p | hsa-miR-545-3p |
| hsa-miR-34a-5p | hsa-miR-19a-3p | hsa-miR-485-5p |
| hsa-miR-130b-3p | hsa-miR-196a-5p | hsa-miR-335-5p |
| hsa-miR-132-3p | hsa-miR-30b-5p | hsa-miR-133a |
| hsa-miR-181b-5p | hsa-miR-378a-3p | hsa-miR-222-3p |
| hsa-miR-211-5p | hsa-miR-302c-5p | hsa-miR-494 |
| hsa-miR-148b-3p | hsa-miR-30e-5p | hsa-miR-498 |
| hsa-miR-17-5p | hsa-miR-130a-3p | hsa-miR-513a-5p |
| hsa-miR-182-5p | hsa-let-7e-5p | hsa-miR-92a-3p |
| hsa-miR-20a-5p | hsa-miR-216a-5p | hsa-miR-495-3p |
| hsa-miR-27a-3p | hsa-miR-450a-5p | hsa-miR-503-5p |
| hsa-miR-301a-3p | hsa-let-7d-3p | hsa-miR-539-5p |
| hsa-miR-204-5p | hsa-miR-26b-5p | hsa-miR-16-2-3p |
| hsa-miR-143-3p | hsa-miR-181c-5p | hsa-miR-302b-5p |
| hsa-miR-1 | hsa-miR-186-5p | hsa-miR-425-3p |
| hsa-miR-9-5p | hsa-miR-519c-3p | hsa-miR-99a-3p |
| hsa-miR-30a-5p | hsa-let-7b-5p | hsa-let-7a-3p |
| hsa-miR-138-5p | hsa-miR-10b-5p | hsa-miR-126-3p |
| hsa-miR-217 | hsa-miR-125b-5p | hsa-miR-20a-3p |
| hsa-miR-19b-3p | hsa-miR-134 | hsa-miR-499a-5p |
| hsa-miR-382-5p | hsa-miR-137 | hsa-let-7g-5p |
| hsa-miR-106a-5p | hsa-miR-150-5p | hsa-miR-152 |
| hsa-miR-107 | hsa-miR-153 | hsa-miR-26a-5p |
| hsa-miR-135a-5p | hsa-miR-15b-5p | hsa-miR-124-3p |
| hsa-miR-93-5p | hsa-miR-16-5p | hsa-miR-203a |
| hsa-miR-21-5p | hsa-miR-195-5p | hsa-miR-24-3p |
| hsa-miR-515-3p | hsa-miR-196b-5p | hsa-miR-301b |
| hsa-miR-106b-3p | hsa-miR-23a-3p | hsa-miR-590-3p |
| hsa-miR-125a-5p | hsa-miR-29c-3p | hsa-miR-1179 |
| hsa-miR-148a-3p | hsa-miR-373-3p | hsa-miR-325 |
| hsa-miR-155-5p | hsa-miR-7-5p | hsa-miR-552 |
| hsa-miR-181a-5p | hsa-miR-214-3p | hsa-miR-185-5p |
| hsa-miR-519d | hsa-miR-421 | hsa-miR-455-3p |
| hsa-miR-96-5p | hsa-miR-15a-5p | hsa-miR-583 |
| hsa-miR-212-3p | hsa-miR-193b-3p | hsa-miR-122-5p |
| hsa-miR-29a-3p | hsa-miR-194-5p | hsa-miR-1305 |
| hsa-miR-98-5p | hsa-miR-223-3p | hsa-miR-139-5p |
| hsa-miR-146a-5p | hsa-miR-30c-5p | hsa-miR-224-3p |
| hsa-miR-18a-5p | hsa-miR-335-3p | hsa-miR-24-1-5p |
| hsa-miR-18b-5p | hsa-miR-374a-5p | hsa-miR-24-2-5p |
| hsa-miR-199b-5p | hsa-miR-410 | hsa-miR-27a-5p |
| hsa-miR-340-5p | hsa-miR-429 | hsa-miR-27b-5p |
| hsa-miR-34c-5p | hsa-miR-497-5p | hsa-miR-29b-1-5p |
| hsa-miR-423-3p | hsa-miR-513a-3p | hsa-miR-302a-5p |
| hsa-miR-489 | hsa-miR-542-3p | hsa-miR-3065-5p |
| hsa-miR-520f | hsa-miR-653 | hsa-miR-30d-3p |
| hsa-miR-520g | hsa-miR-122-3p | hsa-miR-34a-3p |

TABLE 5-continued

Ranking of miRNAs according to selection critria.

| | | |
|---|---|---|
| hsa-miR-605 | hsa-miR-101-5p | hsa-miR-371a-3p |
| hsa-miR-668 | hsa-miR-1178-3p | hsa-miR-373-5p |
| hsa-let-7a-5p | hsa-miR-191-5p | hsa-miR-374a-3p |
| hsa-let-7f-5p | hsa-miR-214-5p | hsa-miR-376a-5p |
| hsa-miR-10a-3p | hsa-miR-302d-5p | hsa-miR-378a-5p |
| hsa-miR-135b-5p | hsa-miR-572 | hsa-miR-424-3p |
| hsa-miR-144-3p | hsa-miR-574-3p | hsa-miR-451a |
| hsa-miR-181d | hsa-miR-26a-2-3p | hsa-miR-452-3p |
| hsa-miR-200b-3p | hsa-miR-611 | hsa-miR-487b |
| hsa-miR-200c-3p | hsa-let-7f-1-3p | hsa-miR-493-5p |
| hsa-miR-218-5p | hsa-let-7i-3p | hsa-miR-500a-3p |
| hsa-miR-23b-3p | hsa-miR-100-5p | hsa-miR-502-3p |
| hsa-miR-25-3p | hsa-miR-106b-5p | hsa-miR-516b-3p |
| hsa-miR-29b-3p | hsa-miR-132-5p | hsa-miR-518e-3p |
| hsa-miR-383 | hsa-miR-135b-3p | hsa-miR-518f-3p |
| hsa-miR-202-3p | hsa-miR-136-3p | hsa-miR-519a-5p |
| hsa-miR-381-3p | hsa-miR-150-3p | hsa-miR-519b-5p |
| hsa-miR-377-3p | hsa-miR-154-3p | hsa-miR-521 |
| hsa-miR-452-5p | hsa-miR-15a-3p | hsa-miR-523-5p |
| hsa-miR-501-3p | hsa-miR-15b-3p | hsa-miR-545-5p |
| hsa-miR-514a-3p | hsa-miR-16-1-3p | hsa-miR-585 |
| hsa-miR-654-3p | hsa-miR-181a-2-3p | hsa-miR-7-2-3p |
| hsa-let-7b-3p | hsa-miR-181c-3p | hsa-miR-93-3p |
| hsa-miR-125a-3p | hsa-miR-186-3p | hsa-miR-96-3p |
| hsa-miR-133b | hsa-miR-195-3p | hsa-miR-99b-3p |
| hsa-miR-192-5p | hsa-miR-20b-3p | |
| hsa-miR-199a-3p | hsa-miR-223-5p | | c) A Multiple microRNAs-One mRNA Paradigm.

Figure 5:
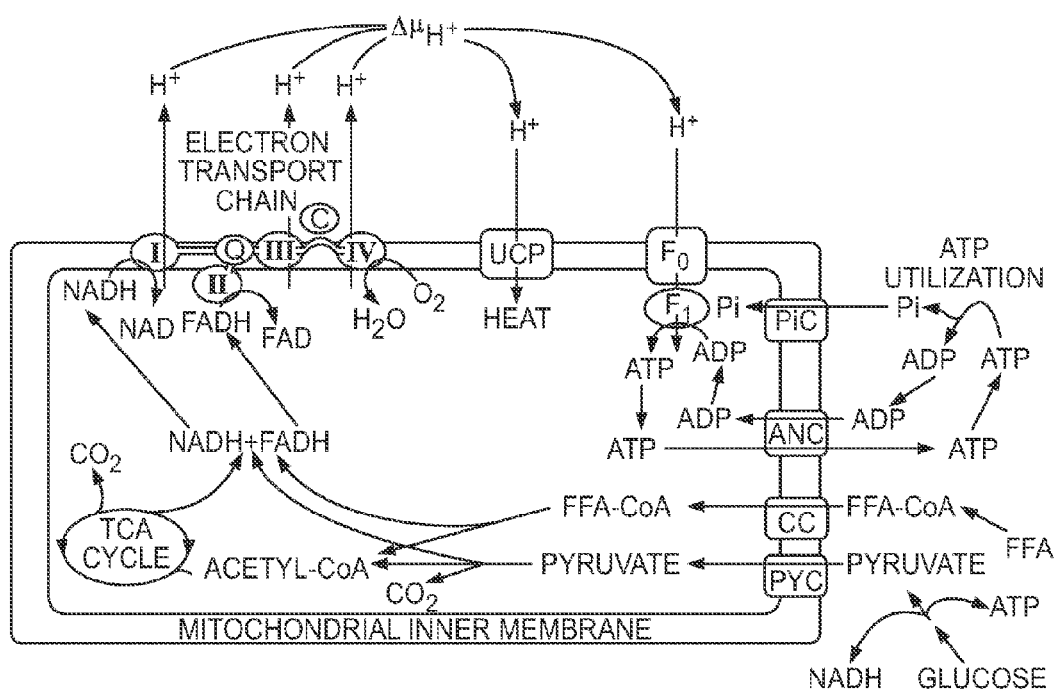
FIG. 5 is a schematic representation of oxidative phosphorylation in mitochondria, illustrating the uncoupling of oxidative phosphorylation from ATP synthesis by UCP1 to generate heat.

A. One exemplary multiple miRNAs-one mRNA paradigm involves UCP1. In adipocytes the key thermogenic regulator ultimately is UCP1 (also named thermogenin) and, thus, all thermogenic regulators must ultimately impact UCP1 activity. UCP1 is a mitochondrial transporter protein that creates proton leaks across the inner mitochondrial membrane, thus uncoupling oxidative phosphorylation from ATP synthesis. As a result, energy is dissipated in the form of heat (adaptive thermogenesis) (see FIG. 5) Lowell et al., Nature (2000); Friedman et al., Bioinformatics (2010); Hsu et al., Nucleic acids research (2011); Rieger et al., Frontiers in Genetics (2011)).

Figure 6:
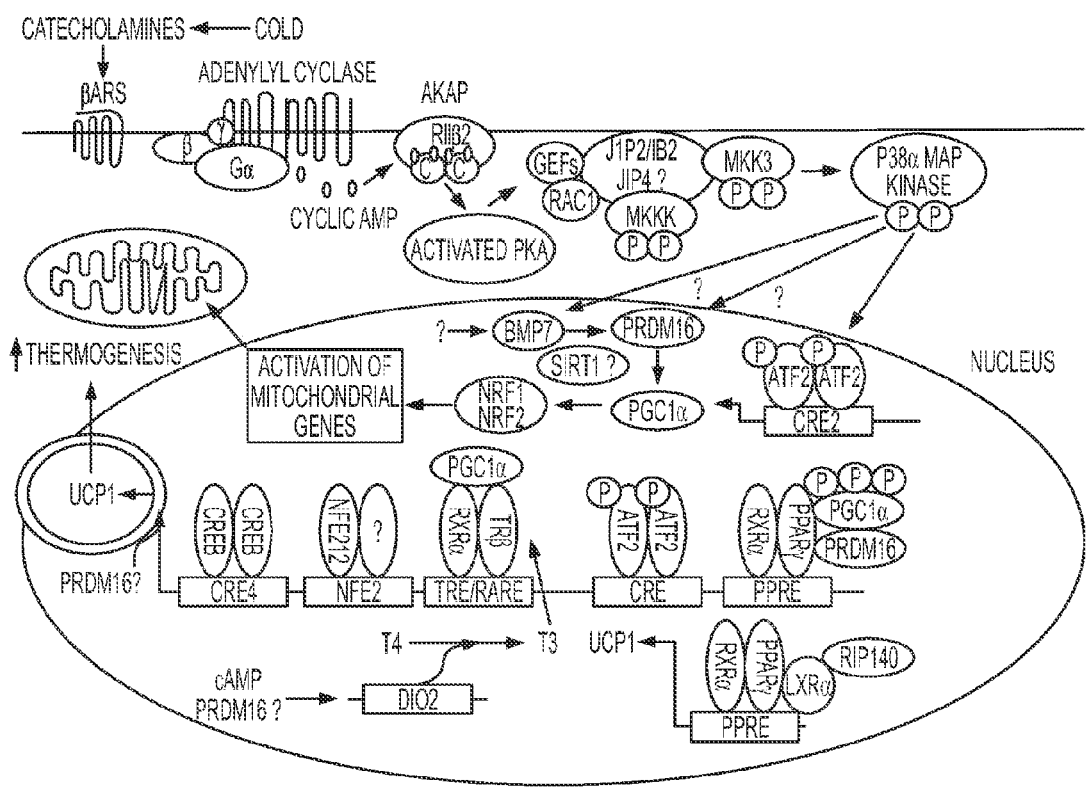
FIG. 6 depicts the transcriptional control of UCP1 by other exemplary thermogenic regulators.
Figure 7:
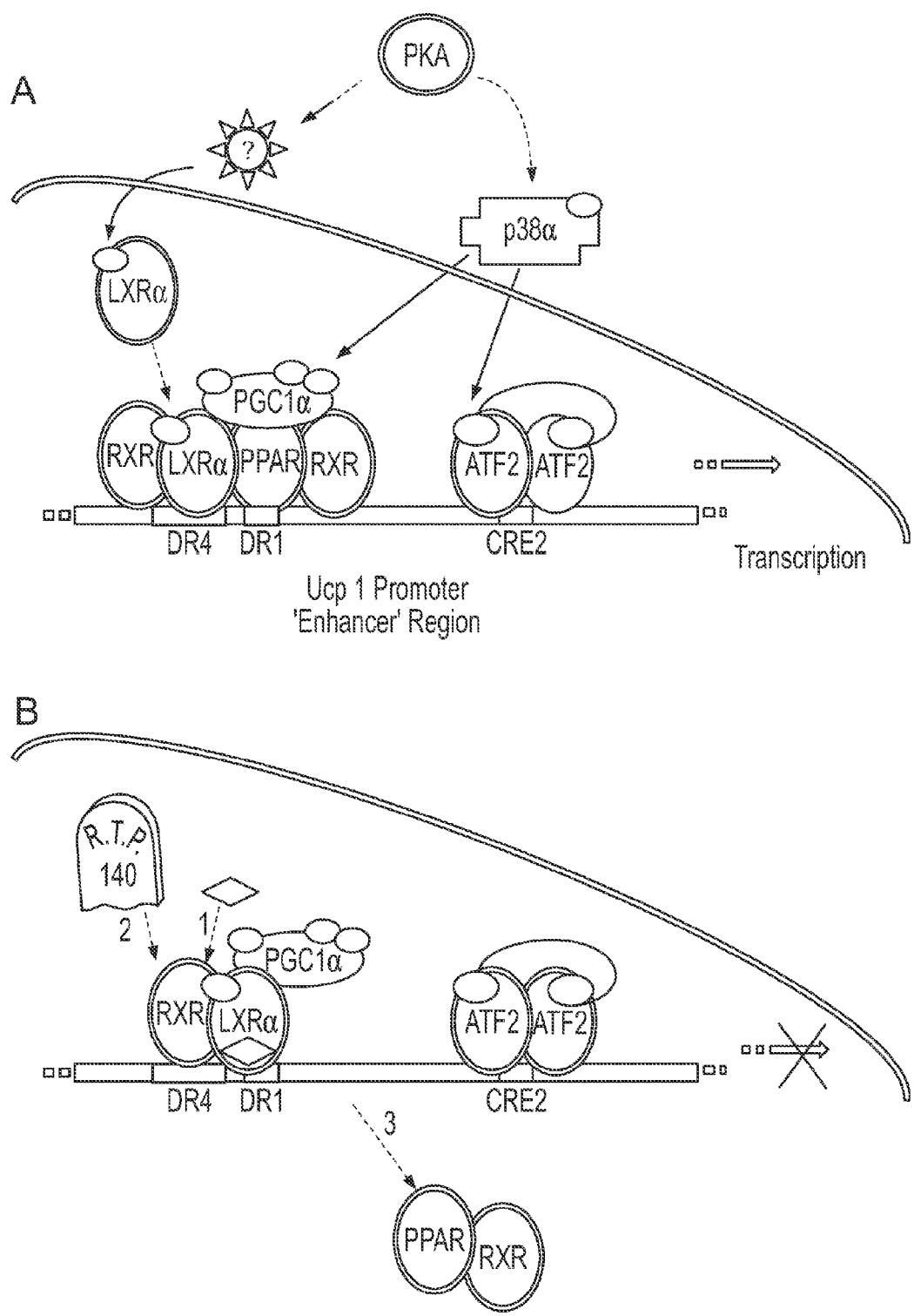
FIG. 7 depicts exemplary positive (A) and negative (B) transcriptional regulators of the UCP1 gene.

UCP1 biosynthesis is mainly controlled at the transcription level. FIG. 6 depicts the transcriptional control of UCP1 by other exemplary thermogenic regulators. The promoter's region of the UCP1 gene contains many distinct regulatory sites, allowing a wide range of proteins to influence its transcription, both positively (see FIG. 7A) and negatively (see FIG. 7B).

Mendelian randomization is a method of using measured variation in genes of known function to examine the causal effect of a modifiable exposure on disease in non-experimental studies. Mendelian randomization can be thought of as a "natural" Randomized Clinical Trial. Genetic polymorphism of the UCP1 gene, such as the −3826 A/G single nucleotide polymorphism in the promoter in exon 2 of UCP1, has been reported to be associated with reduced mRNA expression and obesity. Healthy children with the G/G genotype had a lower capacity for thermogenesis in response to a high-fat meal and acute cold exposure. The same −3826 A/G UCP1 genetic polymorphism diminishes resting energy expenditure and thermoregulatory sympathetic nervous system activity in young females. In a study of 367 Korean women, the G allele of −3826A>G and the C allele of −412A>C were significantly associated with larger areas of abdominal subcutaneous fat in a dominant model (p<0.001 and p<0.0004, respectively); combining them together (ht2[GC]) enhanced this significance (p<0.00005). A study of 100 severe obese adults (BMI>40 kg/m2) and 100 normal-weight control subjects (BMI range=19-24.9 kg/m2) identified 7 variations in the promoter region, 4 in the intronic region and 4 in the exonic region of the UCP1 gene. These variations could contribute to the development of obesity, particularly, g.-451C>T, g.940G>A, and g.IVS4-208T>G could represent "thrifty" factors that promote energy storage. Finally, two polymorphisms (A-3826G and C-3740A), located in the upstream promoter region of the UCP1 gene affect gene expression and are correlated with human longevity.

All aforementioned information supports targeting UCP1 expression and activity as a meaningful way to alter adaptive thermogenesis and consequently treat human obesity. Many strategies could be implemented to achieve this goal, however, the one employed in the methods of the invention uses miRNA agents to modulate simultaneously several elements within the thermogenic pathways to increase UCP1 synthesis and activity. Both direct and indirect interactions between miRNAs and the UCP1 gene are considered. Direct interaction means the direct binding of miRNAs to the various regions of the UCP1 gene, resulting in alterations of the transcription, translation, stability and/or degradation of the UCP1 mRNA. Indirect interaction means that miRNAs alter the transcription, translation, stability and/or degradation of thermogenic mRNAs, whose expressed proteins alter the transcription of the UCP1 gene. Furthermore, indirect interaction means that miRNAs alter the transcription, translation, stability and/or degradation of other miRNAs that modify the transcription of the UCP1 gene.

The promoter region of the human UCP1 gene (gi|237858805|ref|NG_012139.1|Homo sapiens uncoupling protein 1 (mitochondrial, proton carrier) (UCP1), RefSeqGene on chromosome 4) is particularly rich is regulatory element motifs:

UCP1 Gene Regulatory Elements:
1. Brown Fat Response Element 1 (BRE1) Motif: CCTCTCTGCTTCTTCT [SEQ ID NO: 1]
One
Length: 16, Interval: 1,129->1,144, Mismatches: 0.
2. Brown Fat Response Element 2 (BRE2) Motif: CTCCTTGGAA [SEQ ID NO: 2]
One
Length: 10, Interval: 1,269->1,278, Mismatches: 0.
3. CRE2 Motif: ATTCTTTA
Four
Length: 8, Intervals: 1,121->1,128, 3,631->3,638, 10,982->10,989, 15,881->15,888, Mismatches: 0.
4. CREB Motif: ACGTCA
Five
Length: 6, Intervals: 1,082->1,087, 1,345->1,350, 1,348->1,343, 11,439->11,434, 13,831->13,836, Mismatches: 0.
5. DR1 Motif: TTGCCCTTGCTCA [SEQ ID NO: 3]
One
Length: 13, Interval: 1,099->1,111, Mismatches: 0.
6. DR4 Motif: ACGTCATAAAGGGTCA [SEQ ID NO: 4]
One
Length: 16, Interval: 1,082->1,097, Mismatches: 0.
7. DR4 Type RARE Motif: RGKTCANNNNRGKTCA [SEQ ID NO:5]
One
Length: 16, Interval: 1,316->1,301, Mismatches: 0.
8. ERE Motif: GCTCATACTGACCT [SEQ ID NO:6]
One
Length: 14, Interval: 1,107->1,120, Mismatches: 0.

9. PRE Motif: GTTAATGTGTTCT [SEQ ID NO:7]
One
Length: 13, Interval: 1,009->1,021, Mismatches: 0.
10. RARE Motif: TGACCACAGTTTGATCA [SEQ ID NO: 8]
One
Length: 17, Interval: 983->999, Mismatches: 0.
11. RXR Motif: AGGTCA
Twelve
Length: 6, Interval: 1,120->1,115, 1,316->1,311, 3,517->3,522, 3,560->3,555, 3,813->3,808, 5,318->5,313, 6,233->6,238, 6,831->6,836, 8,122->8,127, 9,966->9,971, 11,339->11,334, 11,412->11,407, Mismatches: 0.
12. GC Box 1 Motif: CGCCC
Seven
Length: 5, Interval: 4,593->4,589, 4,615->4,619, 4,615->4,619, 4,747->4,751, 4,765->4,769, 5,914->5,910, 13,715->13,711, Mismatches: 0.
13. GC Box 2 Motif: GCGGG
Nine
Length: 5, Interval: 4,463->4,459, 4,585->4,589, 4,593->4,597, 4,639->4,643, 4,883->4,887, 5,176->5,172, 5,929->5,933, 5,940->5,944, 14,994->14,990, Mismatches: 0.
14. GT Box 1 Motif: CACCC
Twenty Five
Length: 5, Interval: 194->190, 452->448, 1,184->1,188, 1,803->1,807, 2,428->2,424, 3,037->3,041, 3,330->3,334, 4,137->4,141, 4,566->4,562, 4,599->4,595, 4,869->4,865, 5,104->5,108, 5,461->5,457, 6,237->6,241, 6,293->6,289, 8,096->8,092, 8,198->8,194, 9,649->9,645, 9,912->9,908, 12,962->12,958, 13,136->13,132, 13,723->13,719, 14,404->14,400, 14,960->14,964, 15,576->15,572, Mismatches: 0.
15. GT Box 2 Motif: GTGGG
Twenty
Length: 5, Interval: 25->21, 1,805->1,801, 1,809->1,805, 2,119->2,123, 3,854->3,850, 4,310->4,314, 4,339->4,343, 4,765->4,761, 4,867->4,871, 6,291->6,295, 7,554->7,558, 8,280->8,284, 8,681->8,685, 9,615->9,619, 9,689->9,693, 9,906->9,910, 10,363->10,359, 13,074->13,070, 13,640->13,644, 13,941->13,945, Mismatches: 0.
16. CpG Methylation Island Motif: CG
Three Hundred and Sixty Six, including many between positions 4,519 to 5,258 and 5,639 to 6,694.

Figure 8A:
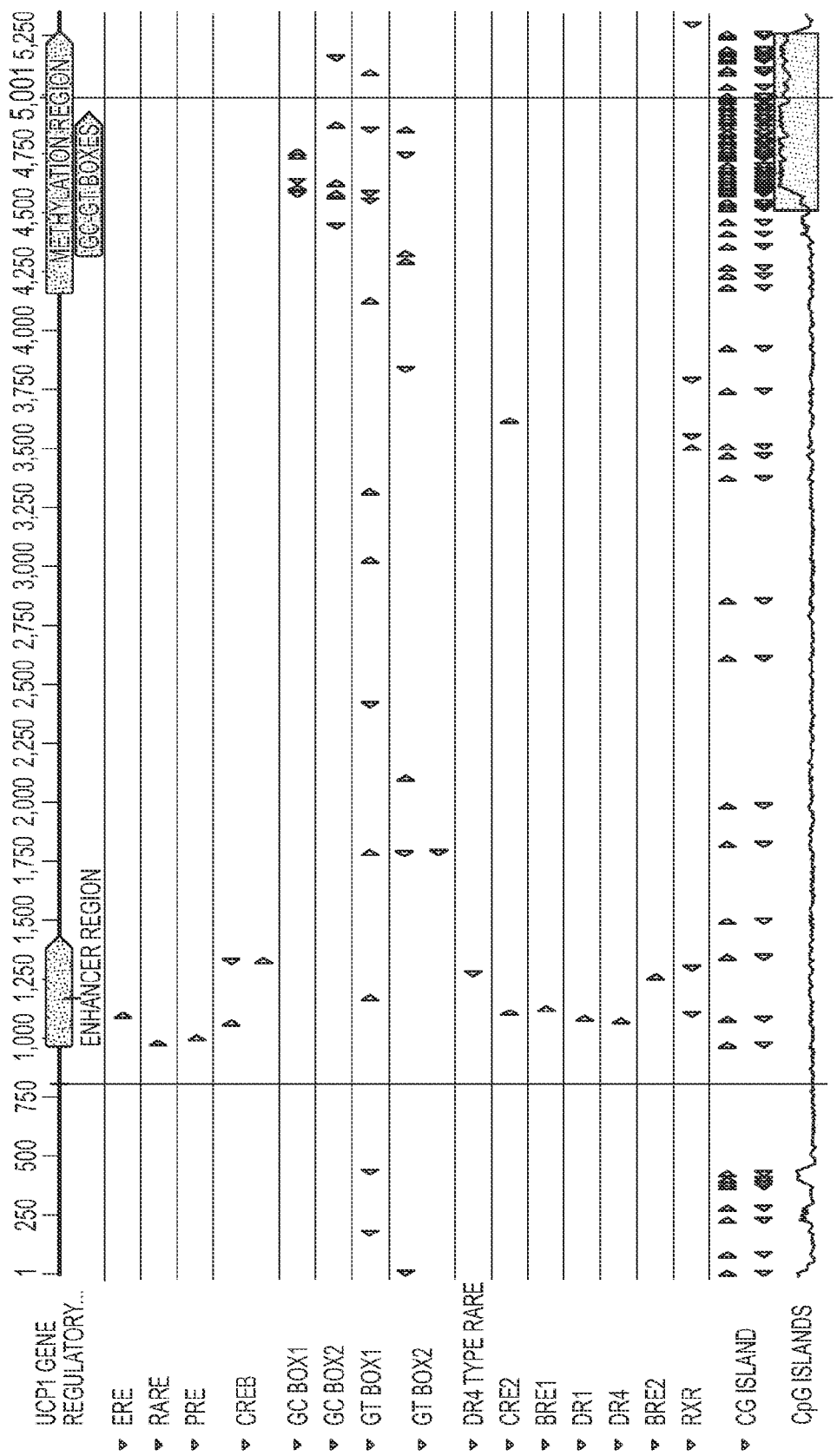
FIG. 8A depicts the location of various regulatory elements in reference to the transcription start site in the 15,910 base pair (bp) human UCP1 gene sequence (NCBI Reference Sequence: gi|237858805|ref|NG_012139.1|Homo sapiens uncoupling protein 1 (mitochondrial, proton carrier) (UCP1), RefSeqGene on chromosome 4).

FIG. 8A depicts the location of these various regulatory elements in reference to the UCP1 transcription start site at nucleotide position 5,001 of the 15,910 base pair human UCP-1 gene (FASTA accession number: >gi|237858805|ref|NG_012139.1|*Homo sapiens* uncoupling protein 1 (mitochondrial, proton carrier) (UCP1), RefSeqGene on chromosome 4; NCBI Reference Sequence: NG_012139.1).

Direct or indirect activation or repression of these regulatory elements by miRNAs will result in alterations of UCP1 gene expression and activity. Under normal conditions, the UCP1 gene expression and activity are repressed by a rich network of regulatory elements, in order to avoid energy wasting. Under stress, such as exposure to a cold environment, the expression of the UCP1 gene is upregulated, via various activators and repressors which are under the control of several miRNAs.

An initial survey of miRNAs targeting the human UCP1 3'UTR with several programs, including microRNA.org, was negative. However, other programs, including MicroCosm Targets, using the UCP1 Ensembl 1,462 base pair transcript ENST00000262999 as a target revealed binding sites for 27 miRNAs at 28 locations in UCP1 3'UTR as shown in Table 6.

TABLE 6

Binding sites for miRNAs in the 3'UTR of UCP1 (NCBI Reference Sequence. NG_012139.1) determined using microCosm Targets.

| Name | Sequence | SEQ ID NO | Minimum | Maximum | Length |
|---|---|---|---|---|---|
| hsa-miR-21 | AATGTAATGCAGATAAGCTA | 9 | 14143 | 14162 | 20 |
| hsa-miR-219-2-3p | ACATGTTTTAATTACAATTC | 10 | 14217 | 14236 | 20 |
| hsa-miR-22 | GATTGGCAGCTT | 11 | 14857 | 14868 | 12 |
| hsa-miR-222a | GATTTTTAATGTTTAGAGTCCAG | 12 | 14500 | 14522 | 23 |
| hsa-miR-290-3p | TTTAGAGCTGGAGGGTACTT | 13 | 14621 | 14640 | 20 |
| hsa-miR-292-3p | TTTAGAGCTGGAGGGTACTT | 14 | 14621 | 14640 | 20 |
| hsa-miR-292-5p | GACAGAGGAACAGTTTGAG | 15 | 14648 | 14666 | 19 |
| hsa-miR-325 | ATTTTGGCAGGATTGCTACTAG | 16 | 14568 | 14589 | 22 |
| hsa-miR-331-5p | TTTTGAGATCTATACCTGG | 17 | 14383 | 14401 | 19 |
| hsa-miR-362-5p | ATTTTAAGCTAAATCCAAGGATT | 18 | 14838 | 14860 | 23 |
| hsa-miR-367 | TGACCATTTCTGGAGTGCAATT | 19 | 14170 | 14191 | 22 |
| hsa-miR-371-5p | ACAGTTTGAT | 20 | 988 | 997 | 10 |
| hsa-miR-371-5p | ACAGTTTGAG | 21 | 14657 | 14666 | 10 |
| hsa-miR-377 | CTGGAGTGCAATTGTGTGA | 22 | 14179 | 14197 | 19 |
| hsa-miR-378 | TTTTAATGTTTAGAGTCCAG | 23 | 14503 | 14522 | 20 |

TABLE 6-continued

Binding sites for miRNAs in the 3'UTR of UCP1 (NCBI Reference Sequence. NG_012139.1) determined using microCosm Targets.

| Name | Sequence | SEQ ID NO | Minimum | Maximum | Length |
|---|---|---|---|---|---|
| hsa-miR-382 | TGATGACATCTCTAACAACTTC | 24 | 14526 | 14547 | 22 |
| hsa-miR-460 | AGAAACTGAGTGAAATGCAG | 25 | 14250 | 14269 | 20 |
| hsa-miR-508-5p | TGACCATTTCTGGAGTG | 26 | 14170 | 14186 | 17 |
| hsa-miR-543 | TACTCTGAATGTT | 27 | 14478 | 14490 | 13 |
| hsa-miR-549 | TTAACCACAGTTGTCA | 28 | 14321 | 14336 | 16 |
| hsa-miR-643 | CAAGTTCACTAGAATACAAG | 29 | 14412 | 14431 | 20 |
| hsa-miR-654-3p | AAGGTTACAGGCTGCCAGACAT | 30 | 14880 | 14901 | 22 |
| hsa-miR-664 | GTGTGAATGAATG | 31 | 14192 | 14204 | 13 |
| hsa-miR-871 | TAGGCATGAACCTACTCTGAATG | 32 | 14466 | 14488 | 23 |
| hsa-miR-883a-3p | AAACTGAGTGAAATGCAGTT | 33 | 14252 | 14271 | 20 |
| hsa-miR-883b-3p | AAACTGAGTGAAATGCAGTT | 34 | 14252 | 14271 | 20 |
| hsa-miR-888-3p | TTTATTAACCACAGTTGTCAGTT | 35 | 14317 | 14339 | 23 |
| hsa-miR-92b | GAGTGCAAT | | 14182 | 14190 | 9 |

Other programs, such as miRWalk, miRGen, miRGator-miRanda, and DIANA microT, using the UCP1 Ensembl 1,462 base pair transcript (ENST00000262999), the UCP1 Ensembl 9,371 base pair gene sequence (ENSG00000109424) or the 15,910 base pair UCP1 sequence (NCBI Reference Sequence: NG_012139.1) as targets, revealed binding sites for a total of 50 miRNAs at 69 locations in UCP1 3'UTR as shown in Table 7.

TABLE 7

Binding sites for miRNAs in the 3'UTR of UCP1 (NCBI Reference Sequence. NG_012139.1) according to several programs.

| | Name | Sequence | SEQ ID NO | Minimum | Maximum | Length |
|---|---|---|---|---|---|---|
| 1 | hsa-miR-1179 | AAGTATCCTTT | 36 | 15346 | 15356 | 11 |
| 2 | hsa-miR-1302 | ATGGGACACA | 37 | 15021 | 15030 | 10 |
| 3 | hsa-miR-130b | TTATTTTCCCT | 38 | 15161 | 15171 | 11 |
| 4 | hsa-miR-146a | TGACAACTGT | 39 | 14327 | 14336 | 10 |
| | hsa-miR-146a | AGGGAACTGA | 40 | 15231 | 15240 | 10 |
| | hsa-miR-146a | TGTGAACTGG | 41 | 15679 | 15688 | 10 |
| 5 | hsa-miR-181c | AACCATAGT | | 15304 | 15312 | 9 |
| 6 | hsa-miR-19b-2 | ACTTTTGCGG | 42 | 14991 | 15000 | 10 |
| 7 | hsa-miR-203 | TTAAATGTT | | 15584 | 15592 | 9 |
| 8 | hsa-miR-204-5p | TTCCTTTATC | 43 | 14006 | 14015 | 10 |
| | hsa-miR-204-5p | TTCCTCTGTC | 44 | 14648 | 14657 | 10 |
| 9 | hsa-miR-21-5p | TAGCTTATCT | 45 | 14153 | 14162 | 10 |
| 10 | hsa-miR-211-5p | TTCCCTATCTC | 46 | 14779 | 14789 | 11 |
| 11 | hsa-miR-214 | CAGCAAGCA | 47 | 15052 | 15060 | 9 |
| 12 | hsa-miR-22-3p | AAGCTGCCAA | 48 | 14859 | 14868 | 10 |
| | hsa-miR-22-5p | AGTTCTTCACA | 49 | 14203 | 14213 | 11 |
| 13 | hsa-miR-26a-2-3p | CATTTTCTTG | 50 | 13918 | 13927 | 10 |
| | hsa-miR-26a-2-3p | CCAATCCTTG | 51 | 14853 | 14862 | 10 |
| | hsa-miR-26a-2-3p | CCTTTTCATG | 52 | 15616 | 15625 | 10 |

TABLE 7-continued

Binding sites for miRNAs in the 3'UTR of UCP1 (NCBI Reference Sequence. NG_012139.1) according to several programs.

| Name | Sequence | SEQ ID NO | Minimum | Maximum | Length |
|---|---|---|---|---|---|
| 14 hsa-miR-30b | GTAACCTTCC | 53 | 14878 | 14887 | 10 |
| 15 hsa-miR-325 | CAGAGTAGGT | 54 | 14475 | 14484 | 10 |
| hsa-miR-325 | CCTTGTAGGC | 55 | 15378 | 15387 | 10 |
| 16 hsa-miR-328 | CTGTTCCTCT | 56 | 14651 | 14660 | 10 |
| 17 hsa-miR-362-5p | ATCCTTGGAT | 57 | 14850 | 14859 | 10 |
| 18 hsa-miR-367-3p | AATTGCACTC | 58 | 14182 | 14191 | 10 |
| 19 hsa-miR-371a-3p | AAGTGCCTGC | 59 | 15435 | 15444 | 10 |
| hsa-miR-371a-5p | TCTCAAACTG | 60 | 14658 | 14667 | 10 |
| 20 hsa-miR-378a-3p | ACTGGCCTTG | 61 | 15816 | 15825 | 10 |
| 21 hsa-miR-382-3p | ATTCATTCAC | 62 | 14194 | 14203 | 10 |
| 22 hsa-miR-382-5p | GAAGTTGTTAGAGAT | 63 | 14533 | 14547 | 15 |
| 23 hsa-miR-383 | AGATTAGAA | 64 | 14545 | 14553 | 9 |
| 24 hsa-miR-421 | ATTAACTGAC | 65 | 14333 | 14342 | 10 |
| hsa-miR-421 | CTCAAAAGAC | 66 | 14380 | 14389 | 10 |
| 25 hsa-miR-422a | ACTGGCCTT | | 15817 | 15825 | 9 |
| 26 hsa-miR-431 | TGTCTGGCA | | 14892 | 14900 | 9 |
| 27 hsa-miR-452 | TTATCTGC | | 14151 | 14158 | 8 |
| hsa-miR-452 | TCTTCTGC | | 14773 | 14780 | 8 |
| hsa-miR-452 | ACATCTGC | | 15009 | 15016 | 8 |
| 28 hsa-miR-455-3p | CAGTCCAT | | 13893 | 13900 | 8 |
| hsa-miR-455-5p | TGTGTGCCTT | 67 | 15641 | 15650 | 10 |
| 29 hsa-miR-491-5p | AATGGGGAAG | 68 | 14975 | 14984 | 10 |
| 30 hsa-miR-501-3p | ATGCATCAGG | 69 | 15547 | 15556 | 10 |
| 31 hsa-miR-504 | AGACCCTGT | | 15325 | 15333 | 9 |
| 32 hsa-miR-508-5p | TATTCTAGTGAACTTG ACTCTTA | 70 | 14405 | 14427 | 23 |
| 33 hsa-miR-512-5p | CACTCAG | | 14255 | 14261 | 7 |
| 34 hsa-miR-514a-3p | TTGACTCTT | | 14406 | 14414 | 9 |
| 35 hsa-miR-515-3p | GACTGCCTT | | 15539 | 15547 | 9 |
| hsa-miR-515-3p | GTGTGCCTT | | 15641 | 15649 | 9 |
| 36 hsa-miR-517a-3p | ATGGTGCATT | 71 | 15650 | 15659 | 10 |
| 37 hsa-miR-545 | CAGCAAGCACT | 72 | 15050 | 15060 | 11 |
| 38 hsa-miR-549 | TGACAACTGT | 73 | 14327 | 14336 | 10 |
| 39 hsa-miR-552 | CACAGGTGA | | 15130 | 15138 | 9 |
| 40 hsa-miR-616-5p | ACTCTAAAC | | 14510 | 14518 | 9 |
| 41 hsa-miR-620 | ATGAATATAG | 74 | 14560 | 14569 | 10 |
| 42 hsa-miR-643 | ACTGGTATGT | 75 | 13933 | 13942 | 10 |
| hsa-miR-643 | TCTTGTATTC | 76 | 14423 | 14432 | 10 |
| hsa-miR-643 | CCTTGTAGGC | 77 | 15378 | 15387 | 10 |
| hsa-miR-643 | ACATGCATGC | 78 | 15553 | 15562 | 10 |
| 43 hsa-miR-651 | TTAAAATAAG | 79 | 13988 | 13997 | 10 |
| hsa-miR-651 | TTAGGTTAAA | 80 | 13993 | 14002 | 10 |
| hsa-miR-651 | TCATGATAAG | 81 | 15700 | 15709 | 10 |
| 44 hsa-miR-654-3p | TATCTCTTCT | 82 | 14775 | 14784 | 10 |
| hsa-miR-654-3p | TATGTATACT | 83 | 15493 | 15502 | 10 |

TABLE 7-continued

Binding sites for miRNAs in the 3'UTR of UCP1 (NCBI Reference Sequence. NG_012139.1) according to several programs.

| Name | Sequence | SEQ ID NO | Minimum | Maximum | Length |
|---|---|---|---|---|---|
| 45 hsa-miR-655 | GTAATACAT | | 15593 | 15601 | 9 |
| 46 hsa-miR-767-3p | CCTGCTCAT | | 14871 | 14879 | 9 |
| 47 hsa-miR-888-3p | GACTGACTCC | 84 | 15772 | 15781 | 10 |
| 48 hsa-miR-92b-3p | ATTGCACTCC | 85 | 14181 | 14190 | 10 |
| 49 hsa-miR-941 | CACCCAGGT | | 14396 | 14404 | 9 |
| 50 hsa-miR-99a-3p | AAGCTGGCTC | 86 | 15117 | 15126 | 10 |

Figure 3:
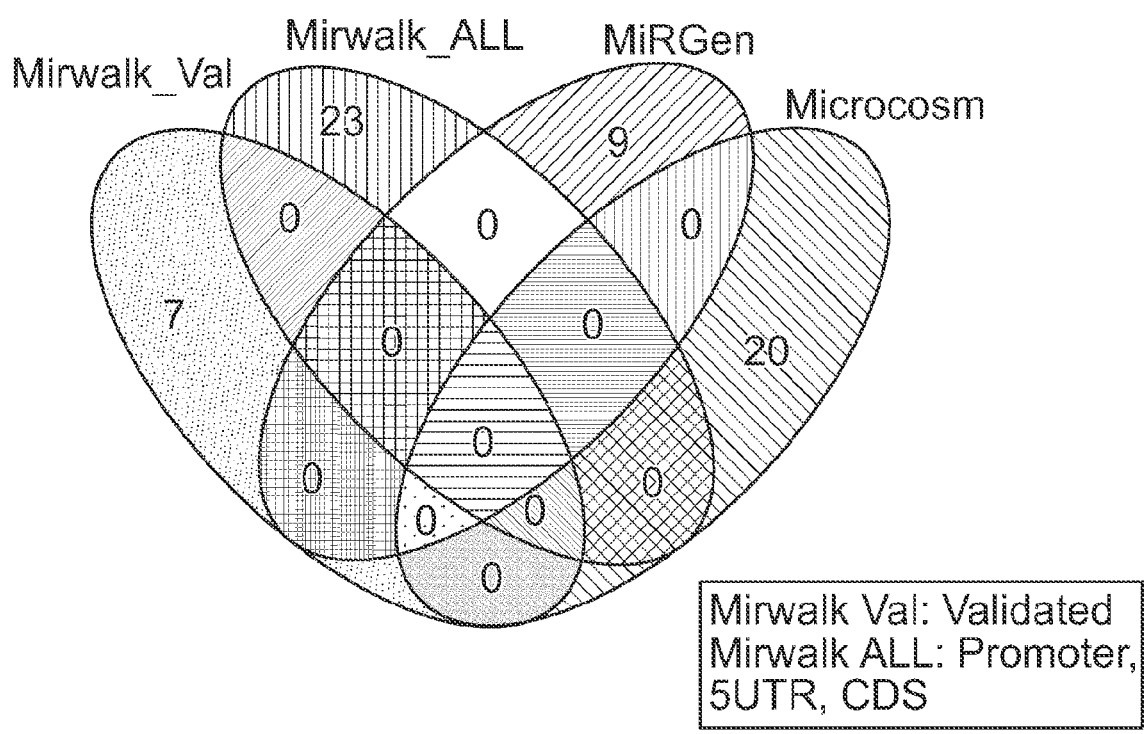
FIG. 3 is a schematic representation of the overlap between the visual inspection and alignment of nucleotide sequences set forth herein, and the results from multiple miRNA prediction programs predicting miRNA binding sites in the 5'UTR, promoter region, coding sequence and 3'UTR of the human UCP1 gene.

Alignment of the sequence of the human UCP1 gene with several miRNA sequences yielded matches in the 5'UTR, the promoter region and the coding regions of the UCP1 gene. Interrogation of the publicly available Internet tools predicting miRNAs targeting the various regions of the UCP1 gene elicited several hits. Surprisingly, the overlap between these prediction tools was zero, as shown in FIG. 3.

Nevertheless, miRNA databases were screened using the alignment program Geneious. A total of 191 human microRNAs were found which have complementary 450 binding sites in the UCP1 gene sequence (Table 8). The length of the matches goes from 7 bases to 12 bases (e.g. hsa-miR-24-2-5p and hsa-miR-192-5p). The number of hits per miRNA varies from 1 to several (e.g. 9 for hsa-miR-19b2 (an abundant adipocyte miRNA), 14 for hsa-miR-26a-2-3p, 11 for hsa-miR-181c, and 12 for hsa-miR-620).

TABLE 8 miRNAs with predicted binding sites in the UCP1 gene sequence (NCBI Reference Sequence: NG_012139.1).

| miRNA | Sequence | SEQ ID NO | Minimum | Maximum | Length | Direction |
|---|---|---|---|---|---|---|
| hsa-let-7c | TAGAGTTTC | | 5918 | 5926 | 9 | reverse |
| hsa-let-7e | GGAGGTAGG | | 13283 | 13291 | 9 | reverse |
| hsa-let-7e | TGAAGTAGG | | 7612 | 7620 | 9 | reverse |
| hsa-let-7e | AGAGGTAGG | | 3306 | 3314 | 9 | reverse |
| hsa-let-7i-3p | CTGTGCAAG | | 3588 | 3596 | 9 | reverse |
| hsa-miR-17 | CAAAGTGCT | | 12200 | 12208 | 9 | reverse |
| hsa-miR-17 | CAAAGTGCT | | 9931 | 9939 | 9 | reverse |
| hsa-miR-17 | CAAAGTGCT | | 218 | 226 | 9 | reverse |
| hsa-miR-19a | TGTGCAAAT | | 3916 | 3924 | 9 | reverse |
| hsa-miR-19a | TGTGCAAAT | | 834 | 842 | 9 | reverse |
| hsa-miR-19b-2 | ACTTTTGCGG | 87 | 14991 | 15000 | 10 | reverse |
| hsa-miR-19b-2 | AGTTTTACAA | 88 | 11998 | 12007 | 10 | reverse |
| hsa-miR-19b-2 | AGTTTTGTAT | 89 | 10023 | 10032 | 10 | reverse |
| hsa-miR-19b-2 | AGTCTTGAAG | 90 | 9399 | 9408 | 10 | reverse |
| hsa-miR-19b-2 | AGGTTTGTAG | 91 | 7758 | 7767 | 10 | reverse |
| hsa-miR-19b-2 | AGTATTGAAG | 92 | 7159 | 7168 | 10 | reverse |
| hsa-miR-19b-2 | AGGCTTGCAG | 93 | 3546 | 3555 | 10 | reverse |
| hsa-miR-19b-2 | AATTTGGCAG | 94 | 529 | 538 | 10 | reverse |
| hsa-miR-19b-2 | AGTTTTGGAA | 95 | 312 | 321 | 10 | reverse |
| hsa-miR-20b | CAAAGTGCT | | 12200 | 12208 | 9 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-20b | CAAAGTGCT | | 9931 | 9939 | 9 | reverse |
| hsa-miR-20b | CAAAGTGCT | | 218 | 226 | 9 | reverse |
| hsa-miR-21-5p | TAGCTTATCT | 96 | 14153 | 14162 | 10 | reverse |
| hsa-miR-22-3p | AAGCTGCCAA | 97 | 14859 | 14868 | 10 | reverse |
| hsa-miR-22-3p | AAGCTTCCAG | 98 | 1482 | 1491 | 10 | reverse |
| hsa-miR-22-5p | AGTTCTTCACA | 99 | 14203 | 14213 | 11 | reverse |
| hsa-miR-22-5p | AATTCTTCAGG | 100 | 8032 | 8042 | 11 | reverse |
| hsa-miR-22-5p | GGTTCTTCAGC | 101 | 5389 | 5399 | 11 | reverse |
| hsa-miR-24-2-5p | TGCCTACTGGCC | 102 | 8651 | 8662 | 12 | reverse |
| hsa-miR-25-3p | CATTGCAC | | 11565 | 11572 | 8 | reverse |
| hsa-miR-25-5p | AGGCGGAG | | 5963 | 5970 | 8 | reverse |
| hsa-miR-26a-2-3p | CCTTTTCATG | 103 | 15616 | 15625 | 10 | reverse |
| hsa-miR-26a-2-3p | CCAATCCTTG | 104 | 14853 | 14862 | 10 | reverse |
| hsa-miR-26a-2-3p | CATTTTCTTG | 105 | 13918 | 13927 | 10 | reverse |
| hsa-miR-26a-2-3p | CCTACTCTTC | 106 | 13505 | 13514 | 10 | reverse |
| hsa-miR-26a-2-3p | ACGATTCTTG | 107 | 13192 | 13201 | 10 | reverse |
| hsa-miR-26a-2-3p | TCTATTCTTT | 108 | 12883 | 12892 | 10 | reverse |
| hsa-miR-26a-2-3p | CATATTTTTG | 109 | 10197 | 10206 | 10 | reverse |
| hsa-miR-26a-2-3p | GCTAGTCTTG | 110 | 9978 | 9987 | 10 | reverse |
| hsa-miR-26a-2-3p | CATATTTTTG | 111 | 9890 | 9899 | 10 | reverse |
| hsa-miR-26a-2-3p | CCTTTTCTTT | 112 | 6631 | 6640 | 10 | reverse |
| hsa-miR-26a-2-3p | CCCATTCTCG | 113 | 4709 | 4718 | 10 | reverse |
| hsa-miR-26a-2-3p | TTTATTCTTG | 114 | 3893 | 3902 | 10 | reverse |
| hsa-miR-26a-2-3p | CCTTTACTTG | 115 | 1885 | 1894 | 10 | reverse |
| hsa-miR-26a-2-3p | GCGATTCTTG | 116 | 376 | 385 | 10 | reverse |
| hsa-miR-27-5p | AGAGCTTAGG | 117 | 2949 | 2958 | 10 | reverse |
| hsa-miR-30b | GTAACCTTCC | 118 | 14878 | 14887 | 10 | reverse |
| hsa-miR-30b | GTAACCATCA | 119 | 12991 | 13000 | 10 | reverse |
| hsa-miR-30b | GTAATCATAC | 120 | 12831 | 12840 | 10 | reverse |
| hsa-miR-30b | GTCAACATCA | 121 | 11401 | 11410 | 10 | reverse |
| hsa-miR-30b | GTAAACATAA | 122 | 9365 | 9374 | 10 | reverse |
| hsa-miR-30b | GTACTCATCC | 123 | 9016 | 9025 | 10 | reverse |
| hsa-miR-30b | CTATACATCC | 124 | 8586 | 8595 | 10 | reverse |
| hsa-miR-30b | CTAAACATCT | 125 | 7495 | 7504 | 10 | reverse |
| hsa-miR-31 | GGCTATGCC | | 7712 | 7720 | 9 | reverse |
| hsa-miR-32 | ATTGCACA | | 11564 | 11571 | 8 | reverse |
| hsa-miR-92b | ATTGCACTCC | 126 | 14181 | 14190 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-92b | ATTGCACTAG | 127 | 11282 | 11291 | 10 | reverse |
| hsa-miR-93 | CAAAGTGCTG | 128 | 12199 | 12208 | 10 | reverse |
| hsa-miR-93 | CAAAGTGCTG | 129 | 217 | 226 | 10 | reverse |
| hsa-miR-93-3p | ACTCCTGGGCT | 130 | 12356 | 12366 | 11 | reverse |
| hsa-miR-93-3p | ACTGATAAGCT | 131 | 11055 | 11065 | 11 | reverse |
| hsa-miR-93-3p | ACTCCTGACCT | 132 | 9966 | 9976 | 11 | reverse |
| hsa-miR-96-3p | AATCATGTGCC | 133 | 8659 | 8669 | 11 | reverse |
| hsa-miR-99a-3p | AAGCTGGCTC | 134 | 15117 | 15126 | 10 | reverse |
| hsa-miR-99a-3p | AAACTCTTTC | 135 | 13344 | 13353 | 10 | reverse |
| hsa-miR-99a-3p | AATCTTGTTC | 136 | 11952 | 11961 | 10 | reverse |
| hsa-miR-99a-3p | AAGCTCCTTT | 137 | 11050 | 11059 | 10 | reverse |
| hsa-miR-99a-3p | AAGCTCCTTT | 138 | 8099 | 8108 | 10 | reverse |
| hsa-miR-99a-3p | AAGCTCTGTC | 139 | 7523 | 7532 | 10 | reverse |
| hsa-miR-99b-3p | CAACCTCGAG | 140 | 13666 | 13675 | 10 | reverse |
| hsa-miR-99b-3p | CGAGCTCCTG | 141 | 13660 | 13669 | 10 | reverse |
| hsa-miR-99b-3p | GAAGCTTGTG | 142 | 6436 | 6445 | 10 | reverse |
| hsa-miR-99b-3p | CAAACTCCTG | 143 | 257 | 266 | 10 | reverse |
| hsa-miR-100 | TCCAGTAGAT | 144 | 11866 | 11875 | 10 | reverse |
| hsa-miR-100 | ACGCGCAGAT | 145 | 5634 | 5643 | 10 | reverse |
| hsa-miR-106b-5p | CAAAGTGCTG | 146 | 12199 | 12208 | 10 | reverse |
| hsa-miR-106b-5p | CAAAGTGCTG | 147 | 217 | 226 | 10 | reverse |
| hsa-miR-126-3P | TCATACAGT | | 12828 | 12836 | 9 | reverse |
| hsa-miR-126-3P | TTGTACTGT | | 11542 | 11550 | 9 | reverse |
| hsa-miR-126-3P | TGGTCCCGT | | 7922 | 7930 | 9 | reverse |
| hsa-miR-126-3P | TCATACAGT | | 932 | 940 | 9 | reverse |
| hsa-miR-130b | TTATTTTCCCT | 148 | 15161 | 15171 | 11 | reverse |
| hsa-miR-130b | CTCTTTTCAGT | 149 | 9670 | 9680 | 11 | reverse |
| hsa-miR-130b | CTCTCTTCACT | 150 | 8977 | 8987 | 11 | reverse |
| hsa-miR-130b | CTCTTTTTCCC | 151 | 8444 | 8454 | 11 | reverse |
| hsa-miR-130b | CTTTTTCCCCT | 152 | 6624 | 6634 | 11 | reverse |
| hsa-miR-130b | CTATTTTCCGT | 153 | 5742 | 5752 | 11 | reverse |
| hsa-miR-130b | TTCCTTTCCCT | 154 | 5007 | 5017 | 11 | reverse |
| hsa-miR-130b | CTCTTTGCCCC | 155 | 1845 | 1855 | 11 | reverse |
| hsa-miR-130b | CTCCTTTCCTT | 156 | 1033 | 1043 | 11 | reverse |
| hsa-miR-133a-1 | TTTGGTGCCC | 157 | 7393 | 7402 | 10 | reverse |
| hsa-miR-140-3p | TACCACAG | | 5893 | 5900 | 8 | reverse |
| hsa-miR-141 | TAACACTG | | 5852 | 5859 | 8 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-143 | GGTGCAGTG | 158 | 4132 | 4140 | 9 | reverse |
| hsa-miR-143-3p | TGAGATGAGG | 159 | 13727 | 13736 | 10 | reverse |
| hsa-miR-143-3p | TGAGATGGAG | 160 | 10172 | 10181 | 10 | reverse |
| hsa-miR-143-3p | TTAGATGAAG | 161 | 9572 | 9581 | 10 | reverse |
| hsa-miR-144-3p | TACAGTATT | | 12825 | 12833 | 9 | reverse |
| hsa-miR-144-3p | TACAATATA | | 8859 | 8867 | 9 | reverse |
| hsa-miR-144-3p | GACAGTATA | | 1491 | 1499 | 9 | reverse |
| hsa-miR-146a | CCTCTGAAA | | 3499 | 3507 | 9 | reverse |
| hsa-miR-146a | TGTGAACTGG | 162 | 15679 | 15688 | 10 | reverse |
| hsa-miR-146a | AGGGAACTGA | 163 | 15231 | 15240 | 10 | reverse |
| hsa-miR-146a | TGACAACTGT | 164 | 14327 | 14336 | 10 | reverse |
| hsa-miR-146a | TAAGAACTAA | 165 | 8935 | 8944 | 10 | reverse |
| hsa-miR-146a | TTAGAACAGA | 166 | 7908 | 7917 | 10 | reverse |
| hsa-miR-146a | TGAGAAGTGC | 167 | 6926 | 6935 | 10 | reverse |
| hsa-miR-146a | TGAAAACTTA | 168 | 3883 | 3892 | 10 | reverse |
| hsa-miR-146a | ACAGAACTGA | 169 | 2259 | 2268 | 10 | reverse |
| hsa-miR-146a | TGAGACCAGA | 170 | 2235 | 2244 | 10 | reverse |
| hsa-miR-146a | TGAGAAATAA | 171 | 1614 | 1623 | 10 | reverse |
| hsa-miR-147 | TGTGTGGATAA | 172 | 7223 | 7233 | 11 | reverse |
| hsa-miR-147 | TTTGTGCAAAT | 173 | 3916 | 3926 | 11 | reverse |
| hsa-miR-154 | AATCATACA | | 12830 | 12838 | 9 | reverse |
| hsa-miR-154 | AATCATACA | | 934 | 942 | 9 | reverse |
| hsa-miR-181c | AACCATAGT | | 15304 | 15312 | 9 | reverse |
| hsa-miR-181c | AACCAAAGA | | 13244 | 13252 | 9 | reverse |
| hsa-miR-181c | AACCATCAC | | 12990 | 12998 | 9 | reverse |
| hsa-miR-181c | ATCCAGCGA | | 11466 | 11474 | 9 | reverse |
| hsa-miR-181c | AAACATCTA | | 7494 | 7502 | 9 | reverse |
| hsa-miR-181c | AAAAATCGA | | 6201 | 6209 | 9 | reverse |
| hsa-miR-181c | AACCCCCGA | | 5540 | 5548 | 9 | reverse |
| hsa-miR-181c | AACCCTCTA | | 3614 | 3622 | 9 | reverse |
| hsa-miR-181c | AGCCAGCGA | | 3471 | 3479 | 9 | reverse |
| hsa-miR-181c | AACCATAGG | | 2801 | 2809 | 9 | reverse |
| hsa-miR-181c | AACCATCAC | | 194 | 202 | 9 | reverse |
| hsa-miR-185 | TGGAGAGAA | | 2979 | 2987 | 9 | reverse |
| hsa-miR-192-5p | CTAACATATGAA | 174 | 114 | 125 | 12 | reverse |
| hsa-miR-194-1 | TGTAACAGCA | 175 | 1895 | 1904 | 10 | reverse |
| hsa-miR-196a | AGGTAGTTT | | 12139 | 12147 | 9 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-199a-5p | CCCTGTGTTC | 176 | 5753 | 5762 | 10 | reverse |
| hsa-miR-200a | TAACACTG | | 5852 | 5859 | 8 | reverse |
| hsa-miR-200b | TAATAATGCC | 177 | 11184 | 11193 | 10 | reverse |
| hsa-miR-200b | GAATACTGCC | 178 | 10340 | 10349 | 10 | reverse |
| hsa-miR-200c-3p | TAATACTGT | | 12466 | 12474 | 9 | reverse |
| hsa-miR-200c-3p | TAATAATGC | | 11185 | 11193 | 9 | reverse |
| hsa-miR-200c-3p | GAATACTGC | | 10341 | 10349 | 9 | reverse |
| hsa-miR-200c-3p | TAATACAGC | | 7594 | 7602 | 9 | reverse |
| hsa-miR-203 | TTAAATGTT | | 15584 | 15592 | 9 | reverse |
| hsa-miR-203 | TGAAATTTT | | 9782 | 9790 | 9 | reverse |
| hsa-miR-203 | TGAAAGGTT | | 4495 | 4503 | 9 | reverse |
| hsa-miR-204-5p | TTCCTCTGTC | 179 | 14648 | 14657 | 10 | reverse |
| hsa-miR-204-5p | TTCCTTTATC | 180 | 14006 | 14015 | 10 | reverse |
| hsa-miR-205 | TCCTTCATT | | 10659 | 10667 | 9 | reverse |
| hsa-miR-208b | ATAAGAAGA | | 9493 | 9501 | 9 | reverse |
| hsa-miR-208b | ATAAGAAGA | | 1770 | 1778 | 9 | reverse |
| hsa-miR-211-5p | TTCCCTATCTC | 181 | 14779 | 14789 | 11 | reverse |
| hsa-miR-211-5p | TCCCCTCTGTC | 182 | 5238 | 5248 | 11 | reverse |
| hsa-miR-211-5p | TTCCCTTGCTC | 183 | 5002 | 5012 | 11 | reverse |
| hsa-miR-211-5p | TTCCCATTCTC | 184 | 4710 | 4720 | 11 | reverse |
| hsa-miR-214 | CAGCAAGCA | | 15052 | 15060 | 9 | reverse |
| hsa-miR-214 | CAGAAGGCA | | 6918 | 6926 | 9 | reverse |
| hsa-miR-214 | CCGCAGGCA | | 5935 | 5943 | 9 | reverse |
| hsa-miR-214 | CACCAGGCA | | 2087 | 2095 | 9 | reverse |
| hsa-miR-218 | TGTGCTTGA | | 10385 | 10393 | 9 | reverse |
| hsa-miR-302c | TTTAACATG | | 2932 | 2940 | 9 | reverse |
| hsa-miR-324-5p | CGCGTCCCCT | 185 | 4876 | 4885 | 10 | reverse |
| hsa-miR-325 | CCTTGTAGGC | 186 | 15378 | 15387 | 10 | reverse |
| hsa-miR-325 | CAGAGTAGGT | 187 | 14475 | 14484 | 10 | reverse |
| hsa-miR-325 | CCAAGTAGCT | 188 | 10066 | 10075 | 10 | reverse |
| hsa-miR-325 | CCAAGTAGCT | 189 | 354 | 363 | 10 | reverse |
| hsa-miR-328 | CTGTTCCTCT | 190 | 14651 | 14660 | 10 | reverse |
| hsa-miR-328 | CTGGCTCCCT | 191 | 8215 | 8224 | 10 | reverse |
| hsa-miR-328 | CTGGCCCTTC | 192 | 8062 | 8071 | 10 | reverse |
| hsa-miR-328 | CTGGCACTCA | 193 | 6653 | 6662 | 10 | reverse |
| hsa-miR-328 | CTGGCTTTCT | 194 | 6496 | 6505 | 10 | reverse |
| hsa-miR-328 | CTGCCCCTCC | 195 | 6048 | 6057 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-328 | CTGGGCCGCT | 196 | 4804 | 4813 | 10 | reverse |
| hsa-miR-328 | CTGGAGCTCT | 197 | 4477 | 4486 | 10 | reverse |
| hsa-miR-328 | CTGACCCTTT | 198 | 1089 | 1098 | 10 | reverse |
| hsa-miR-330 | CAAAGCACAC | 199 | 13845 | 13854 | 10 | reverse |
| hsa-miR-330 | CAAAGCACAC | 199 | 11657 | 11666 | 10 | reverse |
| hsa-miR-331-5p | CTAGGTGTGG | 200 | 7719 | 7728 | 10 | reverse |
| hsa-miR-361-3p | CCCCCAGG |  | 5112 | 5119 | 8 | reverse |
| hsa-miR-362-5p | ATCCTTGGAT | 201 | 14850 | 14859 | 10 | reverse |
| hsa-miR-367-3p | AATTGCACTC | 202 | 14182 | 14191 | 10 | reverse |
| hsa-miR-367-3p | AAATGCACTT | 203 | 999 | 1008 | 10 | reverse |
| hsa-miR-369 | AATAATACA |  | 2266 | 2274 | 9 | reverse |
| hsa-miR-371a-3p | AAGTGCCTGC | 204 | 15435 | 15444 | 10 | reverse |
| hsa-miR-371a-3p | AAGAGCCGAC | 205 | 11455 | 11464 | 10 | reverse |
| hsa-miR-371a-3p | ACGTGCCACC | 206 | 10044 | 10053 | 10 | reverse |
| hsa-miR-371a-3p | AAGTGCCTCT | 207 | 7047 | 7056 | 10 | reverse |
| hsa-miR-371a-3p | AAGTGCACCC | 208 | 5457 | 5466 | 10 | reverse |
| hsa-miR-371a-5p | TCTCAAACTG | 209 | 14658 | 14667 | 10 | reverse |
| hsa-miR-372 | AAAGTGCTG |  | 12199 | 12207 | 9 | reverse |
| hsa-miR-372 | AAAGTGCTG |  | 217 | 225 | 9 | reverse |
| hsa-miR-374a-3p | TCATCAGATT | 210 | 10606 | 10615 | 10 | reverse |
| hsa-miR-377-3p | AGCACACAAA | 211 | 13842 | 13851 | 10 | reverse |
| hsa-miR-378a-3p | ACTGGCCTTG | 212 | 15816 | 15825 | 10 | reverse |
| hsa-miR-378a-3p | ACTGGTCTTG | 213 | 11837 | 11846 | 10 | reverse |
| hsa-miR-378a-5p | CTCCTGCCTC | 214 | 12216 | 12225 | 10 | reverse |
| hsa-miR-378a-5p | CTCCTGCCTC | 215 | 10082 | 10091 | 10 | reverse |
| hsa-miR-378a-5p | CTCCTGTCTC | 216 | 8207 | 8216 | 10 | reverse |
| hsa-miR-378a-5p | CTCCTAACTC | 217 | 7650 | 7659 | 10 | reverse |
| hsa-miR-382-3p | ATTCATTCAC | 218 | 14194 | 14203 | 10 | reverse |
| hsa-miR-383 | AGATTAGAA |  | 14545 | 14553 | 9 | reverse |
| hsa-miR-383 | AGATTAGAA |  | 7912 | 7920 | 9 | reverse |
| hsa-miR-383 | AGAACAGAA |  | 5801 | 5809 | 9 | reverse |
| hsa-miR-412 | ACTTCACCT |  | 737 | 745 | 9 | reverse |
| hsa-miR-421 | CTCAAAAGAC | 219 | 14380 | 14389 | 10 | reverse |
| hsa-miR-421 | ATTAACTGAC | 220 | 14333 | 14342 | 10 | reverse |
| hsa-miR-421 | AACATCAGAC | 221 | 11398 | 11407 | 10 | reverse |
| hsa-miR-421 | ATCAACTGAG | 222 | 3427 | 3436 | 10 | reverse |
| hsa-miR-421 | ATCAACAGGT | 223 | 2443 | 2452 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-421 | ATCAAAAGAT | 224 | 2333 | 2342 | 10 | reverse |
| hsa-miR-422a | ACTGGCCTT | | 15817 | 15825 | 9 | reverse |
| hsa-miR-422a | ACTGGTCTT | | 11838 | 11846 | 9 | reverse |
| hsa-miR-422a | ACTGGACGT | | 5847 | 5855 | 9 | reverse |
| hsa-miR-425 | AGCGGGAAGGT | 225 | 5167 | 5177 | 11 | reverse |
| hsa-miR-431 | TGTCTGGCA | | 14892 | 14900 | 9 | reverse |
| hsa-miR-431 | TGTCTAGCA | | 9218 | 9226 | 9 | reverse |
| hsa-miR-432-5p | TCCTGGAGT | | 13624 | 13632 | 9 | reverse |
| hsa-miR-432-5p | TATTGGAGT | | 10785 | 10793 | 9 | reverse |
| hsa-miR-432-5p | TCTTAGAGT | | 9263 | 9271 | 9 | reverse |
| hsa-miR-432-5p | TCTTAGAGT | | 6666 | 6674 | 9 | reverse |
| hsa-miR-432-5p | TCTTGGAGC | | 2180 | 2188 | 9 | reverse |
| hsa-miR-452 | ACATCTGC | | 15009 | 15016 | 8 | reverse |
| hsa-miR-452 | TCTTCTGC | | 14773 | 14780 | 8 | reverse |
| hsa-miR-452 | TTATCTGC | | 14151 | 14158 | 8 | reverse |
| hsa-miR-452 | TCCTCTGC | | 13488 | 13495 | 8 | reverse |
| hsa-miR-452 | TCATGTGC | | 8660 | 8667 | 8 | reverse |
| hsa-miR-452 | TCATCTGG | | 8221 | 8228 | 8 | reverse |
| hsa-miR-452 | TCATGTGC | | 7945 | 7952 | 8 | reverse |
| hsa-miR-452 | ACATCTGC | | 7508 | 7515 | 8 | reverse |
| hsa-miR-452 | CCATCTGC | | 6787 | 6794 | 8 | reverse |
| hsa-miR-452 | TCATCCGC | | 5912 | 5919 | 8 | reverse |
| hsa-miR-452 | TCATCTGT | | 4053 | 4060 | 8 | reverse |
| hsa-miR-452 | TCATCTCC | | 3667 | 3674 | 8 | reverse |
| hsa-miR-452 | TCCTCTGC | | 3457 | 3464 | 8 | reverse |
| hsa-miR-452 | TCTTCTGC | | 2210 | 2217 | 8 | reverse |
| hsa-miR-455-3p | CAGTCCAT | | 13893 | 13900 | 8 | reverse |
| hsa-miR-455-5p | TGTGTGCCTT | 226 | 15641 | 15650 | 10 | reverse |
| hsa-miR-455-5p | TCTGTGCCTT | 227 | 11203 | 11212 | 10 | reverse |
| hsa-miR-455-5p | TATGTGCTTT | 228 | 10522 | 10531 | 10 | reverse |
| hsa-miR-483-3p | CACTCCTC | | 13536 | 13543 | 8 | reverse |
| hsa-miR-483-3p | CACTCCTC | | 10333 | 10340 | 8 | reverse |
| hsa-miR-483-3p | CACTCCTC | | 6101 | 6108 | 8 | reverse |
| hsa-miR-486-5p | TCATGTACT | | 9835 | 9843 | 9 | reverse |
| hsa-miR-486-5p | TCCTGTCCT | | 6526 | 6534 | 9 | reverse |
| hsa-miR-487a | AATCATACAG | 229 | 12829 | 12838 | 10 | reverse |
| hsa-miR-487a | AATCATACAG | 229 | 933 | 942 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-491-5p | AATGGGGAAG | 230 | 14975 | 14984 | 10 | reverse |
| hsa-miR-491-5p | AGAGGGGACC | 231 | 12315 | 12324 | 10 | reverse |
| hsa-miR-491-5p | AGTTGGGCAC | 232 | 11555 | 11564 | 10 | reverse |
| hsa-miR-491-5p | AGTAGAGAAC | 233 | 6909 | 6918 | 10 | reverse |
| hsa-miR-491-5p | GGTGAGGAAC | 234 | 6005 | 6014 | 10 | reverse |
| hsa-miR-491-5p | AGCGGGGCAC | 235 | 4455 | 4464 | 10 | reverse |
| hsa-miR-491-5p | AGTGGGAAAT | 236 | 3846 | 3855 | 10 | reverse |
| hsa-miR-496 | TTAGTATTA | | 10948 | 10956 | 9 | reverse |
| hsa-miR-496 | TGAGTATAA | | 10768 | 10776 | 9 | reverse |
| hsa-miR-496 | TCAGTATTA | | 9666 | 9674 | 9 | reverse |
| hsa-miR-501-3p | ATGCATCAGG | 237 | 15547 | 15556 | 10 | reverse |
| hsa-miR-501-3p | ATCCACCGGG | 238 | 11497 | 11506 | 10 | reverse |
| hsa-miR-501-3p | AGGCACCAGG | 239 | 2089 | 2098 | 10 | reverse |
| hsa-miR-504 | AGACCCTGT | | 15325 | 15333 | 9 | reverse |
| hsa-miR-504 | AGCCCCTGG | | 12898 | 12906 | 9 | reverse |
| hsa-miR-504 | AGTCCCTGG | | 10591 | 10599 | 9 | reverse |
| hsa-miR-504 | AGACCCGGG | | 4767 | 4775 | 9 | reverse |
| hsa-miR-508-3p | TGATTATAGC | 240 | 13565 | 13574 | 10 | reverse |
| hsa-miR-508-3p | TGAGTGTAGC | 241 | 3231 | 3240 | 10 | reverse |
| hsa-miR-512-3p | CAGTGCTGTC | 242 | 13211 | 13220 | 10 | reverse |
| hsa-miR-512-3p | AAGTGCTCTC | 243 | 7688 | 7697 | 10 | reverse |
| hsa-miR-512-3p | AAGTGCTCTC | 243 | 3184 | 3193 | 10 | reverse |
| hsa-miR-512-5p | CACTCAG | | 14255 | 14261 | 7 | reverse |
| hsa-miR-512-5p | CACTCAG | | 13591 | 13597 | 7 | reverse |
| hsa-miR-512-5p | CACTCAG | | 12291 | 12297 | 7 | reverse |
| hsa-miR-512-5p | CACTCAG | | 6652 | 6658 | 7 | reverse |
| hsa-miR-512-5p | CACTCAG | | 5067 | 5073 | 7 | reverse |
| hsa-miR-514a-3p | TTGACTCTT | | 14406 | 14414 | 9 | reverse |
| hsa-miR-514a-3p | TTGACAGTT | | 13870 | 13878 | 9 | reverse |
| hsa-miR-514a-3p | TTAACACTT | | 11237 | 11245 | 9 | reverse |
| hsa-miR-514a-3p | ATGACACTT | | 10617 | 10625 | 9 | reverse |
| hsa-miR-515-3p | GTGTGCCTT | | 15641 | 15649 | 9 | reverse |
| hsa-miR-515-3p | GACTGCCTT | | 15539 | 15547 | 9 | reverse |
| hsa-miR-515-3p | GAGTGACTT | | 1371 | 1379 | 9 | reverse |
| hsa-miR-516a-3p | TGCTTCCT | | 10301 | 10308 | 8 | reverse |
| hsa-miR-517a-3p | ATGGTGCATT | 244 | 15650 | 15659 | 10 | reverse |
| hsa-miR-517a-3p | ATCTTGCTTC | 245 | 10303 | 10312 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-519b-3p | AAAGTGCAT | | 13782 | 13790 | 9 | reverse |
| hsa-miR-519e-3p | AAGTGCCTC | | 7048 | 7056 | 9 | reverse |
| hsa-miR-520a-5p | CTCCAGATGG | | 6274 | 6283 | 10 | reverse |
| hsa-miR-545 | CAGCAAGCACT | 246 | 15050 | 15060 | 11 | reverse |
| hsa-miR-545 | CAGAACACATT | 247 | 11639 | 11649 | 11 | reverse |
| hsa-miR-545 | CTGCAAACACT | 248 | 3450 | 3460 | 11 | reverse |
| hsa-miR-549 | TGACAACTGT | 249 | 14327 | 14336 | 10 | reverse |
| hsa-miR-551b-3p | GCTACCCAT | | 2411 | 2419 | 9 | reverse |
| hsa-miR-552 | CACAGGTGA | | 15130 | 15138 | 9 | reverse |
| hsa-miR-552 | AACAGGTCA | | 11407 | 11415 | 9 | reverse |
| hsa-miR-552 | AACATGTGA | | 9513 | 9521 | 9 | reverse |
| hsa-miR-552 | AACAGGTTA | | 2441 | 2449 | 9 | reverse |
| hsa-miR-552 | AACAGGTAA | | 1569 | 1577 | 9 | reverse |
| hsa-miR-583 | AAAAGAGGA | | 2921 | 2929 | 9 | reverse |
| hsa-miR-583 | CAAATAGGA | | 2833 | 2841 | 9 | reverse |
| hsa-miR-583 | CAACGAGGA | | 1824 | 1832 | 9 | reverse |
| hsa-miR-583 | CAAAGAAGA | | 1139 | 1147 | 9 | reverse |
| hsa-miR-593-3p | TGTCTCTGT | | 8204 | 8212 | 9 | reverse |
| hsa-miR-593-3p | TGGCTCTGC | | 6852 | 6860 | 9 | reverse |
| hsa-miR-593-3p | TGCCTCTGC | | 231 | 239 | 9 | reverse |
| hsa-miR-593-5p | AGGCACCAG | | 2090 | 2098 | 9 | reverse |
| hsa-miR-593-5p | AGGCACCAG | | 2083 | 2091 | 9 | reverse |
| hsa-miR-598 | ACGTCATC | | 11432 | 11439 | 8 | reverse |
| hsa-miR-611 | GCGAGGTCTC | 250 | 4779 | 4788 | 10 | reverse |
| hsa-miR-611 | GAGAGGCCCC | 251 | 2121 | 2130 | 10 | reverse |
| hsa-miR-611 | GAGAGGACCT | 252 | 1546 | 1555 | 10 | reverse |
| hsa-miR-616-5p | ACTCTAAAC | | 14510 | 14518 | 9 | reverse |
| hsa-miR-619 | GACCTGGA | | 5824 | 5831 | 8 | reverse |
| hsa-miR-620 | ATGAATATAG | 253 | 14560 | 14569 | 10 | reverse |
| hsa-miR-620 | ATGGAAATAT | 254 | 12111 | 12120 | 10 | reverse |
| hsa-miR-620 | TTGGATATAG | 255 | 11026 | 11035 | 10 | reverse |
| hsa-miR-620 | GTGGAGATGG | 256 | 10397 | 10406 | 10 | reverse |
| hsa-miR-620 | ATGGAGATCC | 257 | 6268 | 6277 | 10 | reverse |
| hsa-miR-620 | ATGGAGGGAG | 258 | 5626 | 5635 | 10 | reverse |
| hsa-miR-620 | CTGGAGAAAG | 259 | 3827 | 3836 | 10 | reverse |
| hsa-miR-620 | ATCCAGATAG | 260 | 2959 | 2968 | 10 | reverse |
| hsa-miR-620 | ATGGGGCTAG | 261 | 2843 | 2852 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-620 | AGGGAGAGAG | 262 | 1551 | 1560 | 10 | reverse |
| hsa-miR-620 | CAGGAGATAG | 263 | 1430 | 1439 | 10 | reverse |
| hsa-miR-620 | TTGGAGAGAG | 264 | 1201 | 1210 | 10 | reverse |
| hsa-miR-623 | TCCCTTGC | | 8306 | 8313 | 8 | reverse |
| hsa-miR-623 | TCCCTTGC | | 5004 | 5011 | 8 | reverse |
| hsa-miR-631 | CACCTGGCC | | 9900 | 9908 | 9 | reverse |
| hsa-miR-631 | GACATGGCC | | 8632 | 8640 | 9 | reverse |
| hsa-miR-634 | AACCAGCAC | | 4520 | 4528 | 9 | reverse |
| hsa-miR-636 | TGTGCTTG | | 10386 | 10393 | 8 | reverse |
| hsa-miR-638 | ACGGAGCGCG | 265 | 4905 | 4914 | 10 | reverse |
| hsa-miR-638 | AGGGAGGGCG | 266 | 4615 | 4624 | 10 | reverse |
| hsa-miR-642a-5p | ATCCCTCTC | | 8983 | 8991 | 9 | reverse |
| hsa-miR-642a-5p | GTCCCTCCC | | 4722 | 4730 | 9 | reverse |
| hsa-miR-643 | ACATGCATGC | 267 | 15553 | 15562 | 10 | reverse |
| hsa-miR-643 | CCTTGTAGGC | 268 | 15378 | 15387 | 10 | reverse |
| hsa-miR-643 | TCTTGTATTC | 269 | 14423 | 14432 | 10 | reverse |
| hsa-miR-643 | ACTGGTATGT | 270 | 13933 | 13942 | 10 | reverse |
| hsa-miR-643 | ACTTCTATTC | 271 | 12886 | 12895 | 10 | reverse |
| hsa-miR-643 | ACTTTTCTGC | 272 | 12044 | 12053 | 10 | reverse |
| hsa-miR-643 | GCTTGTAAGC | 273 | 11698 | 11707 | 10 | reverse |
| hsa-miR-643 | AGTTGTATGT | 274 | 10531 | 10540 | 10 | reverse |
| hsa-miR-643 | ACTTGGAAGC | 275 | 8105 | 8114 | 10 | reverse |
| hsa-miR-643 | ACTTGTGTGG | 276 | 7227 | 7236 | 10 | reverse |
| hsa-miR-643 | ACTTGTTTGA | 277 | 1880 | 1889 | 10 | reverse |
| hsa-miR-643 | ACATGTTTGC | 278 | 1695 | 1704 | 10 | reverse |
| hsa-miR-650 | AGGAGGCAC | 279 | 9647 | 9655 | 9 | reverse |
| hsa-miR-650 | AGAAGGCAG | 280 | 6917 | 6925 | 9 | reverse |
| hsa-miR-650 | AGGAGCCAG | 281 | 3474 | 3482 | 9 | reverse |
| hsa-miR-650 | ATGAGGCAG | 282 | 3052 | 3060 | 9 | reverse |
| hsa-miR-651 | TCATGATAAG | 283 | 15700 | 15709 | 10 | reverse |
| hsa-miR-651 | TTAGGTTAAA | 284 | 13993 | 14002 | 10 | reverse |
| hsa-miR-651 | TTAAAATAAG | 285 | 13988 | 13997 | 10 | reverse |
| hsa-miR-651 | TTAGCATAAC | 286 | 12788 | 12797 | 10 | reverse |
| hsa-miR-651 | TTATGATGAG | 287 | 12617 | 12626 | 10 | reverse |
| hsa-miR-651 | TTTGGATGAG | 288 | 11069 | 11078 | 10 | reverse |
| hsa-miR-651 | TGAGTATAAG | 289 | 10767 | 10776 | 10 | reverse |
| hsa-miR-651 | TTACAATAAG | 290 | 10546 | 10555 | 10 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-651 | TAAGGATAAA | 291 | 8265 | 8274 | 10 | reverse |
| hsa-miR-651 | TGTGGATAAG | 292 | 7222 | 7231 | 10 | reverse |
| hsa-miR-651 | GTAGGATAGG | 293 | 5553 | 5562 | 10 | reverse |
| hsa-miR-651 | CTAGGAAAAG | 294 | 2823 | 2832 | 10 | reverse |
| hsa-miR-651 | CTATGATAAG | 295 | 1635 | 1644 | 10 | reverse |
| hsa-miR-651 | TAAGGATAGG | 296 | 1562 | 1571 | 10 | reverse |
| hsa-miR-654-3p | TATGTATACT | 297 | 15493 | 15502 | 10 | reverse |
| hsa-miR-654-3p | TATCTCTTCT | 298 | 14775 | 14784 | 10 | reverse |
| hsa-miR-654-3p | TCTATCTGCT | 299 | 8354 | 8363 | 10 | reverse |
| hsa-miR-654-3p | AATGTCTGGT | 300 | 6720 | 6729 | 10 | reverse |
| hsa-miR-654-3p | TATGTTTCCT | 301 | 6638 | 6647 | 10 | reverse |
| hsa-miR-654-3p | TTTTTCTGCT | 302 | 6586 | 6595 | 10 | reverse |
| hsa-miR-654-3p | TATGTCTTTT | 303 | 6534 | 6543 | 10 | reverse |
| hsa-miR-654-3p | TATATCTGCA | 304 | 6214 | 6223 | 10 | reverse |
| hsa-miR-654-3p | TATGTAGGCT | 305 | 97 | 106 | 10 | reverse |
| hsa-miR-655 | GTAATACAT | | 15593 | 15601 | 9 | reverse |
| hsa-miR-655 | ATAGTACAT | | 4200 | 4208 | 9 | reverse |
| hsa-miR-655 | ATAAGACAT | | 3642 | 3650 | 9 | reverse |
| hsa-miR-655 | ATAATACAG | | 2265 | 2273 | 9 | reverse |
| hsa-miR-655 | ACAATACAT | | 1757 | 1765 | 9 | reverse |
| hsa-miR-656 | AATATTATA | | 657 | 665 | 9 | reverse |
| hsa-miR-664-3p | TATTCATTT | | 9385 | 9393 | 9 | reverse |
| hsa-miR-765 | TGGAGGA | | 5020 | 5026 | 7 | reverse |
| hsa-miR-766 | CTCCAGCCCC | 306 | 12901 | 12910 | 10 | reverse |
| hsa-miR-766 | CTCCAGCCCC | 307 | 5032 | 5041 | 10 | reverse |
| hsa-miR-767-3p | CCTGCTCAT | | 14871 | 14879 | 9 | reverse |
| hsa-miR-767-3p | TCTTCTCAT | | 9155 | 9163 | 9 | reverse |
| hsa-miR-875 | CCTGGAAATA | 308 | 5820 | 5829 | 10 | reverse |
| hsa-miR-875 | CCTAGAAACA | 309 | 5294 | 5303 | 10 | reverse |
| hsa-miR-876 | TGGATTTCT | | 6366 | 6374 | 9 | reverse |
| hsa-miR-876 | TGGATTTCT | | 142 | 150 | 9 | reverse |
| hsa-miR-888-3p | GACTGACTCC | 310 | 15772 | 15781 | 10 | reverse |
| hsa-miR-888-3p | GACTGACAGC | 311 | 9119 | 9128 | 10 | reverse |
| hsa-miR-890 | TACTTGGAAG | 312 | 8106 | 8115 | 10 | reverse |
| hsa-miR-940 | AAGGCAGTG | | 1807 | 1815 | 9 | reverse |
| hsa-miR-941 | CACCCAGGT | | 14396 | 14404 | 9 | reverse |
| hsa-miR-941 | CACCCTGCC | | 13715 | 13723 | 9 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-941 | CACCCCTCT | | 13128 | 13136 | 9 | reverse |
| hsa-miR-941 | CACTCAGCT | | 12289 | 12297 | 9 | reverse |
| hsa-miR-941 | CTCCCGGGT | | 10102 | 10110 | 9 | reverse |
| hsa-miR-941 | CAGCCTGCT | | 10034 | 10042 | 9 | reverse |
| hsa-miR-941 | CACCCACCT | | 9904 | 9912 | 9 | reverse |
| hsa-miR-941 | CACCTGGCC | | 9900 | 9908 | 9 | reverse |
| hsa-miR-941 | CATCTGGCT | | 8219 | 8227 | 9 | reverse |
| hsa-miR-941 | CACTCGACT | | 8148 | 8156 | 9 | reverse |
| hsa-miR-941 | CTCCCAGCT | | 6840 | 6848 | 9 | reverse |
| hsa-miR-941 | CTCACGGCT | | 6031 | 6039 | 9 | reverse |
| hsa-miR-941 | CAGCCCGCT | | 5928 | 5936 | 9 | reverse |
| hsa-miR-941 | CACCTGACT | | 5510 | 5518 | 9 | reverse |
| hsa-miR-941 | CACGCCGCT | | 5142 | 5150 | 9 | reverse |
| hsa-miR-941 | CTCCCTGCT | | 3983 | 3991 | 9 | reverse |
| hsa-miR-941 | CACCAGGCA | | 2087 | 2095 | 9 | reverse |
| hsa-miR-941 | CTCCCGGGT | | 390 | 398 | 9 | reverse |
| hsa-miR-941 | CACCCAGCC | | 186 | 194 | 9 | reverse |
| hsa-miR-941-2 | ATCCGACTGT | 313 | 9657 | 9666 | 10 | reverse |
| hsa-miR-941-2 | TCCCTGCTGT | 314 | 8726 | 8735 | 10 | reverse |
| hsa-miR-941-2 | TCCCAGCTGT | 315 | 6838 | 6847 | 10 | reverse |
| hsa-miR-941-2 | AGCCCGCTGT | 316 | 5926 | 5935 | 10 | reverse |
| hsa-miR-941-2 | ACCCGGGCGT | 317 | 4764 | 4773 | 10 | reverse |
| hsa-miR-1179 | AAGTATCCTTT | 318 | 15346 | 15356 | 11 | reverse |
| hsa-miR-1179 | ATGCATTCTGT | 319 | 3357 | 3367 | 11 | reverse |
| hsa-miR-1179 | ATGCATTCTCT | 320 | 1854 | 1864 | 11 | reverse |
| hsa-miR-1207-5p | TGGCAGGG | | 11441 | 11448 | 8 | reverse |
| hsa-miR-1224-3p | CTCCACCTCC | 321 | 399 | 408 | 10 | reverse |
| hsa-miR-1228-3p | TCCCACCTG | | 13637 | 13645 | 9 | reverse |
| hsa-miR-1228-3p | TCACGCCTG | | 4992 | 5000 | 9 | reverse |
| hsa-miR-1231 | GTGTCTGGC | | 12807 | 12815 | 9 | reverse |
| hsa-miR-1231 | GTGTCCGGG | | 4739 | 4747 | 9 | reverse |
| hsa-miR-1245 | AAGTGATCT | | 8341 | 8349 | 9 | reverse |
| hsa-miR-1245 | AAGTGATCT | | 2020 | 2028 | 9 | reverse |
| hsa-miR-1249 | CGCCCTTC | | 5907 | 5914 | 8 | reverse |
| hsa-miR-1251 | ACTCTAGGT | | 12854 | 12862 | 9 | reverse |
| hsa-miR-1251 | ACTCTATCT | | 8357 | 8365 | 9 | reverse |
| hsa-miR-1251 | ACTCCAGCT | | 4044 | 4052 | 9 | reverse |

TABLE 8-continued miRNAs with predicted binding sites in the UCP1 gene sequence
(NCBI Reference Sequence: NG_012139.1).

| miRNA | Sequence | SEQ ID NO | Minimum | Maximum | Length | Direction |
|---|---|---|---|---|---|---|
| hsa-miR-1251 | AGTCTAGCT | | 457 | 465 | 9 | reverse |
| hsa-miR-1252 | AGAGGGAAAT | 322 | 3819 | 3828 | 10 | reverse |
| hsa-miR-1252 | GGAAGGAAAT | 323 | 1625 | 1634 | 10 | reverse |
| hsa-miR-1268 | CGGGCGTGG | | 4762 | 4770 | 9 | reverse |
| hsa-miR-1270 | CTGGAAATA | | 5820 | 5828 | 9 | reverse |
| hsa-miR-1270 | CTGGAGATG | | 5055 | 5063 | 9 | reverse |
| hsa-miR-1270 | CTGGAGAAA | | 3828 | 3836 | 9 | reverse |
| hsa-miR-1270 | CAGGAGATA | | 1431 | 1439 | 9 | reverse |
| hsa-miR-1272 | GATGATGA | | 10622 | 10629 | 8 | reverse |
| hsa-miR-1275 | GTAGGGGAGA | 324 | 1189 | 1198 | 10 | reverse |
| hsa-miR-1302 | ATGGGACACA | 325 | 15021 | 15030 | 10 | reverse |
| hsa-miR-1302 | TTTGGATATA | 326 | 11027 | 11036 | 10 | reverse |
| hsa-miR-1302 | TTAGGGCATA | 327 | 8421 | 8430 | 10 | reverse |
| hsa-miR-1302 | TTGGAACAGA | 328 | 6076 | 6085 | 10 | reverse |
| hsa-miR-1302 | CTGGGACTTA | 329 | 4819 | 4828 | 10 | reverse |
| hsa-miR-1302 | GTGGGAAATA | 330 | 3845 | 3854 | 10 | reverse |
| hsa-miR-1302 | TTGTGAGATA | 331 | 1944 | 1953 | 10 | reverse |
| hsa-miR-1302 | CTGGGAAATA | 332 | 867 | 876 | 10 | reverse |
| hsa-miR-1324 | TCAAGACAGA | 333 | 9426 | 9435 | 10 | reverse |
| hsa-miR-1827 | TGAGGCAGT | | 3051 | 3059 | 9 | reverse |
| hsa-miR-1911-3p | CACCAGGCA | | 2087 | 2095 | 9 | reverse |
| hsa-miR-1915 | CCCCAGGG | | 5111 | 5118 | 8 | reverse |
| hsa-miR-2909 | TTTAGGGCC | | 3728 | 3736 | 9 | reverse |

B. Another Exemplary Multiple miRNAs-One mRNA Paradigm Involves UCP2.

UCP2 is a mitochondrial transporter protein expressed in WAT, skeletal muscle, pancreatic islets and the central nervous system. Like UCP1, it creates proton leaks across the inner mitochondrial membrane, thus uncoupling oxidative phosphorylation from ATP synthesis (adaptive thermogenesis, see FIG. 5) (Lowell et al., Nature (2000)).

Two recent meta-analyses report an association between polymorphisms in the promoter region of UCP2 and obesity (Liu et al., Gene (2013); Andersen et al., Int J. Obes. (2013)). The first meta-analysis included 14 studies (7,647 cases and 11,322 controls) and concluded that there is a significant association of the A allele of the UCP2 −866G/A polymorphism with reduced risk of obesity, especially in European populations. In the second meta-analysis including 12,984 subjects, the common UCP2 −866G allele is associated with obesity. The same UCP2 −866G allele is associated with decreased insulin sensitivity in 17,636 Danish subjects. In a study, UCP2 mRNA levels in visceral fat were decreased in subjects with the GG phenotype (Esterbauer et al., Nat. Genet. (2001)). A trend toward a negative correlation between subcutaneous adipocyte UCP2 mRNA and percent body fat was found in another study (Wang et al., American Journal of Physiol. (2004)). This information supports targeting UCP2 expression and activity as a meaningful way to alter adaptive thermogenesis and consequently treat human obesity. Many strategies could be implemented to achieve this goal, however, the one employed in the methods of the invention uses miRNA agents to modulate simultaneously several elements within the thermogenic pathways to increase UCP2 synthesis and activity. Both direct and indirect interactions between miRNAs and the UCP2 gene are considered. Direct interaction means the direct binding of miRNAs to the various regions of the UCP2 gene, resulting in alterations of the transcription, translation, stability and/or degradation of the UCP1 mRNA. Indirect interaction means that miRNAs alter the transcription, translation, stability and/or degradation of thermogenic mRNAs, whose expressed proteins alter the transcription of the UCP2 gene. Furthermore, indirect interaction means that miRNAs alter the transcription, translation, stability and/or degradation of other miRNAs that modify the transcription of the UCP2 gene.

The promoter region of the human UCP2 gene (ENSG00000175567, *Homo sapiens* uncoupling protein 2 (mitochondrial, proton carrier) (UCP2), RefSeqGene on chromosome 11) is rich is regulatory element motifs:

UCP2 Gene Regulatory Elements:
1. RXR/T3RE Motif: AGGTCA
Eight
Length: 6, Interval: 1,074->1,079; 3,083->3,088; 3,239->3,244; 4,304->4,309; 6,965->6,970; 7,420->7,425; 7,677->7,682; 13,319->13,324; Mismatches: 0.
2. GC Box 1 Motif: CGCCC
Sixteen
Length: 5, Interval: 2,605->2,609; 4,323->4,327; 4,523->4,527; 4,933->4,937; 4,959->4,963; 5,048->5,052; 5,066->5,070; 5,146->5,150; 5,155->5,159; 5,387->5,391; 5,483->5,487; 6,067->6,071; 8,523->8,527; 9,790->9,794; 10,819->10,823; 11,754->11,758;
Mismatches: 0.
3. GC Box 2 Motif: GCGGG
Five
Length: 5, Interval: 4,263->4,267; 4,757->4,761; 4,860->4,864; 7,619->7,623; 11,262->11,266; Mismatches: 0.
4. GT Box 1 Motif: CACCC
Thirty
Length: 5, Interval: 1,421->1,425; 1,677->1,681; 1,761->1,765; 1,825->1,829; 1,833->1,837; 2,036->2,040; 3,003->3,007; 4,903->4,907; 4,947->4,951; 5,210->5,214; 6,204->6,208; 6,247->6,251; 6,469->6,473; 6,828->6,832; 7,681->7,685; 8,048->8,052; 8,437->8,441; 8,572->8,576; 8,599->8,603; 8,702->8,706; 11,077->11,081; 11,235->11,239; 12,006->12,010; 12,374->12,378; 13,475->13,479; 13,666->13,670; 13,687->13,691; 13,838->13,842; 14,410->14,414; 14,545->14,549; Mismatches: 0.
5. GT Box 2 Motif: GTGGG
Twenty Six
Length: 5, Interval: 123->127; 1,006->1,010; 2,105->2,109; 4,562->4,566; 5,793->5,797; 6,029->6,033; 6,034->6,038; 6,040->6,044; 6,150->6,154; 7,271->7,275; 7,392->7,396; 9,040->9,044; 9,697->9,701; 10,227->10,231; 10,238->10,242; 10,247->10,251; 11,817->11,821; 12,410->12,414; 12,414->12,418; 12,678->12,682; 13,047->13,051; 13,238->13,742; 13,743->13,747; 14,252->14,256; 14,969->14,973; 15,104->15,108; Mismatches: 0.
6. CpG Methylation Island Motif: CG
Two Hundred and Ninety Five, including many between positions 4,071 to 5,212.

Figure 8B:
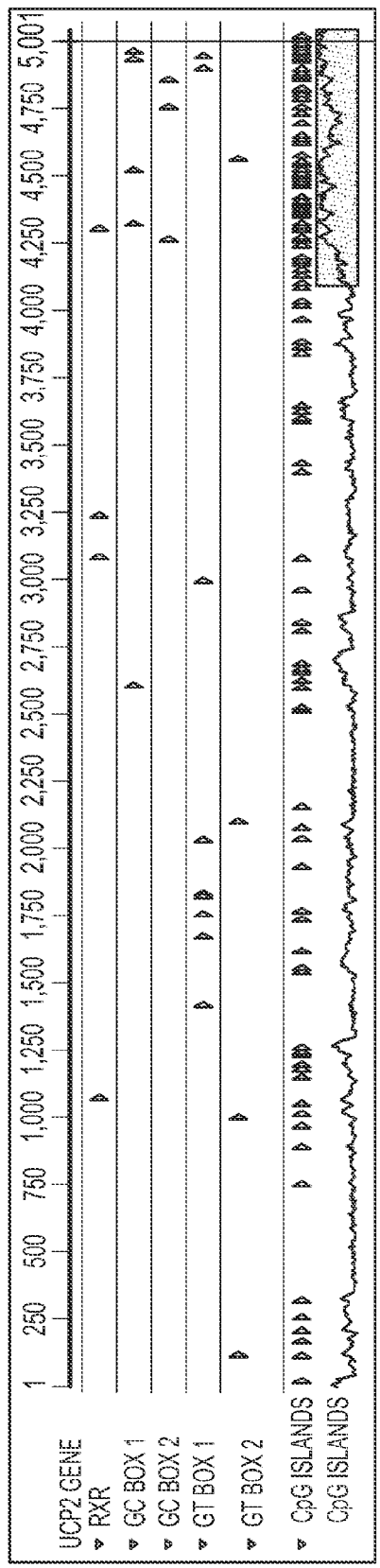
FIG. 8B depicts the location of various regulatory elements in reference to the transcription start site in the 15,174 bp of the human UCP2 gene (ENSG00000175567), including 5,000 bp 5'UTR and 2,000 bp 3'UTR on chromosome 11.

FIG. 8B depicts the location of these various regulatory elements in reference to the UCP2 transcription start site at nucleotide position 5,001 of the 15,174 base pair human UCP2 gene. Direct or indirect activation or repression of these regulatory elements by miRNAs will result in alterations of UCP2 gene expression and activity.

A survey of miRNAs targeting the human UCP2 3'UTR with several prediction programs, using the UCP2 Ensembl 2,113 base pair transcript ENST00000310473 as a target revealed binding sites for 161 miRNAs as shown in Table 9.

TABLE 9 miRNAs with predicted binding sites in the 3'UTR of UCP2 transcript sequence.

| | | |
|---|---|---|
| hsa-miR-1 | hsa-miR-1302-5 | hsa-miR-23b |
| hsa-miR-1-2 | hsa-miR-1302-6 | hsa-miR-24-1 |
| hsa-miR-101-1 | hsa-miR-1302-7 | hsa-miR-24-2 |
| hsa-miR-101-2 | hsa-miR-1302-8 | hsa-miR-27b-5p |
| hsa-miR-103 | hsa-miR-1302-9 | hsa-miR-28 |
| hsa-miR-105-1 | hsa-miR-1303 | hsa-miR-296-3p |
| hsa-miR-105-2 | hsa-miR-130a | hsa-miR-296-5p |
| hsa-miR-106b | hsa-miR-1321 | hsa-miR-3064 |
| hsa-miR-107 | hsa-miR-138-1 | hsa-miR-323a |
| hsa-miR-1204 | hsa-miR-138-2 | hsa-miR-328 |
| hsa-miR-1207 | hsa-miR-149 | hsa-miR-330 |
| hsa-miR-1208 | hsa-miR-150-3p | hsa-miR-331 |
| hsa-miR-1226 | hsa-miR-150-5p | hsa-miR-338 |
| hsa-miR-1246 | hsa-miR-1538 | hsa-miR-342 |
| hsa-miR-1252 | hsa-miR-155 | hsa-miR-3619 |
| hsa-miR-1253 | hsa-miR-15a | hsa-miR-370 |
| hsa-miR-1255a | hsa-miR-15b | hsa-miR-377 |
| hsa-miR-1255b-1 | hsa-miR-16-1 | hsa-miR-378a |
| hsa-miR-1255b-2 | hsa-miR-16-2 | hsa-miR-383 |
| hsa-miR-1260a | hsa-miR-184 | hsa-miR-411 |
| hsa-miR-1262 | hsa-miR-185-3p | hsa-miR-412 |
| hsa-miR-1263 | hsa-miR-185-5p | hsa-miR-422a |
| hsa-miR-1265 | hsa-miR-186 | hsa-miR-424 |
| hsa-miR-1275 | hsa-miR-188 | hsa-miR-425 |
| hsa-miR-1276 | hsa-miR-18a | hsa-miR-4291 |
| hsa-miR-1278 | hsa-miR-18b | hsa-miR-432-3p |
| hsa-miR-1285-1 | hsa-miR-193a | hsa-miR-4505 |
| hsa-miR-1286 | hsa-miR-195 | hsa-miR-450b |
| hsa-miR-1293 | hsa-miR-199b | hsa-miR-453 |
| hsa-miR-1300 | hsa-miR-200a | hsa-miR-4533 |
| hsa-miR-1302-1 | hsa-miR-203 | hsa-miR-4539 |
| hsa-miR-1302-10 | hsa-miR-206 | hsa-miR-4745 |
| hsa-miR-1302-11 | hsa-miR-214 | hsa-miR-4747 |
| hsa-miR-1302-2 | hsa-miR-219-1 | hsa-miR-485-5p |
| hsa-miR-1302-3 | hsa-miR-219-2 | hsa-miR-486 |
| hsa-miR-1302-4 | hsa-miR-221-5p | hsa-miR-490 |
| hsa-miR-491 | hsa-miR-584 | hsa-miR-663b |
| hsa-miR-493 | hsa-miR-608 | hsa-miR-664-5p |
| hsa-miR-497 | hsa-miR-612 | hsa-miR-675 |
| hsa-miR-498 | hsa-miR-613 | hsa-miR-7-1 |
| hsa-miR-503 | hsa-miR-615-3p | hsa-miR-7-2 |
| hsa-miR-505 | hsa-miR-618 | hsa-miR-7-3 |
| hsa-miR-508-3p | hsa-miR-625 | hsa-miR-708 |
| hsa-miR-532 | hsa-miR-626 | hsa-miR-761 |
| hsa-miR-539 | hsa-miR-634 | hsa-miR-765 |
| hsa-miR-541 | hsa-miR-635 | hsa-miR-769 |
| hsa-miR-5481 | hsa-miR-638 | hsa-miR-770 |
| hsa-miR-552 | hsa-miR-645 | hsa-miR-876 |
| hsa-miR-563 | hsa-miR-646 | hsa-miR-877 |
| hsa-miR-575 | hsa-miR-647 | hsa-miR-921 |
| hsa-miR-577 | hsa-miR-652 | hsa-miR-922 |
| hsa-miR-580 | hsa-miR-654 | hsa-miR-92a-1 |
| hsa-miR-583 | hsa-miR-658 | hsa-miR-92a-2-5p |
| | hsa-miR-663a | hsa-miR-92b |

Moreover, a survey of miRNAs targeting the human UCP2 5'UTR with several prediction programs, using the human UCP2 gene (ENSG00000175567, 15,174 base pair (bp) of the, including 5,000 bp 5'UTR as a target revealed binding sites for 54 miRNAs in UCP2 5'UTR as shown in Table 10.

TABLE 10 miRNAs with predicted binding sites in the 5'UTR of UCP2 gene sequence.

| MicroRNA | Seed Length | Start | Sequence | SEQ ID NO | End | P value |
|---|---|---|---|---|---|---|
| hsa-let-7c | 9 | 3052 | UAGAGUUAC | | 3044 | 0.0374 |
| hsa-let-7i-3p | 9 | 3051 | CUGCGCAAG | | 3043 | 0.0374 |

TABLE 10-continued miRNAs with predicted binding sites in the 5'UTR of UCP2 gene sequence.

| MicroRNA | Seed Length | Start | Sequence | SEQ ID NO | End | P value |
|---|---|---|---|---|---|---|
| hsa-miR-1228-5p | 9 | 3419 | UGGGCGGGG | | 3411 | 0.0374 |
| hsa-miR-1229-3p | 9 | 3419 | UCUCACCAC | | 3411 | 0.0374 |
| hsa-miR-129-1-3p | 10 | 2784 | AGCCCUUACC | 334 | 2775 | 0.0095 |
| hsa-miR-1302 | 9 | 4219 | UGGGACAUA | | 4211 | 0.0374 |
| hsa-miR-1303 | 9 | 2159 | UUAGAGACG | | 2151 | 0.0374 |
| hsa-miR-136 | 9 | 4486 | CUCCAUUUG | | 4478 | 0.0374 |
| hsa-miR-155 | 9 | 2160 | UUAAUGCUA | | 2152 | 0.0374 |
| hsa-miR-16 | 10 | 3603 | UAGCAGCACG | 335 | 3594 | 0.0095 |
| hsa-miR-18a-3p | 10 | 3603 | ACUGCCCUAA | 336 | 3594 | 0.0095 |
| hsa-miR-190 | 9 | 2428 | UGAUAUGUU | | 2420 | 0.0374 |
| hsa-miR-191 | 9 | 3052 | CAACGGAAU | | 3044 | 0.0374 |
| hsa-miR-192 | 9 | 4390 | CUGACCUAU | | 4382 | 0.0374 |
| hsa-miR-194 | 9 | 1643 | UGUAACAGC | | 1635 | 0.0374 |
| hsa-miR-197 | 9 | 5001 | UCACCACCU | | 4993 | 0.0374 |
| hsa-miR-19b-2-5p | 10 | 3052 | AGUUUUGCAG | 337 | 3043 | 0.0095 |
| hsa-miR-203 | 9 | 3051 | UGAAAUGUU | | 3043 | 0.0374 |
| hsa-miR-218 | 10 | 3603 | UUGUGCUUGA | 338 | 3594 | 0.0095 |
| hsa-miR-218-1-3p | 9 | 5001 | UGGUUCCGU | | 4993 | 0.0374 |
| hsa-miR-219-1-3p | 9 | 3614 | AGAGUUGAG | | 3606 | 0.0374 |
| hsa-miR-26a-2-3p | 9 | 2163 | CCUAUUCUU | | 2155 | 0.0374 |
| hsa-miR-27a-3p | 10 | 3603 | UUCACAGUGG | 339 | 3594 | 0.0095 |
| hsa-miR-27a-5p | 11 | 3336 | AGGGCUUAGCU | 340 | 3326 | 0.0024 |
| hsa-miR-28-5p | 10 | 3603 | AAGGAGCUCA | 341 | 3594 | 0.0095 |
| hsa-miR-331-3p | 9 | 4134 | GCCCCUGGG | | 4126 | 0.0374 |
| hsa-miR-337-5p | 10 | 115 | GAACGGCUUC | 342 | 106 | 0.0095 |
| hsa-miR-340-3p | 9 | 1872 | CCGUCUCAG | | 1864 | 0.0374 |
| hsa-miR-34c-3p | 11 | 2162 | AAUCACUAACC | 343 | 2152 | 0.0024 |
| hsa-miR-373-5p | 11 | 530 | ACUCAAAAUGG | 344 | 520 | 0.0024 |
| hsa-miR-425 | 9 | 1013 | AAUGACACG | | 1005 | 0.0374 |
| hsa-miR-497 | 9 | 3661 | AGCAGCACA | | 3653 | 0.0374 |
| hsa-miR-501-5p | 9 | 4164 | AUCCUUUGU | | 4156 | 0.0374 |
| hsa-miR-505 | 9 | 1015 | GUCAACACU | | 1007 | 0.0374 |
| hsa-miR-508-3p | 9 | 1274 | GAUUGUAGC | | 1266 | 0.0374 |
| hsa-miR-509-3p | 12 | 2554 | UGAUUGGUACGU | 345 | 2543 | 0.0006 |
| hsa-miR-512-5p | 10 | 987 | ACUCAGCCUU | 346 | 978 | 0.0095 |
| hsa-miR-514 | 9 | 5001 | UUGACACUU | | 4993 | 0.0374 |
| hsa-miR-515-5p | 9 | 59 | UUCUCCAAA | | 51 | 0.0374 |

TABLE 10-continued miRNAs with predicted binding sites in the 5'UTR of UCP2 gene sequence.

| MicroRNA | Seed Length | Start | Sequence | SEQ ID NO | End | P value |
|---|---|---|---|---|---|---|
| hsa-miR-518a-3p | 9 | 19 | GAAAGCGCU |  | 11 | 0.0374 |
| hsa-miR-519e-5p | 11 | 2525 | UCUCCAAAAGG | 347 | 2515 | 0.0024 |
| hsa-miR-548a-3p | 10 | 680 | CAAAACUGGC | 348 | 671 | 0.0095 |
| hsa-miR-550a-3p | 9 | 4312 | GUCUUACUC |  | 4304 | 0.0374 |
| hsa-miR-571 | 9 | 739 | UGAGUUGGC |  | 731 | 0.0374 |
| hsa-miR-578 | 9 | 1377 | CUUCUUGUG |  | 1369 | 0.0374 |
| hsa-miR-606 | 9 | 4420 | AACUACUGA |  | 4412 | 0.0374 |
| hsa-miR-615-5p | 10 | 1140 | GGGGGUCCCC | 349 | 1131 | 0.0095 |
| hsa-miR-638 | 9 | 2710 | GGGAUCGCG |  | 2702 | 0.0374 |
| hsa-miR-657 | 12 | 1316 | GCAGGUUCUCAC | 350 | 1305 | 0.0006 |
| hsa-miR-658 | 9 | 3673 | GGCGGAGGG |  | 3665 | 0.0374 |
| hsa-miR-877-3p | 9 | 4349 | UCCUCUUCU |  | 4341 | 0.0374 |
| hsa-miR-93-3p | 9 | 799 | ACUGCUGAG |  | 791 | 0.0374 |
| hsa-miR-96-3p | 9 | 799 | AAUCAUGUG |  | 791 | 0.0374 |
| hsa-miR-99b-3p | 9 | 2163 | CAAGCUCGU |  | 2155 | 0.0374 | c) A Multiple microRNAs-Multiple mRNAs Paradigm.

Figure 4:
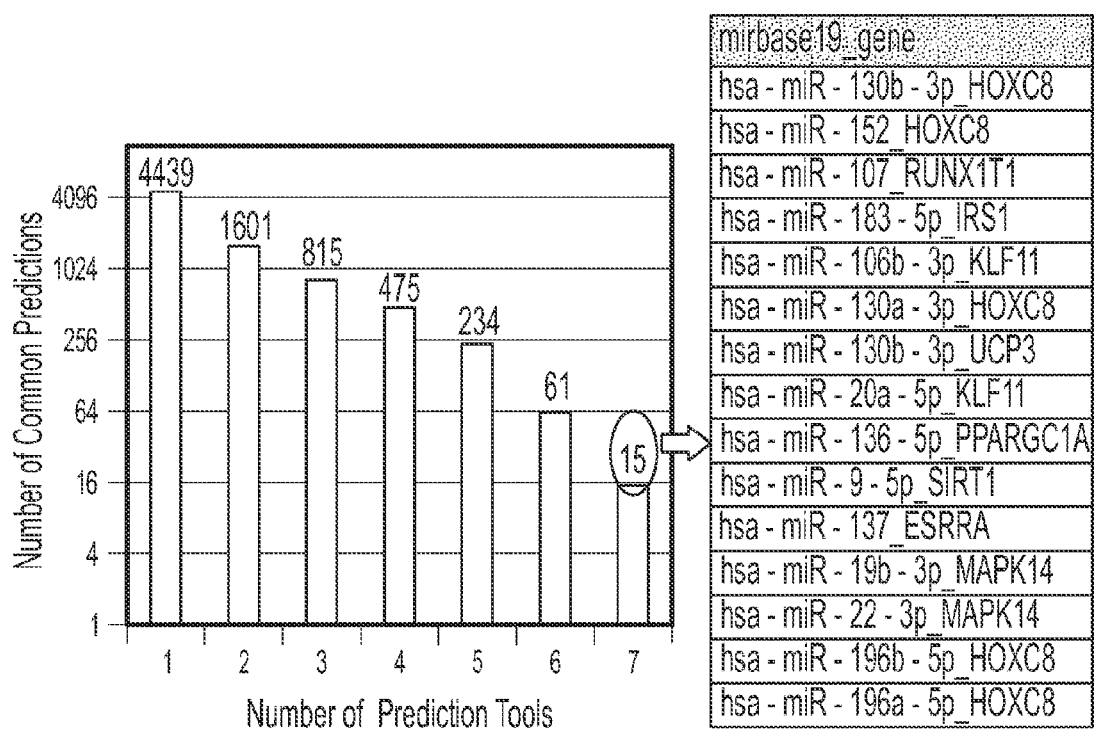
FIG. 4 is a schematic representation of the overlap of results from multiple miRNA prediction programs predicting miRNA binding sites in the 5'UTR, promoter region, coding sequence and 3'UTR of the genes of 83 thermogenic regulators.

The 83 thermogenic regulator molecules selected in Table 1 were screened for high stringency Multiple miRNAs-Multiple mRNAs associations. The results of these analyses with 7 major prediction tools are shown in FIG. 4. The union of these 7 tools produces 4439 miRNA-gene couples. Overlap between these tools decreases as the number of tools increases, reaching only 15 miRNA-gene couples when 7 tools are considered.

of 8 bp, default Weeder model, seed model of 8mer, 100% complementarity homology and 0.25 wobble base-pairing allowed), it was determined that that the motif 5'-UUU-GUACA-3' recognized by hsa-miR-19a/-19b is overrepresented among 15 of the 83 thermogenesis targets with a complementarity p value of $1.7 \times 10^{-04}$ as shown in Table 11. Of note is that hsa-miR-19 has been reported as an abundant adipocyte miRNA.

TABLE 11

Complementarity between the common motif UUUGUACA and hsa-miR-19a/19b.

| miRNA Name | miRNA Seed | Seed Model | Length of Complementarity | Complementary Base-Pairing | Complementartiy P-Value |
|---|---|---|---|---|---|
| hsa-miR-19a hsa-miR-19b | UGUGCAAA | 8mer | 8 | Motif 5' UUUGUACA 3'<br>\|\|\|\|:\|\|\|<br>3' AAACGUGU 5' miRNA Seed | 1.7e-04 | d) An Over-Representation of One microRNA Seed Sequence Motif Among Co-Regulated mRNA Targets Paradigm.

Several approaches can be used to identify pathway-specific miRNAs. For example, searching the 3'-UTRs of putatively co-regulated genes for an over-represented sequence from a miRNA seed region could identify a common regulatory miRNA. To determine if particular miRNA seed sequences were overrepresented among the 3' UTR of the chosen 83 thermogenesis targets, the miRvestigator web application (mirvestigator. systemsbiology.net/) was employed. Using the following parameters (motif size The Minimum Free Energy levels of the hsa-miR-19 mRNA/miRNA duplexes identified by miRvestigator were quite low, favoring tight binding. Accordingly, the miRvestigator analysis was repeated with less stringent levels of complementarity. This analysis identified a further 10 additional targets (CEBPD, PRKAA1, TWIST1, IRS1, NCOA1, NCOA2, NCOA3, KLF5, RPS6KB1, NRIP1) with 95% similarity to the consensus hsa-miR-19 motif. Interestingly, hsa-miR-19 is among the most abundant miRNAs in adipose tissue. The genes identified as containing a sequence complementary to hsa-miR-19 seed region are set forth in Table 12.

TABLE 12

Thermogenic regulators identified as targets for hsa-miR-19.

| Gene | Gene symbol | Sequence of Site | Start Relative to Stop Codon (bp) | % Similarity to Consensus Motif (Quality = \|Medium\|Fair) | Minimum Free Energy (MFE) of mRNA-miRNA Duplex |
|---|---|---|---|---|---|
| 660 | BMP2 | UUUGUACA | 386 | 100.00 | −6.80 |
| 1052 | CEBPD | UUUGUAAA | 263 | 85.44 | −3.40 |
| 7132 | TNFRSF1A | UUUGUACA | 510 | 100.00 | −6.80 |
| 5552 | PRKAA1 | UUUGUAAA | 2400 | 95.44 | −3.40 |
| 5553 | PRKAA2 | UUUGUACA | 542 | 100.00 | −6.80 |
| 555 | BMP7 | UUUGUACA | 1927 | 100.00 | −6.80 |
| 552 | BMP4 | UUUGUACA | 770 | 100.00 | −6.80 |
| 135622 | PRARGC1B | UUUGUACA | 7199 | 100.00 | −6.80 |
| 7474 | WNT5A | UUUGUACA | 1414 | 100.00 | −6.80 |
| 8720 | SREBF1 | UUUGUACA | 510 | 100.00 | −6.80 |
| 2291 | TWIST1 | UUUGUAAA | 649 | 95.44 | −3.40 |
| 3687 | IRS1 | UUUGUAAA | 992 | 95.44 | −3.40 |
| 10498 | NCOA2 | UUUGUAAA | 1381 | 95.44 | −3.40 |
| 8204 | NRIP1 | UUUGUACA | 1718 | 100.00 | −6.60 |
| 8204 | NRIP1 | UUUGUAAA | 1935 | 95.44 | −3.40 |
| 8202 | NCOA3 | UUUGUAAA | 965 | 95.44 | −3.40 |
| 1385 | CREB1 | UUUGUAAA | 1973 | 95.44 | −3.40 |
| 1385 | CREB1 | UUUGUACA | 2822 | 100.00 | −6.80 |
| 1385 | CREB1 | UUUGUACA | 2822 | 100.00 | −6.60 |
| 1355 | CREB1 | UUUGUAAA | 4175 | 85.44 | −3.40 |
| 3543 | INSR | UUUGUAAA | 2105 | 85.44 | −3.40 |
| 8013 | NR4A3 | UUUGUACA | 2347 | 100.00 | −6.80 |
| 880 | RUNX2 | UUUGUACA | 2425 | 100.00 | −6.50 |
| 6776 | STAT5A | UUUGUACA | 1214 | 100.00 | −6.80 |
| 1874 | E2F4 | UUUGUACA | 755 | 100.00 | −6.80 |
| 888 | KLF5 | UUUGUAAA | 549 | 95.44 | −3.40 |
| 6648 | NCOA1 | UUUGUAAA | 381 | 95.44 | −3.40 |
| 6195 | RPS6KB1 | UUUGUAAA | 2531 | 95.44 | −3.40 |

Accordingly, the miRvestigator analysis was repeated with less stringent levels of complementarity (motif size of 8 bp, default Weeder model, seed model of 8mer, 95% complementarity homology and 0.25 wobble base-pairing allowed). This analysis identified a further 10-12 additional targets (CEBPD, CREB1, PRKAA1, TWIST1, INSR, IRS1, NCOA1, NCOA2, NCOA3, KLF5, RPS6KB1, NRIP1) with 95% similarity to the consensus hsa-miR-19 motif. Interestingly, hsa-miR-19 is among the most abundant miRNAs in adipose tissue. The genes identified as containing a sequence complementary to hsa-miR-19 seed region are set forth in Table 13.

TABLE 13

Thermogenic regulators identified as targets for hsa-miR-19a/b with 95% to 100% similarity to consensus motif.

| Gene | Gene symbol | Sequence of Site | Start Stop Relative to Codon (bp) | % Similarity to Consensus Motif (Quality = \|Medium\|Fair) | Minimum Free Energy (MFE) of mRNA-miRNA Duplex |
|---|---|---|---|---|---|
| 650 | BMP2 | UUUGUACA | 386 | 100.00 | -6.80 |
| 1052 | CEBPD | UUUGUAAA | 263 | 95.40 | -3.40 |
| 7132 | TNFRSF1A | UUUGUACA | 510 | 100.00 | -6.80 |
| 4048 | LRP6 | UUUGUACA | 151 | 100.00 | -6.80 |
| 4040 | LRP6 | UUUGUAAA | 4965 | 95.42 | -3.40 |
| 5552 | PRKAA1 | UUUGUAAA | 2400 | 95.42 | -3.40 |
| 5563 | PRKAA2 | UUUGUACA | 542 | 100.00 | -6.80 |
| 655 | BMP7 | UUUGUACA | 1927 | 100.00 | -6.80 |
| 652 | BMP4 | UUUGUACA | 770 | 100.00 | -6.80 |
| 133522 | PPARGC1B | UUUGUACA | 7199 | 100.00 | -6.80 |
| 1874 | E2F4 | UUUGUACA | 755 | 100.00 | -6.80 |
| 7474 | WNT5A | UUUGUACA | 1414 | 100.00 | -6.80 |
| 6720 | SREBF1 | UUUGUACA | 510 | 100.00 | -6.80 |
| 7291 | TWIST1 | UUUGUAAA | 649 | 95.42 | -3.40 |
| 3667 | IRS1 | UUUGUAAA | 992 | 95.42 | -3.40 |
| 10499 | NCOA2 | UUUGUAAA | 1361 | 95.42 | -3.40 |
| 8204 | NRIP1 | UUUGUACA | 1718 | 100.00 | -6.80 |
| 8204 | NRIP1 | UUUGUAAA | 1935 | 95.42 | -3.40 |
| 8202 | NCOA3 | UUUGUAAA | 965 | 95.42 | -3.40 |
| 3643 | INSR | UUUGUAAA | 2105 | 95.42 | -3.40 |
| 8013 | NR4A3 | UUUGUACA | 2347 | 100.00 | -6.80 |
| 6776 | STAT5A | UUUGUACA | 1214 | 100.00 | -6.80 |
| 655 | KLF5 | UUUGUAAA | 549 | 95.42 | -3.40 |
| 8648 | NCOA1 | UUUGUAAA | 381 | 95.42 | -3.40 |
| 860 | RUNX2 | UUUGUACA | 2425 | 100.00 | -6.80 |
| 1385 | CREB1 | UUUGUAAA | 1973 | 95.42 | -3.40 |
| 1385 | CREB1 | UUUGUACA | 2822 | 100.00 | -6.80 |
| 1385 | CREB1 | UUUGUAAA | 4175 | 95.42 | -3.40 |
| 6198 | RPS6KB1 | UUUGUAAA | 2531 | 95.42 | -3.40 |

Without wobbling, the same motif 5'-UUUGUACA-3' is overrepresented among targets of hsa-miR-1283 with a complementarity p value of $1.4 \times 10^{-4}$. Furthermore, hsa-miR-1283 binds to other mRNAs of interest like ABCA1 (cholesterol transporter), the adiponectin receptor and the transcription factor TCF7L2 that is implicated in genetic human obesity.

Similarly, other miRNA over-represented seed sequences were identified for miRNAs expressed in adipocytes. They include the universal hsa-let-7 family (sequence CUAUA-CAA, p value=7.5e-04) and the adipocyte-rich hsa-miR-30 family (sequence UGUAAACA, p value=$1.9 \times 10^{-3}$) to name a few.

With respect to PRDM16, CIDEA, NRIP1, KDM3A, CEPPB, PPARG, PPARGC1A, and PPKAA2, which according to the STRING software package are directly linked to UCP1, it appears that all of them share (at motif size 8 bp, default weeder model, seed model 8mer, 95% complementarity homology and 0.25 wobble base-pairing allowed) a consensus sequence with several miRNAs, including hsa-miR-3658 (p value=1.9e-003) and the hsa-miR-30 family (p value=6.3e-003) as follows:

```
hsa-miR-3658:
Motif 5' UUUUUUAC-3'
         ||s||||
      3'-AAGAAUUU 5' miRNA Seed hsa-miR-30a/b/c/d/e:
Motif 5' UUUUUUAC-3'
         ||||||||
      3'-ACAAAUGU 5' miRNA Seed
``` e) An Intronic miRNA-Multiple mRNAs Pathway-Specific Paradigm.

Many mammalian miRNAs are located within introns of protein-coding genes rather than in their own unique transcription units. Intronic miRNAs are typically expressed and processed with the precursor mRNA in which they reside. Although the intronic miRNAs and their host genes can be regulated independently, an intronic miRNA can down-regulate its own host protein-coding gene by targeting the host gene's UTR. Feedback regulation on host protein-coding genes could be achieved by selecting the transcription factors that are miRNA targets or by protein-protein interactions between intronic miRNA host gene product and miRNA target gene products. As an example, miR-33 acts in concert with the SREBP host genes to control cholesterol homeostasis and the pharmacological inhibition of miR-33a and miR-33b is a promising therapeutic strategy to raise plasma HDL and lower VLDL triglyceride levels for the treatment of dyslipidaemias.

Examination of the 83 thermogenic target genes reveals two intronic miRNAs: miR-378 located in the PPARGC1B gene and miR-4251 located in the PRDM16 gene.

Mining of the Internet tools predicting miRNA targets indicates that miR-378 targets include BMP2, PPARA, PPARGC1A, PRDM16, STAT5 and WNT10A as well as ADIPOQ and IGFR1; and that miR-4251 targets include BMP2, CTBP1, CTBP2, MAPK14, NCOA3, PLACE, PPARA, PPARD, TRPM8, as well as ABCA5, ABCA13, ADIPOQR2, KDM5B, KLF-12, KLF-14 and TCF7L2.

Example 3

High-Content Cellular Phenotypic Screening

High-content screening methods are used to screen for novel miRNA agents that modulate the activity of thermogenic regulators (e.g., UCP1 and UCP2). High-content screening is a drug discovery method that uses images of living cells to facilitate molecule discovery. Such automated image based screening methods are particularly suitable for identifying agents which alter cellular phenotypes.

WAT cells which contain a single large lipid droplet, whereas, in contrast, BAT cells contain numerous smaller droplets and a much higher number of mitochondria, which contain iron and make them appear brown. The large number of mitochondria in BAT leads to an increased oxygen consumption, when compared to WAT. Accordingly, it is possible to distinguish between BAT and WAT cells visually based on their cellular phenotype.

Accordingly, high-content screening methods were used to screen for novel miRNA agents that modulate the activity of thermogenic regulators. Specifically, the phenotypic appearance of cultured human adipocytes and adipose tissue derived mesenchymal stem cells grown in the presence and absence of miRNA agonists or antagonists was assessed over two weeks by phase contrast microscopy of the cultured cells, measurement of the cellular lipid content (using Oil Red O Staining or Nile Red fluorescence); mitochondrial content (e.g., using Life Technologies Mito-Tracker Red FM), and/or oxygen consumption in vitro (e.g., using the Seahorse Bioscience Extra-Cellular Flux Instrument). mRNA expression is measured by targeted q-RT-PCR and universal RNA-Sequencing. Protein expression is measured by targeted Western Blotting and universal proteomic profiling.

A. Differentiation of Human Pre-Adipocytes into Adipocytes.

1. Differentiation Protocol.

In order to assess the effect of miRNA analogs on human pre-adipocytes differentiation into mature adipocytes, human subcutaneous pre-adipocytes (SuperLot 0048 from 8 female donors, ZenBio, NC) were plated on Day 0 into 96-well plates and allowed to attach overnight in preadipocyte medium (DMEM/Ham's F-12 (1:1, v/v), HEPES buffer, Fetal bovine serum and Antibiotics). The next day (Day 1), the medium was removed and replaced with differentiation medium (DMEM/Ham's F-12 (1:1, v/v), 100 µM Ascorbic Acid, 0.85 µM insulin, 20 nM sodium selenite, 0.2 nM, triiodothryonine, 1 µM dexamethasone, 100 µM isobutyl-methylxanthine, 100 nM Rosiglitazone and Antibiotics). The cells were allowed to incubate for 2 days at 37°, 5% $CO_2$. After 2 days (Day 3), the medium was removed and replaced with fresh maintenance medium (DMEM/Ham's F-12 (1:1, v/v), 100 µM Ascorbic Acid, 0.85 µM insulin, 20 nM sodium selenite, 0.2 nM triiodothryonine, and Antibiotics). On Day 3, the cells were transfected with miRNA analogs (Dharmacon specific miRIDIAN Mimics and Hairpin Inhibitors) using the transfecting agent Dharmafect1. All treatments were in triplicate. Post transfection, the negative control was maintenance medium only and the positive control was maintenance medium with 100 nM of the PPARG agonist rosiglitazone. After 2 days, medium was removed and replaced with fresh maintenance medium. The maintenance medium then changed every two days until the end of the treatment period (Day 15). At the end of the treatment (total of 15 days in culture) cells were processed for Phenotyping and Genotyping Screening.

1. Transfection of Pre-Adipocytes.

Transfection reagents are used to facilitate the penetration of miRNA analogs into target cells. As an example, the extent of transfection efficiency we achieved in pre-adipocytes with the transfecting agent Dharmafect 1 (Dharmacon, CO) is depicted herein. Transfection efficiency was assessed in two ways:

a. Measurement of Cellular Epifluorescence after Transfection with Fluorescent miRNA Analogs.

Figure 9:
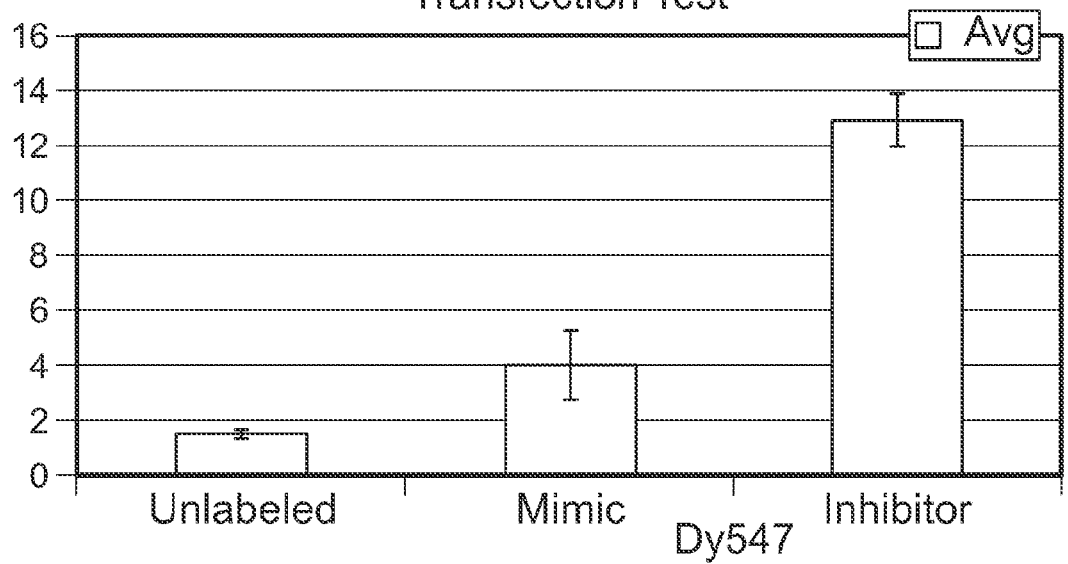
FIG. 9 is a bar graph showing relative fluorescence in unlabeled cells or cells transfected with a Dy547 labeled non-targeting miRIDIAN mimic and hairpin inhibitor.

Fluorescence was measured on Day 15 (540 excitation/590 emission) in cells transfected on Day 3 with the Dy547-labeled non-targeting miRIDIAN Mimic and Hairpin Inhibitor (100 nM). As shown in FIG. 9, there was a significantly greater fluorescence of cells transfected with the fluorescent miRNA analogs, even 12 days after transfection:

b. Reduction of Control Gene Expression.

Figures 10A, 10B:
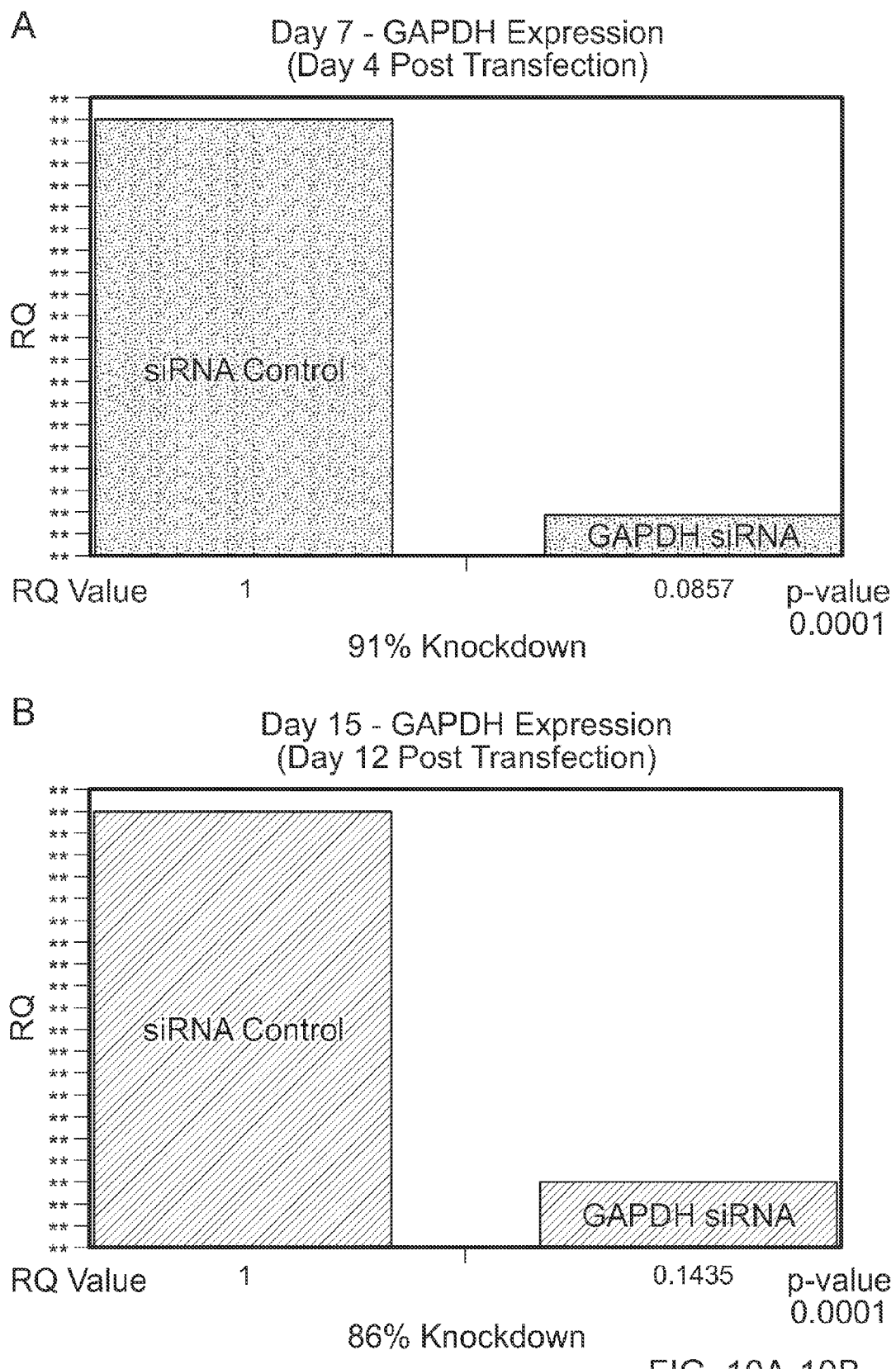
FIG. 10A is a bar graph showing the reduction of GAPDH expression in cells transfected with siRNA control and a GAPDH siRNA 4 days after transfection.
FIG. 10B is a bar graph showing the reduction of GAPDH expression in cells transfected with siRNA control and a GAPDH siRNA 12 days after transfection.

To confirm successful transfection of pre-adipocytes, the reduction of expression of the control gene GAPDH ("housekeeping gene") was measured 4 days (Day 7) (FIG. 10A) and 12 days (Day 15) (FIG. 10B) after transfection of pre-adipocytes with a GAPDH-specific siRNA. Cell lysates were obtained and RT-PCR was conducted using pure RNA obtained by Cells-to-Ct reagents. 91% and 86% knockdowns of the GAPDH mRNA expression were observed at Day 4 and Day 12 post transfection, both highly significant, as shown in FIG. 10.

c. Phenotypic Changes During Human Preadipocytes Differentiation into Adipocytes.

Figures 11A, 11B, 11C, 11D, 11E, 11F:
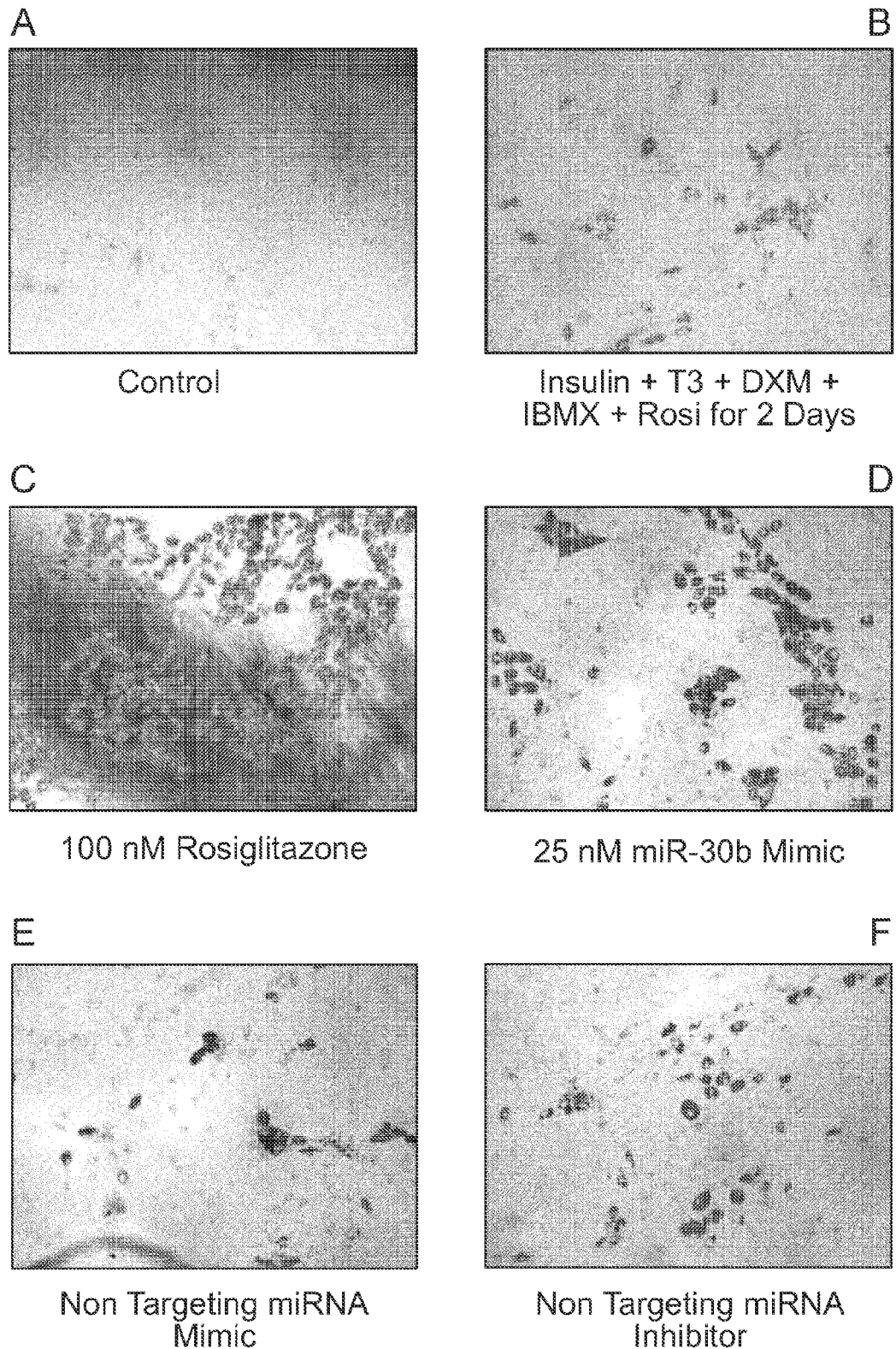
FIG. 11A is a light micrograph of preadipocytes stained with Oil Red O cultured for 2 weeks in maintenance medium without rosiglitazone.
FIG. 11B is a light micrograph of preadipocytes stained with Oil Red O cultured in the presence of insulin, triiodothyronine, dexamethasone, isobutyl-methylxanthine and rosiglitazone for two days followed by maintenance medium for 12 days.
FIG. 11C is a light micrograph of preadipocytes stained with Oil Red O cultured in the presence of insulin, triiodothyronine, dexamethasone, isobutyl-methylxanthine and rosiglitazone throughout the experiment.
FIG. 11D is a light micrograph of preadipocytes stained with Oil Red O cultured in the presence of hsa-miR-30b mimic.
FIG. 11E is a light micrograph of preadipocytes stained with Oil Red O cultured in the presence of non targeting miRNA mimic.
FIG. 11F is a light micrograph of preadipocytes stained with Oil Red O cultured in the presence of non targeting miRNA inhibitor.

At the end of treatment (15 days in culture) cells were stained with Oil Red O for assessment of lipid content. As shown in FIG. 11, in the presence of medium without rosiglitazone, the preadipocytes show little differentiation into lipid-loaded mature adipocytes. In the presence of differentiation medium including 100 nM Rosiglitazone for 2 days followed by maintenance medium for 12 days (negative control), some differentiation into lipid-loaded mature adipocytes is noted. In the presence of 100 nM rosiglitazone throughout the experiment (positive control), most of the cells became lipid-loaded mature adipocytes. As an example, in the presence of 25 nM hsa-miR-30b mimic, about half of the cells became lipid-loaded mature adipocytes. The non targeting miRNA mimic and inhibitor showed patterns similar to the negative control.

d. Genotypic Changes During Human Pre-Adipocyte Differentiation into Adipocytes.

Profiling of mRNA changes occurring during the differentiation of human pre-adipocyte into mature adipocyte induced by rosiglitazone or miRNA analogs was performed by RNA-Seq technology. Small RNA sequencing (RNA-Seq) is a high-throughput next-generation sequencing platform which now allows transcriptome-wide profiling of all small RNAs, known and unknown, with no need for prior sequence or secondary structure information.

RNA samples were extracted from pre-adipocytes (pre-adipocyte negative control) and from pre-adipocytes cultured in the presence of 100 nM rosiglitazone (differentiation positive control) or 25 nM miRNA mimics or inhibitors for 12 days. RNA sequencing was performed on the Illumina Hi-Seq 2000 equipment. The results were mapped against Human Genome 19 (http://genome.ucsc.edu/). It appears that in the presence of a miRNA analog, between 313 and 449 mRNA are significantly differentially expressed in reference to pre-adipocytes. In reference to Rosiglitazone, the number of significantly differentially expressed genes is reduced between 111 and 216, thus suggesting common pathways of activation of adipocyte differentiation between miRNAs and the PPARG analog.

Figure 12A:
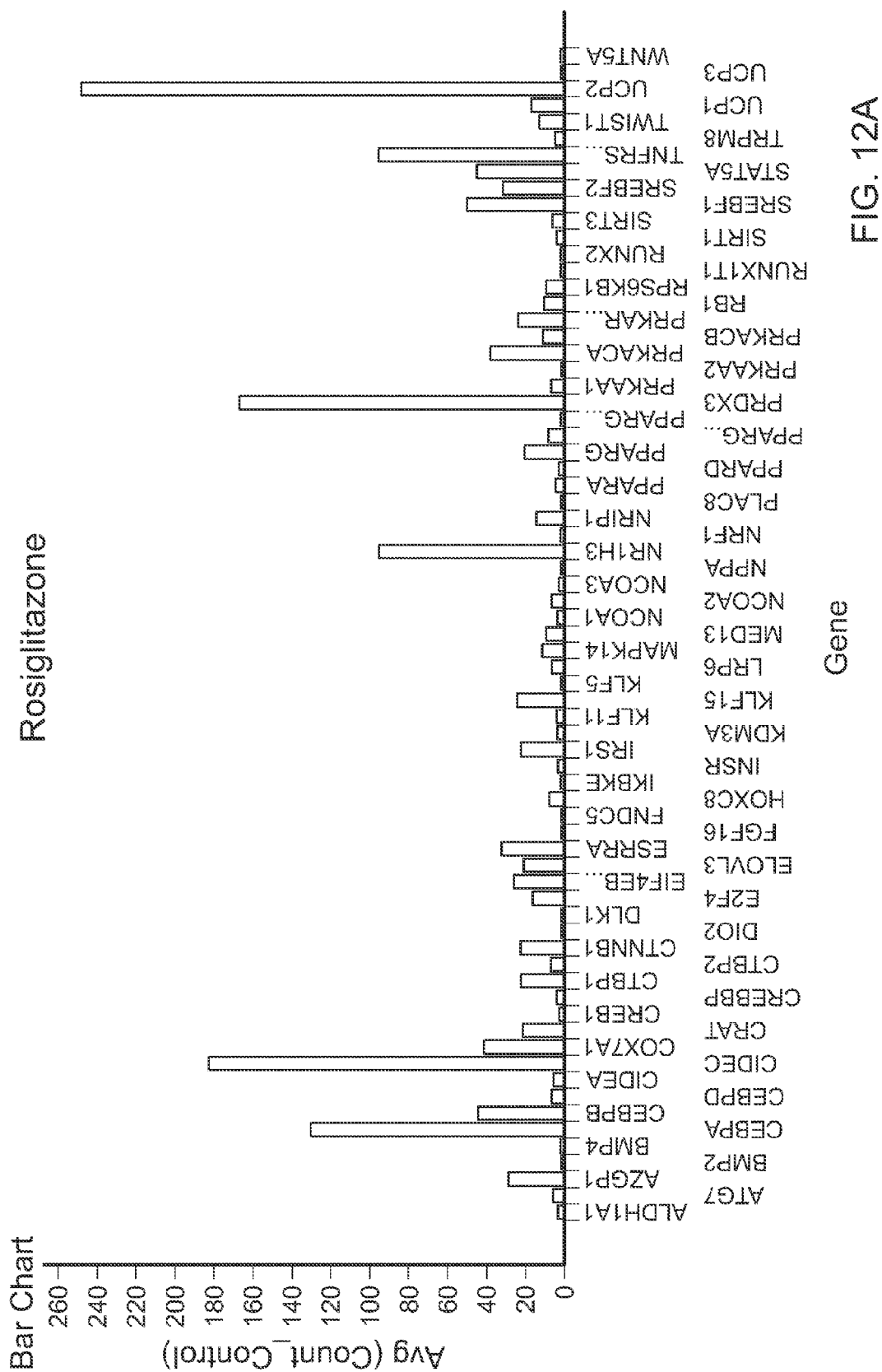
FIG. 12A is a bar graph showing mRNA expression of thermogenesis targets in the presence of rosiglitazone.
Figure 12B:
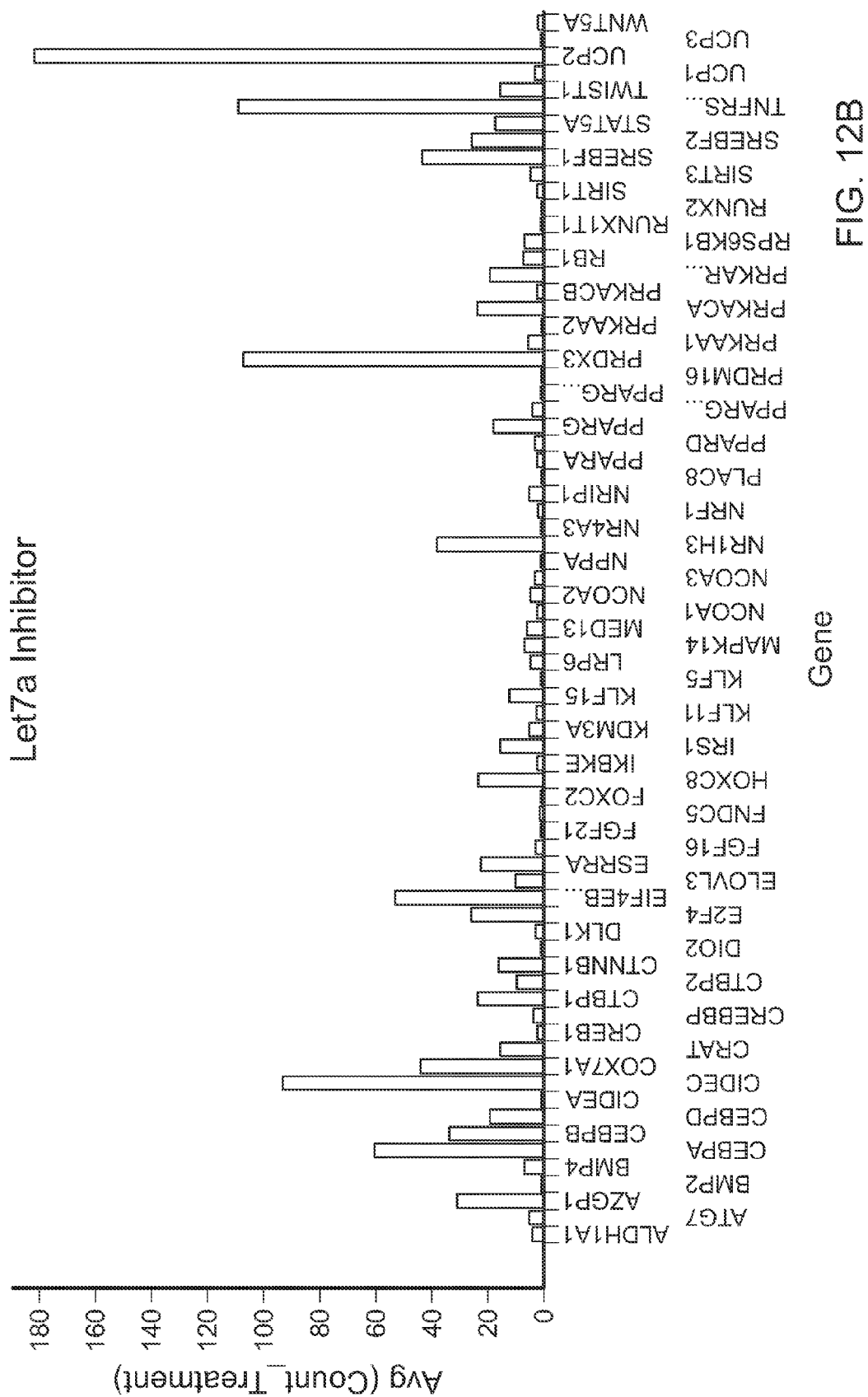
FIG. 12B is a bar graph showing mRNA expression of thermogenesis targets in the presence of hsa-let-7a inhibitor.
Figure 12C:
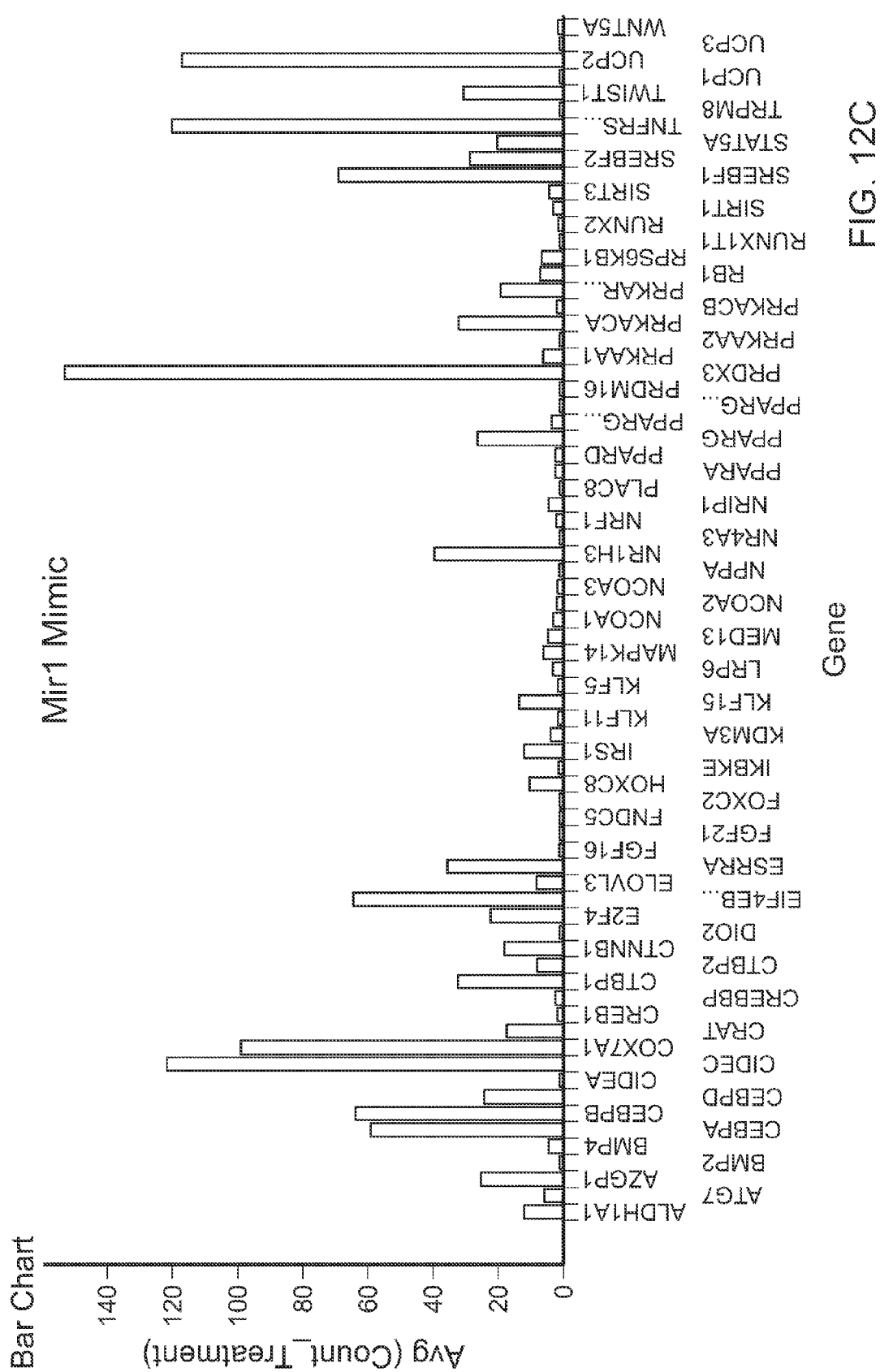
FIG. 12C is a bar graph showing mRNA expression of thermogenesis targets in the presence of hsa-miR-1 mimic.
Figure 12D:
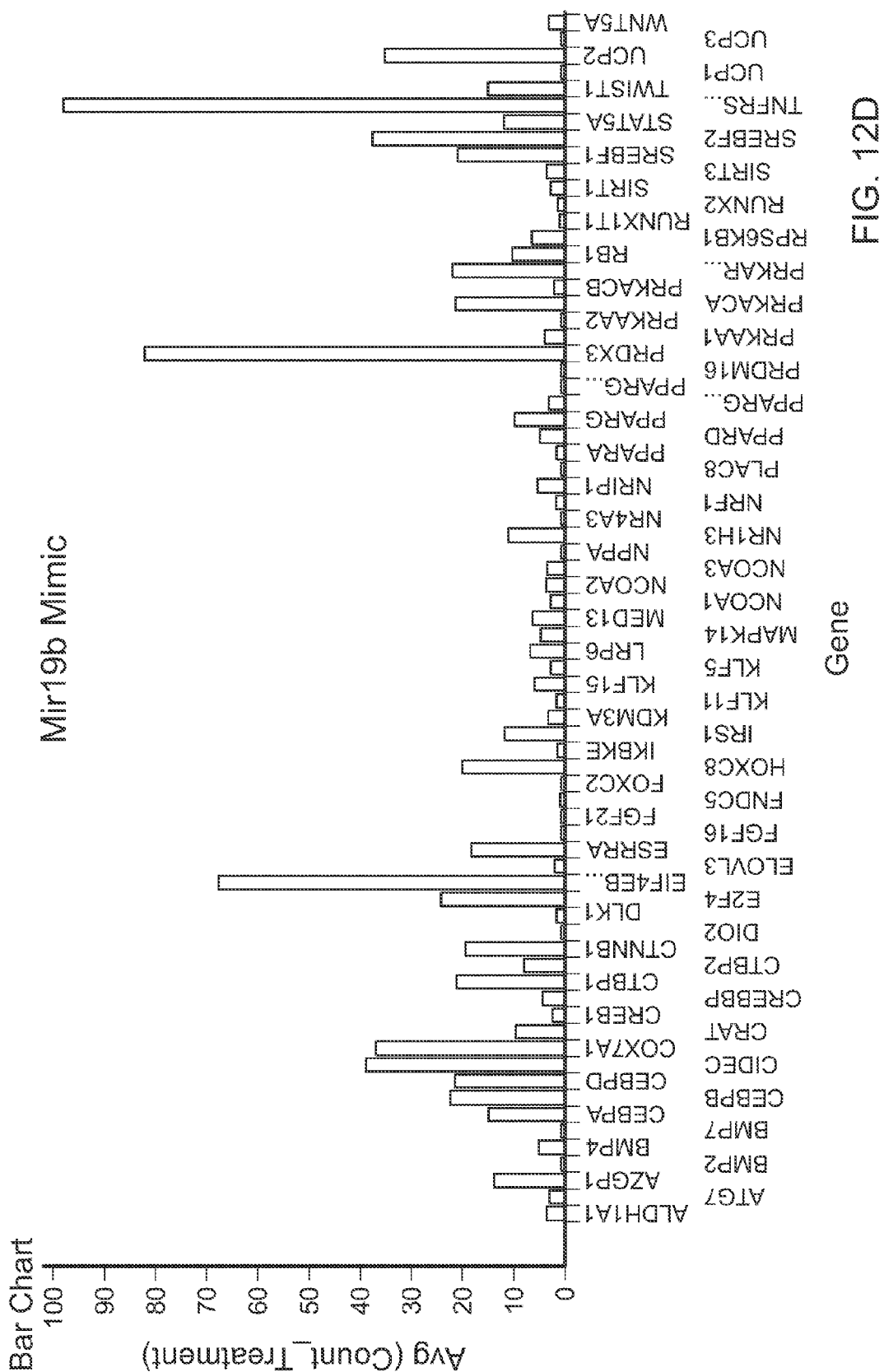
FIG. 12D is a bar graph showing mRNA expression of thermogenesis targets in the presence of hsa-miR-19b mimic.
Figure 12E:
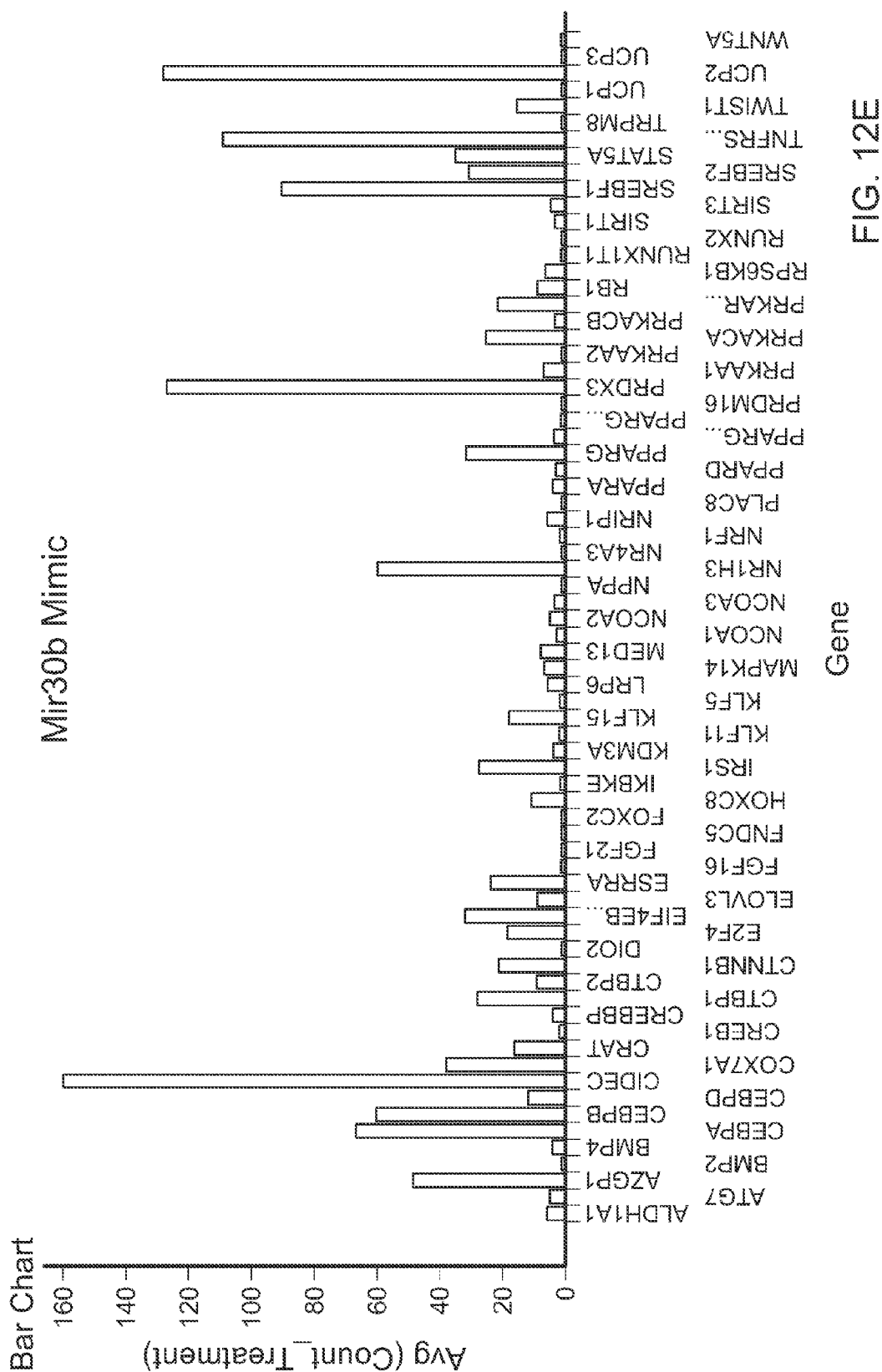
FIG. 12E is a bar graph showing mRNA expression of thermogenesis targets in the presence of and hsa-miR-30b mimic.
Figure 12F:
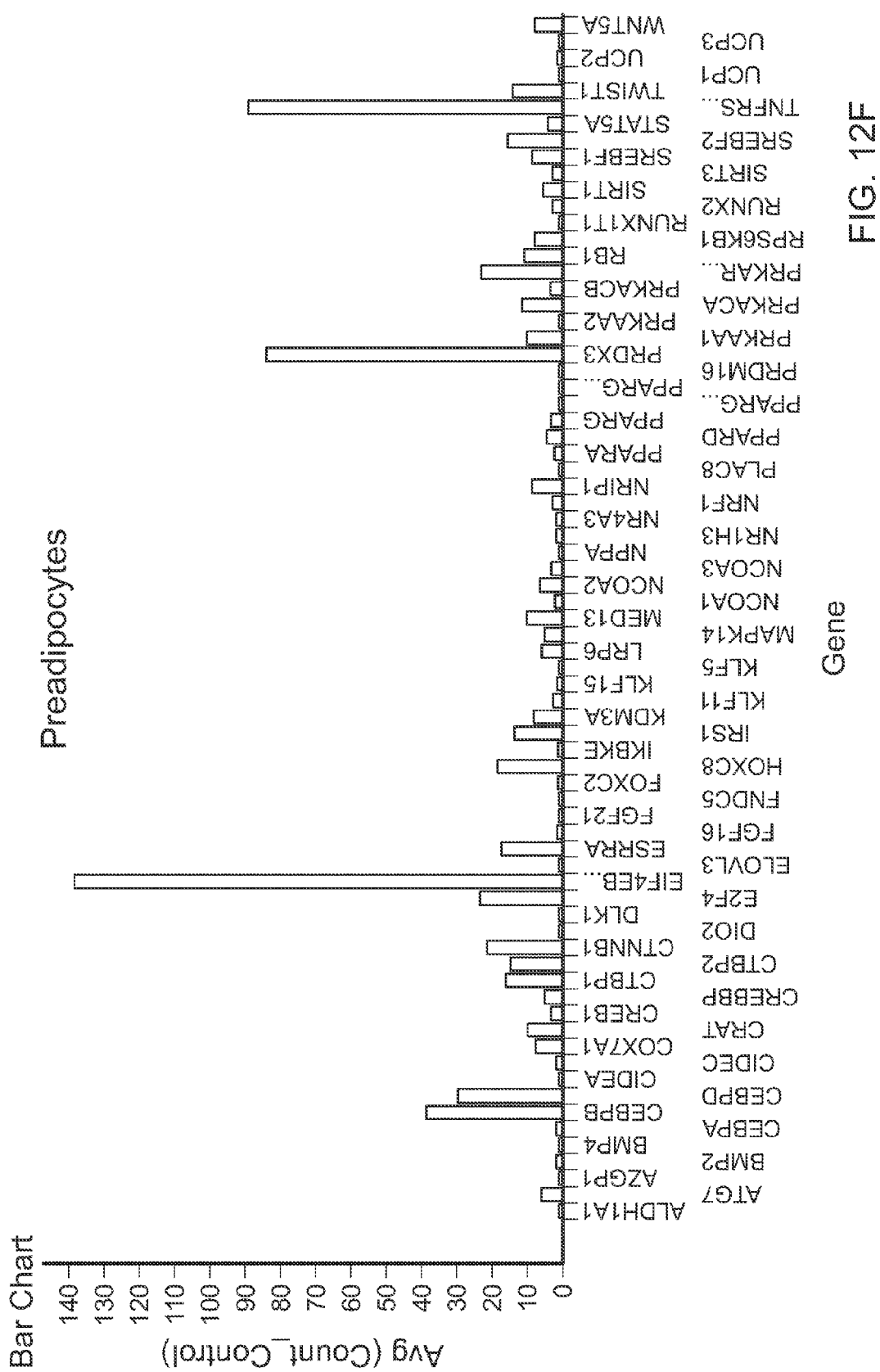
FIG. 12F is a bar graph showing mRNA expression of thermogenesis targets in untreated preadipocytes.

Regarding our 83 thermogenic activators and inhibitors, the expression of 73 of them is altered in the presence of rosiglitazone or miRNA analogs. The changes of mRNA expression of the thermogenesis targets in the presence of rosiglitazone (FIG. 12A) or miRNA analogs hsa-let-7a inhibitor, hsa-miR-1 mimic, hsa-miR-19b mimic, hsa-miR-30b mimic or control adipocytes are shown on FIGS. 12B-F, respectively).

Changes in mRNA expression of UCP1, 2 and 3 were also measured in the presence of rosiglitazone or miRNA analogs, as shown below in Table 14.

TABLE 14

Changes in thermogenic mRNA expression.

| Agent | mRNA Expression changes (log ratios) | | |
|---|---|---|---|
| | UCP1 | UCP2 | UCP3 |
| Rosiglitazone | 15.70 | 263 | 0.26 |
| hsa-let-7a inhibitor | 2.23 | 173 | 0.65 |
| hsa-miR-1 mimic | 0.41 | 110 | 0.40 |
| hsa-miR-19b mimic | 0.18 | 33 | 0.26 |
| hsa-miR-30b mimic | 0.76 | 119 | 0.28 |
| Baseline level in pre-adipocytes | 0.02 | 1.35 | 0.30 |

The expression levels of the three Uncoupling Proteins were low in pre-adipocytes. The expression of UCP1 was significantly increased in the presence of rosiglitazone 100 nM which was renewed with the culture medium every other day. The magnitude of UCP1 mRNA rise with the miRNA analogs was lower than with rosiglitazone, but one has to keep in mind the miRNA analogs concentration used (25 nM) and the fact that only one transfection was performed 12 days before RNA extraction. A major finding is the dramatic increase of UCP2 expression in the presence of rosiglitazone as well as the miRNA analogs. The expression of UCP3 did not change in any condition, as expected for a gene that is mainly expressed in myocytes. This increase in UCP1 and UCP2 expression suggests that administration of these miRNA produces adipocytes with greater potential for thermogenesis and thus are likely effective pharmaceuticals for the treatment of obesity and other metabolic diseases and disorders.

Figure 16:
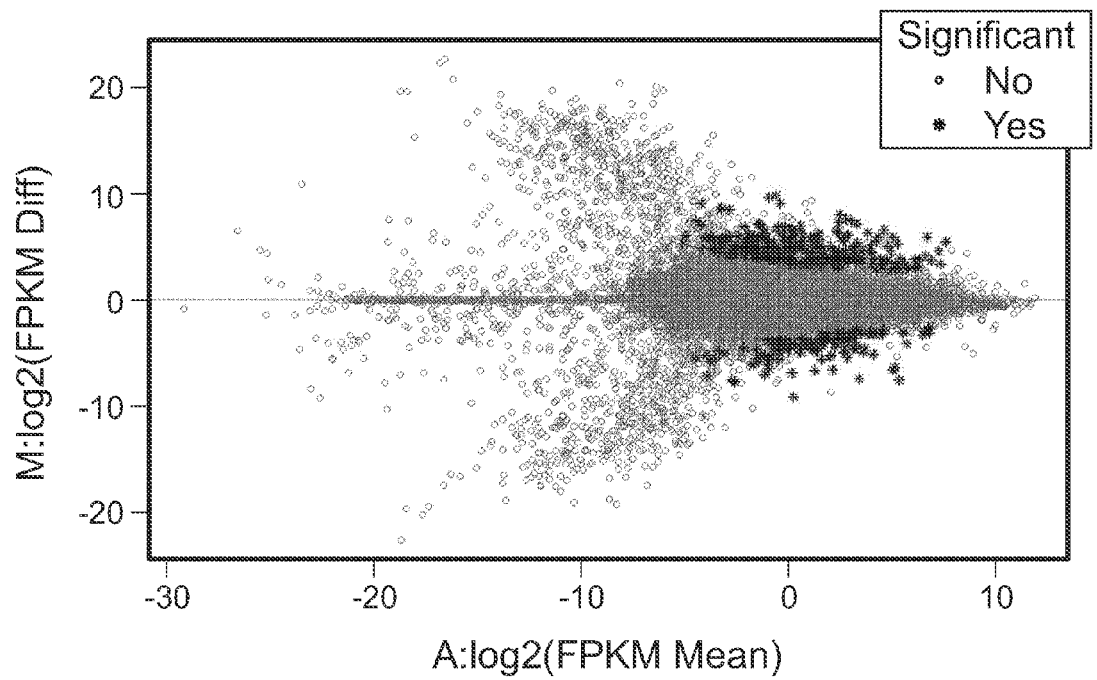
FIG. 16 is an M-A plot showing the mean gene expression on the x-axis and the difference between pairs in logarithmic scale on the y-axis.

Furthermore, we looked at genes differentially expressed during pre-adipocyte culture in the presence of miRNA analogs. As an example shown on FIG. 16, an M-A plot was created to visualize the differences of mRNA expression between pre-adipocytes grown in maintenance medium and pre-adipocytes grown in the presence of hsa-miR-19b mimic. The x-axis is the mean gene expression and the y-axis is the difference between pairs in logarithmic scale. The red dots are the differentially expressed genes (up regulated above zero and down regulated below zero). The gray dots are the genes not differentially expressed between control and hsa-miR-19b mimic (up regulated above zero and down regulated below zero).

Figure 17:
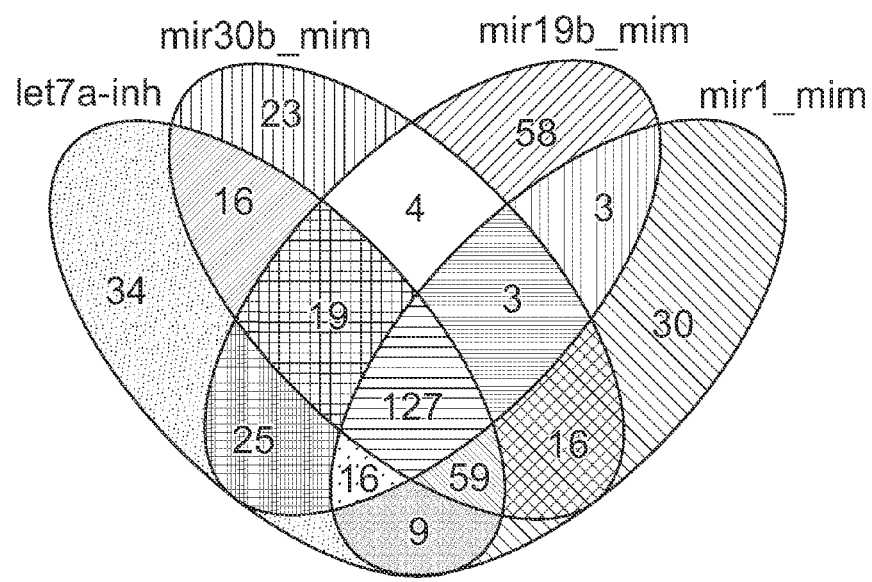
FIG. 17 is a schematic showing a Venn Diagram showing that the numbers of genes significantly upregulated in the presence of the miRNA analogs hsa-let-7a inhibitor, hsa-miR-1 mimic, hsa-miR-19b mimic and hsa-miR-30b mimic were respectively 305, 247, 255 and 267. A set of 127 genes was commonly upregulated by the listed miRNA analogs.

As an example shown on FIG. 17, in reference to pre-adipocytes cultured in maintenance medium only, the numbers of significantly differentially expressed genes in the presence of the miRNA analogs hsa-let-7a inhibitor, hsa-miR-1 mimic, hsa-miR-19b mimic and hsa-miR-30b mimic were respectively 406, 382, 370 and 433. A set of 127 genes was commonly upregulated by these 4 miRNA analogs (Venn Diagram, FIG. 17).

They include not only some of our 83 thermogenic targets like ALDH1A1, AZGP1, CEBPA, PPARGC1A, UCP1 and UCP2 highlighted in green, but also numerous genes involved in lipid metabolism and adipocyte differentiation, highlighted in yellow (Table 15).

TABLE 15

Set of 127 genes commonly upregulated by 4 miRNA analogs.

| | | | |
|---|---|---|---|
| ABCC6 | CHI3L2 | KCNE3 | PPL |
| ABCD2 | CILP | KCNK3 | PPP1R1A |
| ACACB | CKB | KIT | PRKAR2B |
| ACHE | CKMT1B | KLB | PTGDS |
| ACSF2 | CLCA2 | LBP | QPRT |
| ACSM5 | CLMN | LEP | RASL12 |
| ACSS2 | COL14A1 | LGALS12 | RNF157 |
| ADH1B | COL21A1 | LIPE | S100B |
| AIF1L | CPB1 | LPL | SDPR |
| AKR1C3 | CYB5A | LRRC4C | SELENBP1 |
| ALDH1A1 | CYP4F12 | LRRN4CL | SEMA3G |
| AOC3 | CYP4F22 | MAN1C1 | SEPP1 |
| AOC4 | DARC | MAOA | SLC2A4 |
| APCDD1 | DGAT2 | MAOB | SLC2A5 |
| APOC1 | DHCR24 | MARCO | SLC40A1 |
| AQP3 | DPT | MCAM | SLC4O4C1 |
| AQP7 | DTX4 | METTL7A | SMOC2 |
| AQP9 | EPHB6 | MGP | SNCG |
| AZGP1 | FABP4 | MLXIPL | SPARCL1 |
| BBOX1 | FADS2 | MOBKL2B | SPRY1 |
| BHLHE22 | FAM65C | MOSC1 | SVEP1 |
| C11orf87 | FMO1 | MVD | TF |
| C14orf180 | FMO2 | NAT8L | TM7SF2 |
| C1orf115 | G0S2 | NKD2 | TMEM132C |
| C1orf95 | GPD1 | PCSK9 | TMEM176B |
| C3 | GPR109A | PFKFB1 | TMEM37 |
| CA2 | GPR109B | PKD1L2 | TNMD |
| CADM3 | HAVCR2 | PLA2G2A | TPRG1 |
| CDO1 | HRASLS5 | PLIN1 | TRIL |
| CEBPA | IGSF10 | PLIN4 | UCP1 |
| CFD | ITIH1 | PLXDC1 | UCP2 |
| CFHR1 | ITIH5 | PPARGC1A | |

Figure 18:
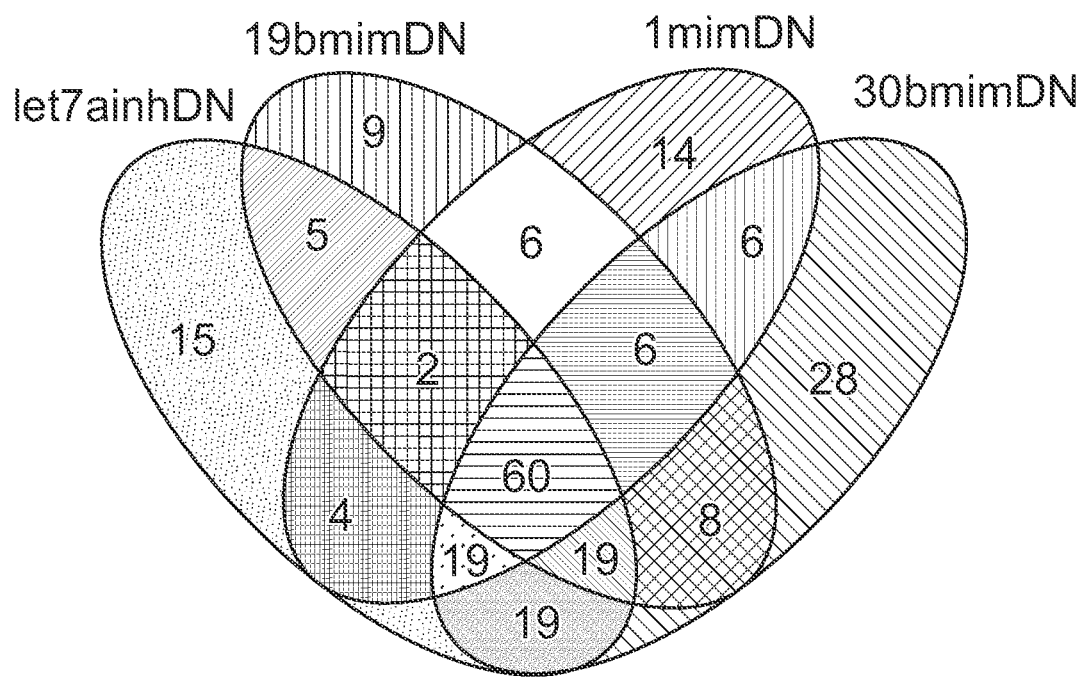
FIG. 18 is a schematic showing a Venn diagram showing that the numbers of genes significantly downpregulated in the presence of the miRNA analogs hsa-let-7a inhibitor, hsa-miR-1 mimic, hsa-miR-19b mimic and hsa-miR-30b mimic were respectively 143, 177, 115 and 165. A set of 60 genes that was commonly downregulated by the listed miRNA analogs.

A set of 60 genes was commonly downregulated by these 4 miRNA analogs (Venn Diagram, FIG. 18).

They include numerous chemokines genes and genes involved in cell proliferation and (Table 16).

TABLE 16

Set of 60 genes commonly downregulated by 4 miRNA analogs.

| | | | |
|---|---|---|---|
| ACTC1 | CENPF | ID1 | KRTAP2-1 |
| ANLN | CKAP2L | ID3 | MALL |
| ARSI | CXCL1 | IER3 | MMP3 |
| ATOH8 | CXCL2 | IL13RA2 | NCAPH |
| AURKB | CXCL3 | IL6 | PHLDA1 |
| BLM | CXCL5 | IL8 | PLK1 |
| BRCA2 | CXCL6 | INHBA | PPAPDC1A |
| BUB1 | E2F7 | IQGAP3 | PTGS2 |
| BUB1B | ESCO2 | KIAA1244 | RELN |
| CASC5 | FAM83D | KIF11 | SHCBP1 |
| CCL26 | GABBR2 | KIF14 | SLC17A9 |
| CDC6 | GREM2 | KIF18B | SLC6A17 |
| CDCA5 | GTSE1 | KIF2C | THBD |
| CDCA8 | HAS1 | KIFC1 | TMSL3 |
| CDH15 | HJURP | KRT34 | TOP2A |

B. Differentiation of Human White Adipocytes into Brown Adipocytes.

1. Differentiation Protocol.

In order to assess the effect of miRNA analogs on human white adipocytes differentiation into brown adipocytes, human subcutaneous pre-adipocytes (SuperLot 0048 from 8 female donors, ZenBio, NC) were plated on Day 0 into 96-well plates and allowed to attach overnight in preadipocyte medium (DMEM/Ham's F-12 (1:1, v/v), HEPES buffer, Fetal bovine serum and Antibiotics). The next day (Day 1), the medium was removed and replaced with differentiation medium-2 (DMEM/Ham's F-12 (1:1, v/v), HEPES buffer, Fetal bovine serum, Biotin, Pantothenate, Human insulin, Dexamethasone, Isobutyl-methylxanthine, Proprietary PPARG agonist and Antibiotics). The cells were allowed to incubate for 7 days at 37° C., 5% $CO_2$. After 7 days (Day 7), a partial medium exchange was performed with AM-1 adipocyte maintenance medium (DMEM/Ham's F-12 (1:1, v/v), HEPES buffer, Fetal bovine serum, Biotin, Pantothenate, Human insulin, Dexamethasone and Antibiotics). The cells were allowed to incubate for an additional 7 days at 37° C., 5% $CO_2$. On Day 17, the cells were transfected with miRNA analogs (Dharmacon specific miRIDIAN Mimics and Hairpin Inhibitors) using the transfecting agent Dharmafect 3. All treatments were in triplicate. Post transfection, the negative control was maintenance medium only and the positive control was maintenance medium with 100 nM of the PPARG agonist rosiglitazone. After 2 days, medium was removed and replaced with fresh maintenance medium. The maintenance medium then changed every two to three days until the end of the treatment period (Day 30). At the end of the treatment (total of 30 days in culture) cells were processed for Phenotyping and Genotyping Screening.

2. Transfection of Adipocytes.

Transfection reagents are used to facilitate the penetration of miRNA analogs into target cells.

As an example, the extent of transfection efficiency we achieved in adipocytes with the transfecting agent Dharmafect 3 (Dharmacon, CO) is depicted herein. Transfection efficiency was assessed in two ways:

a. Measurement of Cellular Epifluorescence after Transfection with Fluorescent miRNA Analogs.

Figure 13:
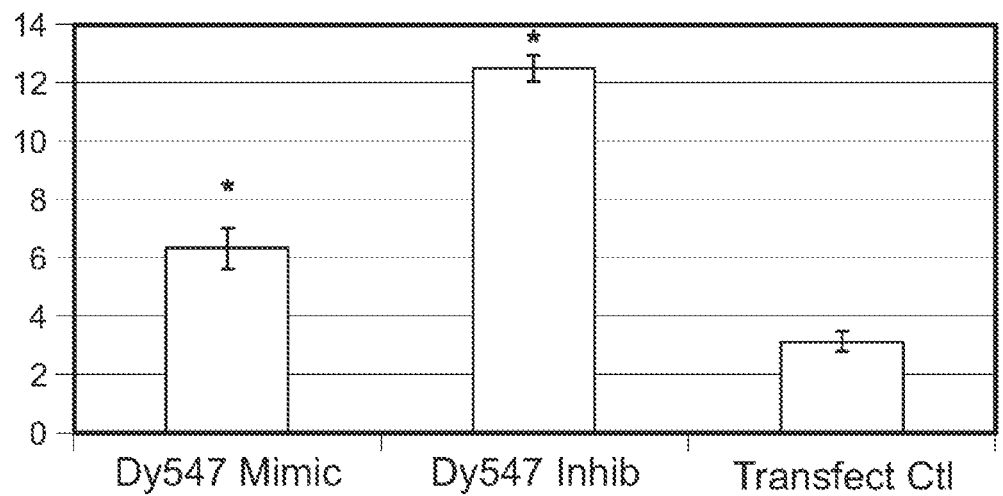
FIG. 13 is a bar graph showing relative fluorescence in unlabeled cells and cells transfected with a Dy547 labeled non-targeting miRIDIAN mimic or hairpin inhibitor.

Fluorescence was measured on Day 30 (540 excitation/ 590 emission) in cells transfected on Day 17 with the Dy547-labeled non-targeting miRIDIAN Mimic and Hairpin Inhibitor (100 nM). As shown in FIG. 13, there was a significantly greater fluorescence of cells transfected with the fluorescent miRNA analogs, even 12 days after transfection:

b. Reduction of Control Gene Expression.

Figure 14A:
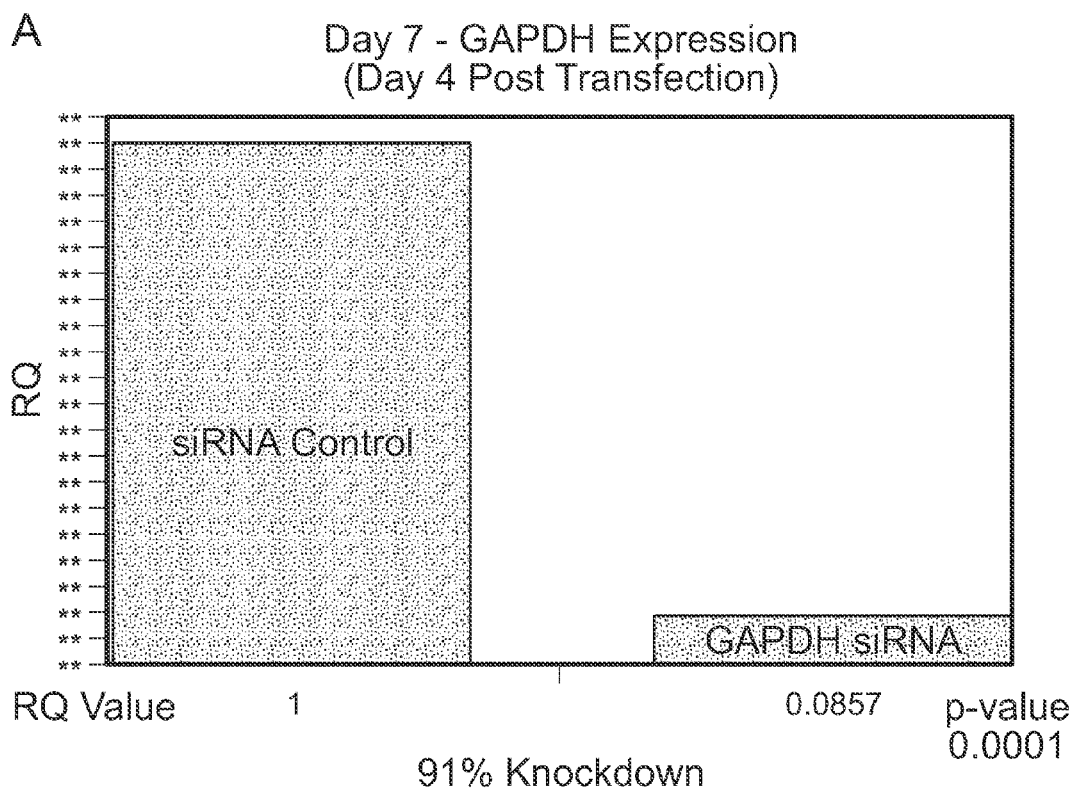
FIG. 14A is a bar graph showing the reduction of GAPDH expression in cells transfected with siRNA control and a GAPDH siRNA 4 days after transfection.
Figure 14B:
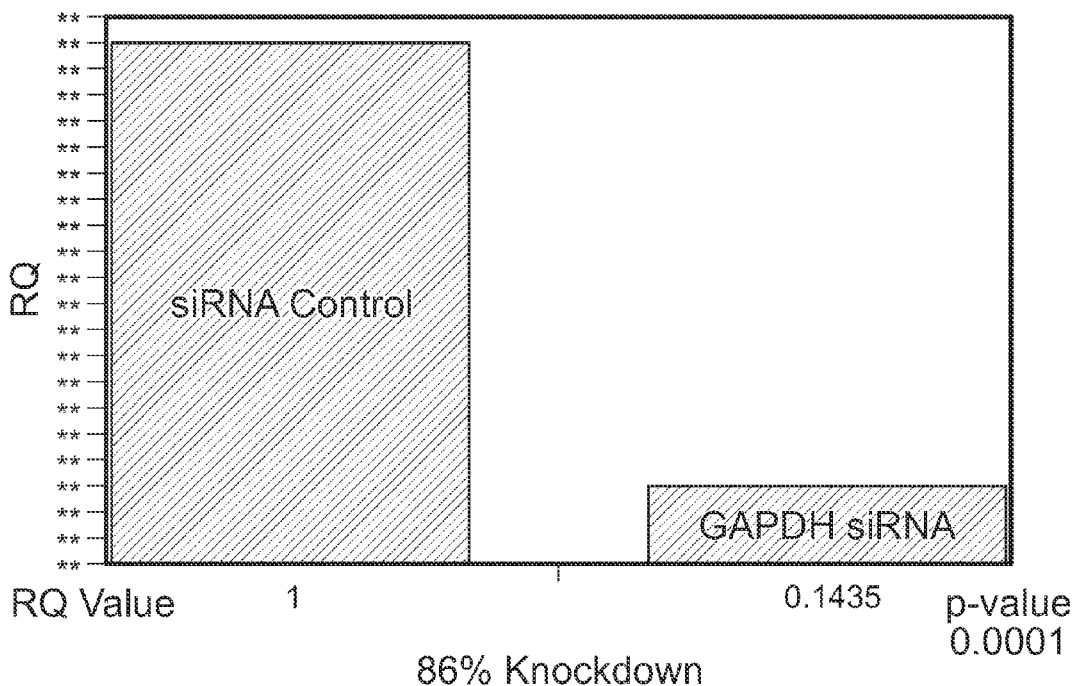
FIG. 14B is a bar graph showing the reduction of GAPDH expression in cells transfected with siRNA control and a GAPDH siRNA 12 days after transfection.

To confirm successful transfection of adipocytes, the reduction of expression of the control gene GAPDH ("housekeeping gene") was measured 4 days (Day 22) and 12 days (Day 30) after Dharmafect 3 (Dharmacon, CO) mediated transfection of adipocytes with a GAPDH-specific siRNA. Cell lysates were obtained and RT-PCR was conducted using pure RNA obtained by Cells-to-Ct reagents. Efficient transfection of mature adipocytes (a cell type known to be difficult to transfect) was achieved with the transfecting agent Dharmafect 3. 54% and 73% knockdowns of the GAPDH mRNA expression were observed at Day 4 and Day 12 post transfection, both highly significant, as shown in FIG. 14.

c. Optimization of Human Mature Adipocyte Transfection.

As efficient transfection of mature adipocytes is known to be difficult to achieve, we tested eleven different transfecting agents and assessed the degree of reduction of mRNA expression of the control gene GAPDH. Human subcutaneous pre-adipocytes were plated in 6-wll plates and differentiated for two weeks following the protocol described above. Subsequently, a miRNA mimic (50 nM) targeting GAPDH was introduced into the differentiated adipocytes using transfecting agents following their manufacters' protocol.

The transfected cells were incubated for 72 hours with reagents and miRNA mimic, then switched to maintenance medium. Fourteen days post-transfection, RNA was isolated using RNeasy Mini kit and RT-PCR reactions for the control gene GAPDH and the reference gene 18S were performed in triplicate using 100 ng of cDNA per well.

Figure 19:
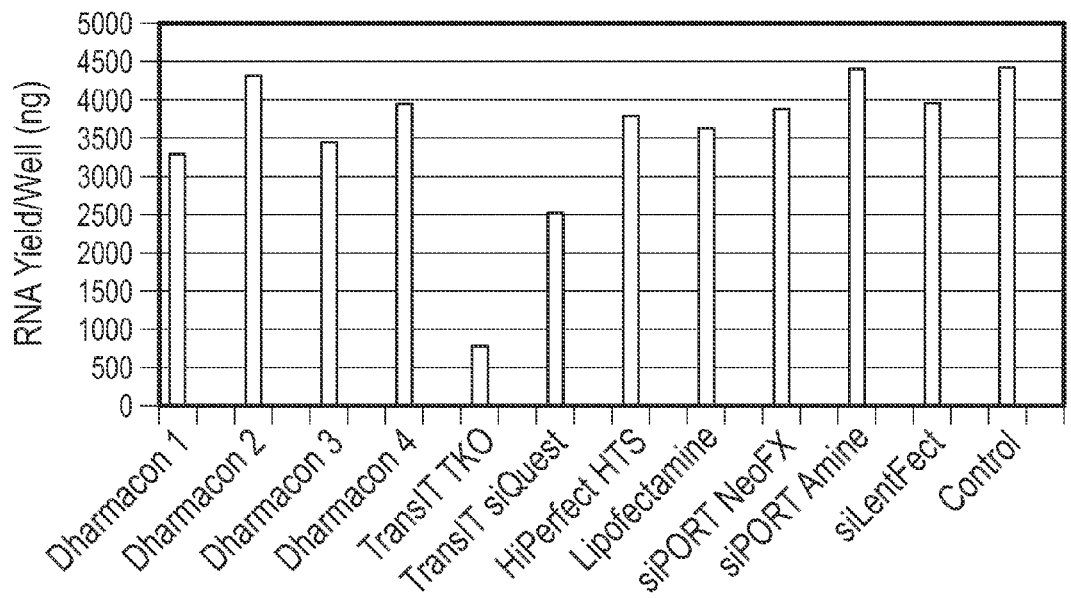
FIG. 19 is a bar graph showing the amounts of RNA extracted from mature adipocytes exposed to various transfecting agents.

The amounts of RNA extracted per well were very similar, except for the transfecting agents TransIT TKO and TransIT siQuest which may produce potential cellular toxicity in the conditions of the experiment (FIG. 19).

Figure 20:
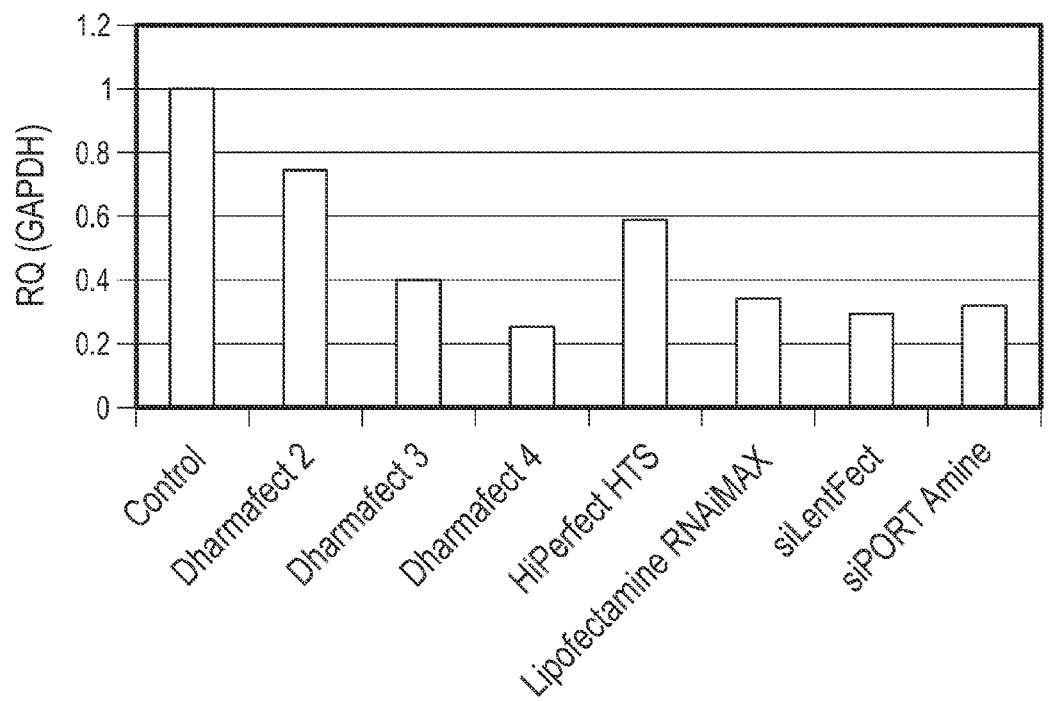
FIG. 20 is a bar graph showing reduction of GAPDH expression in mature adipocytes transfected with a GAPDH-specific miRNA mimic using various transfecting agents.

The cells transfected with Dharmacon 1 and siPORT NeoFX had significantly reduced levels of 18S expression and were excluded from the RT-PCR experiment analysis. Among the remaining 7 transfecting agents analyzed, the often-used transfecting agent Lipofectamine RNAiMAX led to a 66% reduction of GAPDH expression at day 14 post-transfection, Dharmafect 3 and Dharmafect 4 respectively produced 60% and 75% reduction of GAPDH expression (FIG. 20).

3. Phenotypic Changes During Maintenance of Human Adipocytes in Culture for Two More Weeks.

At the end of treatment (total of 30 days in culture) cells were stained with Oil Red O for assessment of lipid content. In the presence of medium without rosiglitazone from Day 16 to Day 30, the adipocytes appear loaded with large lipid droplets. In the presence of differentiation medium including 100 nM Rosiglitazone for 2 days followed by maintenance medium for 12 days (negative control), little change in appearance of the lipid-loaded mature adipocytes is noted. In the presence of 100 nM rosiglitazone throughout the experiment (positive control), the intensity of the red staining seems reduced. As an example, in the presence of 25 nM hsa-miR-30b mimic, the intensity of the red staining seems also reduced and the lipid droplets appear smaller.

The amount of lipids present in the mature adipocytes at Day 30 was measured with the fluorescent Nile Red Dye. As shown in FIG. 15, the highest fluorescence was noted in the adipocytes which were not exposed to rosiglitazone from Day 15 to day 30. A similar fluorescence level was noted in the cells which were transfected with the non targeting miRNA mimic and inhibitor. When the cells were exposed to rosiglitazone for two days, the fluorescence dropped significantly and was further reduced in the presence of rosiglitazone from Day 15 to Day 30. It appears that in the presence of the miRNA inhibitors tested, the level of fluorescence is within the range observed with rosiglitazone 2 day to throughout. In the presence of miRNA mimics, the level of fluorescence appears lower, an indication of lower lipid content.

Example 4

High-Throughput miRNA Target Screening by Luciferase Activity and qRT-PCR

High-throughput screening using luciferase reporter assay constructs are used to identify novel miRNA targets involved in thermogenesis.

Luciferase is commonly used as a reporter to assess the transcriptional activity in cells that are transfected with a genetic construct containing the luciferase gene under the control of a promoter of interest. SwitchGear Genomics has created a genome-wide library of over 18,000 human promoters and 12,000 human 3' UTR regions cloned into an optimized luciferase reporter vector system containing SwitchGear's RenSP reporter cassette (GoClone™) as a component of the LightSwitch™ Luciferase Assay System. This modified form of luciferase greatly facilitates detailed kinetic studies, especially those focusing on repression, which might otherwise be obscured by reporter protein accumulation.

The multiple microRNAs-one mRNA paradigm was tested with the SwitchGear Genomic GoClone system, using UCP1 as the single thermogenic target gene. In order to explore the possible interactions between various huma miRNAs and the 3'UTR region, the 5'UTR region and the promoter/enhancer region of the human UCP1 gene in Hela and HepG2 cells, three reporter constructs were made:
1. A human UCP1 3'UTR construct containing a reporter gene driven by a strong constitutive promoter (RPL10_prom) with a 2,218 bp 3'UTR fragment of the human UCP1 sequence cloned in the 3'UTR region of the reporter gene. The effects of a specific miRNA mimic, inhibitor, or non-targeting control on this reporter's activity are compared to those of an empty 3'UTR and an Actin Beta 3'UTR to identify effects that are specific to the putative UCP1 3'UTR construct.
2. A human UCP1 Promoter construct containing a reporter gene driven by a 4,147 by 5'UTR fragment of the human UCP1 sequence that spans the Transcription Start Site and upstream region covering the methylation region and the enhancer region of the human UCP1 gene sequence. The effects of a specific miRNA mimic, inhibitor, or non-targeting control on this reporter's activity are compared to those of an Actin Beta Promoter to identify effects that are specific to the putative UCP1 5'UTR construct.
3. A human UCP1 Enhancer Region construct containing a reporter gene driven by a short minimal promoter from the HSV-TK locus with a 601 bp 5'UTR fragment of the human UCP1 sequence that spans the Enhancer Region of the human UCP1 gene sequence. The effects of a specific miRNA mimic, inhibitor, or non-targeting control on this reporter's activity are compared to those of an empty 5'Enhancer Region to identify effects that are specific to the putative UCP1 5'Enhancer construct.

In addition, miRNAxxx_3'UTR constructs were made. They contain the reporter gene driven by a strong promoter (RPL10_prom) with a perfect match to the target sequence of miRNAxxx cloned into the 3'UTR region of the reporter gene. The effect of a miRNA mimic, inhibitor, or non-targeting control on this reporter's activity can be compared to EMPTY_3'UTR and Actin B_3'UTR to determine whether a miRNA mimic's or inhibitor's activity can be reasonably detected in the experimental cell type. If the cell type has no endogenous expression of the miRNA in question, the addition of a mimic should knock down the activity of this reporter, and the addition of an inhibitor should have no significant effect. If the cell type has high endogenous expression of the miRNA in question, the addition of an inhibitor should increase the activity of this reporter, and the addition of a mimic should have no significant effect. The range of endogenous miRNA expression in Hela and HepG2 cell types is broad, so the synthetic target activity changes are likely to reflect this variability.

For each miRNA candidate (38 in total), the following conditions were tested:
miRNA mimic (specific)*8 reporter constructs in Hela cells miRNA mimic (specific)*8 reporter constructs in HepG2 cells
miRNA mimic non-targeting control*8 reporter constructs inHela cells
miRNA mimic non-targeting control*8 reporter constructs in HepG2 cells
miRNA inhibitor (specific)*8 reporter constructs in Hela cells
miRNA inhibitor (specific)*8 reporter constructs in HepG2 cells
miRNA inhibitor non-targeting control*8 reporter constructs in Hela cells
miRNA inhibitor non-targeting control*8 reporter constructs in HepG2 cells To the extensive list of miRNAs that may bind to the UCP1 sequence, 8 filters were applied (in addition to required binding to UCP1 3'UTR region) to reduce the number of miRNA candidates to be tested. These filters were length of binding sites, number of binding sites, binding to the 5'UTR region, chromosomal clustering with other miRNAs, intronic location, binding to the Enhancer Region, binding to the Methylation Region and proof of experimental evidence of a relation to UCP1. 38 miRNAs that met at least 3 of these criteria were tested (Table 17).

TABLE 17 miRNA with putative binding sites in the UCP1 gene sequence.

|    | miRNA | # of criteria | Binding length | # of sites | 3'UTR | 5'UTR | Clustering | Intronic | Enhancer | Methylation | Exp. Evidence |
|----|-------|---------------|----------------|------------|-------|-------|------------|----------|----------|-------------|---------------|
| 1  | hsa-miR-130b-5p | 7 | 11 | 3 | + | + | 22 | | + | + | + |
| 2  | hsa-miR-328 | 6 | 10 | 4 | + | + | | | + | + | + |
| 3  | hsa-miR-655 | 6 | 10 | 5 | + | + | 14 | | | + | + |
| 4  | hsa-miR-19b-2-5p | 5 | 10 | 4 | + | + | X | | | | + |
| 5  | hsa-miR-26a-2-3p | 5 | 10 | 7 | + | + | | | | + | + |
| 6  | hsa-miR-367-3p | 5 | 10 to 18 | 3 | + | + | 4 | + | | | |
| 7  | hsa-miR-371a-5p | 5 | 10 to 12 | 9 | + | + | 19 | | | | + |
| 8  | hsa-miR-377-3p | 5 | 10 to 14 | 5 | + | + | 14 | | | | + |
| 9  | hsa-miR-378a-3p | 5 | 7 to 13 | 19 | + | + | | + | | | + |
| 10 | hsa-miR-382-3p/5p | 5 | 15 | 2 | + | + | 14 | | | | |
| 11 | hsa-miR-421 | 5 | 10 | 5 | + | + | X | | | | + |
| 12 | hsa-miR-515-3p | 5 | 9 | 3 | + | + | 19 | | + | | + |
| 13 | hsa-miR-620 | 5 | 10 | 7 | + | + | | | + | | + |
| 14 | hsa-miR-941/2 | 5 | 9 | 5 | + | + | 20 | | | + | |
| 15 | hsa-miR-1179 | 4 | 11 | 3 | + | + | 15 | | | | |
| 16 | hsa-miR-1302 | 4 | 10 | 5 | + | + | | | | + | |
| 17 | hsa-miR-146a | 4 | 9 to 10 | 8 | + | + | | | | | + |
| 18 | hsa-miR-181c | 4 | 9 | 5 | + | + | 19 | | | | + |
| 19 | hsa-miR-203 | 4 | 9 | 1 | + | | 14 | | | + | + |
| 20 | hsa-miR-331-5p | 4 | 8 to 15 | 6 | + | + | 12 | | | | |
| 21 | hsa-miR-422a | 4 | 7 to 14 | 6 | + | + | | | | | + |
| 22 | hsa-miR-452 | 4 | 8 | 7 | + | + | X | | | | + |
| 23 | hsa-miR-491-5p | 4 | 10 | 3 | + | + | | | | | |
| 24 | hsa-miR-501-3p | 4 | 10 | 2 | + | + | X | | | | + |
| 25 | hsa-miR-543 | 4 | 10 to 14 | 4 | + | + | 14 | | | | |
| 26 | hsa-miR-545 | 4 | 11 | 2 | + | + | X | | | | + |
| 27 | hsa-miR-549 | 4 | 13 to 14 | 3 | + | + | | | | | + |
| 28 | hsa-miR-643 | 4 | 10 to 14 | 9 | + | + | | | | | + |
| 29 | hsa-miR-651 | 4 | 10 | 6 | + | + | | | | | + |
| 30 | hsa-miR-654-3p | 4 | 8 to 10 | 11 | + | + | 14 | | | | |
| 31 | hsa-miR-21-5p | 3 | 10 to 14 | 2 | + | + | | | | | + |
| 32 | hsa-miR-211-5p | 3 | 11 | 1 | + | | | | | + | + |
| 33 | hsa-miR-22-3p | 3 | 9 | 5 | + | + | | | | | + |
| 34 | hsa-miR-30b-5p | 3 | 10 | 1 | + | | 8 | | | | + |
| 35 | hsa-miR-325 | 3 | 7 to 8 | 11 | + | + | | | | | + |
| 36 | hsa-miR-362-5p | 3 | 10 | 1 | + | | X | | | | + |
| 37 | hsa-miR-504 | 3 | 9 | 2 | + | + | | | | + | + |
| 38 | hsa-miR-552 | 3 | 9 | 3 | + | + | | | | | + |

In these Luciferase reporter gene assay experiments, a miRNA candidate was considered to interact with UCP1 if both the specific miRNA inhibitor increases the luciferase signal and the specific miRNA mimic decreases the luciferase signal with an Inhibitor/Mimic Ratio ≥1.5 and or/a p value <0.05. These selection criteria identify 9 miRNAs (miR-19b-2-5p, miR-21-5p, miR-130b-5p, miR-211, miR-325, miR-382-3p/5p, miR-543, miR-515-3p, and miR-545) (Table 18). A few more barely missed these selection criteria; they are miR-331-5p, miR-552, miR-620, and miR-1179.

TABLE 18 miRNA identified as regulators of UCP1 by luciferase reporter assay.

| | Cell Line | miRNA | # of criteria | Binding length | # of sites | 3'UTR | 5'UTR | Clustering | Intronic | Enhancer | Methylation | Exp. Evidence |
|---|---|---|---|---|---|---|---|---|---|---|---|---|
| 1 | Hela | hsa-miR-130b-5p | 7 | 11 | 3 | + | + | 22 | | + | + | + |
| 2 | | hsa-miR-328 | 6 | 10 | 4 | + | + | | | + | + | + |
| 3 | | hsa-miR-655 | 6 | 10 | 5 | + | + | 14 | | | + | + |
| 4 | Hela + HepG2 | hsa-miR-19b-2-5p | 5 | 10 | 4 | + | + | X | | | | + |
| 5 | | hsa-miR-26a-2-3p | 5 | 10 | 7 | + | + | | | | + | + |
| 6 | | hsa-miR-367-3p | 5 | 10 to 18 | 3 | + | + | 4 | + | | | |
| 7 | | hsa-miR-371a-5p | 5 | 10 to 12 | 9 | + | + | 19 | | | | + |
| 8 | | hsa-miR-377-3p | 5 | 10 to 14 | 5 | + | + | 14 | | | | + |
| 9 | | hsa-miR-378a-3p | 5 | 7 to 13 | 19 | + | + | | + | | | + |
| 10 | HepG2 | hsa-miR-382-3p/5p | 5 | 15 | 2 | + | + | 14 | | | | |
| 11 | | hsa-miR-421 | 5 | 10 | 5 | + | + | X | | | | + |
| 12 | Hela | hsa-miR-515-3p | 5 | 9 | 3 | + | + | 19 | | + | | + |
| 13 | | hsa-miR-620 | 5 | 10 | 7 | + | + | | | + | | + |
| 14 | | hsa-miR-941/2 | 5 | 9 | 5 | + | + | 20 | | | + | |
| 15 | | hsa-miR-1179 | 4 | 11 | 3 | + | + | 15 | | | | |
| 16 | | hsa-miR-1302 | 4 | 10 | 5 | + | + | | | | + | |
| 17 | | hsa-miR-146a | 4 | 9 to 10 | 8 | + | + | | | | | + |
| 18 | | hsa-miR-181c | 4 | 9 | 5 | + | + | 19 | | | | + |
| 19 | | hsa-miR-203 | 4 | 9 | 1 | + | | 14 | | | + | + |
| 20 | | hsa-miR-331-5p | 4 | 8 to 15 | 6 | + | + | 12 | | | | |
| 21 | | hsa-miR-422a | 4 | 7 to 14 | 6 | + | + | | | | | + |
| 22 | | hsa-miR-452 | 4 | 8 | 7 | + | + | X | | | | + |
| 23 | | hsa-miR-491-5p | 4 | 10 | 3 | + | + | | | | | |
| 24 | | hsa-miR-501-3p | 4 | 10 | 2 | + | + | X | | | | + |
| 25 | Hela | hsa-miR-543 | 4 | 10 to 14 | 4 | + | + | 14 | | | | |
| 26 | | hsa-miR-545 | 4 | 11 | 2 | + | + | X | | | | + |
| 27 | | hsa-miR-549 | 4 | 13 to 14 | 3 | + | + | | | | | + |
| 28 | | hsa-miR-643 | 4 | 10 to 14 | 9 | + | + | | | | | + |
| 29 | | hsa-miR-651 | 4 | 10 | 6 | + | + | | | | | + |
| 30 | | hsa-miR-654-3p | 4 | 8 to 10 | 11 | + | + | 14 | | | | |
| 31 | Hela + HepG2 | hsa-miR-21-5p | 3 | 10 to 14 | 2 | + | + | | | | | + |
| 32 | Hela | hsa-miR-211-5p | 3 | 11 | 1 | + | | | | | + | + |
| 33 | | hsa-miR-22-3p | 3 | 9 | 5 | + | + | | | | | + |
| 34 | | hsa-miR-30b-5p | 3 | 10 | 1 | + | | 8 | | | | + |
| 35 | Hela + HepG2 | hsa-miR-325 | 3 | 7 to 8 | 11 | + | + | | | | | + |
| 36 | | hsa-miR-362-5p | 3 | 10 | 1 | + | | X | | | | + |
| 37 | | hsa-miR-504 | 3 | 9 | 2 | + | + | | | | + | + |
| 38 | | hsa-miR-552 | 3 | 9 | 3 | + | + | | | | | + |

Out of these 9 selected miRNAs, 3 appear to bind to the 3 regions of UCP1 which were studied (miR-21-5p, miR-211, and miR-515-3p); 3 appear to bind to 2 regions of UCP1 (miR-19b-2-5p, miR-130b-5p, and miR-325), and 3 bind to a single region of UCP1 (miR-331-5p, miR-543, and miR-545). All but miR-331-5p appear to bind to the 3'UTR region of UCP1 (Table 19).

TABLE 19 miRNA identified as regulators of UCP1 by luciferase reporter assay.

| | miRNA | UCP1 3' UTR | UCP1 Enhancer | UCP1 Promoter |
|---|---|---|---|---|
| 1 | mir-21-5p | X | X | X |
| 2 | miR-211 | X | X | X |
| 3 | mir-515-3p | X | X | X |
| 4 | mir-19b-2-5p | X | | X |
| 5 | mir-130b-5p | X | X | |
| 6 | mir-325 | X | X | |
| 7 | miR-331-5P | | | X |
| 8 | mir-543 | X | | |
| 9 | mir-545 | X | | |

Further screening is performed by transfection of the promoter/3'UTR library into human adipocytes or adipose-derived mesenchymal stem cells in cell culture, followed by addition of miRNA agents (e.g., agomirs or antagomirs) to the cell culture. Measurement of luciferase activity and identification of mRNAs is performed 24 hours after transfection and addition of miRNA agents.

In order to confirm the results of the transfection experiments set forth above over a longer time frame, lentiviral transduction experiments are performed using lentiviral vectors containing the miRNA agents of interest (from System Biosciences (SBI) collection of miRNA precursors expressed in the pMIRNA1 SBI vectors allowing the expression of the copGFP fluorescent marker). Specifically, cells containing the promoter/3'UTR library are transduced with lentiviral particles at an MOI of 1:10 and GFP-positive cells are sorted by FACS, according to the supplier's instructions. The level of expression of the mature miRNAs and their targeted mRNAs is assessed at several time points (0, 3, and 6 hr.; 1, 4, and 7 days) by Taqman Quantitative Real-time PCR in control cells (HEK293 cells), Human Adipose-Derived Mesenchymal Stem Cells, Human Subcutaneous Preadipocytes, and Human Proliferating Subcutaneous Adipocytes. Pooling of RNAs from 5 different time points after transduction is optionally employed to reduce the complexity of the qRT-PCR based screening approach while preserving the detection sensitivity.

Example 5

Proteomic Profiling

Proteomic Profiling is also used to identify novel miRNA targets involved in thermogenesis.

Shotgun proteomics is a method of identifying proteins in complex mixtures using high performance liquid chromatography (HPLC) combined with mass spectrometry (MS). Transfected and transduced cells with miRNA agents and promoter/3'UTR library (as described in Example 4) are harvested and lysed to produce crude soluble (cytosolic) and insoluble (nuclear) fractions. Peptides are from these fractions are then separated by HPLC and analyzed using nanoelectrospray-ionization tandem MS using the isotopic labeling technique SILAC to quantify protein abundance. Spectra are searched against the Ensembl release 54 human protein-coding sequence database using Sequest (Bioworks version 3.3.1, Thermo Scientific).

To avoid missing low abundance proteins, a targeted proteomics approach is also employed to accurately quantify a set of proteins that are known regulators of adipogenesis, adipocyte differentiation and BAT function. Some examples include UCP1, KDM3A, PRDM16, PPARA, PPARGC1A, CEBPB, CIDEA, BMP7, COX7A1, SIRT1, SIRT3, DIO2, FABP4, ADIPOQ. These proteins are analyzed via ELISA based or Luminex based immunoassays using commercially available antibodies.

Optionally, the protein fractions are analyzed using Multiple Reaction Monitoring-Mass Spectrometry on a proteomics platform, whereby only one protein (e.g. UCP1) of the thermogenic pathway is accurately quantified using LC-MS-MS.

Example 6

Reconciliation of the Phenotypic, Luciferase/qRT-PCR, and Proteomic Datasets

The results of the in vitro experiments set forth in Examples 3-5, herein, are reconciled. Specifically, to narrow further the initial set of microRNAs, mRNAs and target proteins and pathways to a relevant yet manageable number of targets, the experimental data is integrated with Network Searches and Analyses Packages (DAVID, Ingenuity Systems IPA and ARIADNE Pathway Studio.

Global analysis of the results of the in vitro experiments set forth in Examples 3-5, herein, is performed the Business Intelligence tool TIBCO Spotfire. This allows for a visualization of the relationships between the miRNA agents and target gene.

Example 7

Animal Models of Obesity

Several animal models of obesity have been developed and validated (Kanasaki K et al., J Biomed Biotechnol., 2011:197636 (2011); Speakman J et al., Obesity reviews: an official journal of the International Association for the Study of Obesity, 8 Suppl 1:55-61 (2007)). The most commonly used are the Leptin Signaling Defects $Lep^{ob/ob}$ and $Lepr^{db/db}$ Mouse Models as well as the High-Fat Diet model in C57BL/6J mice (Wang C Y et al., Methods in molecular biology, 821:421-433 (2012). This diet-induced obesity (DIO) model closely mimics the increased availability of the high-fat/high-density foods in modern society.

A DIO mouse model is used for in vivo validation of the effectiveness of the miRNA analogs described herein for the increase in thermogenesis and/or the treatment of obesity and other metabolic disorders (Yin H et al., Cell Metab., 17(2):210-224 (2013)).

DIO mice are administered one or more of an hsa-let-7a agomir, hsa-let-7a antagomir, hsa-miR-1 agomir, hsa-miR-1 antagomir, hsa-miR-19b agomir, hsa-miR-19b antagomir, hsa-miR-30b agomir, and hsa-miR-30b antagomir. Rosiglitazone is used as a positive control. Food intake, blood metabolic parameters, body composition (body weight, body fat, bone mineral and lean mass, body fat distribution, body temperature, O2 consumption and CO2 production, exercise induced thermogenesis, cold induced thermogenesis and resting thermogenesis are measured in the mice prior to treatment and after treatment. A reduction in body mass or body fat or an increase in body temperature or any kind of thermogenesis indicate the in vivo effectiveness of the administered composition.

Example 8

Nucleic Acid Sequences of Human UCP1 and UCP2 Genes and Transcripts

The nucleic acid sequence of the 1,462 base pair (bp) transcript ENST00000262999 of the human UCP1 gene is as follows (Exons in capital letters) [SEQ ID NO: FROM 351-363]

| No | Exon/Intron | Start | End | Start Phase | End Phase | Length | Sequence | SEQ ID NO: |
|---|---|---|---|---|---|---|---|---|
| | 5' upstream sequence | | | | | | ...gtcgttcaaaaacagaaatcgggtttgctgcccggcgacaggcgtga | 351 |
| 1 | ENSE00001081761 | 141,489,959 | 141,489,758 | — | 0 | 202 | AGAGCAAGGG AAAGGAACTT CCTCCACCTT CGGGGCTGGA GCCCTTTTCC TCTGCATCTC CAGTCTCTGA GTGAAGATGG GGGGCCTGAC AGCCTCGGAC GTACACCCGA CCCTGGGGGT CCAGCTCTTC TCAGCTGGAA TAGCGGCGTG CTTGGCCGAC GTGATCACCT TCCCGCTGGA CACGGCCAAA GTCCGGCTCC AG | 352 |
| | Intron 1-2 | 141,489,757 | 141,489,132 | | | 626 | gtagctaggc agagggtaa gacaa...tgttc tgcaccttc ttattcccag | 353 |
| 2 | ENSE00001009006 | 141,489,131 | 141,488,933 | 0 | 1 | 199 | GTCCAAGGTG AATGCCCGAC GTCCAGTGTT ATTAGGTATA AAGTGTCCT GGAACAATC ACCGCTGTGG TAAAAACAGA AGGGCGGATG AAACTCTACA GCGGGCTGCC TGCCGGGCTT CAGCGGCAAA TCAGCTCCGC CTCTCTAGG ATCGGCCTCT ACGACACGGT CCAGGAGTTC CTCACCCGCA GGAAAGAAA | 354 |
| | Intron 2-3 | 141,488,932 | 141,484,673 | | | 4,260 | gtaagccgtg agcgttcctg ggagg...aataa ttttttct ctctggatag | 355 |
| 3 | ENSE00001081759 | 141,484,672 | 141,484,472 | 1 | 1 | 201 | CAGCACCTAG TTTAGGAAGC AAGATTTTAG CTGGTCTAAC GACTGGAGGA GTGGCAGTAT TCATTGGGCA ACCCACAGAG GTCGTGAAAG TCAGACTTCA AGCACAGCCA TCTCCACGGA ATCAAACCTC GCTACACGGG GACTTATAAT GCGTACAGAA TAATAGCAAC AACCGAAGGC TTGACGGGTC TTTGGAAAG | 356 |
| | Intron 3-4 | 141,484,471 | 141,484,366 | | | 106 | gtaactaact tcaaaatggg tttta...acatt ttcttttt ttttcccag | 357 |
| 4 | ENSE00001081762 | 141,484,365 | 141,484,264 | 1 | 1 | 102 | GGACTACTCC CAATCTGATG AGAAGTGTCA TCATCAATTG TACAGAGCTA GTAACATATG ATCTAATGAA GGAGGCCTTT GTGAAAAACA ACATATTAGC AG | 358 |
| | Intron 4-5 | 141,484,263 | 141,483,528 | | | 736 | gtaacttccc atttcatata acaaa...gacc tgttcatcg atccatttta g | 359 |
| 5 | ENSE00001081763 | 141,483,527 | 141,483,347 | 1 | 2 | 181 | ATGACGTCCC CTGCCACTTG GTGTCGGCTC TTATCGCTGG ATTTTGCGCA ACAGTATGT CCTCCCCGGT GGATGTAGTA AAAACCAGAT TTATTAATTC TCCACCAGGA CAGTACAAAA GTGTGCCCAA CTGTGCAATG AAAGTGTTCA CTAACGAAGG ACCACGGCT TTCTTCAAGG G | 360 |

| No | Exon/Intron | Start | End | Start Phase | End Phase | Length | Sequence | SEQ ID NO: |
|---|---|---|---|---|---|---|---|---|
| | Intron 5-6 | 141,483,346 | 141,481,165 | | | 2,182 | gtaagatatg atcttgtgta tctgt...cgaac gatgacatgc actttctag | 361 |
| 6 | ENSE00001081760 | 141,481,164 | 141,480,586 | 2 | — | 577 | GTTGGTACCT TCCTTCTTGC GACTTGGATC CTGGAACGTC ATTATGTTTG TGTGCTTTGA ACAACTGAAA CGAGAACTGT CAAAGTCAAG GCAGACTATG GACTGTGCCA CATAATCAGC TTCAAGAAAA TGATGTAACA TACCAGTGGG AATCTTGCTG ACTGGATCAT AAAACAAAC AAAACTTATT CACTTATTTT AACCTAAAA GATAAAGGAA TTTTGGCAGA GAATTTTGGA CTTTTTTATA TAAAAAGAG GAAAATTAAT GCCTATTTCA TATAACTTTT TTTTTTTCTC AGTGTCTTAA GAAGGGGAAA GCAAAACATT CAGCATATAC CCTGCAAAT GTAATGCAGA TAAGCTACTG CATTGACCA TTTCTGGAGT GCAATTGTGT GAATGAATGT GAAGAACTTT AACATGTTTT AATTACAATT CCAACTGTG CTTAAAAATG TGAGTGAAAT GCAGTTTATA AATATTAGT TTTTATTAAC CACAGTGTC AGTTAATATA TTCAATAAAA GTATTGCTAA TACCTTTT | 362 |
| | 3' downstream sequence | | | | | | aaagtttgctctttgagatctataccctggtgtaagagtcaagttcacta... | 363 |

The nucleic acid sequence of the 9,371 base pair (bp) of the human UCP1 gene (ENSG00000109424) is as follows (Exons are highlighted) [SEQ ID NO: 364]:

```
>chromosome:GRCh37:4:141479988:141490559:-1
AGAGAAGGCC GCAAGGTGCC TGCAAGATGT CTGGGGAGTT GGAGGAATGG AAGAGTGCCC      60
CGCTCTTCCT TCTGGGAGAG CTCCAGCTAG GCAGAACCTT TCACCAAGGC TCTGATATCG     120
TGCTGGTTTC CGAAAGCCCC AGCCGAAGGT GTGCAGCCAA AGGGTGACAG AAGGTGAGGC     180
ACGTGCGGGG GCGCGGGTGC TGACCGCCGC GGTGCGCCCT CCCTCCGACG TGCGGTGTGC     240
GGGGCGCAGA CAACCAGCGG CCGGCCCAGG GCTTTCGGGG AGCGAAGCAG GGCTCCCGAG     300
GCACCGAGCG AGAATGGGAA TGGGAGGGAC CCGGTGCTCC CGGACACGCC CCCGGCAGGT     360
CCCACGCCCG GGTCTTCTGA GACCTCGCGC GGCCCAGCCC GGGAGCGGCC CAGCTATATA     420
AGTCCCAGCG GAAGACCGGA ACGCAGAGGG TCCTGCTGGC GCGAGGGTGG GTAGGAGGGG     480
ACGCGGGGAC TCGGCCCCCA ACACCGCGCT CCGTCTGCAG CCGCCGCCTC TGCACCGCCG     540

CTGCCCGGCG GTCGGTTCAA AAAACAGAAA TCGGGTTTGC TGCCCGGCGG ACAGGCGTGA     600
AGAGCAAGGG AAAGGAACTT CCTCCACCTT CGGGGCTGGA GCCCTTTTCC TCTGCATCTC     660
CAGTCTCTGA GTGAAGATGG GGGGCCTGAC AGCCTCGGAC GTACACCCGA CCCTGGGGGT     720
CCAGCTCTTC TCAGCTGGAA TAGCGGCGTG CTTGGCGGAC GTGATCACCT TCCCGCTGGA     780
CACGGCCAAA GTCCGGCTCC AGGTAGCTAG GCAGAGGGGT AAGACAAGGG GTCTCAGGAC     840
AGAGGGGACG CTGTTGCGTG CATTCCATTT ATTCTCTGCT TTGGTGTAAC CACTGTTTCT     900
AGGTAGGGTA GGTGACCTTC CAAAGCAGTC TGGCCTTGTC CCAGGGCTGG TGCTTTAGGA     960
TGGGAAACTG GAACTTTTTC TGGGATTAGC TGAAGAACCA CCAGGGCCAC AGAGAATGGG    1020
TTGACCATGA CTACTACCAA ATTCTCCCAA AATTTAGGGT GCACTTAGTA TTTTAAGAGC    1080
TGAGAATATT GGCCTCTCCT GAGTTTACTA GTCAGGTGCT TTTTCCTTTC TTTGATTCTT    1140
CGGGGGTTCT GTCCTATCCT ACTGCCCTAG GGGTTCTGGA GAGTTCCTGG GGAGGGGAT     1200

ATTCAAAATG TGCATTGTAG CCAGCCTCCC TCCATCTGCG CGTGAGCGAA CACACACACA    1260
CACACACACA CACACACACA CACACACACA CACACACGGT AGAGGGAGGG GGATGGAAGA    1320
GGAATGTTGC TGAGAAAAGA AACGGAAAAT AGGAACACAG GGGGAAATCT TGGCTTAAGA    1380
GTGAACTCAA TTTCGCTCCC TTCTGTTCTG CACCTTTCTT ATTTCCAGGT CCAAGGTGAA    1440
TGCCCGACGT CCAGTGTTAT TAGGTATAAA GGTGTCCTGG GAACAATCAC CGCTGTGGTA    1500
AAAACAGAAG GGCGGATGAA ACTCTACAGC GGGCTGCCTG CGGGGCTTCA GCGGCAAATC    1560
AGCTCCGCCT CTCTCAGGAT CGGCCTCTAC GACACGGTCC AGGAGTTCCT CACCGCAGGG    1620
AAAGAAAGTA AGCCGTGAGC GTTCCTGGGA GGGGCAGAAA AGCCTTGGGC TCCGCTCTGT    1680
TCCAAAAAGT GTAACACACA GAGGAGTGGT TTTCATAACA AATTGGCGAG AAAACATTCA    1740
TATTTGAACT CTCCCTTCCC CAAACATTAG CTCATTGTTC ATAGAAAAAA GTATGCAAAA    1800
TCGATTTTTT AGATGCAGAT ATATACTTGT AAAGGTCACC CAGTCATGGA AGTTTTGTGC    1860

CCAGTTTGGA TCTCCATCTG GAGAATATGG GTGGGCTACA GAAAAATGTT TAACTTAAAG    1920
TTCTCCAAAG AGGGAAGTAT ATCAGAAACA TCTATGGAGC TTGTCAGAAA TCCAAACGAG    1980
GACTACCATG GTCCTCTGAG TCTGAATCCT CAGGCTAGAG ACCAGAGTGT CTTTCCACAA    2040
GCTTCCCTCA TCATTTGTGT ATGCAACAAA GTTCAAAGCC TTCTGTTTGA AGCAAAGAAA    2100
GCCAGACTTT GTGAAGAGAG TTGAAAGGAC AGGAAAAGAC ATATTTCCTC TTAAGAGGTT    2160
CCTCATCAGG TCCAGGAAAG ACCAGAGCAG AAAAAGTGGA CGAATGCTGC AGGGAGTTTG    2220
TTTAGGGGAA AAAGAAAAGG AAACATATTT CCTGAGTGCC AGTGCACTCT AAGAATTCCT    2280
GTCACTTTAG GTAGCATTTA TTTGAGGGCT TAACTATGAA CCAGACATTG TTCTAAGTGC    2340
TTCAGATACA TTATAACTGG AAGGGTATTA GTACCATTAT CCCTTGGCAG ATGGGAAAAC    2400
TGAACACAGA GCAGATTCAT CACTTGCCCA AGGTCACACA GCTGGGAGGG GGCAGAGCCA    2460

GGGTTCAAAC CCAGGCAGTC TGGCCTCGGA CTCCAGGCTC CTAACCCTGT TCTCTACTGC    2520
CTTCTGCACT TCTCATATGA TTCTGCCCAT CATTCAAACC GCACAACACT GCTGTGAGTA    2580
AAAAGTGTTA GCCGAATATC AGGGTAGTTA AGTAACATGC ACAAAATCAC ACAGCTAATC    2640
AACATCAGAG GCACTTTCAT GTGGAGTAGA CAAGCCAGAG AGAAGATGTG CTGATGGCAC    2700
AATGAATACA TTAAGTGAAA TCCACCTTGT AGATTTCATC ATTTCTGCTG TGAGTAACCT    2760
TCAATACTAT AATTTTATGG GATAATTTAT AAATGTTGTC TATACAAATA TATAAGTTAT    2820
ACTTATCCAC ACAAGTACTT TCAAAGTGAA GATAAAGTCT GGATGTTACT AGATCAAAAC    2880
TGCATTTTTT TATTTATAGA TGTAGCAAGA GAGGAAACAC AAAGGAGGTA AAGCTGCCCG    2940
TTCAGGTGGT TTTCTTCACA GATTGACTGT TCTACCAATT GTTGTGGACT TTGGGCACCA    3000
AATTAATAGG ATATATGTTG GCAGTGTTCT ATGTTATATA GATTCAGTTT ATTTAGTAGG    3060

CTTTATTGAA CTGCCATGTG CCAGTAACTA TGTTAGATGT TTAGATGGCA GATGTGTCTC    3120
TAGACAGAGC TTACAGTTGA GAGTATGGGT TGTGTGGGGA GAAGTGAATA GATGACTATA    3180
TTCCATGATA CATGCTGTAT TACAATACAG TCCTACTTCA CTTAACGATG GGGATACATT    3240
CTCAGAAATG AGTTAGGAGG CAAATTGGTT GTTGAATGAA CATCACAGAG AGCACTTACA    3300
CAAACCTAGA TGGCATAGCC ACACCTAGGC TATATGGTAT AATCTATTGC TCCTAGGCTA    3360
CAAACCTGTG CAGCATGTTG GTATTGAATA CTACAGGCAA TTGTTACATA AAGTTAAGTG    3420
TTTGTGTACC TAAAAATAGA AAAGGTAATG CATTACACTA CAGTCTTATG GGGCTGGGAT    3480
GTCACTAGGT GATAGGAATT TTTCAGCTCT GTTCTAATCT TACGGGACCA CCATCATGA    3540
TGCAGCACAT GACTAACTGT AATTACAAGA TGGTGGCTAT ATTAAACACA ACTACTTAAG    3600
CTAGCCATGG AGGTATGGTC CGTGAGATTT TCCTGAAGAA TTAACGTCTG GATCAATTCT    3660
GGAAGGGCCA GCAGGAGTAC TCCAGGCAAA GGGGTGAGAA AGGAGCTTCC AAGTAGAGTG    3720

AAGGTCATGT GCAAAGACTC AGTGAGGAGT CGAGTGAACA TAGCACAGGG AGGACATGTT    3780
GGTGAGGAAG GAGGGGTGAA GCCACAGAGA CAGGAGGGAG CCAGATGACA GAAGGCCTTG    3840
CAGGCGGTGC TAAGGAGTTT GGATTTTATC CTTACAGTGG TGGGAAGTCA TTGTAAAAAT    3900
ATTAAGCAAG GGAGTGGCAT AAACAATTTA CATTTTCAAA AGATCACTTT GGCAGCAGAT    3960
AGAGTATATA TGTAAAAGGA GTAAGAAAGA GGTAAGTTAG AAAGCAAGAA ATGATCAGGG    4020
TATGCCCTAA AACACTGGCA ATAGGGAAAA AGAGATGTCA ATCAGAAAGA TTGAGAAAGT    4080
ATAATTGAAT TGACTTGGTG AACAAATAGA AGTAAGGCAT AAGGGACAGG TAGAAATATG    4140
AGATGACTTC CAAGTTTCTG TTTAAAGATA CCCTTTATTG AGAGAGGATG TATAGAAGCT    4200
GTCTTAGGGG GAAGACAAGA AATTTGGTTT AGGCCATGTC AACAGGTAAT GGCCAGTAGG    4260
CACATGATTC AGTTTATTTA GTGGGCTCCT TTTAGGAGAA AATCTGAGCC AGATTCCAGG    4320
```

```
AAGTCACAGC AGGGACTACC AATAGGGTCA AACAGCAGAG AGTGTGGAAA GGACTGAAAA      4380
GTGATCATTG TACATAACAA ATAGAAGCTC ACTGATTTTC TAGCAAAAAC ATCTTCAGCA      4440
GAGTAGCGTG GTATAAGCTA TATTGTAGGG GACTGAGGAA GAAATGGGCT CTGAGAAGTA      4500
AAGACAAACA ATATGTTTTG TAAATAAATT TCTTTTAGTT CTTAAAAAAA AAGCCTCTTT      4560
TCCAGCTTGA TTGGGAAGTG AAGAGAGGGA TTTGAAAGTT GGAGATTGGA GGATAGGATG      4620
AGTACATCAA GATACACTAC GTTGTAGTGC AGTGCATTAC AAATGTGAGC TAAAAGTGAA      4680
GGCATTTGTA ATCATATGAT ATTGCTAATT AAAAGACAGC TGTCAGTCAT ATGCCCAGCT      4740
CCTGGTAAAG CATGATGAGA AGAGTACAAT CATGGTAGTG ATTTAAAAAT TGCTGCCAGT      4800
TTTGTGGATT TTCTTTATGC TAGACAGTGT AAGCTCTTTA TCAATATTAT TTAACTCACA      4860
CAACTCTAAG AGGTAGATAT TATTATCCCT TTTTGACAAA TTAGGAAACA GAATTATAAT      4920
GACTGAGAAA GTCTCTGCTG AGTAAATGTT ACTGAACCTT AATTTTATGT TTACTTAATG      4980
ATAGAAATGA ATATTGGGCT TCAAGACTAT TTGTACTTAA TGAAATCTGT CTTGAGCAAC      5040
ATAAGCTATT TTTTTCAAAA TTTTAAGACA AAAATCACTT TCTTCTCTCC TGTCTTCTTA      5100
TTTTTGTTCC CTTCACATGT TGTAGCCTAA CACTACTTGA TGGCCCATTT TGGTGCAGTT      5160
TGTCCACTGG GCTTCATCTA AGGCCACCAA GTCCCATAAT TAACATGATC ATTCGTGGGA      5220
GAAAGATCAA GCCTCATTGG TGATGGGTGC CTCCTCACAG TCGGATAATA CTGAAAAGAG      5280
AGCTAAATGT GGGAAAGAAC CAAGTTGAAC ACAGGAAAGA ATCAGGCCAC TGTGAAAATA      5340
AGCATTGTGT TTTCTTGTTC CTTGAAAGTC TTCATTTTTA AAAAATTTCA GACACCTGAA      5400
GTTTTCTAGC CTTACTCTGA GTTGACGCAC ATTTAGTACA TGATCAACAC ATAAACAAGC      5460
ATTAGAGAAA TAGAAAAGCT GTAAGAATAC AAAAATATGG GCCAGGTGGG TGGCTCATAC      5520
CTGTAATCCT AGCACTTTGG GAGGCCGAGG CAGACGGATC ACCTGAGGTC AGGAGTTCAA      5580
GACTAGCCTG GCCAATATAG TGAAACCCTG TCTCTACTAA AAATACAAAA CTTAGCAGGC      5640
TGTGGTGGCA CGTGCCTATA ATCCCAGCTA CTTGGGAGGC TGAGGCAGGA GAATCTCTTG      5700
AACCCGGGAG GCGGAGATTG CAGTGAGCCA AGATCACACC ACTGCACTCT AGCCTAGATA      5760
ACAGAGCAAG ACTCCATCTC AAAAAAAAAA AAAATACAAA AATATGAACC ACTGAAAATT      5820
AAAAAGACAT GCATGCATTC TAGGTGTTTA ATTTTTTTTC TTAATAATTT TTTTTCTCTC      5880
TGGATAGCAG CACCCTAGTTT AGGAAGCAAG ATTTTAGCTG GTCTAACGAC TGGAGGAGTG      5940
GCAGTATTCA TTGGGCAACC CACAGAGGTC GTGAAAGTCA GACTTCAAGC ACAGAGCCAT      6000
CTCCACGGAA TCAAACCTCG CTACACGGGG ACTTATAATG CGTACAGAAT AATAGCAACA      6060
ACCGAAGGCT TGACGGGTCT TTGGAAAGGT AACTAACTTC AAAATGGGTT TTATAACCAC      6120
CAAAGCACAT ACATACAACT AGCAACTTAT TGTAAAGTAG AGTTAATAAA CATTTTCTTT      6180
TTTTTTTTCC CCAGGGACTA CTCCCAATCT GATGAGAAGT GTCATCATCA ATTGTACAGA      6240
GCTAGTAACA TATGATCTAA TGAAGGAGGC CTTTGTGAAA AACAACATAT TAGCAGGTAA      6300
CTTCCCATTT CATATAACAA ACAGGTCTGC ACCTTTAGAA GTTCATCTTG GAGCTTCTGC      6360
AGCCACCTTA TACTCAATCT CTTAACTCCA ATAGTTTTCT CTTTTTAAAA ATTAAGTAAT      6420
TTTGAACCAT ATACTTTG TGTGAGAAGCA GGAAAAGACC AAAATATTAA GTTTAAGAAG      6480
TTTTGCCACA ACAAAAATAT TTGCAACAA AAATAACAGG CAATTTCATG TCAGCATTAT      6540
TCTCATTTAA TACTAATATA TGGGACTTTT GTTAGAATCT TATTCTTTAT ACAGCAGAAT      6600
TCAGGAGGTA AGTCCATCCT GCATACTATA TCCAAAAGAT CTAGTTATAA AAGGAGCTTA      6660
TCAGTGGTCT CATCCAAAAA GTAATACCAT AAGATAGGTT CTTAAAAATA ATATTCTAAC      6720
AACTTCTAGA GACATTGAAA TTTCCCTTAT TTCAATAAAA AAGTATTAGA TGCTCATATA      6780
TTAGGCATTA TTACAGGCCT TAAAGGCACA GAGGAAACTA ACAGTTTACT TTCCTAAAGT      6840
GTTAACAATC TATTAAGCCA TTTACTCTTT ACCTTCTTTT TCTAGTGCAA TACCTTTCTT      6900
ATTTTATTTT ATTTATTTAT AAGACATCTT CATTGACCTA CTGTTATCAA TAGGTTTATA      6960
AAGATATGAC AGATAACTAA ATTGCAAGCC CCCAAAAGTC TGATGTTGAC CTGTTTCATC      7020
GATCCATTTT AGATGACGTC CCCTGCCACT TGGTGTCGGC TCTTATCGCT GGATTTTGCG      7080
CAACAGCTAT GTCCTCCCCG GTGGATGTAG TAAAAACCAG ATTTATTAAT TCTCCACCAG      7140
GACAGTACAA AAGTGTGCCC AACTGTGCAA TGAAAGTGTT CACTAACGAA GGACCAACGG      7200
CTTTCTTCAA GGGGTAAGAT ATGACTTGT GTATCTGTAA TGTGTTCTGG CTGTCTGTGT      7260
GCTTTGGGAC ACTCTCATGT CAAGCAACCG ACATTTAGCT TACAAGCCTT AGTATATTCA      7320
TATACTTAGT ATTGACTTTT CCTTGCCACA GATTTCTCCA ATCCACCAAT TCCACTGTGC      7380
CAGAAAGTAA AAAGCCATGA TATTCAAATT TTCTCAACTT TGATCAAAGG CTCATTCAAG      7440
ACCAGTGCCT TTTCCACTGG TCCCAATCTA CTGGAAATGC AGACAGTATT TTGCCTTCTC      7500
TGGGCAGAA AGTTATAAAG TAGAGGGAAA TCATAATAGA GAGCTATGAG AGAACAAGAT      7560
TTGATTTGAT TTAATTTGAT GGACTCAAGT TTTAACATTG TAAAACTAGA GATAAGACAT      7620
CACCACCAAT CTAGAAAAGT GATGCAGAAA AGTATTTGAT TTGGGTAATT ATTACACTCA      7680
CCTAGAAACA AGTGTTGTGT AATAGATTAC ATATTTCCAT AATGCAATGT TGTATCAGAA      7740
ACTACCTTCC TAAGAAAATA TAGTATGGGC TCGGCGTGGT GGCTCGCACC TGTAATCCCA      7800
GCACTTTGGG AGATGGAGGC AGGAGGATCA CTTGAGCCCA GACTGGGCAA CAAAGCGAGA      7860
CCCTGTCTCA ACAAAAAATT TAAAAATTAG CTGAGTGTGG TGGCACGCAC TGATGGTCCC      7920
CTCTACTTGG GAAGCTGAGG CAAGAGGATC TCCTGAGCCC AGGAGTTCAA GGTTTCAGCG      7980
AGCTATGATT GTGCCACTGC ACTCCAGCCT GGGAGACAGA GCAAGTCCCT GTCTCAAAAA      8040
AGAAGAAGGA GAAGGAGGAG AAAATACAGT ATTAAGTAAT CTGTCAATAT ATTCCACAAG      8100
GATTACACTA GTGGTTTAAT AATAAAATTA TATTACTTTT TTAAATTGTA AGGCCATTCC      8160
TCAAGCTTTA TAAATTAAGC ATGAATGCAT CATACACATT TTATAAAAAG TTCCAACTCA      8220
TCATAATCTG TACTTATGAT ACATTAATAC AAATGAAGTT CATTATAAAA TTAACTTAAA      8280
ATGGATATAC CAGTTATTAA ACCATTAACC ATTTAATAAT TTTATTTTTT TCAAATTTAA      8340
AAACCTTTTG GGGAAGAAAT ACTACAACAT GGATGAACCT TGAAAACGTT ATGCTAAGTG      8400
AAATAAGCCA GACACAAAAG GACAAATACT GTATGATTAC ACTTAAATGA GGTACCTAGA      8460
GTAGTCAAAT TCATAGAGAC AGAAAGAATA GAAGTTACCA GGGGCTGGAG GTAGGAAAAA      8520
ATGGAGAGCT GTTTAATGGG TAGAGAGTTT CTTTTTGGGG TACAAAAAG GTTCTAGAGA      8580
TGGATAGTGG TGATGGTTAC ACACAATGTG TGTGTACTTA ATGCTACTGA AATGTAATTT      8640
TATGATTTTT TTTTTTTGCA GCAAAATACC CCACATTGGG AAGTGAAGAG AAACATGTTA      8700
AGAGACTTGA AGGAAAAAAA TTGGGGCAGA GGGGTGTTTT TTATAGGTTA AACAATAAAA      8760
GCCATTTAAA CAGTAACAAT TTCTCTAAGG ACAAGAATCG TCAAGATTGA GACAGCACTG      8820
ATTTCTTGAC TCTACTCAAT ACTTCTTTGG TTTCTCTTCT TCCTTCCCCC TTCTAATAGT      8880
TTCCTACCTC CCATTCAGAA AGCAAAGCAA AACAAGCAAA AATTCCCCCT TCCCTCAAAA      8940
AAGGAAAGAG TTTTTGAAAA AGTTCATGTC AGTGAAGAAA AGACATGTTT GGGAGTGAA       9000
GGATATTTGT GGATTTGTAT AGATGTGATC ATCAGGGCTG TGTTGTTTTG AAGTAATATA      9060
GGACATCTAG AGGAAAATTT ATTTTCAGCA GAGGAGGGAA AGATGAAGAG TAGGTACTTT      9120
TAAGCATCTT CACTTGAGGA GTGGCAAAAT GAGAAGCATA ACCTGCTATA ATCACTTTAA      9180
GAATTTCAGG CTGAGTGTGG TGGTGCAGTC TCTAGTCCCA GTTACTCCAG GAGGCTCAGG      9240
TGGGAGGATC ACTTAAGCCC AGGAGCTCGA GGTTGCAGTG AGCTATGATT ACACTACTGC      9300
```

-continued

```
ATTCCAGCCT GGGCGGCAGG GTGAAGCCTC ATCTCAAAAA TTAAAAAAAA AAAAAATCAA      9360
ACAAATTAAT CGAACGATGA CATGCACTTT TCTAGGTTGG TACCTTCCTT CTTGCGACTT      9420
GGATCCTGGA ACGTCATTAT GTTTGTGTGC TTTGAACAAC TGAAACGAGA ACTGTCAAAG      9480
TCAAGGCAGA CTATGGACTG TGCCACATAA TCAGCTTCAA GAAAATGATG TAACATACCA      9540
GTGGGAATCT TGCTGACTGG ATCATAAAAA CAAACAAAAC TTATTCACTT ATTTTAACCT      9600
AAAAAGATAA AGGAATTTTG GCAGAGAATT TTGGACTTTT TTATATAAAA AAGAGGAAAA      9660
TTAATGCCTA TTTCATATAA CTTTTTTTTT TTCTCAGTGT CTTAAGAAGG GGAAAGCAAA      9720
ACATTCAGCA TATACCCTGG CAAATGTAAT GCAGATAAGC TACTGCATTT GACCATTTCT      9780
GGAGTGCAAT TGTGTGAATG AATGTGAAGA ACTTTAACAT GTTTTAATTA CAATTCCAAC      9840
TGGTGGAAAA GAAACTGAGT GAAATGCAGT TTATATTTAT AAATACTTAA AAATGAAGTT      9900
ATTAAAAATA TTAGTTTTTA TTAACCACAG TTGTCAGTTA ATATATTCAA TAAAGTATTG      9960
CTAATACCTT TTAAAGTTTG TCTTTTGAGA TCTATACCTG GGTGTAAGAG TCAAGTTCAC     10020
TAGAATACAA GACTGCCCAA TAGCAAATGC AGGTCTTTAG AATCATAGGC ATGAACCTAC     10080
TCTGAATGTT ATTAGTATAG ATTTTTAATG TTTAGAGTCC AGATTTGATG ACATCTCTAA     10140
CAACTTCTAA TCTAAGACAC TATATTCATT TTGGCAGGAT TGCTACTAGA GTCTTGGTAT     10200
CTGTGCTAGC ATCACATAAT TTTAGAGCTG GAGGGTACTT CTGGGAAGAC AGAGGAACAG     10260
TTTGAGATTC CTACTGAGAT GAAAACGAAT CTTCATGGAA TCTTTCAGCA AAGCCAAATT     10320
CAAATTCATC ATTAGCACCT GTAGTAACCT TTTCAATGCC TACAAACTGC ATGCAGAAGA     10380
GATAGGGAAA CAGTAAAACA GATATTAAAA GAAGTTTTTA AGACAAAGCC CAGCCTGATT     10440
TTAAGCTAAA TCCAAGGATT GGCAGCTTGG ATGAGCAGGA AGGTTACAGG CTGCCAGACA     10500
TCATTCTAGT TCTGTTTTAA TCAACTCCAT GTTACATTTA CTATCAGGGA TTCTCACCTC     10560
ACCCTCATGC AT                                                        10572
```

20

The nucleic acid sequence of the 15,901 base pair (bp) human UCP1 sequence (gi|237858805|ref|NG_012139.1| *Homo sapiens* uncoupling protein 1 (mitochondrial, proton carrier) (UCP1), RefSeqGene on chromosome 4) is as follows [SEQ ID NO: 365]:

```
CTGTACAGCT CTCCGACAAT CCCACATCTA GATGCCAAGC TGAGGTTGGC ATTCTCACTA        60

ATTTGCTGTT ATAAATATTA AGCTATCATA AGCGTTAGCC TACATATGAC TCTTTCATAT       120

GTTAGTTAAT TATTTTAGGG TAGAAATCCA AAAGTGGAGT TACCAGAAGT GGATATAGAC       180

ATTCTGGCTG GGTGTGATGG TTCATGCCTG TAATCCCAGC ACTTTGGGAG GCAGAGGCAG       240

GCGGATCACT TGAGGCCAGG AGTTTGAGAT CAGCCTGGGC AACACACGCG AAACCCCATC       300

TCTACTAAAA ATTCCAAAAC TAGCCAGGCA TAGTGGCACA TGCCTGTACT CCCAGCTACT       360

TGGGAGGCTA AGACACAAGA ATCGCTTGAA CCCGGGAGGG AGGTGGAGGT TGCGGTGAGC       420

TGAGATTGTG CCACCGTACT CCAGCCTGGG TGACACAGCT AGACTCTGTT TCAAAAAAA       480

AAAGAAAAAG AAAAGAAAAA AATAGACTTT CTCTTGGCTC AGTGTATACT GCCAAATTGT       540

TTTCCAAAAA AATTGTGTCA ATGTATAACA CCATCACTAA TATAGTATTG ATATTATGGT       600

TATTACATTT TAAAATTCAT AATTTGTAAT TATAACATTC ATAATTTATT ACTATTTATA       660

ATATTAATGT AAATGTATAT TATATATAAA TGTTATAGTA ATTATAACTT TGGTAGTGAC       720

AAAGTATTAA TTTATTAGGT GAAGTATATG CTTTTTTATT AGTGATAATA AATATATCCT       780

CTCTCCCATT ATAAAAGTTT GTATTTCTTC TTTTAGAAAT TGATTCTTCT GTCATTTGCA       840

CATTTATCTG TATAATTATA ACAGGGTATT TCCCAGTGGT GGCTAATGAG AGAATTATGG       900

GAAAGTATAG AACACTATTC AAATGCAAAG CACTGTATGA TTTTTATTTA ATAGGAAGAC       960

ATTTTGTGCA GCGATTTCTG ATTGACCACA GTTTGATCAA GTGCATTTGT TAATGTGTTC      1020

TACATTTTCA AAAAGGAAAG GAGAATTTGT TACATTCAGA ACTTGCTGCC ACTCCTTTGC      1080

TACGTCATAA AGGGTCAGTT GCCCTTGCTC ATACTGACCT ATTCTTTACC TCTCTGCTTC      1140

TTCTTTGTGC CAGAAGAGTA GAAATCTGAC CCTTTGGGGA TACCACCCTC TCCCCTACTG      1200

CTCTCTCCAA CCTGAGGCAA ACTTTCTCCT ACTTCCCAGA GCCTGTCAGA AGTGGTGAAG      1260

CCAGCCTGCT CCTTGGAATC CAGAACTACT TTCAGAATCT TGAACTTCTG TGACCTCTCA      1320

GGGTCCCCTT GTGTGAAGTT TTTGACGTCA GCTTCTCCTG TGACCCTTAG AAGTCACTCT      1380

TGTGTCTAGC ACATCCCAGG TGCTCAGTCA CCATTGAACT ACAGTCATAC TATCTCCTGG      1440
```

-continued

```
CAAAGGCTCT TAACTGTCCA TGTTAGCCTG ATATTAATAT CCTGGAAGCT TATACTGTCG    1500

TTCTTCCTTC CAGGTTTAAA TAAGGCAGCC CCTTTATCCT GTCACAGGTC CTCTCTCCCT    1560

ACCTATCCTT ACCTGTTTTG GATAACAACC TTTCTTATTT CTAATAGATT TATTTATTTC    1620

TCACATTTCC TTCCCTTATC ATAGTTTTCC TCTCACTTTC TCCTCTAGTT TGTCATACTC    1680

TGGCTTTAAA ACATGCAAAC ATGTGCCTTA TGGGGAAAAA AAGACAATTT TAATTTACCT    1740

TGCTTCTTCT TTACAAATGT ATTGTGGCTT CTTCTTATAG TCCAAATCTA AAACTCTTTA    1800

CCCACCCACT GCCTTGAACT CCTTCCTCGT TGTGAAAGTA GGATGGGGCA AAGAGAGAAT    1860

GCATGCCCCT CCCAACTGCT CAAACAAGTA AAGGTGCTGT TACAGTTATC TTTTGCTACC    1920

TTAATACAAT AATTATTTTA TTATATCTCA CAATTTTATG GATCAGGAAT TTAGACTGGG    1980

CTCAGCTAGG CGATTCTTCT GCTTTACTGA CATCATAGGA GATCACTTGG TGGTATTCAA    2040

CTGTCAGGTA GGCTTATCTG GAGGGTCCAA GATAGCTGTA CTCTGGTGCC TGGTGCCTTG    2100

GTAAAGAGGG ATGATGATGT GGGGCCTCTC CAGCATGAAC AGCCTCAGAG AAGTTTGCTT    2160

TCTTACATGC TGGCCCAGGG CTCCAAGAGC AAATGTTGCA GTGAGTAAAG CAGAAGATAC    2220

AAGGACTTTT ATAATCTGGT CTCAGAAGCC ACATGGCATC AGTTCTGTAT TATTCTATTG    2280

GTCAAAACAT TCATAAGCCT GCCAGATGCA AGGGGAAGGC ATATGTACCC TCATCTTTTG    2340

ATGGGAGGAA TGTGATGGAT TTGCAATTAT GTTTTAAAAC TACTACAGAC AGAACCACTG    2400

AGAAAGATTC ATGGGTAGCT TTGGGGTGAG GACTGGGAAT TAACCTGTTG ATAGCAGAGG    2460

TTCACTAGAG TCAACAAGGA ATAAGGTCTC CTCTTGTACA CTTTAGTCAT ACTATACCAA    2520

CATTCTTAAC CACTGCTTAG CCATCAGCCT CACAACATAA CAACTCCATC ATAGTTGTAC    2580

TCCCTAAGAT CACCAACAAT GTTAGAGTCA ATCCGGTAG GTTTTTCTTT GTTTTTGTCC    2640

TCCTGACATT TTTTCTAAAC TTGACACTGG TCAGACCCAA TCTTTCTTTA ATCATATTCT    2700

TAAATACCAG TTCTATCACT GGATATGTTA CTGTTTCTTG TTCTCACTCT ACCTTTGACA    2760

AAGCCATTCT TTCCAGACTA TAACTCTGGG TCTGGGTCCC CCTATGGTTT GGCCCTTGAA    2820

TTCTTTTCCT AGTCCTATTT GACTAGCCCC ATTTTCCCGT GAAAAGCATG CCCCTTTCAT    2880

TGCATCCATA TCATGACTAC CAAATACCTC CTCTATTTCT TCCTCTTTTA GCATGTTAAA    2940

TGCAGCTTCC TAAGCTCTCT ATCTGGATAT CAACAGTATT CTCTCCAAAT AATTCTAAGA    3000

CTTTAAAAAT TGGTTTAATC TTCTTACCCC TAAAATCACC CCCCTTACCA ACTGCCTCAT    3060

GACAATCATT GGTACTGTCA CTGAGCTTGC AACCCATGTT CTTAAACATA GAGTAATCTT    3120

TGACTCCACA TCTAATCATT CATAAAGCTG TATTGTCTAT CAAATTAAAT CTGACATTTA    3180

TGTGAGAGCA CTTCATAGTC TGTAAAGCAC TACACAGGTG ATAACATGAA GCTACACTCA    3240

TAATGGATTT GCAGGCTCTG CTTCTCATTT GGCTTCTACA GCCTCATCCC TCACCAACTT    3300

CTTGCCCTAC CTCTCTCTTT CTTCCCCATC ACCCAATTTC CCAGTCAGTC AGGCCAACAG    3360

AATGCATTCT ATATACGCGA CTTGCTTTCC CCAACATCTT TGCCTGTATG CATGCCACTT    3420

ATTTGCCTCA GTTGATCTTT ATTTCAACAA GTGTTTGCAG AGGAGAAACC TCGCTGGCTC    3480

CTTCTCCTTT CTATTTTTTT TCAGAGGCTA CCCGTCAGGT CAACATTGCC TTTTTCAGGG    3540

AAGCTCTGCA AGCCTGACCT CCCTTGGAAG TGCCTTAGGA CTGGCTTCTT GCACAGTACA    3600

CAACCTTTAC TTATAGAGGG TTTGGAGATT ATTCTTTATT CATGTCTTAT TTCTCCTGCT    3660

CCTGGAGGAG ATGACTCTGA CTTCCACTGA CTCTTTTGGG GGGCTTAAGT CAGGGTTGAG    3720

TACCAGAGGC CCTAAATAGC TGGACGTGGA TTCTGGTAAT ATCAAATCCA TCTTTGGCTT    3780

AACTGAGAGG TTCTGAAAGC TGGGACCTGA CCTTGTCCAT TTCCCTCTTT CTCCAGTTTC    3840

CTATTATTTC CCACTGTTTT TTTTAAAAGT TTTTTGTTTT CTTAAGTTTT CACAAGAATA    3900
```

```
                                   -continued
AACATTGAAA ATAAAATTTG CACAAAGATC GAACTAGGAA AGGCCACACA ACCAACACAT      3960

ATTACATCAT TATAGGTAAG TTAGCAGGGA GATTTCAGAC CTGGGCTAGC TCTGGAACCA      4020

CATTTTACAC TGTTGAAAAT AAAAGCTGGA GTACAGATGA CTTTCCCAGG TTCACAGAGT      4080

TGGTAAGCTG GAGAGCTGCA CCTGGAGCCA AGCAACCTGC CCTGTCCTTT CCACTGCACC      4140

CTCTAAGAAA TCTAATTAGA AGGAACAGGT GGTATCTCAT TTTGTACGGT GCTTTAGCAA      4200

TGTACTATTT GCTTTCTAGT GTGTCTATTG TCTCGTTTGA CATCTTCTCT CAAAAAGTGA      4260

TGAAACGAAA CGCTCTTTTT GACAAGTTCA GAGTGCTCTT GGTTCCTGTG TGGGATTCTT      4320

CCAAGTCTGA ATTTGGTAGT GGGAAGAGAA GGAATCCGGA GGAAGGAGGA TGAGAAGTTT      4380

AAAGGAGAGG AAAGGGAAGC AGAGAAGGCC GCAAGGTGCC TGCAAGATGT CTGGGGAGTT      4440

GGAGGAATGG AAGAGTGCCC CGCTCTTCCT TCTGGGAGAG CTCCAGCTAG GCAGAACCTT      4500

TCACCAAGGC TCTGATATCG TGCTGGTTTC CGAAAGCCCC AGCCGAAGGT GTGCAGCCAA      4560

AGGGTGACAG AAGGTGAGGC ACGTGCGGGG GCGCGGGTGC TGACCGCCGC GGTGCGCCCT      4620

CCCTCCGACG TGCGGTGTGC GGGGCGCAGA CAACCAGCGG CCGGCCCAGG GCTTTCGGGG      4680

AGCGAAGCAG GGCTCCCGAG GCACCGAGCG AGAATGGGAA TGGGAGGGAC CCGGTGCTCC      4740

CGGACACGCC CCCGGCAGGT CCCACGCCCG GGTCTTCTGA GACCTCGCGC GGCCCAGCCC      4800

GGGAGCGGCC CAGCTATATA AGTCCCAGCG GAAGACCGGA ACGCAGAGGG TCCTGCTGGC      4860

GCGAGGGTGG GTAGGAGGGG ACGCGGGGAC TCGGCCCCCA ACACCGCGCT CCGTCTGCAG      4920

CCGCCGCCTC TGCACCGCCG CTGCCCGGCG GTCGGTTCAA AAAACAGAAA TCGGGTTTGC      4980

TGCCCGGCGG ACAGGCGTGA AGAGCAAGGG AAAGGAACTT CCTCCACCTT CGGGGCTGGA      5040

GCCCTTTTCC TCTGCATCTC CAGTCTCTGA GTGAAGATGG GGGGCCTGAC AGCCTCGGAC      5100

GTACACCCGA CCCTGGGGGT CCAGCTCTTC TCAGCTGGAA TAGCGGCGTG CTTGGCGGAC      5160

GTGATCACCT TCCCGCTGGA CACGGCCAAA GTCCGGCTCC AGGTAGCTAG GCAGAGGGGT      5220

AAGACAAGGG GTCTCAGGAC AGAGGGGACG CTGTTGCGTG CATTCCATTT ATTCTCTGCT      5280

TTGGTGTAAC CACTGTTTCT AGGTAGGGTA GGTGACCTTC CAAAGCAGTC TGGCCTTGTC      5340

CCAGGGCTGG TGCTTTAGGA TGGGAAACTG GAACTTTTTC TGGGATTAGC TGAAGAACCA      5400

CCAGGGCCAC AGAGAATGGG TTGACCATGA CTACTACCAA ATTCTCCCAA AATTTAGGGT      5460

GCACTTAGTA TTTTAAGAGC TGAGAATATT GGCCTCTCCT GAGTTTACTA GTCAGGTGCT      5520

TTTTCCTTTC TTTGATTCTT CGGGGGTTCT GTCCTATCCT ACTGCCCTAG GGGTTCTGGA      5580

GAGTTCCTGG GGAGGGGGAT ATTCAAAATG TGCATTGTAG CCAGCCTCCC TCCATCTGCG      5640

CGTGAGCGAA CACACACACA CACACACACA CACACACACA CACACACACA CACACACGGT      5700

AGAGGGAGGT GGATGGAAGA GGAATGTTGC TGAGAAAAGA AACGGAAAAT AGGAACACAG      5760

GGGGAAATCT TGGCTTAAGA GTGAACTCAA TTTCGCTCCC TTCTGTTCTG CACCTTTCTT      5820

ATTTCCAGGT CCAAGGTGAA TGCCCGACGT CCAGTGTTAT TAGGTATAAA GGTGTCCTGG      5880

GAACAATCAC CGCTGTGGTA AAAACAGAAG GCGGATGAA  ACTCTACAGC GGGCTGCCTG      5940

CGGGGCTTCA GCGGCAAATC AGCTCCGCCT CTCTCAGGAT CGGCCTCTAC GACACGGTCC      6000

AGGAGTTCCT CACCGCAGGG AAAGAAAGTA AGCCGTGAGC GTTCCTGGGA GGGGCAGAAA      6060

AGCCTTGGGC TCCGCTCTGT TCCAAAAAGT GTAACACACA GAGGAGTGGT TTTCATAACA      6120

AATTGGCGAG AAAACATTCA TATTTGAACT CTCCCTTCCC CAAACATTAG CTCATTGTTC      6180

ATAGAAAAAA GTATGCAAAA TCGATTTTTT AGATGCAGAT ATATACTTGT AAAGGTCACC      6240

CAGTCATGGA AGTTTTGTGC CCAGTTTGGA TCTCCATCTG GAGAATATGG GTGGGCTACA      6300
```

```
GAAAAATGTT TAACTTAAAG TTCTCCAAAG AGGGAAGTAT ATCAGAAACA TCTATGGAGC      6360

TTGTCAGAAA TCCAAACGAG GACTACCATG GTCCTCTGAG TCTGAATCCT CAGGCTAGAG      6420

ACCAGAGTGT CTTTCCACAA GCTTCCCTCA TCATTTGTGT ATGCAACAAA GTTCAAAGCC      6480

TTCTGTTTGA AGCAAAGAAA GCCAGACTTT GTGAAGAGAG TTGAAAGGAC AGGAAAAGAC      6540

ATATTTCCTC TTAAGAGGTT CCTCATCAGG TCCAGGAAAG ACCAGAGCAG AAAAAGTGGA      6600

CGAATGCTGC AGGGAGTTTG TTTAGGGGAA AAAGAAAAGG AAACATATTT CCTGAGTGCC      6660

AGTGCACTCT AAGAATTCCT GTCACTTTAG GTAGCATTTA TTTGAGGGCT TAACTATGAA      6720

CCAGACATTG TTCTAAGTGC TTCAGATACA TTATAACTGG AAGGGTATTA GTACCATTAT      6780

CCCTTGGCAG ATGGGAAAAC TGAACACAGA GCAGATTCAT CACTTGCCCA AGGTCACACA      6840

GCTGGGAGGG GGCAGAGCCA GGGTTCAAAC CCAGGCAGTC TGGCCTCGGA CTCCAGGCTC      6900

CTAACCCTGT TCTCTACTGC CTTCTGCACT TCTCATATGA TTCTGCCCAT CATTCAAACC      6960

GCACAACACT GCTGTGAGTA AAAAGTGTTA GCCGAATATC AGGGTAGTTA AGTAACATGC      7020

ACAAAATCAC ACAGCTAATC AACATCAGAG GCACTTTCAT GTGGAGTAGA CAAGCCAGAG      7080

AGAAGATGTG CTGATGGCAC AATGAATACA TTAAGTGAAA TCCACCTTGT AGATTTCATC      7140

ATTTCTGCTG TGAGTAACCT TCAATACTAT AATTTTATGG GATAATTTAT AAATGTTGTC      7200

TATACAAATA TATAAGTTAT ACTTATCCAC ACAAGTACTT TCAAAGTGAA GATCAATTCT      7260

GGATGTTACT AGATCAAAAC TGCATTTTTT TATTTATAGA TGTAGCAAGA GAGGAAACAC      7320

AAAGGAGGTA AAGCTGCCCG TTCAGGTGGT TTTCTTCACA GATTGACTGT TCTACCAATT      7380

GTTGTGGACT TTGGGCACCA AATTAATAGG ATATATGTTG GCAGTGTTCT ATGTTATATA      7440

GATTCAGTTT ATTTAGTAGG CTTTATTGAA CTGCCATGTG CCAGTAACTA TGTTAGATGT      7500

TTAGATGGCA GATGTGTCTC TAGACAGAGC TTACAGTTGA GAGTATGGGT TGTGTGGGGA      7560

GAAGTGAATA GATGACTATA TTCCATGATA CATGCTGTAT TACAATACAG TCCTACTTCA      7620

CTTAACGATG GGGATACATT CTCAGAAATG AGTTAGGAGG CAAATTGGTT GTTGAATGAA      7680

CATCACAGAG AGCACTTACA CAAACCTAGA TGGCATAGCC ACACCTAGGC TATATGGTAT      7740

AATCTATTGC TCCTAGGCTA CAAACCTGTG CAGCATGTTG GTATTGAATA CTACAGGCAA      7800

TTGTTACATA AAGTTAAGTG TTTGTGTACC TAAAAATAGA AAAGGTAATG CATTACACTA      7860

CAGTCTTATG GGGCTGGGAT GTCACTAGGT GATAGGAATT TTTCAGCTCT GTTCTAATCT      7920

TACGGGACCA CCATCATGTA TGCAGCACAT GACTAACTGT AATTACAAGA TGGTGGCTAT      7980

ATTAAACAGA ACTACTTAAG CTAGCCATGG AGGTATGGTC CGTGAGATTT TCCTGAAGAA      8040

TTAACGTCTG GATCAATTCT GGAAGGGCCA GCAGGAGTAC TCCAGGCAAA GGGGTGAGAA      8100

AGGAGCTTCC AAGTAGAGTG AAGGTCATGT GCAAAGACTC AGTGAGGAGT CGAGTGAACA      8160

TAGCACAGGG AGGACATGTT GGTGAGGAAG GAGGGGTGAA GCCACAGAGA CAGGAGGGAG      8220

CCAGATGACA GAAGGCCTTG CAGGCGGTGC TAAGGAGTTT GGATTTTATC CTTACAGTGG      8280

TGGGAAGTCA TTGTAAAAAT ATTAAGCAAG GGAGTGGCAT AAACAATTTA CATTTTCAAA      8340

AGATCACTTT GGCAGCAGAT AGAGTATATA TGTAAAAGGA GTAAGAAAGA GGTAAGTTAG      8400

AAAGCAAGAA ATGATCAGGG TATGCCCTAA AACACTGGCA ATAGGGAAAA AGAGATGTCA      8460

ATCAGAAAGA TTGAGAAAGT ATAATTGAAT TGACTTGGTG AACAAATAGA AGTAAGGCAT      8520

AAGGGACAGG TAGAAATATG AGATGACTTC CAAGTTTCTG TTTAAAGATA CCCTTTATTG      8580

AGAGAGGATG TATAGAAGCT GTCTTAGGGG GAAGACAAGA AATTTGGTTT AGGCCATGTC      8640

AACAGGTAAT GGCCAGTAGG CACATGATTC AGTTTATTTA GTGGGCTCCT TTTAGGAGAA      8700

AATCTGAGCC AGATTCCAGG AAGTCACAGC AGGGACTACC AATAGGGTCA AACAGCAGAG      8760
```

```
AGTGTGGAAA GGACTGAAAA GTGATCATTG TACATAACAA ATAGAAGCTC ACTGATTTTC    8820

TAGCAAAAAC ATCTTCAGCA GAGTAGCGTG GTATAAGCTA TATTGTAGGG GACTGAGGAA    8880

GAAATGGGCT CTGAGAAGTA AAGACAAACA ATATGTTTTG TAAATAAATT TCTTTTAGTT    8940

CTTAAAAAAA AAGCCTCTTT TCCAGCTTGA TTGGGAAGTG AAGAGAGGGA TTTGAAAGTT    9000

GGAGATTGGA GGATAGGATG AGTACATCAA GATACACTAC GTTGTAGTGC AGTGCATTAC    9060

AAATGTGAGC TAAAAGTGAA GGCATTTGTA ATCATATGAT ATTGCTAATT AAAAGACAGC    9120

TGTCAGTCAT ATGCCCAGCT CCTGGTAAAG CATGATGAGA AGAGTACAAT CATGGTAGTG    9180

ATTTAAAAAT TGCTGCCAGT TTTGTGGATT TTCTTTATGC TAGACAGTGT AAGCTCTTTA    9240

TCAATATTAT TTAACTCACA CAACTCTAAG AGGTAGATAT TATTATCCCT TTTTGACAAA    9300

TTAGGAAACA GAATTATAAT GACTGAGGAA GTCTCTGCTG AGTAAATGTT ACTGAACCTT    9360

AATTTTATGT TTACTTAATG ATAGAAATGA ATATTGGGCT TCAAGACTAT TTGTACTTAA    9420

TGAAATCTGT CTTGAGCAAC ATAAGCTATT TTTTTCAAAA TTTTAAGACA AAAATCACTT    9480

TCTTCTCTCC TGTCTTCTTA TTTTTGTTCC CTTCACATGT TGTAGCCTAA CACTACTTGA    9540

TGGCCCATTT TGGTGCAGTT TGTCCACTGG GCTTCATCTA AGGCCACCAA GTCCCATAAT    9600

TAACATGATC ATTCGTGGGA GAAAGATCAA GCCTCATTGG TGATGGGTGC CTCCTCACAG    9660

TCGGATAATA CTGAAAAGAG AGCTAAATGT GGGAAAGAAC CAAGTTGAAC ACAGGAAAGA    9720

ATCAGGCCAC TGTGAAAATA AGCATTGTGT TTTCTTGTTC CTTGAAAGTC TTCATTTTTA    9780

AAAAATTTCA GACACCTGAA GTTTTCTAGC CTTACTCTGA GTTGACGCAC ATTTAGTACA    9840

TGATCAACAC ATAAACAAGC ATTAGAGAAA TAGAAAAGCT GTAAGAATAC AAAAATATGG    9900

GCCAGGTGGG TGGCTCATAC CTGTAATCCT AGCACTTTGG GAGGCCGAGG CAGACGGATC    9960

ACCTGAGGTC AGGAGTTCAA GACTAGCCTG GCCAATATAG TGAAACCCTG TCTCTACTAA    10020

AAATACAAAA CTTAGCAGGC TGTGGTGGCA CGTGCCTATA ATCCCAGCTA CTTGGGAGGC    10080

TGAGGCAGGA GAATCTCTTG AACCCGGGAG GCGGAGATTG CAGTGAGCCA AGATCACACC    10140

ACTGCACTCT AGCCTAGATA ACAGAGCAAG ACTCCATCTC AAAAAAAAAA AAAATACAAA    10200

AATATGAACC ACTGAAAATT AAAAAGACAT GCATGCATTC TAGGTCTTTA ATTTTTTTTC    10260

TTAATAATTT TTTTTCTCTC TGGATAGCAG CACCTAGTTT AGGAAGCAAG ATTTTAGCTG    10320

GTCTAACGAC TGGAGGAGTG GCAGTATTCA TTGGGCAACC CACAGAGGTC GTGAGAAGCA    10380

GACTTCAAGC ACAGAGCCAT CTCCACGGAA TCAAACCTCG CTACACGGGG ACTTATAATG    10440

CGTACAGAAT AATAGCAACA ACCGAAGGCT TGACGGGTCT TTGGAAAGGT AACTAACTTC    10500

AAGATAGGTT TTATAACCAC CAAAGCACAT ACATACAACT AGCAACTTAT TGTAAAGTAG    10560

AGTTAATAAA CATTTCTTT TTTTTTTTCC CCAGGGACTA CTCCCAATCT GATGAGAAGT    10620

GTCATCATCA ATTGTACAGA GCTAGTAACA TATGATCTAA TGAAGGAGGC CTTTGTGAAA    10680

AACAACATAT TAGCAGGTAA CTTCCCATTT CATATAACAA ACAGGTCTGC ACCTTTAGAA    10740

GTTCATCTTG GAGCTTCTGC AGCCACCTTA TACTCAATCT CTTAACTCCA ATAGTTTTCT    10800

CTTTTTAAAA ATTAAGTAAT TTGAACCAT ATATAACTTT GTGAGAAGCA GGAAAAGACC    10860

AAAATATTAA GTTAAGAAG TTTTGCCACA ACAAAAATAT TTTGCAACAA AATAACAGG    10920

CAATTTCATG TCAGCATTAT TCTCATTTAA TACTAATATA TGGGACTTTT GTTAGAATCT    10980

TATTCTTTAT ACAGCAGAAT TCAGGAGGTA AGTCCATCCT GCATACTATA TCCAAAAGAT    11040

CTAGTTATAA AAGGAGCTTA TCAGTGGTCT CATCCAAAAA GTAATACCAT AAGATAGGTT    11100

CTTAAAAATA ATATTCTAAC AACTTCTAGA GACATTGAAA TTTCCCTTAT TTCAATAAAA    11160
```

```
AAGTATTAGA TGCTCATATA TTAGGCATTA TTACAGGCCT TAAAGGCACA GAGGAAACTA    11220

ACAGTTTACT TTCCTAAAGT GTTAACAATC TATTAAGCCA TTTACTCTTT ACCTTCTTTT    11280

TCTAGTGCAA TACCTTTCTT ATTTTATTTT ATTTATTTAT AAGACATCTT CATTGACCTA    11340

CTGTTATCAA TAGGTTTATA AAGATATGAC AGATAACTAA ATTGCAAGCC CCCAAAAGTC    11400

TGATGTTGAC CTGTTTCATC GATCCATTTT AGATGACGTC CCCTGCCACT TGGTGTCGGC    11460

TCTTATCGCT GGATTTTGCG CAACAGCTAT GTCCTCCCCG GTGGATGTAG TAAAAACCAG    11520

ATTTATTAAT TCTCCACCAG GACAGTACAA AAGTGTGCCC AACTGTGCAA TGAAAGTGTT    11580

CACTAACGAA GGACCAACGG CTTTCTTCAA GGGGTAAGAT ATGATCTTGT GTATCTGTAA    11640

TGTGTTCTGG CTGTCTGTGT GCTTTGGGAC ACTCTCATGT CAAGCAACCG ACATTTAGCT    11700

TACAAGCCTT AGTATATTCA TATACTTAGT ATTGACTTTT CCTTGCCACA GATTTCTCCA    11760

ATCCACCAAT TCCACTGTGC CAGAAAGTAA AAAGCCATGA TATTCAAATT TTCTCAACTT    11820

TGATCAAAGG CTCATTCAAG ACCAGTGCCT TTTCCACTGG TCCCAATCTA CTGGAAATGC    11880

AGACAGTATT TTGCCTTCTC TGGGCAAGAA AGTTATAAAG TAGAGGGAAA TCATAATAGA    11940

GAGCTATGAG AGAACAAGAT TTGATTTGAT TTAATTTGAT GGACTCAAGT TTTAACATTG    12000

TAAAACTAGA GATAAGACAT CACCACCAAT CTAGAAAAGT GATGCAGAAA AGTATTTGAT    12060

TTGGGTAATT ATTACACTCA CCTAGAAACA AGTGTTGTGT AATAGATTAC ATATTTCCAT    12120

AATGCAATGT TGTATCAGAA ACTACCTTCC TAAGAAAATA TAGTATGGGC TCGGCGTGGT    12180

GGCTCGCACC TGTAATCCCA GCACTTTGGG AGATGGAGGC AGGAGGATCA CTTGAGCCCA    12240

GACTGGGCAA CAAAGCGAGA CCCTGTCTCA ACAAAAAATT TAAAAATTAG CTGAGTGTGG    12300

TGGCACGCAC TGATGGTCCC CTCTACTTGG GAAGCTGAGG CAAGAGGATC TCCTGAGCCC    12360

AGGAGTTCAA GGTTTCAGCG AGCTATGATT GTGCCACTGC ACTCCAGCCT GGGAGACAGA    12420

GCAAGTCCCT GTCTCAAAAA AGAAGAAGGA GAAGGAGGAG AAAATACAGT ATTAAGTAAT    12480

CTGTCAATAT ATTCCACAAG GATTACACTA GTGGTTTAAT AATAAAATTA TATTACCTTT    12540

TTAAATTGTA AGGCCATTCC TCAAGCTTTA TAAATTAAGC ATGAATGCAT CATACACATT    12600

TTATAAAAAG TTCCAACTCA TCATAATCTG TACTTATGAT ACATTAATAC AAATGAAGTT    12660

CATTATAAAA TTAACTTAAA ATGGATATAC CAGTTATTAA ACCATTAACC ATTTAATAAT    12720

TTTATTTTTT TCAAATTTAA AAACCTTTTG GGGAAGAAAT ACTACAACAT GGATGAACCT    12780

TGAAAACGTT ATGCTAAGTG AAATAAGCCA GACACAAAAG GACAAATACT GTATGATTAC    12840

ACTTAAATGA GGTACCTAGA GTAGTCAAAT TCATAGAGAC AGAAAGAATA GAAGTTACCA    12900

GGGGCTGGAG GTAGGAAAAA ATGGAGAGCT GTTTAATGGG TAGAGAGTTT CTTTTTGGGG    12960

TGACAAAAAG GTTCTAGAGA TGGATAGTGG TGATGGTTAC ACACAATGTG TGTGTACTTA    13020

ATGCTACTGA AATGTAATTT TATGATTTTT TTTTTTTGCA GCAAAATACC CCACATTGGG    13080

AAGTGAAGAG AAACATGTTA AGAGACTTGA AGGAAAAAAA TTGGGGCAGA GGGGTGTTTT    13140

TTATAGGTTA AACAATAAAA GCCATTTAAA CAGTAACAAT TTCTCTAAGG ACAAGAATCG    13200

TCAAGATTGA GACAGCACTG ATTTCTTGAC TCTACTCAAT ACTTCTTTGG TTTCTCTTCT    13260

TCCTTCCCCC TTCTAATAGT TTCCTACCTC CCATTCAGAA AGCAAAGCAA AACAAGCAAA    13320

AATTCCCCCT TCCCTCAAAA AAGTGAAGAG TTTTTGAAAA AGTTCATGTC AGTGAAGAAA    13380

AGACATGTTT TGGGAGTGAA GGATATTTGT GGATTTGTAT AGATGTGATC ATCAGGGCTG    13440

TGTTGTTTTG AAGTAATATA GGACATCTAG AGGAAAATTT ATTTTCAGCA GAGGAGGGAA    13500

AGATGAAGAG TAGGTACTTT TAAGCATCTT CACTTGAGGA GTGGCAAAAT GAGAAGCATA    13560

ACCTGCTATA ATCACTTTAA GAATTTCAGG CTGAGTGTGG TGGTGCAGTC TCTAGTCCCA    13620
```

```
GTTACTCCAG GAGGCTCAGG TGGGAGGATC ACTTAAGCCC AGGAGCTCGA GGTTGCAGTG    13680

AGCTATGATT ACACTACTGC ATTCCAGCCT GGGCGGCAGG GTGAAGCCTC ATCTCAAAAA    13740

TTAAAAAAAA AAAAAATCAA ACAAATTAAT CGAACGATGA CATGCACTTT TCTAGGTTGG    13800

TACCTTCCTT CTTGCGACTT GGATCCTGGA ACGTCATTAT GTTTGTGTGC TTTGAACAAC    13860

TGAAACGAGA ACTGTCAAAG TCAAGGCAGA CTATGGACTG TGCCACATAA TCAGCTTCAA    13920

GAAAATGATG TAACATACCA GTGGGAATCT TGCTGACTGG ATCATAAAAA CAAACAAAAC    13980

TTATTCACTT ATTTTAACCT AAAAAGATAA AGGAATTTTG GCAGAGAATT TTGGACTTTT    14040

TTATATAAAA AAGAGGAAAA TTAATGCCTA TTTCATATAA CTTTTTTTTT TTCTCAGTGT    14100

CTTAAGAAGG GGAAAGCAAA ACATTCAGCA TATACCCTGG CAAATGTAAT GCAGATAAGC    14160

TACTGCATTT GACCATTTCT GGAGTGCAAT TGTGTGAATG AATGTGAAGA ACTTTAACAT    14220

GTTTTAATTA CAATTCCAAC TGGTGGAAAA GAAACTGAGT GAAATGCAGT TTATATTTAT    14280

AAATACTTAA AAATGAAGTT ATTAAAAATA TTAGTTTTTA TTAACCACAG TTGTCAGTTA    14340

ATATATTCAA TAAAGTATTG CTAATACCTT TTAAAGTTTG TCTTTTGAGA TCTATACCTG    14400

GGTGTAAGAG TCAAGTTCAC TAGAATACAA GACTGCCCAA TAGCAAATGC AGGTCTTTAG    14460

AATCATAGGC ATGAACCTAC TCTGAATGTT ATTAGTATAG ATTTTTAATG TTTAGAGTCC    14520

AGATTTGATG ACATCTCTAA CAACTTCTAA TCTAAGACAC TATATTCATT TTGGCAGGAT    14580

TGCTACTAGA GTCTTGGTAT CTGTGCTAGC ATCACATAAT TTTAGAGCTG GAGGGTACTT    14640

CTGGGAAGAC AGAGGAACAG TTTGAGATTC CTACTGAGAT GAAAACGAAT CTTCATGGAA    14700

TCTTTCAGCA AAGCCAAATT CAAATTCATC ATTAGCACCT GTAGTAACCT TTTCAATGCC    14760

TACAAACTGC ATGCAGAAGA GATAGGGAAA CAGTAAAACA GATATTAAAA GAAGTTTTTA    14820

AGACAAAGCC CAGCCTGATT TTAAGCTAAA TCCAAGGATT GGCAGCTTGG ATGAGCAGGA    14880

AGGTTACAGG CTGCCAGACA TCATTCTAGT TCTGTTTTAA TCAACTCCAT GTTACATTTA    14940

CTATCAGGGA TTCTCACCTC ACCCTCATGC ATGTCTTCCC CATTCATTAC CCGCAAAAGT    15000

GTCTTGTAGC AGATGTCTTC TGTGTCCCAT ACATACCATT TTGCTCTTTA GTGCTTGCTG    15060

GCCTGACTTC CTATTGTCAT GTCAGCATCT GCCCTTTTTA GGGTCTCTGG CCACCAGAGC    15120

CAGCTTTACT CACCTGTGCA TGGCATTCTA GAAGAGCAGC AGGGAAAATA ACACAGCCCC    15180

AGTGCAGCCC TTAACCACCA ATAACTGGTA GTAGTTGGTG TACAAATATC TCAGTTCCCT    15240

CAACTGTCAG GTGGAATACC GCTGAGGGAT CAAACTCTAG TAACACACAG TAGTGTTTTG    15300

CTTACTATGG TTAACTAAAA AATCACAGGG TCTTCATGCA TTTGGAAAGG ATACTTTATT    15360

TCTTACAAAG GGTTACAGCC TACAAGGTGG TCATTCTGCA GGCTAGAAAG CGTAACCTCC    15420

AGCAAAGACC GGAGGCAGGC ACTTCTAGGG AAGGAAGAGT AAGACAGAAA TTTAAATTGA    15480

ATGGGTTGGC CAAGTATACA TATTCAACAG GCTACAGGTG GATTCATGAA TATTCATGAA    15540

GGCAGTCCTG ATGCATGCAT GTTACACCTT GGGGTGGAGG CTTAACATTT AAATGTATTA    15600

CAGTTAGGCC CTATACATGA AAAGGTGAAG CAGTAACACG AAGGCACACA ATGCACCATT    15660

TCTGTAAACA GGCCAGAGCC AGTTCACAGT GGTTGGTCTC TTATCATGAG AAAGCTACTA    15720

AAATCCTCTT GTCCAGTTAA AACTGTAGTT ATGGCTGGTG GAAAATGGGC TGGAGTCAGT    15780

CAACACTTGG TGAAGCTGCA GTTGCTTCAG ACACTCAAGG CCAGTGTTTG TTTAGCTGCT    15840

CGAGAAAAAG AAAAATCTTG TGGCAGTTAG AACATAGTTT ATTCTTTAAG TGTAGGAGTG    15900

TGTGACTTAA //
```

The nucleic acid sequence of the 2,113 base pair (bp) transcript ENST00000310473 of the human UCP2 gene is as follows (Eight Coding Exons in capital letters) (SEQ ID NO: 366-382):

| No | Exon/Intron | Start | End | Start Phase | End Phase | Length | Sequence | SEQ ID NO |
|---|---|---|---|---|---|---|---|---|
| | 5' upstream sequence | | | | | | ...aatcgacagc gaggccggtc gcgaggcccc agtcccgccc tgcaggagcc | 366 |
| 1 | ENSE00002287650 | 73,694,352 | 73,693,766 | — | — | 587 | AGCCGCCGCGC TCGCTCGCAG GAGGGTGGGT AGTTTGCCAGCGTAGGGGG<br>GCTGGGCCCA TAAAAGAGGA AGTGCACTTA AGACACGGCC<br>CCGCTGGACG CTGTTAGAAA CCGTCCTGGC TGGGAAGGCA<br>AGAGGTGTGT GACTGGACAA GACTTGTTTC TGGCGGTCAG TCTTGCCATC<br>CTCACAGAGG TTGGCCGCCC GAGAGAGTGT GAGGCAGAGG<br>CGGGAGTGG CAAGGGAGTG ACCATCTCGG GGAACGAAGG<br>AGTAAACCG GTGATGGGAC GCACGAAAAC GGGAGTGGAG<br>AAAGTCATGG AGAGAACCCT AGGCGGGGCG GTCCCCGCG<br>AAAGGCGCT GCTCCAGGGT CTCCGCACCC AAGTAGGAGC<br>TGGCAGGCCC GGCCCCGCCC CGCAGGCCCC ACCCGGGCC<br>CCGCCCCCGA GGCTTAAGCC GCGCCGCCGC CTGGCGCGAG CCCCACTGCG<br>AAGCCCCAGT GCGCGGCCCT TGGGATTGAC TGTCCACGCT CGCCCGGCTC<br>GTCCGACCGG CCCTCCGCCA GCCGACAGAC ACAGCCGCAC<br>GCACTGCCGT GTTCTCCCTG CGGCTCG | 367 |
| | Intron 1-2 | 73,693,765 | 73,692,678 | | | 1,088 | gtgagcctgg cccagccct gcgcc...actct ctgcctttgc tcaccacag | 368 |
| 2 | ENSE00001184362 | 73,692,677 | 73,692,521 | — | — | 157 | GACACATAGT ATGACCATTA GGTGTTTCGT CTCCCACCCA TTTTCTATGG<br>AAAACCAAGG GGATCGGGCC ATGATAGCCA CTGGCAGCTT<br>TGAAGAACGG GACACCTTTA GAGAAGCTTG ATCTTGGAGG<br>CCTCACCGTG AGACCTTACA AAGCCGG | 369 |
| | Intron 2-3 | 73,692,520 | 73,689,523 | | | 2,998 | gtaagagtcc agtccaagga agagg...tgggg ctttttccct cttggcttag | 370 |
| 3 | ENSE00001184370 | 73,689,522 | 73,689,298 | — | 0 | 225 | AATTCCGGCAG AGTTCCTCTA TCTCGTCTTG TTGCTGATTA AAGGTGCCCC<br>TGTCTCCAGT TTTTCTCCAT CTCCTGGGAC GTAGCAGGAA ATCAGCATCA<br>TGGTTGGGTT CAAGGCCACA GATGTGCCCC CTACTGCCAC TGTGAAGTTT<br>CTTGGGGCTG GCACAGCTGC CTGCATCGCA GATCTCATCA CCTTTCCTCT<br>GGATACTGCT AAAGTCCGGT TACAG | 371 |
| | Intron 3-4 | 73,689,298 | 73,689,142 | | | 156 | gtgagggggat gaagcctggg agtct...tagct accctgtctt ggccttgcag | 372 |
| 4 | ENSE00001252503 | 73,689,141 | 73,688,931 | 0 | 1 | 211 | ATCCAAGGAG AAAGTCAGGG GCCAGTGCGC GCTACAGCCA<br>GCGCCAGTA CCGCGGTGTG ATGGGCACCA TTCTGACCAT<br>GGTGCGTACT CCGGGCCCCC GAAGCCTCTA CAATGGGCTG GTTGCCGGCC<br>TGCACGCCA AATGAGCTTT GCCTCTGTCC GCATCGCCT GTATGATTCT<br>GTCAAACAGT TCTACACCAA GGGCTCTGAG C | 373 |
| | Intron 4-5 | 73,688,930 | 73,688,063 | | | 868 | gtgagtatgg agcaaggtg taggc...cactg acccatggc tcgcccacag | 374 |
| 5 | ENSE00001184355 | 73,688,062 | 73,687,868 | 1 | 1 | 195 | ATGCCAGCAT TGGGAGCCGC CTCCTAGCAG GCAGCACCAC<br>AGTGCCCTG GCTGTGCTG TGGCCCAGCC CACGGATGTG<br>GTAAAGGTCC GATTCCAAGC TCAGGCCCGG GCTGGAGGTG | 375 |

-continued

| No | Exon/Intron | Start | End | Start Phase | End Phase | Length | Sequence | SEQ ID NO |
|---|---|---|---|---|---|---|---|---|
| | Intron 5-6 | 73,687,867 | 73,687,788 | | | 80 | GTCGGAGATA CCAAAGCACC GTCAATGCCT ACAAGACCAT TGCCCGAGAG GAAGGGTTCC GGGGCCTCTG GAAAG gtgtacca gttgttttcc cttcc...accca ggatcttcct cctcctacag | 376 |
| 6 | ENSE00003147097 | 73,687,787 | 73,687,686 | 1 | 1 | 102 | GGACCTCTCC CAATGTTGCT CGTAATGCCA TTGTCAACTG TGCTGAGCTG GTGACCTATG ACCTCATCAA GGATGCCCTC CTGAAAGCCA ACCTCATGAC | 377 |
| | Intron 6-7 | 73,687,685 | 73,686,717 | | | 969 | gtgagtcatg aggtagacgg tgctg...tgcct tgcctgctcc tccttggcag | 378 |
| 7 | ENSE00001184349 | 73,686,716 | 73,686,536 | 1 | 2 | 181 | ATGACCTCCC TTGCCACTTC ACTTCTGCCT TTGGGGCAGG CTTCTGCACC ACTGTCATCG CCTCCCCTGT AGACGTGGTC AAGACGAGAT ACATGAACTC TGCCCTGGGC CAGTACAGTA GCGCTGGCCA CTGTGCCCTT ACCATGCTCC AGAAGGAGGG GCCCCGAGCC TTCTACAAAGG | 379 |
| | Intron 7-8 | 73,685,535 | 73,686,167 | | | 369 | gtgagcctct ggtcctcccc accca...atgac ctgtgatttt tctcctctag | 380 |
| 8 | ENSE00001184368 | 73,685,166 | 73,685,712 | 2 | - | 455 | GTTCATGCCC TCCTTTCTCC GCTTGGGTTC CTGGAACGTG GTGATGTTCG TCACCTATGA GCAGTGAAAA CGAGCCCTCA TGGCTGCCTG CACTTCCCGA GAGGCTCCCT TCTGAGCCTC TCCTGCTGCT GACCTGATCA CCTCTGGCTT TGTCCTAGC CGGGCCATGC TTTCCTTCTTT CTCTCCCCTC CTTCCCCTCT CTCCTCCCCT CTTCCCCCAC CTCTTCCTTC CGCTCCTTTA CCTCCCTTTC TCCCTCTTTC TACATTCTCA TCTACTCATT GTCTCAGTGC TGGTGGAGTT GACATTTGAC AGTGTGGGAG GCCTCGTACC AGCCAGGATC CCAAGCGTCC CGTCCCCTGG AAAGTTCAGC CAGAATCTTC GTCCTGCCCC CGACAGCCCA GCCTAGCCCA CTTGTCATCC ATAAAGCAAG CTCAACCTTG GCGTC | 381 |
| | 3' downstream sequence | | | | | | tcctccctct cttgtagctc ttaccagagg tcttggtcca atggcctttt... | 382 |

The nucleic acid sequence of the 15,174 base pair (bp) of the human UCP2 gene (ENSG00000175567), including 5,000 bp 5'UTR and 2,000 bp 3'UTR, is as follows (Exons are highlighted) [SEQ ID NO: 383]:

```
TCCAGCCTGG GCAACAAGAG TGAAACTCGG TCTCAAAAAA AAAAAAAAGA GAAGAAGAAG     60
AAAGAAAACT AGGTGGAGTG TGGTGGCTTG CACCTATAAT CCCAGCACTT TGGGAGGCCG    120
AGGTGGGTGG ATCTATTGAG GCTAGGAGTT CAAGATCAAC CTGCCAACAT GACGAAACCC    180
CACCTCTACT AAAAATACAA AAAATTAGCA CGGCGTGGTG TGTGTGCCTG TAATCCTAGC    240
TACTTGGAAG GCTGAGGCAG GAATCGCTTG AACCTGGGGG GCAGAGGTTG CAGTGAGCCA    300
AGATCTTGCC ACTGCACTCC AGGCTGGGCG ACACAGCACA ACTCTATCTC AAAAAAAAAA    360
AGAAAAAACA AAAGAAAACT AATATATCAA AATAATTTCT AGTTAGTTGG ATTCACTCAC    420
TTATTCATTC AATGACTTAT TGAATTATCA TATATTACTA GTGCTTTTTA ATACATACCT    480
TCTACAATTT TCAACTGAA AATTACTTCA TTGATCAGGG CTCTTTAAAC TGATCTCCAT     540
TTGCATTGTT TTACTAACTA TAGTTATTAT TCATGTATTA GCACTCTGAG CCTACTGTAA    600
TGATGTGTAC CTTAATAAAG AACTGAATAT TTGTAATGGC TGGCAGTGAA TTTAGTAGTT    660
CTTGAATTTA GAGCTCAAAA TATGGGAGTA ATTTGCTGCT TTATTTCCTT TGAGAGGTAA    720
TAGAGGAAAA ACAGAATCTA ATAACAATCA CAGATTTTCG GGAAAGCACT GTAAAACCAT    780
ATGATCAATT CTAGCTTCTT ATGTAAACAT GGAAAGATTG CCAGCTGAAC ACCTGTCATG    840
CTCTAAGAAG TTGGGGAGAA TTTGCATTTT TAGAACTGTG AGCAAAATGA GAACGACTGC    900
TATGTTCATG CTTTGTGAAT TTAGCTTTAT TTCATTCACA CAATTCATGG GAAAAAATGC    960
ATCTTTTAAC TCGGTGTTTT TCAATTCAAC TTTTAAAATA CAGGAGTGGG CCAGACCCGG   1020
TGGCTCACAC CTGTAATCTC ATCACTTTGG GAGGCCGAGG CAGGTGGACC ACAAGGTCAA   1080
GAGATAGACA CCATCCTGGC CAACATGGTG AAACCCCATC TCCACTAAAA ATACAAAAAT   1140
TAGCTGGGCA TGTTGGCACG TACCTGTAAT CCCAGCTACT CGGGAGACTG AGGCAGGAGA   1200
ATCGCTTGAA CCTGGGAGAT GGAGGTTACA GTAAGCCGAG ATCGCGCCAC TGCACTCCAG   1260
CCTGGCGACA GAGCAAGACT CCATCTCAAA AAAAAAAAAA AAAAAAAAAA AAAAAAAAAA   1320
AAAAAACCAG GATGTGTTAC CAAGGAAAAT TCATTTACAA TGGTTAATTA TGTGACAAAC   1380
ATGTCAAGTA ATTCCATCTG GCTTTGTGTC ACCATTTCCC CACCCTTTTT TCAGAAACCA   1440
AAACCAAGAA GAAGAACAAA CATCAAAATG GACATGGAAA TTAACAAATA TATGATTCAA   1500
TTTAATCTCC TAAGAGGTTT TTTAAAATTA TTTTATTTTG AGACGGAGTC TTGCTCTGTC   1560
GCCAGGCTGG AGTGCAGTGG CAGGATCTCA GCTCACTGCA ACCTCCATCT CCCAGGTTCA   1620
AGCGATTCTC CTGCTTCAGC CTCCCAAGTA GCTGGAACTA CAGGCAAGCA CCACCACACC   1680
CAGCTAATGT TTGTATTTTT GGTAGAGATG GGGTTTCACC ATGTTGGCCA GGATGGTCTC   1740
GATCTCTTGA CCTCATGATC CACCCGCCTT GGCCTCCCAA AGTGCTGGGA TTACAGGTAT   1800
TTTTTATTTT TTTTGAGACA GGGTCACCCT GTCACCCAGG CTGGAGTGTA GTGGCACAAT   1860
CATGGCTCAC TGCAGCCTCA ACCTCCCAGG CTCAGGTGAT CCTCCATGTC AGCCTCCCAA   1920
GTAGCTGGAA CTATAGGCGT GCAACACCAT GCCCAGCTAA TTTTTGTATT TTTTGTAGAG   1980
ACAGGGATTT GCCATGTTGG CCAGGCTGGT CTTCAACTCC TGGCCTCAAG TGATCCACCC   2040
GTCTCAACCT CCCAAACTGC TAGGATTACA GGTGTGAGCC ACCGTGCCCC ATCTCATCTG   2100
CTAAGTGGGT TTAAAGAAAT TCAGTTTCAT GTCAATTTTT AAAATGTATG GTTATCAAAT   2160
TCGACTTCTT TTTAAAAATG CAATCAGATA ACTGTATGCT TGTTTGATGA GGGGAGGAAA   2220
GTTAATATAG CCAATCTACT CAATATTTTT AGCAGAAATT ATCAGAGACT AAGGAAATGT   2280
TTAAGTTTTT CTCATGTTGG TTTTAATTAC CTAATGTTTT CAGTTTTCTC TTTCATTCTT   2340
GTGTCTTTTT TTCATTTTCA GTGTTTCAAA TACAGTTTGT ATTTAAAGAT TTAGAAGTTC   2400
CAAAACTGTA AGCACAGTGG ATTGTTCCT GGGATGATGT TAAAATTATA CAACAAAATA    2460
TATGAAACTT TGTCAATTTG GTTATTGGCA CATACAAAAT ATTTACAAAT AAACGTGTGT   2520
GTGTGTGCGT GTACACACAA TTCAATGAAA TAGATGTGAA ACAAGTTTTC TTTTTTTTTT   2580
TTTTGAGACA GAGTCTTGCT CTGTCGCCCA GGCTGGAGTG CAATGTCGCA GTCTCAGCTC   2640
ACTGCAACCT CTGCCTCCCG GGTTCAAGCG ATTCTCCTGC CTCAGCCTCC CGAGTAGCTG   2700
GGACTACAGG CACCTACCAC CACTCCCAGC TAATTTTTGT GTTTTTAGTA GAGACAGGGT   2760
TTCACCATGT TAGCCAGGCT AGTCTCCAAC TCCTGACCTC AGGTGATCTG CCCGCCTCAG   2820
CCTCCCAAAG TGCTGGGATT GCAGGCGTGA GCCACCTCAC CTGGCTACAA GTTTTCAAAA   2880
TACATTTATC TGTACCCATA CATTCTCCAG TTTGTCCACA GGACATCTTA TGACTTGAGC   2940
AAGCTGCTAA AAATCCAAGG GTGCAGCGTT TGTATGTCTA TAGGATTGCT CAGATCTGCC   3000
CCCACCCTGA AAGAATTTAA GAGAATTTCT TGAGGCCAGG CACAGTGGCT CACACCTGTA   3060
ATTCCAGTAC TGTGAGAGTC CGAGGTCAGA GGACTGCTTG AGGCCAGGAG TTCAAGAGCA   3120
GCCTGGACAA CATAGGGAGA CCTGTCACTA CAAAGAATAA ATAAATTAGC CAGGCTTAGT   3180
GGCTCATCCC TGTGGTCCCA GCTACTAGGG AGGCAGAAGT AGGACTGCTT GTCCCAGGAG   3240
GTCAAGACTG CAGTGAGCTG AGACCCGACC ACCTGCATTC CAGCCTGGGC AACAAAAAGA   3300
GACCCTGTCT CAAAAAATAA GTTAAATAAA TAAATAATAA AAATAGTTTA AACCCTAAAC   3360
ACATCTTCTT TTTCAAAGAG GACTTCTTAA GGACTTCATG CTGCGTCCTG TTGATCTCCA   3420
CTTCCCTTTT TCAGCGTCCA CACTTTTAAC AGTCTCTTTT GCCAAGGATA ATAAGTATAT   3480
AGTTTCTGGA ATCCAGATTC TTCCCTGTTT GGACAGCCAG GGGGACAATT TTTGGTCTGC   3540
AGGCCTTTGC ATCTGTTCTG CTGTTGCTCA GCAATCTCAC AGCAAATTTG CCGAGCCTCT   3600
CCGGAATGCA CAGCCAGACA GAGCTCAGCG CAAAAGCTAG AGAACCTGGC GGAGGGAGAC   3660
TCACAGTGCC ACAAAAAAAC TTTATCTTTT CTTTTTTTTT TTCTTTTCTT TCTTTCTCTT   3720
```

```
TCTTTCTTGT CTTTCTGTCT TTCCTCTCTC TCTCTCTGTC TTTCTTTCCT CTCTTTCTTT    3780
CTTTTTTCCT ACATGGCAAG ATCTCCTCAT GGCAGAAATA ATCTGCCTTG ACTTCTGTTT    3840
CCACGCTGCT TCTGCCAGGA CCATGCGCTC GGCGTGTTTT TCTTTCCGCT ATAATTATCC    3900
AGGCCCATCC CAGCTCTGGT CCCCTCAGCT GTTCCCTGGC AGTCCCTTCT GCTGGTGAAA    3960
ACACATATGG CGCCGGCCTG ACCAGGGTGT AAGTGTGTGA ATATCAGGAA GATGACTGAA    4020
CGTCTTTGGG ACTCCGTTTC CTCATTGTAA AATGGAGGTT AATACCAGCC TTCTTCTACT    4080
CCCCAAACGC ACGTGTTTGT CCCGGCCAGA GGGCCCAATT GTTGGCTGTT CACGCGTCAG    4140
TTACCCCCAC AGGACGGGTC AGCCAATTAA AGGCGAACCA GGCCCGGTCC ATCTCCTGAC    4200
GCCTTTTCTC ATCCCAGGGC TGGACAGGCA GCTGGCCTGG GCCCGACCTCT GCCTTGTCAC    4260
GTGCGGGGGC CGGCCCGTTT GCTTGTCTGT GTGTAGGAGC GTGAGGTCAC GCTGGGTGCT    4320

CCCGCCCCGC CGGGGCCTTT AGTGTCCTGG TCCCTAAACG CCAGGCCGCT CCACCGGGGG    4380
AGAAGGCGCG AACCCCAGCC GAGCCCAACG GCTGTTGTCG GTTGCCGGGC CACCTGTTGC    4440
TGCAGTTCTG ATTGGTTCCT TCCCCCGACA ACGCGGCGGC TGTAACCAAT CGACAGCGAG    4500
GCCGGTCGCG AGGCCCCAGT CCCGCCCTGC AGGAGCCAGC CGCGCGCTCG CTCGCAGGAG    4560
GGTGGGTAGT TTGCCCAGCG TAGGGGGGCT GGGCCCATAA AAGAGGAAGT GCACTTAAGA    4620
CACGGCCCCG CTGGACGCTG TTAGAAACCG TCCTGGCTGG GAAGGCAAGA GGTGTGTGAC    4680
TGGACAAGAC TTGTTTCTGG CGGTCAGTCT TGCCATCCTC ACAGAGGTTG GCGGCCCGGA    4740
AGAGTGTGAG GCAGAGGCGG GGAGTGGCAA GGGAGTGACC ATCTCGGGGA ACGAAGGAGT    4800
AAACGCGGTG ATGGGACGCA CGGAAACGGG AGTGGAGAAA GTCATGGAGA GAACCCTAGG    4860
CGGGGCGGTC CCCGCGGAAA GGCGGCTGCT CCAGGGTCTC CGCACCCAAG TAGGAGCTGG    4920

CAGGCCCGGC CCCGCCCCGC AGGCCCCACC CCGGGCCCCG CCCCCGAGGC TTAAGCCGCG    4980
CCGCCGCCTG CGCGGAGCCC CACTGCGAAG CCCAGCTGCG CGCGCCTTGG GATTGACTGT    5040
CCACGCTCGC CGGCTCGTC CGACGCGCCC TCCGCCAGCC GACAGACACA GCCGCACGCA    5100
CTGCCGTGTT CTCCCTGCGG CTCGGTGAGC CTGGCCCCAG CCCTGCGCCC TTTGCGCCCC    5160
CCACGCTTGT TCTGCGTGCG CTGCCCGCTC TTCCATTTAC CTTCTCTCCC ACCCAAGTTT    5220
GTACTCTTTT CTTTCTCTCG GTTTTATTTT TTGTTTTTGT TTGTTTGTTT GAGACAGGCT    5280
TTCGCTCTGT CTCCCAGGCT GGAGTGCAGT GGCGCGATCT CGGCTCACTG CAGCCTCCAC    5340
CTCCCAGGTT CAAGCGATCC GCCTGCCGAG TAGCTGGGAT TACAGGCGCC CGCCACCACG    5400
CCTGCTAAT TTTTGTGTTT TGTAGAGATG GGGTTTCGCC ATGTTGGCCA GGCTGGCCTC    5460
GAACTGCTGA GCTCAAGCAA TCCGCCCGCC TCGGCCTCAC AAAGTCCTAG AATTTTAGGC    5520
ATGAGCCTCC GGGTCCGGCC TGTGCTAATC CTTTCTGTCC TTGGTTCTTT ATTTCTCTTC    5580

TCTCTTTTTC TTAGTCCCTT TTGTTCTTTC CCTCTCCCGT TCAGTTGGCT GTCGTTTGAG    5640
CCTCCACCTT TTCACTCCCT CCTTTCCACC ACGATGCCGA GCCCTGCCTT GGATGGGGAC    5700
CATCAGCGAT GACCACAATG ACCTCTCCCT TACCAGGCAG CTCCAGGCAG TGTTCCTGCA    5760
CCGCCTTTCC CAGGGCTTGG GGGCTTTTTT TAGTGGGCTT TGAGCTGCTC AATCTGGCCT    5820
CTGCAGGGCC GGCTCCCAGC CCTTCCAACC TCCTCACAGC CCGACCTGGG ACCTAGCCAA    5880
TTCCCGGAGA GTCTCTGTCC CATCGTGACC CCCTCACAAC TCTCCCACTC ACCAAAGTCT    5940
GATGACTGTG CTAGGGGGTG CTTATATAGA GTACTGAGTG TTACAAAAGC AGAAGTCTGG    6000
ATGAGAACCA ATTTGTGATA TTAAGCAGGT GGGGTGGGGG TGGGAGTGT ACCTAGGTTC    6060
ATTTTCCGCC CTGCTTTTCC CCTTTCCAGT GTGTGCACTT AACCAGTCCC TGGGCCCTGT    6120

TCCCCATCCC CCTCCAAGGC ATGGATTGGG TGGGCTTGTG TGTCTTGGGG CAGGTGGCCC    6180
TTTCTAAACT CTCTGCCTTT GCTCACCCAC AGGACACATA GTATGACCAT TAGGTGTTTC    6240
GTCTCCCACC CATTTTCTAT GGAAAACCAA GGGGATCGGG CCATGATAGC CACTGGCAGC    6300
TTTGAAGAAC GGGACACCTT TAGAGAAGCT TGATCTTGGA GGCCTCACCG TGAGACCTTA    6360
CAAAGCCGGG TAAGAGTCCA GTCCAAGGAA GAGGTCTCTT GCTGCCTCCT AACCCTGTGG    6420
TCTAGGGGCA GGAGTCAGCA GGGCATTAAC AAAAATAATT ACCATCCCCA CCCCCGACAG    6480
TGAAGTGGCT CTTTCCAGTT CACAGAGCAC TCTCACACCT CCCCGCTCTC ATTCTGGCCC    6540
TTCAGCTGAC TCGGACAAGC CAAGGATCTT GGTCCCCATT TTATAAAGGA GAAAACTGAG    6600
GCCCACGTGT AACAGTGATT GGCCCCAAGT CATCCCGGGA GCCAGCAGAA GAGCTAGGAC    6660
AGGAACCTAT TGTTCTAACT TCATATTGAT GCTAGCTTTT GACTATCCCT GAAACCGAGA    6720
TTGGTAATCA GCCCGGCTCT GAAACTGGTT ATTTGCTGGG GACTGTAAAA TAGGATTAAC    6780

TATTTCTAGT CCTGCATTTT AATTGCTGTT AGTAGGGCCA TCTTACCCAC CCTCTGAAGG    6840
ACCTGACTTG GCAAGCCCAA GGCAACATTC AGAATATGGC AGCTGAACCT CTGTGCACTT    6900
GTCTTTGGGC AGCAGCTGGG TCTTATTCTT CTCTGGCCTT CACACATCC TGCAACCCAG    6960
CTCAAGGTCA GGAATGTGAC AGACTCATGT CATCATATCT CTGATGCCCA GAGAAGGGAT    7020
ACCATTTGCC TGAGCCTTCT CAGTACTGTT TAATCAGCCT GTGAGAACTT TCCTTGTGAA    7080
AGGCCCTGTC TGTGCCTGGG GCTGATAAAA CAGCAAGAAC GAACTGAGGA GCTGGGCAGC    7140
AGTGCAAAGC AAATACTACC AGCTTTGGTG CCTGTAAGTG TGGCTCTTAC TCATCTCACA    7200
TGGAAATAAG GCAGCCACC TTGCAGGGCT GCTCTGAGGA TTGAGCTAAT ACAGTGCCCT    7260
GGGCGTTGGG GTGGGAAAG TTGTGGAGCA CCTCCTGGGG GAAGGGGGTG TCAGAGCAGG    7320
GAATCTGGGG AGTCCGAGGG CACCTTCATC AACCCAATCT GTCATTTGAG CACCAGTCTT    7380
CACTGAGCCT CGTGGGCAAG CTGGAGGGAA ACAGGAATAA GGTCAGGCCC TGTTCTATAG    7440

GTCCCAGTGT AGTTGCTATG GTGAGTATCT TCATTTCCCT GCTTGCCCCA GCCACCTGGA    7500
GTGAGAAGCC CAAGAGGAAG CTGGGTGAGC TGTTTGTTTC CATGGGTCTC TGTGTTCACA    7560
GCTGACTCCC TTCACCAGCC AGCCCTTTCA CCTGAGCCCC AGCAACAAAG GCAGTCAGGC    7620
GGGGCTCAAA GCAGCTGCTC CAATGAAGTC AAAGAAATAA GCTCAGGGGA AGAAGCAGGT    7680
CACCCTCCCC CACTAGGGTG CTGGGCTCAC TTCCTCCTGG GGCAGTGGAG GAGGGTGTGG    7740
TTCCAACTCA GAACAAAATG GGGCTTTTGG TTTACTTTAT CACTCTTCAC AGCTCTGACC    7800
TGGACCCCTC ATCCCTGCCT GTCTTGTGGT GTAAGTGCGG ATCCCCCTGA GTTGGAGGAA    7860
AGGAAACTGG CCCAAACAAA AGGAGAGCA GTTTTCTCTG CATCACATGG TAGGCCAGGA    7920
GGAGTCTAAT GCCCCAGAGT TTACTCTCAG CCCCCAAAAT CACCTAGCTA AATGTTACCT    7980
TATCTAAGAA GTCCTTAGGT TTTTTGGGGT TTGTTTTTTT TTTTTTGAG ACAAGGTCTC    8040

ACTCTCTCAC CCAGACTGGA GCACAGTGGC ACAATCACAG CTCACTGCAG CCTCAACCTC    8100
CTGGGCTCAA GCAATCGTCC CAAGTAGCTG GGACTATAGG CCTGCACCAC CATGTCCAGC    8160
TAATTTATTT TTATTTATAT TTTTTAGACA GGGTCTCATT ATGTTGCCCT GGCTGGTCTT    8220
GAACTCCTGG GTTCAAGCAG TCCTCCCACC TCTGCCTCCC AAAGTGCTAG GTTTTTTTT    8280
GTTTGTTTGT CTGTTTTTTG AAACAGAGTC TTGCTCTGTC GCCTAGGCTG GAGTGCAGTG    8340
GCACGATCTC AGCTACTGCA ACCTCCACCT CCTGGGTTCA AGTGATTCTC CTGCCTCAGC    8400
CTCCTAAGTA GTTGGGAATA CAGGCGTGTG CCAACACACC CAGCTCATTT TTGTATTTTT    8460
AGCGGAGATG GGGTTTTGCC ATGTTGGCCA AGCTGGTCTC AAACTCCTGA CCTCAGGTGA    8520
TTCGCCCGCC TCAGCCTCCC AAAGTGCTGG GTTTACAGGC GTGAGCCACC ACACCCAGCC    8580
CAAGAAGTCT TTTCTGATCA CCCACTCTTC CTTCTCTCCC AATGGCATTA GTTGTTCCCT    8640
```

```
CCTTTGCATT TTGAGAGTAT GTCCTGTAAG CCCCAAATGC AGCTTGAATC ATCTGCCCAT      8700
CCACCCCCTG TGCCCAACAG TAAGCCTCCT CTAGAGTAGA TACTATCTCC TGCATCTCAG      8760
TGAACCACTG CCCAGCAAAG CAGTCTTGCT AAAACAATGA CTCTAGAGAT CCTAAGCTGT      8820
GTGAGAGCTG GAGGAGAGAA TTAGACTGAT GGTCTGGGAA GGGATTGAAT TAGTCATCTT      8880
GTACCTTTTC TTCTTGACTT AAGTTCCAGA CCTGTAGCAA CCATTCCTGC TTAGACATCC      8940
AGAACATAAG CCTATGGGTC TGTGCCTGTT GGGTCTTAGT CTGGGTGAAA CTTTTCTCTA      9000
CTTCTGTCAG CTCTCCAGAT GAACCACAGA AGCAGGAATG TGGGCATCAT CAGTGAAATC      9060
TCTGCATACA GCAGACAAAG GGCTGGTCCA GTGCTGTTT ATGAGGCAGC GCTAGGAGAG       9120
CTCTGATCCA GACTCTCCCT GCAGTGAAAG GGAGGGAGCC CTTCATGAAG TATTGACTGC      9180
TTGAGCAGGA ATTGCTTCAC CAGCACCTAA CTGAGTGCCT CTCGAGCTCA CATCGGTTTT      9240
CCCTCATGAG GCCACTTGGA GTCTTGCTGA GGGACTTGGT TCTATTAGGG AAGGTGAGTT      9300

TGGGGATGGT GAGCAGGGAG GGCCTGGGGA CATTGTGGCT AATGGGGCTT TTCTCCTCTT      9360
GGCTTAGATT CCGGCAGAGT TCCTCTATCT CGTCTTGTTG CTGATTAAAG GTGCCCCTGT      9420
CTCCAGTTTT TCTCCATCTC CTGGGACGTA GCAGGAAATC AGCATCATGG TTGGGTTCAA      9480
GGCCACACAG GTGCCCCCTA CTGCCACTGT GAAGTTTCTT GGGGCTGGCA CAGCTGCCTG      9540
CATCGCAGAT CTCATCACCT TTCCTCTGGA TACTGCTAAA GTCCGGTTAC AGGTGAGGGG      9600
ATGAAGCCTG GGAGTCTTGA TGGTGTCTAC TCTGTTCCCT CCCCAAAGAC ACAGACCCCT      9660
CAAGGGCCAG TGTTTGGAGC ATCGAGATGA CTGGAGGTGG GAAGGGCAAC ATGCTTATCC      9720
CTGTAGCTAC CCTGTCTTGG CCTTGCAGAT CCAAGGAGAA AGTCAGGGGC CAGTGCGCGC      9780
TACAGCCAGC GCCCAGTACC GCGGTGTGAT GGGCACCATT CTGACCATGG TGCGTACTGA      9840
GGGCCCCCGA AGCCTCTACA ATGGGCTGGT TGCCGGCCTG CAGCGCCCAA TGAGCTTTGC      9900
CTCTGTCCGC ATCGGCCTGT ATGATTCTGT CAAACAGTTC TACACCAAGG GCTCTGAGCG      9960
TGAGTATGGA GCAAGGGTGT AGGCCCCTTG GCCCTTTTTT CTCAGTGATG ATTGATCTTA     10020

GTTCATTCAG CCATATAGTT TTTTAGGCCC CACGATCCCT AGGAAGATCA GGGGAACAGA     10080
GAACTGGAAG GGGCCCTGGT CCTCCACATA GTTCCTAAGC ACCTGGGCTA TACCAGGCTC     10140
TGAGCAGGGC GTCATCCCAT CACAGTCTTC AACACCACCT TGGGAGTAGG TAGTATCATC     10200
CCAGTGTTAT AGAAGAAGAG ACTGAGGTGG GAAGGCAGTG GGTAGAGTGG GGACTTGGCC     10260
AGGGGCACAC AGTAGAGAGC CAGAAAACAC ACAGTAGAGA GCCAGGACAC TCGTCTCTAA     10320
GGCCAGCGTT CTTCCCTTTC ACCTCCTTAG TATGCCATGC CAACCCTCCA TTTTACACAT     10380
GACGAAACAG AGCCCCAGAC AAAAGGTTGT CTTTCCCAGA TCACATGGCA GGAAGAAGTA     10440
AAGCTGACCT GAGATCCCAA GTCTTAGGAA TCCCAGTCCT CAGAAAGCCA CTTCTCTCTG     10500
AGCCTTGGTT TTCACATTTG TCAGATGGAA ATGATTGTGA TTTCTCAGGG CTGTTGAGCA     10560
GGTAAATGAA AATGTTTTAT GAAAGAAAGC ACCAAGTTTC ATTTTGGTCT TAGCCCTTGC     10620

TATGTCCCTA GCAAGAAGTA GATATTCATA GGGATATTTT GTTTGATGTG AGGAGTTCTT     10680
ACAGCAAGAG CTTGTAGAAG GCCAAAAGCT TCTGGATTCT ATTCCCAAAA GCAGGAGATG     10740
ACAGTGACAG GGTGGTTTTG GTGAGGAGAG ATGAGGTAGA AATGAGTGC AAGCCCGCTG      10800
GCCACTGACC CCATGGCTCG CCCACAGATG CCAGCATTGG GAGCCGCCTC CTAGCAGGCA     10860
GCACCACAGG TGCCCTGGCT GTGGCTGTGG CCCAGCCCAC GGATGTGGTA AAGGTCCGAT     10920
TCCAAGCTCA GGCCCGGGCT GGAGGTGGTC GGAGATACCA AAGCACCGTC AATGCCTACA     10980
AGACCATTGC CCGAGAGGAA GGGTTCCGGG GCCTCTGGAA AGGTGTGTAC CAGTTGTTTT     11040
CCCTTCCCCT TTTCCTCCTC CCCGATACTC TGGTCTCACC CAGGATCTTC CTCCTCCTAC     11100
AGGGACCTCT CCCAATGTTG CTCGTAATGC CATTGTCAAC TGTGCTGAGC TGGTGACCTA     11160
TGACCTCATC AAGGATGCCC TCCTGAAAGC CAACCTCATG ACAGGTGAGT CATGAGGTAG     11220

ACGGTGCTGG GTCTCACCCT TCCCCCATGC CAGGAGCAGG TGCGGGGGTG TAGCTGACAC     11280
CAGAAGACCA CATCTTTTCA TCCTATTTGC CCTTTGCAGG GAGAGTAAGA TATCTCTTAC     11340
TTGCCATATT GAAGCCAATT GGGATGAAGC TCCCACTTTG CACATTGGAG AACTGAGGCT     11400
AGATTGGCAA AATGACTCTT TCAGGTCCTC AGAAGATGTC TCAGCTGGAG TCCCTGTCTG     11460
TTTTTGTTTT TTTGTTTGTT TGTTTTTTGT TTTTTTTGAG ATAGAGTCTC ACTCTGTTAC     11520
CCGTGTAATC TCAGCTCACT GCAACCTTCC TCCTCCTAGGG TCAAGCGATT CTTGTGCCTC    11580
AGCCTCCCGA GTAGCTGGGA TGACAGGTGT GCACCAGCAC ACTGGCTAAT TTTTGTATTT     11640
TTAGTAGAGA TGGAGTTTCA CCATGTTAGC CAGGCTGGTC TCGAACTCCT GGCCTCAAGT     11700
GATCTGCCCA CCTTGGCCTC CCAATGTGCT GGGATTACAG GTGTGAGCCT CTGCGCCCCA     11760
TCCTCTTGTT TGTTTTTTGA GACAGGGTCT TGCTCGGTTG CCCAGGCTGG AGTGCAGTGG     11820

GGTGATTAAT GGCTCATTGC AGCCTCGACC TCCCTGACTC AAGCAATCCT CCCACCTCAG     11880
CCTCCTGAGT AGCTGGGGCT GACTACAGGC ATGCACACTG TGCCTGGCTA ATTTTTGTAT     11940
TTTGTAGAGA CAGGGTTTTT GCCATGTTAC CCAGTCTGGT CTTGAACTCC TGGGCTCAAG     12000
TGATCCACCC ACCTCGGCCT CCAAAAGAAG TCCTGGATTA CAGGCATGAG ACATTGTGCC     12060
CAGCCTCTCT GTCTCTTTAA AATCATGAAA ACTCGTAGCT ACTTAAGTAA TTCTCCTGCA     12120
TTCTGGAATG ATGGGTGAAG ATCTTGACTG CCTTGCCTGC TCCTCCTTGG CAGATGACCT     12180
CCCTTGCCAC TTCACTTCTG CCTTTGGGGC AGGCTTCTGC ACCACTGTCA TCGCCTCCCC     12240
TGTAGACGTG GTCAAGACGA GATACATGAA CTCTGCCCTG GGCCAGTACA GTAGCGCTGG     12300
CCACTGTGCC CTTACCATGC TCCAGAAGGA GGGGCCCGA GCCTTCTACA AAGGGTGAGC      12360
CTCTGGTCCT CCCCACCCAG TTCAGGCCTC TTGGCTATGC ATGTCTATTG TGGGTGGGAG     12420

AGAACCACCT GGAAGTGAGT AGCAGCCAAG TGTGACTATT TCTGATCCTG GTCCTGGCAT     12480
TTCACCAGCA TTCACCTATC CCCTTAATTC CTTCCTCCCA GAATTGCTAC CATCACTGTT     12540
TATTAGGTGT TAAATGGAGA CTCAAGGGA ATTCATGCTT ATAGCCAAGC AGCTGTGAGC      12600
TCAGTTCATT GAGTCCTCCC AGCCTCCTTT GGGACAGAGC AACTGGGTTG GATTGAATAC     12660
CAGGCCCAGT GAGGGAAGTG GGAGGTGGAG GTGCCCCCAT GACCTGTGAT TTTTCTCCTC     12720
TAGGTTCATG CCCTCCTTTC TCCGCTTGGG TTCCTGGAAC GTGGTGATGT TCGTCACCTA     12780
TGAGCAGCTG AAACGAGCCC TCATGGCTGC CTGCACTTCC CGAGAGGCTC CCTTCTGAGC     12840
CTCCCTGCT GCTGACCTGA TCACCTCCTG CTTTGTCTCT AGCCGGGCCA TGCTTTCCTT     12900
TTCTTCCTTC TTTCTCTTCC TCCCTTCCCT TCTCTCCTTC CCTCTTTCCC CACCCTCTTCC    12960
TTCCGCTCCT TTACCTACCA CCTTCCCTCT TTCTACATTC TCATCTACTC ATTGTCTCAG    13020
TGCTGGTGGA GTTGACATTT GACAGTGTGG GAGGCCTCGT ACCAGCCAGG ATCCCAAGCG    13080
```

```
TCCCGTCCCT TGGAAAGTTC AGCCAGAATC TTCGTCCTGC CCCCGACAGC CCAGCCTAGC    13140
CCACTTGTCA TCCATAAAGC AAGCTCAACC TTGGCGTCTC CTCCCTCTCT TGTAGCTCTT    13200
ACCAGAGGTC TTGGTCCAAT GGCCTTTTTG GTACCTGGTG GGCAGGGGAG GAACCACCTG    13260
ACTTTGAAAA TGGGTGTGAT CCACCTTCCA CCTCCAGCAT CCAATCTGAA GCCCGTGTAG    13320
GTCATCTGGT CCATTTCTCT CTAGACCCAG GCCCTGTACT AACATGGGGA GTGCAGGAGC    13380
CACCTGAGAG ACAGCAGTGC CTCCCCTTCC TTTGCGGGC CACTTGAGCT CTTACTCAGA     13440
ATCTGGTACT CTAGTGCCTG CCATCCCAAC CCCCCACCCC AGCCGCAGGC CTGTTTATCT    13500
GCACAACAAG AGTGCTCCTG TGTGCCCTGC ATCTCCTGCA GTTCCAGAGG AACATGAGAC    13560
TCTTAGATGC TGTTGACTTT ATTTTATTCC ATTTTACAAA TGGAAGGAAG ACCCACCTCC    13620
CCCAAAGTCC CAGACCTTGT GAGAACAAGT CAGTCAGCCT CCTTCCACCC TCCACAGCCA    13680
CAGCCACACC CACAGAGGAA ATGTTACTGA ACTGGGTGGA GCAGGCCCTG ACTCCACAGA    13740

GGGTGGGTGG AGGCTGCAGG GCAAACATCT GGTCTCTGCC TGAGGATACT TTCCATTTGT    13800
GTTTTTTGTT GTTTTGAGAC AGAGTCTCAC TTGCTGTCAC CCAGGCTGGA GTGCAGTGGT    13860
GCAATCTTGG CTCACTGCAA CCTCTCCCAG GTTCAGGCGA TTCTCCTGCC TCAGCCTCCC    13920
AAGTAGCTGG GATTACAGGC ATACACCATC ATACCTGGCT AATTTTTGTG TTTTTGGTAG    13980
AAACGGGGTT TTGCCATGTT GGCCAGGCTG GTCTCAAACT CCTGACCTCA AGTGATCCAC    14040
CTACCTCAGC CTCCCAAAGT GCTGGGATTA CAGGCATGAG CCACTGTGCC TGGCCAGGAT    14100
ATTTTCCATT TGGAGTCTCA CCACCACAAC CCCCCTCCAC CTGCCCCTGC CCCAGCTAGG    14160
CATCCAAGGA GGCCGCAAGA AGCCAGGGCC TTGGCTGCAC AGGGGTCTCC GCTTCTCTGT    14220
CCCTGTTCTT ATCACCTGCA CTCAGAGGCA GGTGGGCAGG GGTACTACAA TTTCAAGGAG    14280
TGGAGACTGT GAGGTCCTGG AATCCCAAGG CATCTCCTGT AGGGCTGGGC CCTTAGAATT    14340

ATGTCACTCA GACCCAGTTT GTAGGTGTCT GAAGAAACTG AGGCCTGACA CAGGTGATGC    14400
AGGCAAGAAC ACCCAGAAAG TCCACTACTG AACTGGGACC GGGACCCAGT CCTCCTTCCC    14460
CTTGTGGACT CCCCCAGAGA CCAGTGCTGG GGTCCTTGGG GAAGCCTGTT TGGCAGCTGT    14520
GGAGCTAGGC CCTGAGAACA CGACCACCCT CCCTCTTCCC TCAGCCTCAA GCCGCTGAAG    14580
CCACTGCTGC TTCGCCGCCT CGTAAGCCCA ATGGTCAGAG CTGGAGGCTA GACCCTTCAG    14640
TGCTTGGGTT GAGGGCCAGG GTGTTAGATT GGTTTTTGGA GAAGGAACGA GGGCCCAGGA    14700
TTCTTCAGCT TCTTAGTTTT TGACAAATTG AGCTGAGGCC CCATAGTCCT CGGGAGGGAC    14760
AGGGTTGAGT GCCATAAGTC GGCAAACCAG GGTAAAGGTG ACAGCCAGCT CAGCCAGGCT    14820
GCAGGGGGTG GCATATACAG AGGACCTGGC CACTACTTTA TGTACCTTCT TACACTAATT    14880
CTGTGAGGCA GGCTGTTTGT TAGCTCTGCT CTGGACGGGA AGAAGTAGGG GCAGTTTGGT    14940

AGGTGTGTGT CAAAGCTAAA CAGGCTGGGT GGGCATGAGC AAGTCAGCTG GTTCATTCAG    15000
CAGCCTTAAT AGACACGAGG CTACCCAACT TCACTGTGGT TCTGGGTGTG GCCTTAGGAC    15060
AATGAGCTGG GAACAGTGGT AGGAACCACT GGAAAACATA CCAGTGGGTC TCATTCATTC    15120
TGATCACAGG TAGATCACTT CTCTTTGGTT CCCAACCCTT TAATGCCTAT TAAG          15174
```

---

The invention claimed is:

1. A method of modulating respiratory chain uncoupling in a cell or thermogenesis in a tissue, the method comprising contacting the cell or tissue with an antagomir of miR-22, miR-22-3p or miR-22-5p, wherein the antagomir modulates activity of at least one of UCP1 or UCP2.

2. The method of claim 1, wherein the tissue is brown fat, white fat, subcutaneous adipose tissue, liver or muscle.

3. A method of reducing body fat in a human subject in need thereof, the method comprising administering to the human subject an effective amount of an antagomir of miR-22, miR-22-3p or miR-22-5p, wherein the antagomir modulates activity or expression of at least one of UCP1 or UCP2.

4. The method of claim 3, wherein the human subject in need thereof is obese.

5. The method of claim 3, wherein the miRNA agent is linked to targeting moiety.

6. The method of claim 3, wherein the targeting moiety is an aptamer.

7. The method of claim 3, wherein the targeting moiety delivers the miRNA agent to a specific cell type or tissue.

8. The method of claim 3, wherein the miRNA agent directly binds to the mRNA or promoter region of at least one mitochondrial uncoupler.

9. The method of claim 3, wherein the miRNA agent directly binds to the 5'UTR or coding sequence of the mRNA of at least one mitochondrial uncoupler.

10. The method of claim 3, wherein the miRNA agent modulates the activity of an activator or repressor of a mitochondrial uncoupling protein.

11. The method of claim 3, wherein the mRNA expression, protein expression, or mitochondrial uncoupling activity of the mitochondrial uncoupling protein is upregulated.

12. The method of claim 3, wherein the antagomir is an antagomir of miR-22-3p or mir-22-5p.

13. The method of claim 12, wherein the antagomir is an antagomir of miR-22-3p.

14. The method of claim 3, wherein the human subject selected for treatment has a genetic or epigenetic predisposition to obesity.

\* \* \* \* \*